US012559496B2

(12) United States Patent
Goldberg et al.

(10) Patent No.: US 12,559,496 B2
(45) Date of Patent: Feb. 24, 2026

(54) IMIDAZOPYRIMIDINES AS MODULATORS OF IL-17

(71) Applicant: Janssen Pharmaceutica NV, Beerse (BE)

(72) Inventors: Steven Goldberg, San Diego, CA (US); Connor Martin, San Diego, CA (US); Timothy B. Rhorer, San Diego, CA (US); Virginia M. Tanis, Vista, CA (US); Xiaohua Xue, San Diego, CA (US)

(73) Assignee: JANSSEN PHARMACEUTICA NV (BE)

( * ) Notice: Subject to any disclaimer, the term of this patent is extended or adjusted under 35 U.S.C. 154(b) by 558 days.

(21) Appl. No.: 17/997,437

(22) PCT Filed: Apr. 28, 2021

(86) PCT No.: PCT/IB2021/053517
§ 371 (c)(1),
(2) Date: Oct. 28, 2022

(87) PCT Pub. No.: WO2021/220183
PCT Pub. Date: Nov. 4, 2021

(65) Prior Publication Data

US 2023/0242537 A1 Aug. 3, 2023

Related U.S. Application Data

(60) Provisional application No. 63/017,679, filed on Apr. 30, 2020.

(51) Int. Cl.
*C07D 487/04* (2006.01)
*A61P 37/02* (2006.01)

(52) U.S. Cl.
CPC ............ *C07D 487/04* (2013.01); *A61P 37/02* (2018.01)

(58) Field of Classification Search
CPC ............................... C07D 487/04; A61P 37/02
See application file for complete search history.

(56) References Cited

U.S. PATENT DOCUMENTS

| | | | |
|---|---|---|---|
| 10,515,026 | B2 | 12/2019 | Piel |
| 12,024,524 | B2 | 7/2024 | Goldberg et al. |
| 2023/0167497 | A1 | 6/2023 | Blain et al. |
| 2023/0183249 | A1 | 6/2023 | Oehlrich et al. |

FOREIGN PATENT DOCUMENTS

| | | | |
|---|---|---|---|
| CN | 105992768 | A | 5/2016 |
| RU | 2016128438 | A1 | 1/2018 |
| WO | 2013116682 | A1 | 8/2013 |
| WO | WO 2015/086499 | A1 | 6/2015 |
| WO | 2016046755 | A1 | 3/2016 |
| WO | 2017087590 | A1 | 5/2017 |
| WO | 2018229079 | A1 | 12/2018 |
| WO | 2019138017 | A1 | 7/2019 |
| WO | 2019223718 | A1 | 11/2019 |
| WO | 2019241796 | A1 | 12/2019 |
| WO | 2020011731 | A1 | 1/2020 |

OTHER PUBLICATIONS

Abu El-Asrar A. et al., "Cytokine profiles in aqueous humor of patients with different clinical entities of endogenous uveitis", Clin. Immunol., vol. 139(2), pp. 177-184, 2011.
Adamopoulos, I.E. et al., "Alternative pathways of osteoclastogenesis in inflammatory arthritis", Nat. Rev.;  Rheumatol., vol. 11, pp. 189-194, 2015.
Amatya, N. et al., "IL-17 Signaling: The Yin and the Yang", Trends in Immunology, vol. 38 No. 5, pp. 310-322, 2017.
Appel, H. et al., "Analysis of IL-17+ cells in facet joints of patients with spondyloarthritis suggests that the innate immute pathway might be of greater relevance than the Th17-mediated adaptive immune response", Arthritis Research & Therapy, vol. 13 Issue 03, 9 pages, 2011.
Baeten, D. et al., "Risankizumab, an IL-23 inhibitor, for ankylosing spondylitis: results of a randomised, double-blind, placebo-controlled, proof-of-concept, dose-finding phase 2 study", Ann Rheum Dis, vol. 77 Issue 09, pp. 1295-1302, 2018.
Bharate, et al., Synthesis and evaluation of pyrazolo[3,4-b]pyridines and its structural analogues as TNF- and IL-6 inhibitors, Bioorganic & Medicinal Chemistry, 2008, pp. 7167-7176, vol. 16 Issue 15.
Blauvelt et al., "The Immunologic Role of IL-17 in Psoriasis and Psoriatic Arthritis Pathogenesis", Clinical Reviews Allergy & Immunology, vol. 55 Issue 03, pp. 379-390, Aug. 14, 2018.
Camargo, LDN et al., "Effects of Anti-IL-17 Inflammation, Remodeling, and Oxidative Stress in an Experimental Model of Asthma Exacerbated by LPS", Frontiers in Immuno., vol. 8, Article 1835, 14 pages, Jan. 2018.
Chakievska, L et al., "IL-17A is functionally relevant and a potential therapeutic target in bullous pemphigoid", Journal of Autoimmunity, vol. 96, pp. 104-112, 2019.

(Continued)

*Primary Examiner* — Paul V Ward
(74) *Attorney, Agent, or Firm* — JANSSEN PHARMACEUTICA NV

(57) ABSTRACT

The present application discloses compounds of Formula I or pharmaceutically acceptable salt thereof, wherein $R^1$, $R^2$, $R^3$, $R^4$, and $R^5$ are defined in the specification, as well as methods of making and using the compounds disclosed herein for treating or ameliorating an IL-17 mediated syndrome, disorder and/or disease.

I

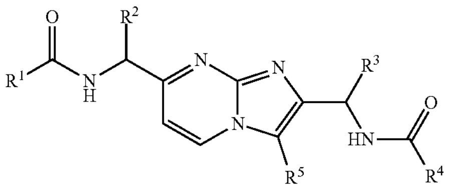

37 Claims, No Drawings

Specification includes a Sequence Listing.

(56) References Cited

OTHER PUBLICATIONS

Chakir, J. et al., "Airway remodeling-associated mediators in moderate to severe asthma: Effect of steroids on TGF-β, IL-11, IL-17, and type I and type III collagen expression", J. Allergy Clin Immunol., vol. 111 No.06, pp. 1293-1298, Jun. 2003.
Chen, X. et al., "Plasma IL-17A Is Increased in New-Onset SLE Patients and Associated with Disease Activity", J. Clin. Immunol., vol. 30, No. 2, pp. 221-225, 2010.
Chen, Y. et al., "The Effects of Th17 Cytokines on the inflammatory Mediator Production and Barrier Function of ARPE-19 Cells", PLoS ONE , vol. 6 Issue 3, Mar. 2011, 6 pages, e18139.
Christenson, S. et al., "An Airway Epithelial IL-17A Response Signature Identifies a Steroid-Unresponsive COPD Patient Subgroup", J Clin Invest., vol. 129, No. 1, pp. 169-181, Jan. 2019.
ClinicalTrials.gov Identifier: NCT03099538, "Ixekizumab in the Treatment of Bullous Pemphigoid", Last Update Posted May 21, 2020, 10 pages.
Cross, et al., "Rules for The Nomenclature of Organic Chemistry", Section E: Stereochemistry, Pure and Appl. Chem., vol. 45, pp. 11-30, 1976.
Deodhar, A. et al., "Three Multicentre, Randomized , Double-Blind, Placebo-Controlled Studies Evaluating the Efficacy and Safety of Ustekinumab in Axial Spondyloarthritis", Arthritis And Rheumatology, vol. 71 No. 02, pp. 258-270, Feb. 2, 2019.
Dick, A. et al., "Secukinumab in the Treatment of Noninfectious Uveitis: Results of Three Randomized, Controlled Clinical Trials", Ophthalmology, vol. 120 No. 4, pp. 777-787, 2013.
Dolff, S. et al., "Disturbed Th1, Th2, Th17 and Treg balance in patients with systemic lupus erythematosus", Clin. Immunol., vol. 141, Issue 2, pp. 197-204, Nov. 2011.
Dos Santos TM. et al., "Effect of Anti-IL-17 Antibody Treatment Alone and in Combination With Rho-Kinase Inhibitor in a Murine Model of Asthma", Frontiers in Physiology, vol. 09, Article 1183, 19 pages, 2018.
Eby, J. et al., "Immune responses in a mouse model of vitiligo with spontaneous epidermal de- and repigmentation", Pigment Cell and Melanoma Res., vol. 27, Issue 6, pp. 1075-1085, 2014.
Gaffen, S., "Structure and signaling in the IL-17 receptor family", Nature Reviews, Immunology, vol. 09, pp. 556-567, Aug. 2009.
Havrdova, E. et al., "Activity of Secukinumab, an anti-IL-17A antibody, on brain lesions in RRMS: results from a randomised, proof-of-concept study", J Neurol., vol. 263, pp. 1287-1295, 2016.
Hawkes et al., "Psoriasis Pathogenesis and the Development of Novel Targeted Immune Therapies", J Allergy Clin Immunol., vol. 140 No. 3, pp. 645-653, 2017.
International Search Report and Written Opinion for PCT International application No. PCT/IB2021/053517 mailed Jun. 28, 2021, 18 pages.
Jansen, D. et al., "IL-17-producing CD4+ T cells are increased in early, active axial spondyloarthritis including patients without imaging abnormalities", Rheumatology, vol. 54 Issue 04, pp. 728-735, 2015.
Jawad, S. et al., "Elevated Serum Levels of Interleukin-17A in Uveitis Patients", Ocul. Immunol. Inflamm., vol. 21 No. 6, pp. 434-439, Dec. 2013.
Kelly, G. et al., "Dysregulated Cytokine Expression in Lesional and Nonlesional skin in hidradenitis suppurativa", British Journal of Dermatology, vol. 173 Issue 06, pp. 1431-1439, 2015.
Khattri, S. et al., "Efficacy and Safety of Ustekinumab treatment in adults with moderate-to-severe atopic dermatitis", Experimental Dermatology, vol. 26 Issue 01, pp. 28-35, 2017.
Koga, C. et al., "Possible Pathogenic Role of Th17 Cells for Atopic Dermatitis", Journal of Investigative Dermatology, vol. 128, pp. 2625-2630, 2008.
Koga, T. et al.,"The role of IL-17 in systemic lupus erythematosus and its potential as a therapeutic target", Expert Rev. of Clin. Immunol., vol. 15, No. 6, pp. 629-637, 2019.
Kuiper, J. et al., "Intraocular Interleukin-17 and Proinflammatory Cytokines in HLA-A29—Associated Birdshot Chorioretinopathy", American J. Ophthalmol., vol. 152, No. 2, pp. 177-182, 2011.
Le Jan, S. et al., "Innate Immune Cell Produced IL-17 Sustains Inflammation in Bullous Pemphigoid", Journal of Investigative Dermatology, vol. 134, No. 12, pp. 2908-2917, 2014.
Lemancewicz, D. et al., "The Role of Interleukin-17A and Interleukin-17E in multiple myeloma patients", Med Sci Monit., vol. 18 Issue 01, pp. 54-59, 2012.
Letko, E. et al., "Efficacy and Safety of Intravenous Secukinumab in Noninfectious Uveitis Requiring Steroid-Sparing Immunosuppressive Therapy", Ophthalmology, vol. 122, No. 5, pp. 939-948, 2015.
Lock, C. et al., "Gene-Microarray Analysis of Multiple Sclerosis lesions yields new targets validated in Autoimmune encephalomyelitis", Nature Medicine, vol. 8, No. 5, pp. 500-508, May 2002.
Ma, J. et al., "The imbalance between regulatory and IL-17-secreting CD4+ T cells in lupus patients", Clin. Rheumatol., vol. 29, No. 11, pp. 1251-1258, 2010.
Matusevicius, D. et al., "Interleukin-17 mRNA expression in blood and CSF mononuclear cells is augmented in multiple sclerosis", Multiple Sclerosis, vol. 5, pp. 101-104, 1999.
Mease PJ, et al., "A head-to-head comparison of the efficacy and safety of ixekizumab and adalimumab in biological-naïve patients with active psoriatic arthritis: 24-week results of a randomised, open-label, blinded-assessor trial", Ann Rheum Dis., vol. 79, pp. 123-131, 2020.
Mease, P. et al., "Comparative effectiveness of Secukinumab and Etanercept in Biologic-Naïve Patients with Psoriatic Arthritis assessed by Matching-adjusted indirect Comparison", Eur J Rheumatol, vol. 6 No. 03, pp. 113-121, 2019.
Menon, B. et al., "Interleukin-17+ CD8+ T Cells are Enriched in the Joints of Patients With Psoriatic Arthritis and Correlate With Disease Activity and Joint Damage Progression", Arth Rheumatology, vol. 66, No. 5, pp. 1272-1281, May 2014.
Molet, S. et al., "IL-17 is Increased in Asthmatic Airways and Induces Human Bronchial Fibroblasts to Produce Cytokines", J Allergy Clin Immuno., vol. 108 Issue 03, pp. 430-438, Sep. 2001.
Moran, B. et al., "Hidradenitis Suppurativa Is Characterized by Dysregulation of the Th17:Treg Cell Axis, Which Is Corrected by Anti-TNF Therapy", J of Investigative Dermatology, vol. 137, Issue 11, pp. 2389-2395, 2017.
Mugheddu, C. et al., "Successful Ustekinumab Treatment of Noninfectious uveitis and Concomitant severe psoriatic Arthritis and Plaque Psoriasis", Dermatologic Therapy, vol. 30 Issue 05, pp. 1-4, 2017.
Nash, P. et al., "Secukinumab Versus Adalimumab for Psoriatic Arthritis: Comparative Effectiveness up to 48 Weeks Using a Matching-Adjusted Indirect Comparison", Rheumatol Ther., vol. 05 Issue 01, pp. 99-122, 2018.
Prabhala, R. et al., "Targeting IL-17A in Multiple Myeloma: a potential novel therapeutic approach in myeloma", Leukemia, vol. 30 Issue 02, pp. 379-389, 2016.
Prelog V. et al., "Basic Principles of the CIP-System and Proposals for a Revision", Angew. Chem. Int. Ed. Engl., vol. 21, pp. 567-583, 1982.
Prussick, L. et al., "Open-label, investigator-initiated, single-site exploratory trial evaluating secukinumab, an anti-interleukin-17A monoclonal antibody, for patients with moderate-to-severe hidradenitis suppurativa", Brit. J of Dermatology, vol. 181 Issue 03, pp. 609-611, 2019.
Robert M. et al., "IL 17 in Rheumatoid Arthritis and Precision Medicine: From Synovitis Expression to Circulating Bioactive Levels", Front. Med., vol. 05, Article 364, 10 pages, Jan. 2019.
Schlapbach, C. et al., "Expression of the IL-23/Th17 pathway in lesions of Hidradenitis Suppurativa", J. American Academy Dermatology, vol. 65, No. 04, pp. 790-798, Oct. 1, 2011.
Setiadi AF et al., "IL-17A is Associated with the breakdown of the blood-brain barrier in relapsing-remitting multiple sclerosis", J Neuroimmuno., vol. 332, pp. 147-154, 2019.
Shen, H. et al., "Frequency and Phenotype of Peripheral Blood Th17 Cells in Ankylosing Spondylitis and Rheumatoid Arthritis", Arthritis Rheumatism, vol. 60, No. 06, pp. 1647-1656, Jun. 2009.

(56) References Cited

OTHER PUBLICATIONS

Singh, R. et al., "The role of IL-17 in vitiligo: A review", Autoimmun. Rev., vol. 15, pp. 397-404, 2016.
Stamp, L. et al., "Interleukin-17: the missing link between T-cell accumulation and effector cell actions in rheumatoid arthritis?", Immunol. Cell Biol., vol. 82, No. 1, pp. 1-9, 2004.
Strand, V. et al., "Matching-adjusted indirect Comparison: secukinumab versus infliximab in biologic-naive patients with psoriatic arthritis", J. of Comparative Effectiveness Research, vol. 8, No. 07, pp. 497-510, 2019.
Thomi, R. et al., "Association of Hidradenitis Suppurativa With T Helper 1/ T Helper 17 Phenotypes—A Semantic Map Analysis", JAMA Derma., vol. 154, No. 05, pp. 592-595, May 2018.
Tzartos, J. et al., "Interleukin-17 Production in Central Nervous System—Infiltrating T Cells and Glial Cells Is Associated with Active Disease in Multiple Sclerosis.", American J. of Pathology, vol. 172 No. 1, pp. 146-155, Jan. 2008.
Van Vollenhoven, R. et al., "Efficacy and safety of ustekinumab, an IL-12 and IL-23 inhibitor, in patients with active systemic lupus erythematosus: results of a multicentre, double-blind, phase 2, randomised, controlled study", Lancet, vol. 392, pp. 1330-1339, 2018.
Vargas-Rojas M. et al., "Increase of Th17 in peripheral blood of patients with chronic obstructive pulmonary disease", Respir. Med., vol. 105, No. 11, pp. 1648-1654, 2011.
Wen, Z. et al., "Interleukin-17 Expression Positively Correlates with Disease Severity of Lupus Nephritis by Increasing Anti-Double-Stranded DNA Antibody Production in a Lupus Model Induced by Activated Lymphocyte Derived DNA", PLoS ONE., vol. 8, Issue 3, e58161, 10 pages, Mar. 2013.
Wendling, D. et al., "Serum IL-17, BMP-7, and bone turnover markers in patients with ankylosing spondylitis", Joint Bone Spine, vol. 74, pp. 304-305, 2007.
Willing A. et al., "Production of IL-17 by MAIT Cells Is Increased in Multiple Sclerosis and is Associated with IL-7 Receptor Expression", J. of Immunology, vol. 200, No. 03, pp. 974-982, 2018.
Wong, C. et al., "Elevation of Proinflammatory Cytokine (IL-18, IL-17, IL-12) and Th2 Cytokine (IL-4) Concentrations in patients with systemic lupus Erythematosus", Lupus, vol. 9, pp. 589-593, 2000.
Wong, C. et al.,"Hyperproduction of IL-23 and IL-17 in patients with systemic lupus erythematosus: Implications for Th17-mediated inflammation in auto-immunity", Clinical Immunology, vol. 127, pp. 385-393, 2008.
Xing Q. et al., "Elevated Th17 cells are accompanied by FoxP3+ Treg cells decrease in patients with lupus nephritis", Rheumatol. Int., vol. 32, pp. 949-958, 2012.
Zhang L. et al., "Increased Frequencies of Th22 Cells as well as Th17 Cells in the Peripheral Blood of Patients with Ankylosing Spondylitis and Rheumatoid Arthritis", PLoS one, vol. 7, Issue 04, 9 pages, Apr. 2012.
Zhang, R. et al., "Suppression of Experimental Autoimmune Uveoretinitis by Anti-IL-17 Antibody", Curr. Eye Res., vol. 34, No. 4, pp. 297-303, 2009.
Zhao X-F. et al., "Increased serum interleukin 17 in patients with systemic lupus erythematosus", Mol. Biol. Rep., vol. 37, pp. 81-85, 2010.
Dyson G., May P. "*Himiâ sinteticeskih lekarstvennyh sredstv*" [Chemistry of Synthetic Drugs], Moscow: "Mir", 1964, pp. 12-19.
V.G. Belikov "*Farmacevticeskaâ himiâ*" [Pharmaceutical Chemistry], Textbook, 2007, Moscow, "*MEDpress—Inform*", pp. 27-29.
K. Kümmerer "Pharmaceuticals in the environment", Annual Review of Environment and Resources, 2010, v. 35, pp. 57-75, doi: 10.1146/annurev-environ-052809-161223.
"*Kratkij kurs molekulârnoj farmakologii*" [Short course in molecular pharmacology] edited by Sergeev P.V, Moscow, 1975, p. 10.
Holodov L.E. et al."*Kliniceskaâ farmakokinetika*" [Clinical pharmacokinetics], Moscow: "Medicina", 1985, pp. 83-98, 134-138, 160, 378-380.
"*Rukovodstvo po provedeniû doklinicheskih issledovanij lekarstvennyh sredstv*" [Guidelines for conducting preclinical studies of medicinal products], Chapter 1, Moscow: "Grif i K", 2012, 944 pages, pp. 486-501, 624-639, 738-745.

SEQUENCE LISTING

```
<160> NUMBER OF SEQ ID NOS: 2

<210> SEQ ID NO 1
<211> LENGTH: 182
<212> TYPE: PRT
<213> ORGANISM: artificial
<220> FEATURE:
<223> OTHER INFORMATION: Human IL17A with a FLAg tag

<400> SEQUENCE: 1

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gly Ser Asp Tyr Lys Asp
            20                  25                  30

Asp Asp Asp Lys Gly Ser Gly Ser Gly Ser Leu Glu Val Leu Phe Gln
        35                  40                  45

Gly Pro Gly Ile Thr Ile Pro Arg Asn Pro Gly Cys Pro Asn Ser Glu
    50                  55                  60

Asp Lys Asn Phe Pro Arg Thr Val Met Val Asn Leu Asn Ile His Asn
65                  70                  75                  80

Arg Asn Thr Asn Thr Asn Pro Lys Arg Ser Ser Asp Tyr Tyr Asn Arg
                85                  90                  95

Ser Thr Ser Pro Trp Asn Leu His Arg Asn Glu Asp Pro Glu Arg Tyr
            100                 105                 110

Pro Ser Val Ile Trp Glu Ala Gln Cys Arg His Leu Gly Cys Ile Asn
        115                 120                 125

Ala Asp Gly Asn Val Asp Tyr His Met Asn Ser Val Pro Ile Gln Gln
    130                 135                 140
```

Glu Ile Leu Val Leu Arg Arg Glu Pro Pro His Cys Pro Asn Ser Phe
145 150 155 160

Arg Leu Glu Lys Ile Leu Val Ser Val Gly Cys Thr Cys Val Thr Pro
165 170 175

Ile Val His His Val Gln
180

<210> SEQ ID NO 2
<211> LENGTH: 323
<212> TYPE: PRT
<213> ORGANISM: artificial
<220> FEATURE:
<223> OTHER INFORMATION: IL17A with a His tag

<400> SEQUENCE: 2

Met Lys Phe Leu Val Asn Val Ala Leu Val Phe Met Val Val Tyr Ile
1 5 10 15

Ser Tyr Ile Tyr Ala Leu Arg Leu Leu Asp His Arg Ala Leu Val Cys
20 25 30

Ser Gln Pro Gly Leu Asn Cys Thr Val Lys Asn Ser Thr Cys Leu Asp
35 40 45

Asp Ser Trp Ile His Pro Arg Asn Leu Thr Pro Ser Ser Pro Lys Asp
50 55 60

Leu Gln Ile Gln Leu His Phe Ala His Thr Gln Gln Gly Asp Leu Phe
65 70 75 80

Pro Val Ala His Ile Glu Trp Thr Leu Gln Thr Asp Ala Ser Ile Leu
85 90 95

Tyr Leu Glu Gly Ala Glu Leu Ser Val Leu Gln Leu Asn Thr Asn Glu
100 105 110

Arg Leu Cys Val Arg Phe Glu Phe Leu Ser Lys Leu Arg His His His
115 120 125

Arg Arg Trp Arg Phe Thr Phe Ser His Phe Val Val Asp Pro Asp Gln
130 135 140

Glu Tyr Glu Val Thr Val His His Leu Pro Lys Pro Ile Pro Asp Gly
145 150 155 160

Asp Pro Asn His Gln Ser Lys Asn Phe Leu Val Pro Asp Cys Glu His
165 170 175

Ala Arg Met Lys Val Thr Thr Pro Cys Met Ser Ser Gly Ser Leu Trp
180 185 190

Asp Pro Asn Ile Thr Val Glu Thr Leu Glu Ala His Gln Leu Arg Val
195 200 205

Ser Phe Thr Leu Trp Asn Glu Ser Thr His Tyr Gln Ile Leu Leu Thr
210 215 220

Ser Phe Pro His Met Glu Asn His Ser Cys Phe Glu His Met His His
225 230 235 240

Ile Pro Ala Pro Arg Pro Glu Glu Phe His Gln Arg Ser Asn Val Thr
245 250 255

Leu Thr Leu Arg Asn Leu Lys Gly Cys Cys Arg His Gln Val Gln Ile
260 265 270

Gln Pro Phe Phe Ser Ser Cys Leu Asn Asp Cys Leu Arg His Ser Ala
275 280 285

-continued

```
Thr Val Ser Cys Pro Glu Met Pro Asp Thr Pro Glu Pro Ile Pro Asp
    290                 295                 300

Tyr Met Pro Leu Trp Gly Ser Gly Gly His His His His His His His
305                 310                 315                 320

His His His
```

IMIDAZOPYRIMIDINES AS MODULATORS OF IL-17

CROSS-REFERENCE TO RELATED APPLICATIONS

This application is a 371 national stage of PCT Application No. PCT/IB2021/053517, filed on Apr. 28, 2021, which claims priority to and benefit under 35 U.S.C. 119(e) of U.S. Provisional Patent Application Ser. No. 63/017,679, filed Apr. 30, 2020, the disclosure of which is hereby incorporated by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "JBI6283WOPCT1SeqListing4-22-20.txt", creation date of Apr. 22, 2020, and having a size of 5 KB. The sequence listing submitted via EFS-Web is part of the specification and is herein incorporated by reference in its entirety.

FIELD

Disclosed herein are imidazopyrimidine compounds, and pharmaceutical compositions thereof, which modulate Interleukin-17A. Also disclosed herein is the therapeutic use of such compounds, for example, in treating and/or ameliorating an IL-17A mediated inflammatory syndrome, disorder, or disease.

BACKGROUND

Interleukin-17 ("IL-17"), also known as IL-17A and CTLA-8, is produced mainly by CD4+ Th17 cells, and also by other immune cells such as CD8+ T cells, γδT cells, NK cells, NKT cells, and innate lymphoid cells (ILCs). IL-17A exists as a homodimer (A/A) or as a heterodimer (A/F) with IL-17F and signals through binding to dimeric receptor complex IL-17RA and IL-17RC. IL-17RA is ubiquitously expressed at particularly high levels by haematopoietic cell types, whereas IL-17RC is preferentially expressed by non-haematopoietic cells (Gaffen, S. Structure and signaling in the IL-17 receptor family. Nat. Rev. Immunol. 2009, 9, 556-567). IL-17A/IL-17R signaling induces de novo gene transcription by triggering NF-kB, C/EBP and MAPK pathways through ACT1-TRAF6-TRAF4. It can also stabilize target mRNA transcripts through the ACT1-TRAF2-TRAF5 complex (Amatya N et al., Trends in Immunology, 2017, 38, 310-322). IL-17A stimulates the release of inflammatory mediators including IL-6, IL-8, G-CSF, TNF-α and IL-1β that recruit and activate lymphocytes to the site of injury or inflammation and maintain a proinflammatory state.

As discussed below, preclinical and clinical data have demonstrated the significant pathological role of IL-17A in multiple autoimmune and inflammatory diseases.

For psoriasis: IL-17A mRNA and/or protein levels are elevated in the lesional skin and blood of patients with psoriasis and correlate with disease severity. IL-17A acts directly in synergy with other cytokines (such as TNFα, IFNγ or IL-22) on keratinocytes triggering a self-amplifying inflammatory response in the skin and leading to the formation of psoriatic plaques. The blockade of IL-17A by means of antibodies to IL-17A or IL-23 results in complete reversal of the molecular and clinical disease features in majority of psoriasis patients, manifesting the significant role of IL-17A and IL-17-producing T-cells in the immunopathogenesis of psoriasis. (Hawkes et al. Psoriasis Pathogenesis and the Development of Novel, Targeted Immune Therapies. J. Allergy Clin. Immunol. 2017, 140(3): 645-653). The development and approval of IL-17 monoclonal antibodies such as secukinumab, ixekizumab, and brodalumab and their transformational efficacy for psoriasis have demonstrated IL-17A as a valid target for psoriasis treatments. (Blauvelt A. and Chiricozzi A. The Immunologic Role of IL-17 in Psoriasis and Psoriatic Arthritis Pathogenesis. Clin Rev Allergy Immunol. 2018, 55(3):379-390)

For psoriatic arthritis (PsA): IL-17A is mechanistically relevant to PsA through NFκB activation that triggers transcription of several PsA related genes including the receptor activator of nuclear factor KB ligand (RANKL). RANKL triggers the differentiation of osteoclast precursor cells into activated osteoclasts, resulting in bone resorption and subsequently joint deformity in PsA (Adamopoulos I E and Mellins E D. Nature reviews Rheumatology 2015; 11:189-94). PsA joint is enriched for IL-17+CD8+ T cells, and the levels of this T cell subset are correlated with disease activity (Menon B. et al. Arthritis & Rheumatology 2014; 66: 1272-81). Synovial fibroblasts isolated from PsA patients also contain elevated IL-17R expression and secrete increased IL-6, CXCL8 and MMP3 ex vivo compared to osteoarthritis patients. Both secukinumab and ixekizumab are FDA approval drugs for PsA. In matching-adjusted indirect comparison analysis, secukinumab was associated with higher ACR 20/50/70 response rates in patients with active PsA than anti-TNFα antibodies (Mease P. et al. Eur. J. Rheumatol. 2019 Jul. 1; 6(3):113-121; Strand V. et al. J. Comp. Eff Res. 2019, 8(7):497-510; Nash P. et al., Rheumatol. Ther. 2018, 5(1):99-122. In a recent head-to-head study, ixekizumab was superior to adalimumab in achieving simultaneous improvement of joint and skin disease (ACR50 and PASI100) in patients with PsA and inadequate response to conventional synthetic disease-modifying antirheumatic drug (Mease, P J et al. Ann Rheum Diss 2020; 79:123-131). By hitting the same target, IL-17A small molecule inhibitor compounds may exert similar or better efficacy than biologics considering that small molecules generally have better tissue penetration.

For rheumatoid arthritis (RA): IL-17A has been recognized as critical to the progression of rheumatoid arthritis. "The recognition of IL-17 as a pro-inflammatory T cell derived cytokine, and its abundance within rheumatoid joints, provides the strongest candidate mechanism to date through which T cells can capture and localize macrophage effector functions in rheumatoid arthritis" Stamp, L. K., M. J. James, et al. Immunol. Cell Biol. 2004, 82(1): 1-9. Moreover, in rheumatoid arthritis IL-17A acts locally on synoviocytes and osteoblasts contributing to synovitis and joint destruction. Robert and Miossec have proposed the use of synovial biopsies and/or biomarkers to precisely identify patients that would respond to IL-17A inhibition. Their work concludes that IL-17 inhibitors should now be considered in the development of precision medicine in RA. (Robert M and Miossec P, Front. Med., 2019, 5:364)

For Ankylosing Spondylitis (AS): Various studies have reported elevated IL-17A and Th17 and other cells producing IL-17 in AS blood samples (Wendling D. et al. Joint Bone Spine. 2007; 74:304-305; Shen H. et al. Arthritis Rheum. 2009; 60(6):1647-56; Zhang L. et al. PLoS One. 2012; 7(4):e31000; Jansen D T et al. Rheumatology (Oxford). 2015 April; 54(4):728-735). In situ analysis of AS spine has revealed increased IL-17A-producing cells in bone of facet (zygapophyseal) joints (Appel H. et al. Arthritis Res Ther. 2011; 13(3):R95). Two advanced IL-17A neutralizing antibodies, secukinumab, approved by FDA for AS, and ixekizumab, have demonstrated efficacy over placebo even in anti-TNF inadequate responders. In contrast, anti-IL-23 p40 and p19 biologics failed to demonstrate beneficial effect (Deodhar A. et al Arthritis Rheumatol. 2019, 71(2):258-270; Baeten D. et al. Ann Rheum Dis. 2018, 77(9):1295-1302), indicating the differential underling mechanism along IL-23/IL-17 pathway in AS and providing a strong evidence to support continuing developing IL-17A inhibitors.

For hidradenitis suppurativa (HS): Increased IL-17 and IL-17-producing T helper cells in the skin lesions of HS patients were reported and molecular proteomics and gene expression data indicate that the IL-23/Th17 pathway is upregulated in HS lesions (Schlapbach et al., J. Am. Acad. Dermatol. 2011; 65(4):790; Kelly G. et al. British J. Dermatol. 2015 December; 173(6):1431-9; Moran et al., J. Invest. Dermatol. 2017; 137(11):2389; Thomi et al., JAMA Dermatol. 2018; 154(5):592). Seven of nine (78%) patients with moderate-to-severe HS achieved HiSCR in an open-label pilot-trial with Secukinumab (Prussick L. et al. British J. Dermatol. 2019 September; 181(3):609-611), and more clinical trials with anti-IL-17 mAbs in HS are on-going.

For bullous pemphigold (BP): IL-17 is elevated in the blister fluid and perilesional skin of BP patients. (Le Jan S. et al. J. Invest. Dermatol. 2014; 134 (12):2908-2917; Chakievska L. J Autoimmun. 2019, 96:104-112). Exome sequencing of BP patients revealed mutations in twelve IL-17-related genes in one third of patients, providing the genetic link between IL-17 pathway and BP (Chakievska L. J Autoimmun. 2019, 96:104-112). In experimental murine BP, IL-17A−/− mice are protected, and anti-IL-17A treatment significantly reduced skin lesions in wild type (Chakievska L. J Autoimmun. 2019, 96:104-112). Ixekizumab Phase 2 of treatment naive and refractory BP patients is on-going (NCT03099538)

For atopic dermatitis (AD): IL-17 was found to be elevated in peripheral blood and lesions in AD patients and Th17 cells infiltrated more markedly in acute than chronic lesions, suggesting its role in acute phase of AD (Koga C. et al. Journal of Investigative Dermatology 2008, 128, 2625-2630). Molecular profile analysis from ustekinumab Phase II suggest likely contribution of IL-23/Th17/IL-17 pathway in AD (Khattri S. et al. Exp. Dermatol. 2017 January; 26(1): 28-35).

For vitiligo: Many studies in vitiligo patients have demonstrated an increased frequency of Th17 cells and higher level of IL-17 in both circulation and lesions that positively correlates with disease duration, extent, and activity (Singh R K et al. Autoimm. Rev 2016, April; 15(4):397-404). Mouse studies demonstrated that depigmentation correlates with greater IL-17 expression/secretion, which modulates vitiligo development (Eby J M et al. Pigment Cell Melanoma Res. 2014, November; 27(6):1075-85).

For multiple sclerosis (MS): IL-17 expression is increased in PBMCs, cerebrospinal fluid (CSF) as well as in brain lesions and cells from MS patients (Lock, C G et al., Nat. Med. 2002, 8: 500-508; Matusevicius, D et al. Mult. Scler. 1999, 5: 101-104; Tzartos, J S et al. Am. J. Pathol. 2008, 172: 146-155). IL-17-producing T cells are enriched in active MS lesions (Tzartos, J S et al. Am. J. Pathol. 2008, 172: 146-155; Willing A. et al. J. Immunol. 2018, 200(3): 974-982). IL-17A levels were elevated in the CSF of relapsing-remitting MS (RRMS) patients and correlated with the CSF/serum albumin quotient, a measure of blood-brain barrier (BBB) dysfunction, together with in vitro data that IL-17A in combination with IL-6 reduced the expression of tight junction-associated genes and disrupted monolayer integrity in a BBB cell line, highlighting the potential importance of targeting IL-17A in preserving BBB integrity in RRMS (Setiadi A F et al. J Neuroimmunol. 2019, 332: 147-154). Secukinumab yielded promising first results in a proof-of-concept study in MS patients (Havrdová, E A et al. J. Neurol. 2016, 263: 1287-1295).

For Asthma: IL-17 expression is increased in the lung, sputum, bronchoalveolar lavage fluid, and sera in patients with asthma, and the severity of airway hyperresponsiveness is positively correlated with IL-17 expression levels. (Chakir J. et al. J. Allergy Clin. Immunol. 2003, 111(6):1293-8). IL-17 was reported to be increased in asthmatic airways and induce human bronchial fibroblasts to produce cytokines (Molet S. et al. J. Allergy Clin. Immunol. 2001, 108(3):430-8). Anti-IL-17 antibody modulates airway responsiveness, inflammation, tissue remodeling, and oxidative stress in chronic mouse asthma models (Camargo L D N et al. Front Immunol. 2018; 8:1835; dos Santos T M et al. Front Physiol. 2018, 9:1183).

For Chronic Obstructive Pulmonary Disease (COPD): An increase in Th17 cells was observed in patients with COPD compared with current smokers without COPD and healthy subjects, and inverse correlations were found between Th17 cells with lung function (Vargas-Rojas et al., Respir. Med. 2011 November; 105(11):1648-54). In three recent human COPD studies, gene expression profile in bronchial epithelia showed that higher IL-17 signature expression is associated with a lack of response to inhaled corticosteroid, suggesting that there is a COPD subgroup that may benefit from IL-17 inhibitor therapy (Christenson S A et al., J. Clin. Invest. 2019; 129(1):169-181).

For Uveitis: IL-17 promotes the release of inflammatory mediators from retinal pigment epithelium cell line, disrupting the retinal pigment epithelium barrier function (Chen Y. et al., PLoS One. 2011; 6:e18139). IL-17 levels were elevated in the serum or aqueous humor of uveitis patients (El-Asrar A M A et al., Clin. Immunol. 2011; 139(2):177-84; Jawad S et al. Ocul. Immunol. Inflamm. 2013; 21(6):434-9; Kuiper J J W. Am. J. Ophthalmol. 2011; 152(2):177-182). Anti-IL-17 antibody delayed the onset of ocular inflammation and markedly inhibited the development of experimental autoimmune uveitis in rats (Zhang R. et. al. Curr. Eye Res. 2009 April; 34(4):297-303). The analysis of secondary efficacy data from subcutaneous (sc) secukinumab phase 3 trials in uveitis suggested a beneficial effect of secukinumab in reducing the use of concomitant immunosuppressive medication (Dick A D et al. Ophthalmology. 2013; 120(4): 777-87). Later study of intravenous secukinumab in uveitis demonstrated greater efficacy than sc dosing, suggesting requiring optimal exposure for efficacy and confirming the therapeutic potential of IL-17A inhibition (Letko E. et al. Ophthalmology 2015, 122(5), 939-948). Ustekinumab that blocks IL-23/IL-17 pathway was also reported to successfully treat a noninfectious uveitis patient who had severe concomitant psoriasis and PsA and failed to respond to conventional immune suppressants (Mugheddu C. et al. Dermatol. Ther. 2017 September; 30(5); e12527).

For multiple myeloma (MM): IL-17A serum levels were significantly higher in MM patients and also in patients with advanced stage compared with healthy subjects (Lemancewicz D. et al., Med. Sci. Monit. 2012; 18(1): BR54-BR59). Administration of secukinumab in the SCIDhu model of human myeloma weekly for 4 weeks after the first detection of tumor in mice led to a significant inhibition of tumor growth and reduced bone damage compared to isotype control mice (Prabhala R. et al., Leukemia. 2016 February; 30(2): 379-389).

For systemic lupus erythematosus (SLE): Increased serum or plasma levels of IL-17, expansion of IL-17-producing T cells in the peripheral blood, and infiltration of Th17 cells in target organs like the kidneys was observed in SLE patients (Wong C K et al. Lupus. 2000; 9(8):589-593; Wong C K et al. Clinical Immunology. 2008; 127(3):385-393; Zhao X F et al. Mol. Biol. Rep. 2010 January; 37(1): 81-5; Chen X Q et al. J. Clin. Immunol. 2010 March; 30(2):221-5; Xing Q. et al. Rheumatol. Int. 2012 April; 32(4):949-58). Imbalance between Th17 cells and regulatory T (Treg) cells has been observed in SLE patients including quiescent stage (Ma J. et al. Clinical Rheumatology. 2010; 29(11):1251-1258; Dolff S. et al. Clinical Immunology 2011, 141(2):197-204). Overexpression of IL-17A using adenovirus enhanced the severity of lupus nephritis, while blockade of IL-17A using neutralizing antibody resulted in decreased severity of lupus nephritis (Wen, Z. et al. PLoS One. 2013, 8: e58161). In a phase 2 study, ustekinumab, an anti-IL-12/23 p40 monoclonal antibody blocking IL-23/IL-17 pathway, has demonstrated efficacy in SLE patients (van Vollenhoven R F et al. Lancet 2018; 392: 1330-39). Human expression studies, animal models, and clinical trials indicate that IL-17 blockade may become a promising therapeutic strategy for SLE (Koga T. et al., Expert Rev. Clin. Immunol. 2019, 15 (6) 629-637).

In summary, animal and human studies have shown that IL-17A plays crucial role in pathogenesis of the multiple diseases and/or conditions discussed above. The significance of targeting IL-17A has been demonstrated by the transformational efficacy of IL-17A neutralizing antibodies in patients. While no oral small molecule IL-17A inhibitors have progressed into late stage clinical trials yet, they are in an attractive area for discovery as their development may broaden treatment options for many patients without access to biologics. In addition, a safe and efficacious small molecule IL-17A inhibitor may offer significant benefits to patients such as convenient dosing regimens and cost savings, which in turn may provide effective long-term disease management. Accordingly, there is a need for new small molecule IL-17A modulators (e.g., inhibitors).

SUMMARY

The present application discloses a compound of Formula I:

I

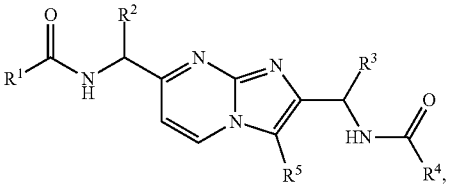

or a pharmaceutically acceptable salt thereof, wherein:

$R^1$ is —$C_{(1-6)}$alkyl or —$C_{(0-3)}$alkyl$C_{(3-6)}$cycloalkyl; wherein the —$C_{(1-6)}$alkyl and the —$C_{(0-3)}$alkyl$C_{(3-6)}$cycloalkyl are unsubstituted or substituted with one to six fluorine atoms;

$R^2$ is —$C_{(3-5)}$cycloalkyl;

$R^3$ is —$C_{(0-1)}$alkyl$C_{(3-6)}$cycloalkyl, wherein the —$C_{(0-1)}$alkyl$C_{(3-6)}$cycloalkyl is unsubstituted or substituted with one to five fluorine atoms;

$R^4$ is —$C_{(3-4)}$cycloalkyl or a 5- to 6-membered heteroaryl having 1 to 4 heteroatoms selected from N, O, and S;

wherein the $C_{(3-4)}$cycloalkyl is unsubstituted or substituted with one to three $R^{4a}$ groups; and wherein the 5- to 6-membered heteroaryl is unsubstituted or substituted with one or two $R^{4b}$ groups;

each $R^{4a}$ group is independently selected from —$C_{(1-4)}$alkyl that is unsubstituted or substituted with one to six fluorine atoms; and each $R^{4b}$ group is independently selected from —$C_{(0-2)}$alkyl$C_{(3-4)}$cycloalkyl or —$C_{(1-5)}$alkyl, wherein the —$C_{(0-2)}$alkyl$C_{(3-4)}$cycloalkyl and —$C_{(1-5)}$alkyl are unsubstituted or substituted with one to six fluorine atoms;

$R^5$ is H or F;

wherein when $R^4$ is —$C_{(3-4)}$cycloalkyl then the compound of Formula I is a compound of Formula Ia:

Ia

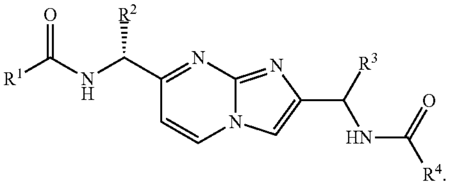

In some embodiments, disclosed herein is a pharmaceutical composition comprising a compound of Formula I, or pharmaceutically acceptable salt thereof, and a pharmaceutically acceptable carrier.

Also described herein is a method for treating and/or ameliorating an IL-17A mediated inflammatory syndrome, disorder, or disease (e.g., psoriasis, psoriatic arthritis, rheumatoid arthritis, ankylosing spondylitis, etc.) comprising administering to a subject in need thereof a therapeutically effective amount of a compound of Formula I, or a pharmaceutically acceptable salt thereof.

In some embodiments, disclosed herein is the use of a therapeutically effective amount of compound of Formula I, or a pharmaceutically acceptable salt thereof, for treating and/or ameliorating an IL-17A mediated inflammatory syndrome, disorder, or disease (e.g., psoriasis, psoriatic arthritis, rheumatoid arthritis, ankylosing spondylitis, etc.).

In some embodiments, disclosed herein is the use of a compound of Formula I, or pharmaceutically acceptable salt thereof, in the manufacture of a medicament for treating and/or ameliorating an IL-17A mediated inflammatory syndrome, disorder, or disease (e.g., psoriasis, psoriatic arthritis, rheumatoid arthritis, ankylosing spondylitis, etc.).

In some embodiments, provided herein are processes and intermediates disclosed herein that are useful for preparing a compound of Formula I or pharmaceutically acceptable salts thereof.

The disclosure also provides a compound or method as described herein.

DETAILED DESCRIPTION

Definitions

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

In an attempt to help the reader of the application, the description has been separated in various paragraphs or sections, or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples.

The term "administering" with respect to the methods of the invention, means a method for therapeutically or prophylactically preventing, treating or ameliorating a syndrome, disorder or disease as described herein by using a compound of Formula I, or pharmaceutically acceptable salt thereof, composition thereof, or medicament thereof. Such methods include administering a therapeutically effective amount of a compound of Formula I, or pharmaceutically acceptable salt thereof, composition thereof, or medicament thereof, at different times during the course of a therapy or concurrently or sequentially as a combination therapy.

The term "subject" refers to a patient, which may be an animal, preferably a mammal, most preferably a human, whom will be or has been treated by a method according to an embodiment of the application. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

The term "therapeutically effective amount" or "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, "IL-17" or "IL-17A" refers to interleukin 17A. It is also named IL17, CTLA8, CTLA-8. Interleukin 17A is a pro-inflammatory cytokine. This cytokine is produced by a group of immune cells in response to their stimulation. An exemplary amino acid sequence of human IL-17 is represented in GenBank Accession No. NP_002181.1, which can be encoded by a nucleic acid sequence such as that of GenBank Accession No. NM_002190.3.

The term "modulator" as used herein refers to any agents or molecules that can bind to IL-17, including small molecule compounds.

As used herein, the term "composition" is intended to encompass a product comprising the specified ingredients in the specified amounts, as well as any product which results, directly or indirectly, from combinations of the specified ingredients in the specified amounts.

As used herein, the term "treat", "treating", or "treatment" of any disease, condition, syndrome or disorder refers, in one embodiment, to ameliorating the disease, condition, syndrome or disorder (i.e., slowing or arresting or reducing the development of the disease or at least one of the clinical symptoms thereof). In another embodiment, "treat", "treating", or "treatment" refers to alleviating or ameliorating at least one physiological or biochemical parameter associated with or causative of the disease, condition, syndrome or disorder, including those which may not be discernible by the patient. In a further embodiment, "treat", "treating", or "treatment" refers to modulating the disease, condition, syndrome or disorder either physically (e.g. stabilization of a discernible symptom), physiologically, (e.g. stabilization of a physical parameter), or both. In yet another embodiment, "treat", "treating", or "treatment" refers to preventing or delaying the onset or development or progression of the disease, condition, syndrome or disorder.

As used herein, the term "QD" means once daily.

As used herein, the term "BID" means twice daily.

The term "alkyl" is a straight or branched saturated hydrocarbon. For example, an alkyl group can have 1 to 12 carbon atoms (i.e., $(C_1\text{-}C_{12})$alkyl) or 1 to 6 carbon atoms (i.e., $(C_1\text{-}C_6)$alkyl). Examples of alkyl groups include, but are not limited to, methyl (Me, $—CH_3$), ethyl (Et, $—CH_2CH_3$), 1-propyl (n-Pr, n-propyl, $—CH_2CH_2CH_3$), isopropyl (i-Pr, i-propyl, $—CH(CH_3)_2$), 1-butyl (n-Bu, n-butyl, $—CH_2CH_2CH_2CH_3$), 2-butyl (s-Bu, s-butyl, $—CH(CH_3)CH_2CH_3$), tert-butyl (t-Bu, t-butyl, $—CH(CH_3)_3$), 1-pentyl (n-pentyl, $—CH_2CH_2CH_2CH_2CH_3$), 2-pentyl ($—CH(CH_3)CH_2CH_2CH_3$), 1-hexyl ($—CH_2CH_2CH_2CH_2CH_2CH_3$), 2-hexyl ($—CH(CH_3)CH_2CH_2CH_2CH_3$), heptyl ($—(CH_2)_6CH_3$), octyl ($—(CH_2)_7CH_3$), 2,2,4-trimethylpentyl ($—CH_2C(CH_3)_2CH_2CH(CH_3)_2$), nonyl ($—(CH_2)_8CH_3$), decyl ($—(CH_2)_9CH_3$), undecyl ($—(CH_2)_{10}CH_3$), and dodecyl ($—(CH_2)_{11}CH_3$). Any alkyl group may be unsubstituted or substituted.

The term "$C_{(a\text{-}b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1\text{-}4)}$ denotes a radical containing 1, 2, 3 or 4 carbon atoms.

The term "heterocycle" or "heterocyclyl" refers to a single saturated or partially unsaturated ring that has at least one atom other than carbon in the ring, wherein the atom is selected from the group consisting of oxygen, nitrogen and sulfur. Exemplary heterocycles include, but are not limited to oxetanyl, aziridinyl, azetidinyl, pyrrolidinyl, piperidinyl, piperazinyl, morpholinyl, tetrahydropyranyl, tetrahydrofuranyl, and thiomorpholinyl.

The term "cycloalkyl" refers to a saturated or partially unsaturated all carbon ring system having 3 to 8 carbon atoms (i.e., $C_{(3-8)}$cycloalkyl), and preferably 3 to 6 carbon atoms (i.e., $C_{(3-6)}$cycloalkyl), wherein the cycloalkyl ring system has a single ring or multiple rings in a spirocyclic or bicyclic form. Exemplary cycloalkyls include, but are not limited to, cyclopropyl, cyclobutyl, cyclopentyl, cyclohexyl, cycloheptyl, and cyclooctyl. Unless otherwise stated specifically in the specification, a cycloalkyl group may be unsubstituted or substituted. Some cycloalkyl groups may exist as spirocycloalkyls, wherein two cycloalkyl rings are fused through a single carbon atom; for example and without limitation, an example of a spiropentyl group is

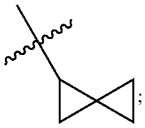 [SMILES: *C1CC12CC2];

for example and without limitation, examples of spirohexyl groups include

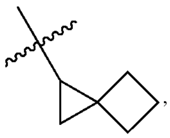, 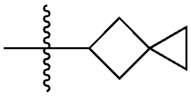, and

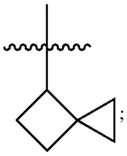;

for example and without limitation examples of cycloheptyl groups include

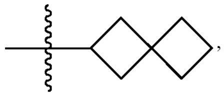, 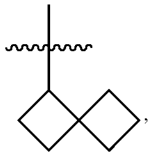,

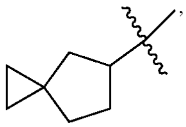, and 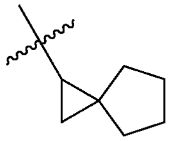;

for example and without limitation examples of cyclooctyl groups include

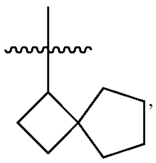, 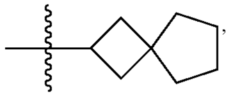,

-continued

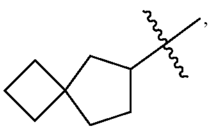, 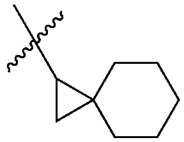,

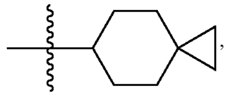, and 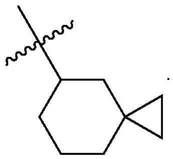.

Unless otherwise stated specifically in the specification, a siprocycloalkyl group may be unsubstituted or substituted. Bicyclic cycloalkyl ring systems also include

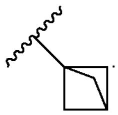.

The term "heteroaryl" refers to a single aromatic ring that has at least one atom other than carbon in the ring, wherein the atom is selected from the group consisting of oxygen, nitrogen and sulfur. The term "heteroaryl" includes single aromatic rings of from 1 to 6 carbon atoms and 1 to 4 heteroatoms selected from the group consisting of oxygen, nitrogen and sulfur. Exemplary heteroaryl ring systems include but are not limited to pyridinyl, pyrimidinyl, pyrazinyl, pyridazinyl, pyrimidinyl, pyrazolyl, oxazolyl, oxadiazolyl, isoxazolyl, triazolyl, imidazolyl, tetrazolyl, thienyl, thiazolyl, isothiazolyl, thiadiazolyl, or furyl.

The term "halogen" refers to bromo (—Br), chloro (—Cl), fluoro (—F) or iodo (—I).

Where the compounds of Formula I disclosed herein have at least one stereo center, they may accordingly exist as enantiomers or diastereomers. It is to be understood that all such isomers and mixtures thereof are encompassed within the scope of the present invention.

"Diastereoisomers" are stereoisomers that have at least two asymmetric atoms, but which are not mirror images of each other.

"Enantiomers" are a pair of stereoisomers that are non-superimposable mirror images of each other. A "racemic" mixture is a 1:1 mixture of a pair of enantiomers. A "scalemic" mixture of enantiomers is mixture of enantiomers at a ratio other than 1:1.

Where the processes for the preparation of the compounds according to the invention give rise to mixture of stereoisomers, these isomers may be separated by conventional techniques such as preparative chromatography. The compounds may be prepared in racemic form, a scalemic mixture, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral column vial HPLC or SFC. In some instances rotamers of compounds may exist which are observable by $^1H$ NMR leading to complex multiplets and peak integration in the $^1H$ NMR spectrum.

The absolute stereochemistry is specified according to the Cahn-Ingold-Prelog R-S system. Chiral centers, of which the absolute configurations are known, are labelled by prefixes R and S, assigned by the standard sequence-rule procedure, and preceded when necessary by the appropriate locants (*Pure & Appl. Chem.* 45, 1976, 11-30). Certain examples contain chemical structures that are depicted or labelled as an (R*) or (S*). When (R*) or (S*) is used in the name of a compound or in the chemical representation of the compound, it is intended to convey that the compound is a pure single isomer at that stereocenter; however, absolute configuration of that stereocenter has not been established. Thus, a compound designated as (R*) refers to a compound that is a pure single isomer at that stereocenter with an absolute configuration of either (R) or (S), and a compound designated as (S*) refers to a compound that is a pure single isomer at that stereocenter with an absolute configuration of either (R) or (S). For example, N—((S)-(7-((R)-cyclopropyl ((S*)-4,4,4-trifluoro-3-methylbutanamido)methyl)imidazo [1,2-a]pyrimidin-2-yl)(4,4-difluorocyclohexyl)methyl)-1-isopropyl-1H-1,2,4-triazole-5-carboxamide:

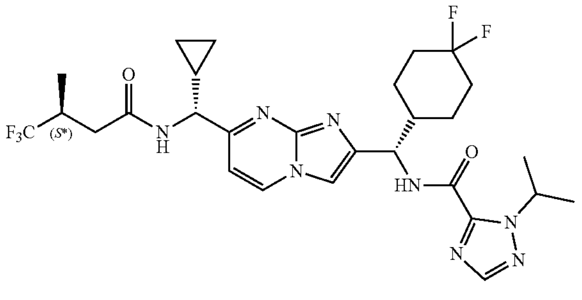 [SMILES: CC(C)n1ncnc1C(=O)N[C@H](c1cn2ccc([C@H](NC(=O)C[C@H](C)C(F)(F)F)C3CC3)nc2n1)C1CCC(F)(F)CC1]

refers to a compound that is:

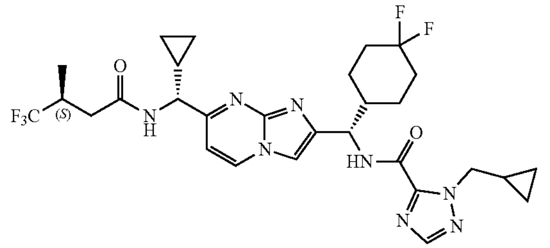

or

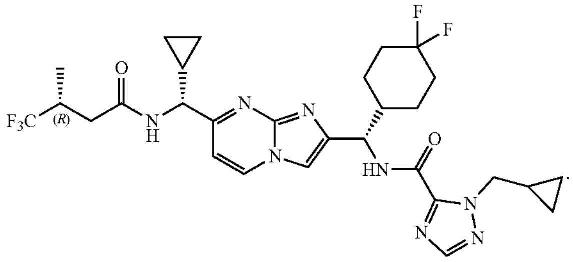

Pseudoasymmetric stereogenic centers are treated in the same way as chiral centers, but are given lower-case symbols, r or s (*Angew. Chem. Int. Ed. Engl.* 1982, 21, 567-583).

During any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Furthermore, it is intended that within the scope of the present invention, any element, in particular when mentioned in relation to a compound of Formula I, or pharmaceutically acceptable salt thereof, shall comprise all isotopes and isotopic mixtures of said element, either naturally occurring or synthetically produced, either with natural abundance or in an isotopically enriched form. For example, a reference to hydrogen includes within its scope $^1H$, $^2H$ (i.e., deuterium or D), and $^3H$ (i.e., tritium or T). In some embodiments, the compounds described herein include a $^2H$ (i.e., deuterium) isotope. By way of example, the group denoted $—C_{(1-6)}$alkyl includes not only $—CH_3$ but also $CD_3$; not only $CH_2CH_3$, but also $CD_2CD_3$, etc. Similarly, references to carbon and oxygen include within their scope respectively $^{12}C$, $^{13}C$ and $^{14}C$ and $^{15}O$ and $^{16}O$ and $^{17}O$ and $^{18}O$. The isotopes may be radioactive or non-radioactive. Radiolabelled compounds of Formula I may include a radioactive isotope selected from the group comprising $^3H$, $^{11}C$, $^{18}F$, $^{35}S$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Compounds of Formula I

The present application discloses a compound of Formula I:

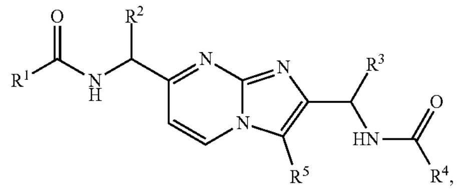

I or a pharmaceutically acceptable salt thereof, wherein:

$R^1$ is $—C_{(1-6)}$alkyl or $—C_{(0-3)}$alkyl$C_{(3-6)}$cycloalkyl;
- wherein the $—C_{(1-6)}$alkyl and the $—C_{(0-3)}$alkyl $C_{(3-6)}$cycloalkyl are unsubstituted or substituted with one to six fluorine atoms;

$R^2$ is $—C_{(3-5)}$cycloalkyl;

$R^3$ is $—C_{(0-1)}$alkyl$C_{(3-6)}$cycloalkyl, wherein the $—C_{(0-1)}$alkyl$C_{(3-6)}$cycloalkyl is unsubstituted or substituted with one to five fluorine atoms;

$R^4$ is $—C_{(3-4)}$cycloalkyl or a 5- to 6-membered heteroaryl having 1 to 4 heteroatoms selected from N, O, and S;
- wherein the $C_{(3-4)}$cycloalkyl is unsubstituted or substituted with one to three $R^{4a}$ groups; and
- wherein the 5- to 6-membered heteroaryl is unsubstituted or substituted with one or two $R^{4b}$ groups;

each $R^{4a}$ group is independently selected from $—C_{(1-4)}$alkyl that is unsubstituted or substituted with one to six fluorine atoms; and each $R^{4b}$ group is independently selected from —$C_{(0-2)}$alkyl$C_{(3-4)}$cycloalkyl or —$C_{(1-5)}$alkyl, wherein the —$C_{(0-2)}$alkyl$C_{(3-4)}$cycloalkyl and —$C_{(1-5)}$alkyl are unsubstituted or substituted with one to six fluorine atoms;

$R^5$ is H or F;

wherein when $R^4$ is —$C_{(3-4)}$cycloalkyl then the compound of Formula I is a compound of Formula Ia:

Ia

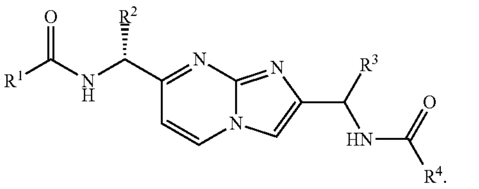

In some embodiments, disclosed herein is a compound of Formula I, or a pharmaceutically acceptable salt thereof, wherein $R^1$ is —$C_{(1-6)}$alkyl or —$C_{(0-3)}$alkyl$C_{(3-6)}$cycloalkyl; wherein the —$C_{(1-6)}$alkyl and the —$C_{(0-3)}$alkyl$C_{(3-6)}$cycloalkyl are unsubstituted or substituted with one to six fluorine atoms;

$R^2$ is —$C_{(3-5)}$cycloalkyl;

$R^3$ is —$C_{(0-1)}$alkyl$C_{(3-6)}$cycloalkyl, wherein the —$C_{(0-1)}$alkyl$C_{(3-6)}$cycloalkyl is unsubstituted or substituted with one to five fluorine atoms;

$R^4$ is a 5- to 6-membered heteroaryl having 1 to 4 heteroatoms selected from N, O, and S; wherein the 5- to 6-membered heteroaryl is unsubstituted or substituted with one or two $R^{4b}$ groups; and each $R^{4b}$ group is independently selected from —$C_{(0-2)}$alkyl$C_{(3-4)}$cycloalkyl or —$C_{(1-5)}$alkyl, wherein the —$C_{(0-2)}$alkyl$C_{(3-4)}$cycloalkyl and —$C_{(1-5)}$alkyl are unsubstituted or substituted with one to six fluorine atoms;

$R^5$ is H or F.

In some embodiments, disclosed herein is a compound of Formula I, or a pharmaceutically acceptable salt thereof, wherein $R^5$ is H.

In some embodiments, disclosed herein is a compound of Formula I, or a pharmaceutically acceptable salt thereof, wherein $R^1$ is —$C_{(1-4)}$alkyl or —$C_{(0-3)}$alkyl$C_{(3-5)}$cycloalkyl; wherein the —$C_{(1-4)}$alkyl and the —$C_{(0-3)}$alkyl$C_{(3-5)}$cycloalkyl are unsubstituted or substituted with one to six fluorine atoms.

In some embodiments, disclosed herein is a compound of Formula I, or a pharmaceutically acceptable salt thereof, wherein $R^1$ is —$C_{(1-3)}$alkyl or —$C_{(0-3)}$alkyl$C_{(3-5)}$cycloalkyl; wherein the —$C_{(1-3)}$alkyl and the —$C_{(0-3)}$alkyl$C_{(3-5)}$cycloalkyl are unsubstituted or substituted with one to six fluorine atoms.

In some embodiments, disclosed herein is a compound of Formula I, or a pharmaceutically acceptable salt thereof, wherein $R^1$ is —$C_{(1-3)}$alkyl, wherein the —$C_{(1-3)}$alkyl is unsubstituted or substituted with one to three fluorine atoms.

In some embodiments, disclosed herein is a compound of Formula I, or a pharmaceutically acceptable salt thereof, wherein $R^1$ is $C_{(0-3)}$alkyl$C_{(3-5)}$cycloalkyl, wherein the —$C_{(0-3)}$alkyl$C_{(3-5)}$cycloalkyl is unsubstituted or substituted with one to six fluorine atoms.

In some embodiments, disclosed herein is a compound of Formula I, or a pharmaceutically acceptable salt thereof, wherein $R^1$ is $C_{(1-2)}$alkyl$C_{(3-5)}$cycloalkyl, wherein the —$C_{(1-2)}$alkyl$C_{(3-5)}$cycloalkyl is unsubstituted or substituted with one to three fluorine atoms.

In some embodiments, disclosed herein is a compound of Formula I, or a pharmaceutically acceptable salt thereof, wherein $R^1$ is:

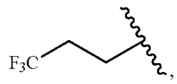,
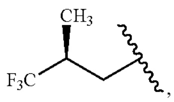,
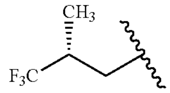
or
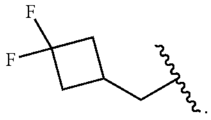.

In some embodiments, disclosed herein is a compound of Formula I, or a pharmaceutically acceptable salt thereof, wherein $R^1$ is:

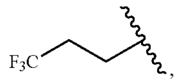,
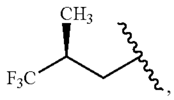,
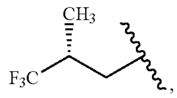,
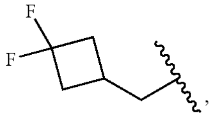,
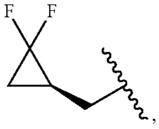,
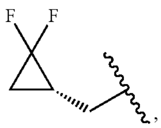,
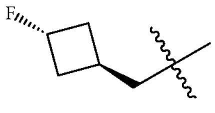,
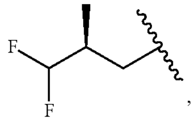,
or
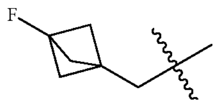.

In some embodiments, disclosed herein is a compound of Formula I, or a pharmaceutically acceptable salt thereof, wherein $R^1$ is:

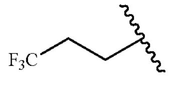
or
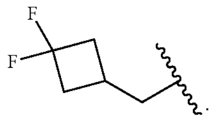.

In some embodiments, disclosed herein is a compound of Formula I, or a pharmaceutically acceptable salt thereof, wherein $R^2$ is cyclopropyl.

In some embodiments, disclosed herein is a compound of Formula I, or a pharmaceutically acceptable salt thereof, wherein $R^3$ is $—C_{(0)}$alkyl$C_{(5-6)}$cycloalkyl, wherein the $—C_{(0)}$alkyl$C_{(5-6)}$cycloalkyl is unsubstituted or substituted with one to five fluorine atoms.

In some embodiments, disclosed herein is a compound of Formula I, or a pharmaceutically acceptable salt thereof, wherein $R^3$ is $—C_{(0)}$alkyl$C_{(5-6)}$cycloalkyl, wherein the $—C_{(0)}$alkyl$C_{(5-6)}$cycloalkyl is unsubstituted or substituted with one to three fluorine atoms.

In some embodiments, disclosed herein is a compound of Formula I, or a pharmaceutically acceptable salt thereof, wherein $R^3$ is $—C_{(0)}$alkyl$C_{(6)}$cycloalkyl, wherein the $—C_{(0)}$alkyl$C_{(6)}$cycloalkyl is unsubstituted or substituted with one to two fluorine atoms.

In some embodiments, disclosed herein is a compound of Formula I, or a pharmaceutically acceptable salt thereof, wherein $R^3$ is

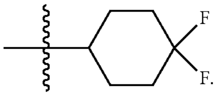

In some embodiments, disclosed herein is a compound of Formula I, or a pharmaceutically acceptable salt thereof, wherein $R^4$ is a 5- to 6-membered heteroaryl having 1 to 4 heteroatoms selected from N and O;

wherein the 5- to 6-membered heteroaryl is unsubstituted or substituted with one or two $R^{4b}$ groups;

each $R^{4b}$ group is independently selected from $—C_{(0-1)}$alkyl$C_{(3)}$cycloalkyl or $—C_{(1-3)}$alkyl, wherein the $—C_{(0-1)}$alkyl$C_{(3)}$cycloalkyl and $—C_{(1-3)}$alkyl are unsubstituted or substituted with one to four fluorine atoms;

In some embodiments, disclosed herein is a compound of Formula I, or a pharmaceutically acceptable salt thereof, wherein $R^4$ is pyridinyl that is unsubstituted or substituted with $C_{(1-2)}$alkyl that is unsubstituted or substituted with one to three fluorine atoms.

In some embodiments, disclosed herein is a compound of Formula I, or a pharmaceutically acceptable salt thereof, wherein $R^4$ is

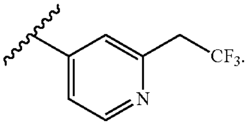 [SMILES: *c1ccnc(CC(F)(F)F)c1]

In some embodiments, disclosed herein is a compound of Formula I, or a pharmaceutically acceptable salt thereof, wherein $R^4$ is pyrazolyl, triazolyl, isoxazolyl, or oxadiazolyl that is unsubstituted or substituted with one or two $R^{4b}$ groups, each $R^{4b}$ group is independently selected from $—C_{(0-1)}$alkyl$C_{(3)}$cycloalkyl or $—C_{(1-3)}$alkyl, wherein the $—C_{(0-1)}$alkyl$C_{(3)}$cycloalkyl and $—C_{(1-3)}$alkyl are unsubstituted or substituted with one to four fluorine atoms.

In some embodiments, disclosed herein is a compound of Formula I, or a pharmaceutically acceptable salt thereof, wherein $R^4$ is pyrazolyl, triazolyl, isoxazolyl, or oxadiazolyl that is unsubstituted or substituted with one or two $R^{4b}$ groups, each $R^{4b}$ group is independently selected from $—C_{(1)}$alkyl$C_{(3)}$cycloalkyl or $—C_{(1-3)}$alkyl, wherein the $—C_{(1)}$alkyl$C_{(3)}$cycloalkyl and $—C_{(1-3)}$alkyl are unsubstituted or substituted with one to three fluorine atoms.

In some embodiments, disclosed herein is a compound of Formula I, or a pharmaceutically acceptable salt thereof, wherein $R^4$ is pyrazolyl, triazolyl, isoxazolyl, or oxadiazolyl that is unsubstituted or substituted with one or two $R^{4b}$ groups, each $R^{4b}$ group is independently $—C_{(1-3)}$alkyl, wherein the $—C_{(1-3)}$alkyl is unsubstituted or substituted with one to three fluorine atoms.

In some embodiments, disclosed herein is a compound of Formula I, or a pharmaceutically acceptable salt thereof, wherein $R^4$ is 1H-pyrazolyl, 1H-1,2,3-triazolyl, 2H-1,2,3-triazolyl, 1H-1,2,4-triazolyl, isoxazole-4-yl, or 1,2,5-oxadiazolyl that is unsubstituted or substituted with one or two $R^{4b}$ groups.

In some embodiments, disclosed herein is a compound of Formula I, or a pharmaceutically acceptable salt thereof, wherein $R^4$ is 1H-pyrazolyl, 1H-1,2,3-triazolyl, 2H-1,2,3-triazolyl, 1H-1,2,4-triazolyl, isoxazole-4-yl, isoxazole-3-yl or 1,2,5-oxadiazolyl that is unsubstituted or substituted with one or two $R^{4b}$ groups.

In some embodiments, disclosed herein is a compound of Formula I, or a pharmaceutically acceptable salt thereof, wherein $R^4$ is 1H-pyrazol-3-yl, 1H-pyrazol-4-yl, 1H-pyrazol-5-yl, 1H-1,2,3-triazol-5-yl, 2H-1,2,3-triazol-4-yl, 1H-1,2,4-triazol-5-yl, isoxazole-4-yl, or 1,2,5-oxadiazol-3-yl that is unsubstituted or substituted with one or two $R^{4b}$ groups.

In some embodiments, disclosed herein is a compound of Formula I, or a pharmaceutically acceptable salt thereof, wherein $R^4$ is 1H-pyrazol-3-yl, 1H-pyrazol-4-yl, 1H-pyrazol-5-yl, 1H-1,2,3-triazol-5-yl, 2H-1,2,3-triazol-4-yl, 1H-1,2,4-triazol-5-yl, isoxazole-4-yl, isoxazole-3-yl or 1,2,5-oxadiazol-3-yl that is unsubstituted or substituted with one or two $R^{4b}$ groups.

In some embodiments, disclosed herein is a compound of Formula I, or a pharmaceutically acceptable salt thereof, wherein $R^4$ is:
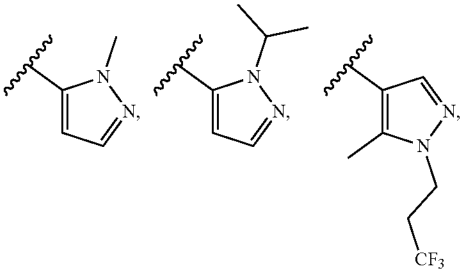
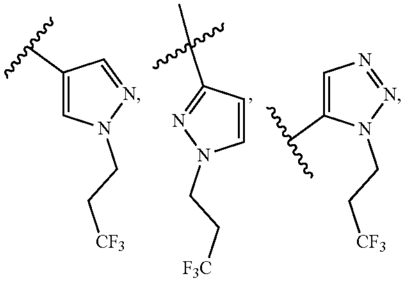
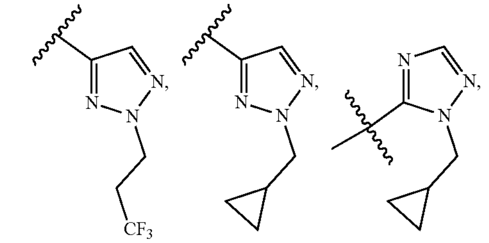
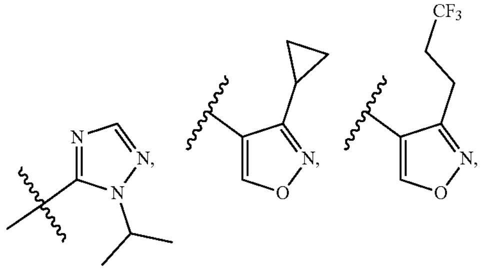
or
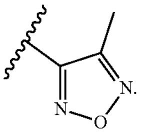
In some embodiments, disclosed herein is a compound of Formula I, or a pharmaceutically acceptable salt thereof, wherein
$R^4$ is:
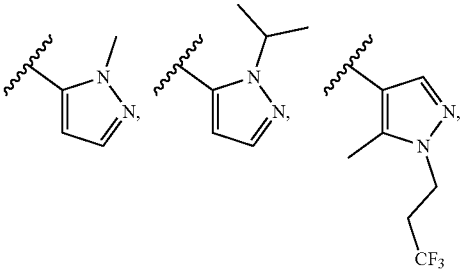
-continued
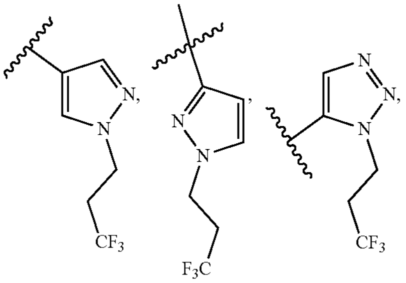
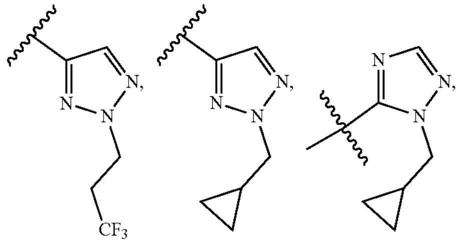
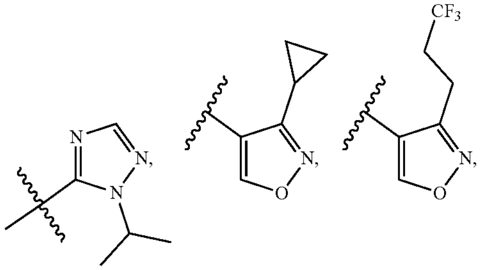
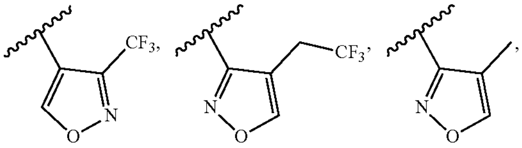
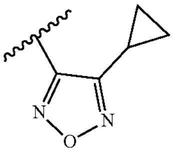
or
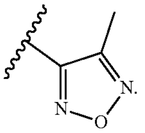
In some embodiments, disclosed herein is a compound of Formula I, or a pharmaceutically acceptable salt thereof, wherein
$R^4$ is:
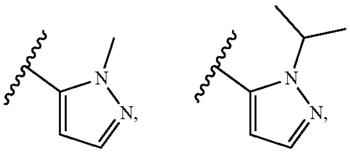

-continued

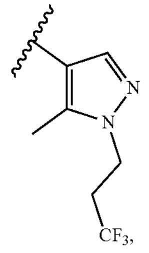

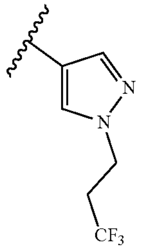

or

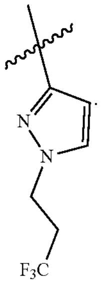

In some embodiments, disclosed herein is a compound of Formula I, or a pharmaceutically acceptable salt thereof, wherein $R^4$ is:

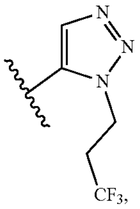

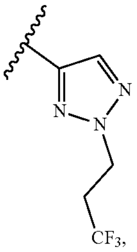

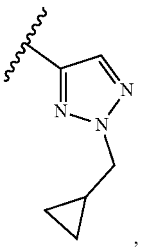

,

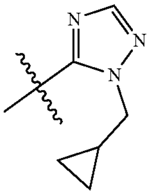

or

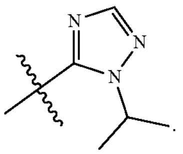

In some embodiments, disclosed herein is a compound of Formula I, or a pharmaceutically acceptable salt thereof, wherein $R^4$ is:

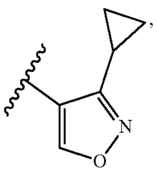

or

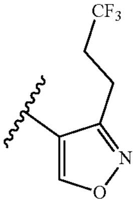

-continued

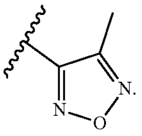

In some embodiments, disclosed herein is a compound of Formula I, or a pharmaceutically acceptable salt thereof, wherein $R^4$ is:

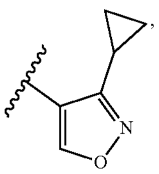

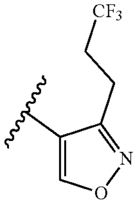

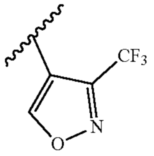

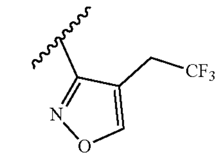

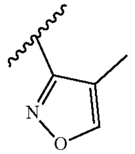

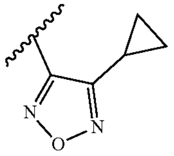

or

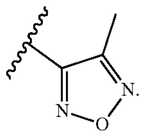

In some embodiments, disclosed herein is a compound of Formula I, or a pharmaceutically acceptable salt thereof, wherein:

$R^4$ is $-C_{(3)}$cycloalkyl;

wherein the $C_{(3)}$cycloalkyl is unsubstituted or substituted with one to three $R^{4a}$ groups; and each $R^{4a}$ group is independently selected from $-C_{(1-2)}$alkyl that is unsubstituted or substituted with one to three fluorine atoms; and wherein the compound of Formula I is a compound of Formula Ia:

Ia

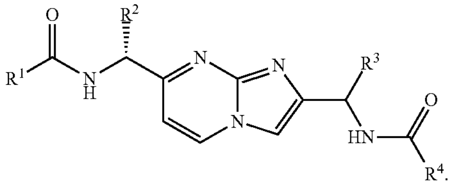

In some embodiments, disclosed herein is a compound of Formula I, or a pharmaceutically acceptable salt thereof, wherein:

$R^4$ is $-C_{(3)}$cycloalkyl that is unsubstituted or substituted with one $-CF_3$ and wherein the compound of Formula I is a compound of Formula Ia:

Ia

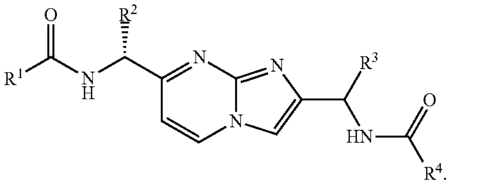

In some embodiments, disclosed herein is a compound of Formula I, or a pharmaceutically acceptable salt thereof, wherein:

$R^4$ is

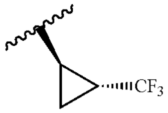

or

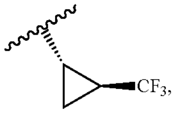

and wherein the compound of Formula I is a compound of Formula Ia:

Ia

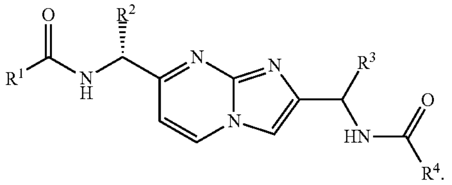

In some embodiments, disclosed herein is a compound of Formula I, or a pharmaceutically acceptable salt thereof, which is a compound of Formula Ia:

Ia

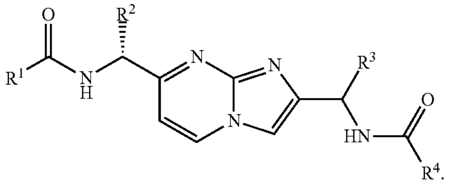

In some embodiments, disclosed herein is a compound of Formula I, or a pharmaceutically acceptable salt thereof wherein the compound is selected from the compounds below in Table 1A.

TABLE 1A

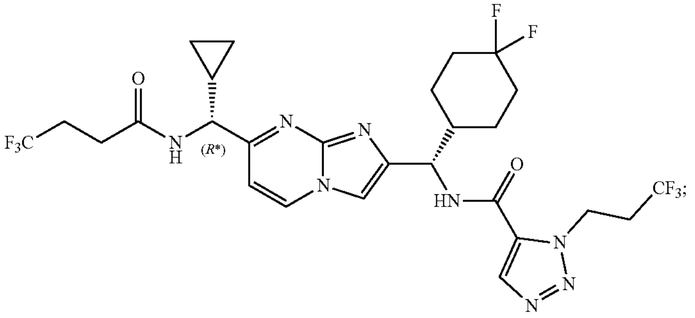 [SMILES: O=C(CCC(F)(F)F)N[C@@H](c1ccn2cc([C@@H](NC(=O)c3cnnn3CCC(F)(F)F)C3CCC(F)(F)CC3)nc2n1)C1CC1]

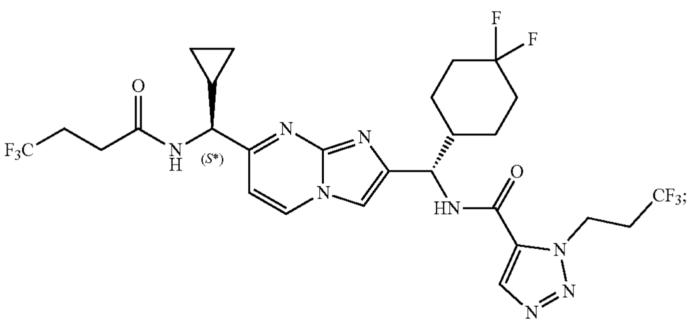 [SMILES: O=C(CCC(F)(F)F)N[C@H](c1ccn2cc([C@@H](NC(=O)c3cnnn3CCC(F)(F)F)C3CCC(F)(F)CC3)nc2n1)C1CC1]

TABLE 1A-continued
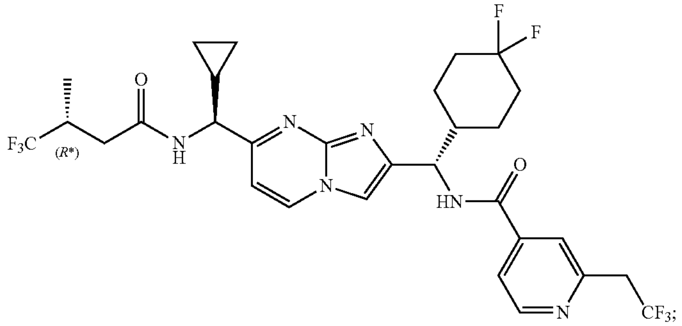 [SMILES: C[C@H](CC(=O)N[C@H](c1ccn2cc([C@@H](NC(=O)c3ccnc(CC(F)(F)F)c3)C3CCC(F)(F)CC3)nc2n1)C1CC1)C(F)(F)F]
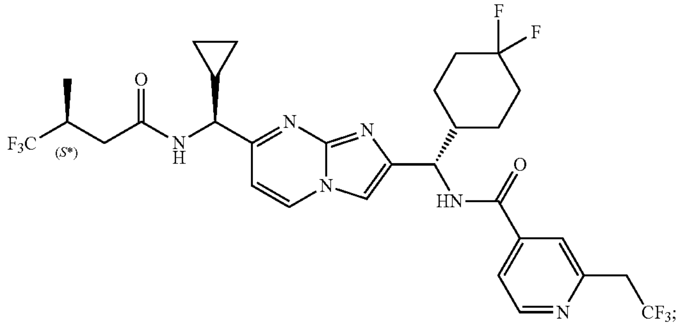 [SMILES: C[C@@H](CC(=O)N[C@H](c1ccn2cc([C@@H](NC(=O)c3ccnc(CC(F)(F)F)c3)C3CCC(F)(F)CC3)nc2n1)C1CC1)C(F)(F)F]
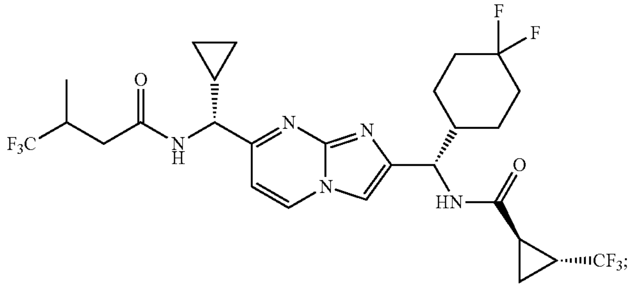 [SMILES: CC(CC(=O)N[C@@H](c1ccn2cc([C@@H](NC(=O)[C@@H]3C[C@H]3C(F)(F)F)C3CCC(F)(F)CC3)nc2n1)C1CC1)C(F)(F)F]
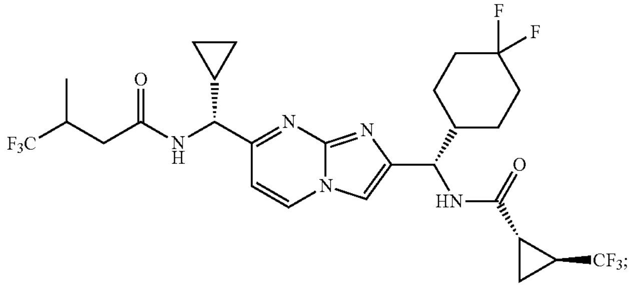 [SMILES: CC(CC(=O)N[C@@H](c1ccn2cc([C@@H](NC(=O)[C@H]3C[C@@H]3C(F)(F)F)C3CCC(F)(F)CC3)nc2n1)C1CC1)C(F)(F)F]
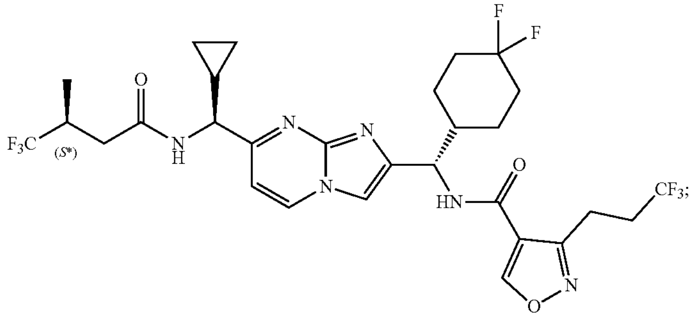 [SMILES: C[C@@H](CC(=O)N[C@H](c1ccn2cc([C@@H](NC(=O)c3conc3CCC(F)(F)F)C3CCC(F)(F)CC3)nc2n1)C1CC1)C(F)(F)F]

TABLE 1A-continued
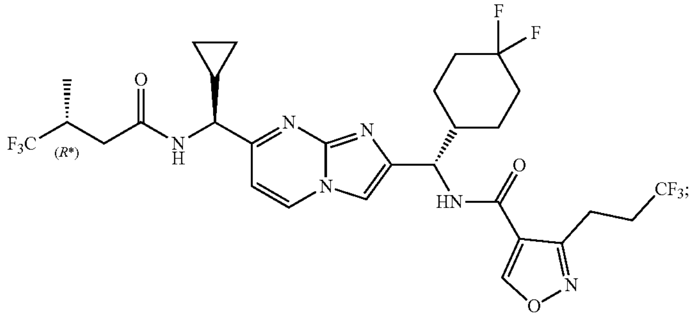 [SMILES: C[C@H](CC(=O)N[C@H](c1ccn2cc([C@@H](NC(=O)c3conc3CCC(F)(F)F)C3CCC(F)(F)CC3)nc2n1)C1CC1)C(F)(F)F]
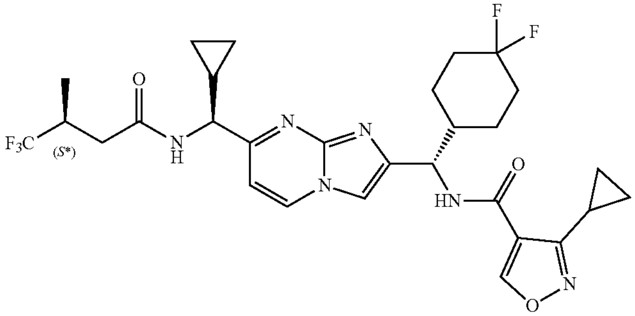
;
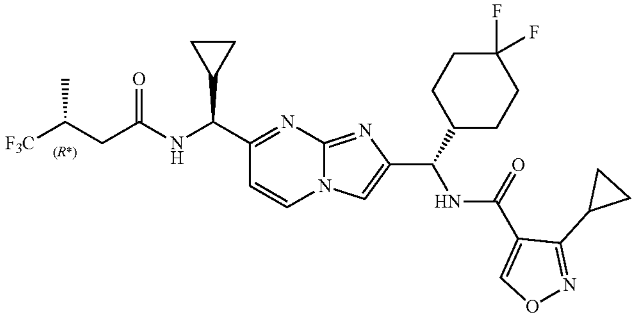
;
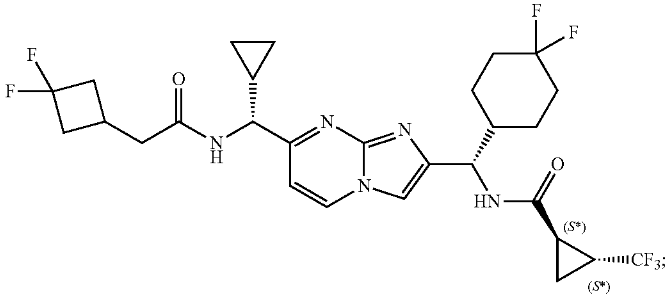 [SMILES: O=C(CC1CC(F)(F)C1)N[C@@H](c1ccn2cc([C@@H](NC(=O)[C@@H]3C[C@H]3C(F)(F)F)C3CCC(F)(F)CC3)nc2n1)C1CC1]
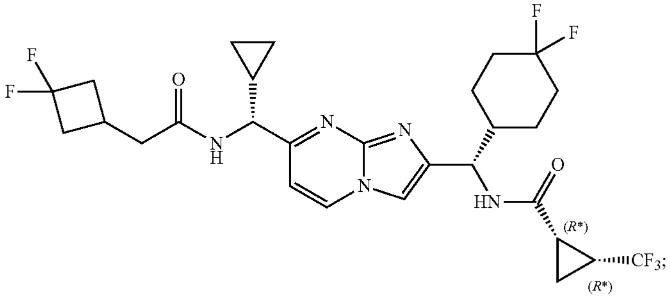 [SMILES: O=C(CC1CC(F)(F)C1)N[C@@H](c1ccn2cc([C@@H](NC(=O)[C@H]3C[C@H]3C(F)(F)F)C3CCC(F)(F)CC3)nc2n1)C1CC1]

TABLE 1A-continued
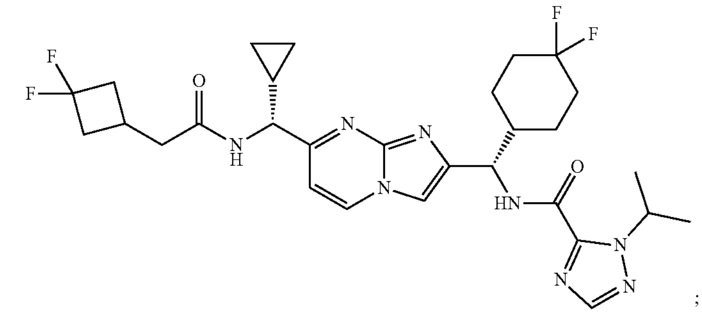 [SMILES: CC(C)n1ncnc1C(=O)N[C@H](c1cn2ccc([C@H](NC(=O)CC3CC(F)(F)C3)C3CC3)nc2n1)C1CCC(F)(F)CC1]
;
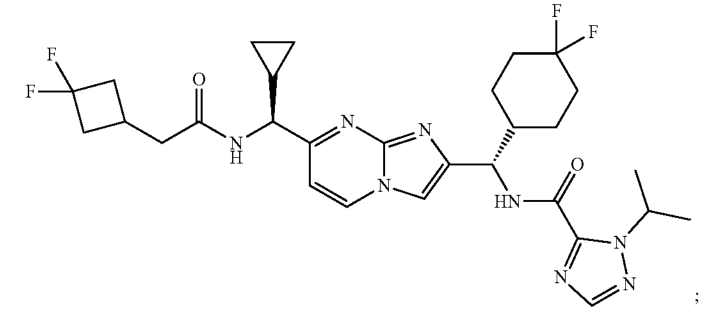 [SMILES: CC(C)n1ncnc1C(=O)N[C@H](c1cn2ccc([C@@H](NC(=O)CC3CC(F)(F)C3)C3CC3)nc2n1)C1CCC(F)(F)CC1]
;
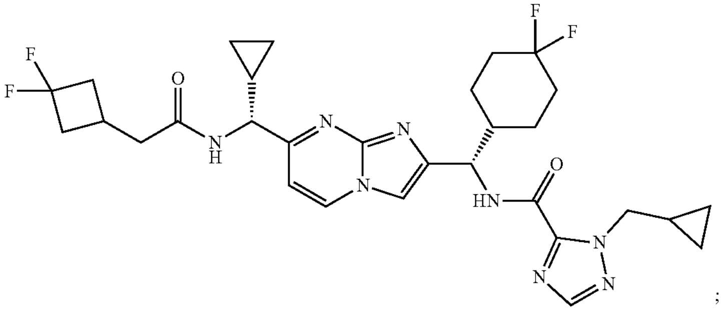 [SMILES: O=C(CC1CC(F)(F)C1)N[C@@H](c1ccn2cc([C@@H](NC(=O)c3ncnn3CC3CC3)C3CCC(F)(F)CC3)nc2n1)C1CC1]
;
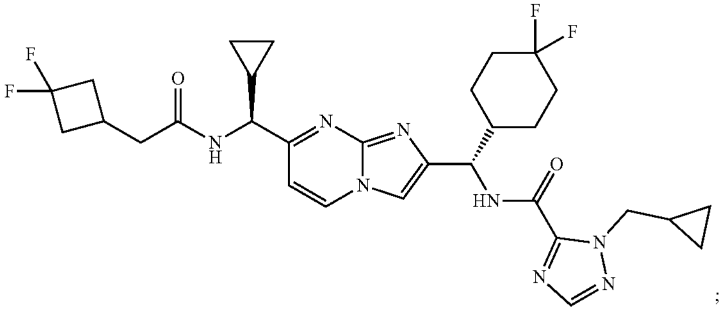 [SMILES: O=C(CC1CC(F)(F)C1)N[C@H](c1ccn2cc([C@@H](NC(=O)c3ncnn3CC3CC3)C3CCC(F)(F)CC3)nc2n1)C1CC1]
;
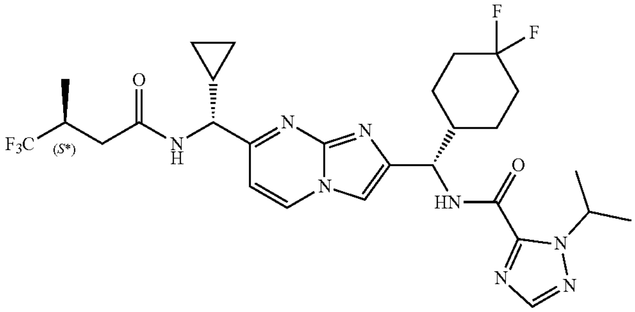
;

TABLE 1A-continued
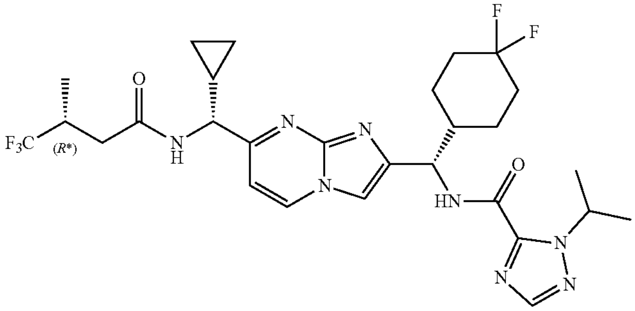
;
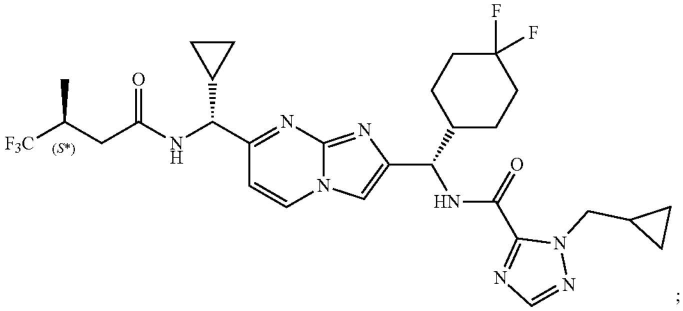 [SMILES: C[C@@H](CC(=O)N[C@@H](c1ccn2cc([C@@H](NC(=O)c3ncnn3CC3CC3)C3CCC(F)(F)CC3)nc2n1)C1CC1)C(F)(F)F]
;
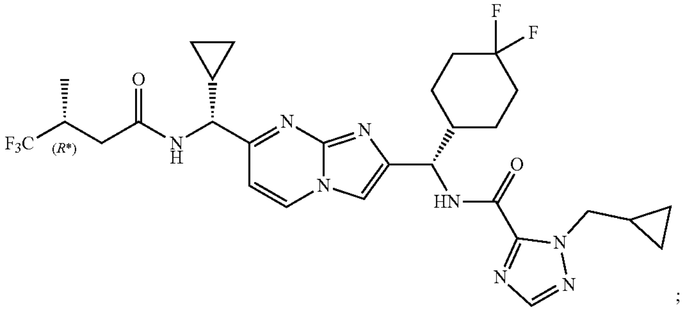 [SMILES: C[C@H](CC(=O)N[C@@H](c1ccn2cc([C@@H](NC(=O)c3ncnn3CC3CC3)C3CCC(F)(F)CC3)nc2n1)C1CC1)C(F)(F)F]
;
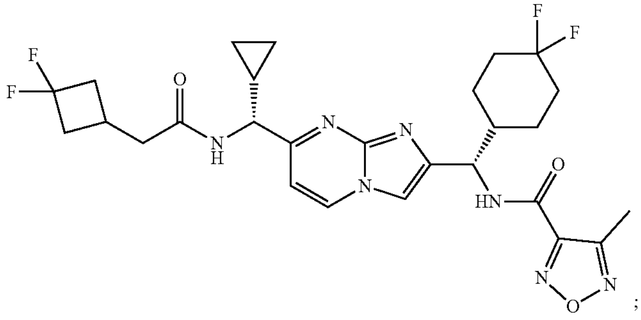 [SMILES: Cc1nonc1C(=O)N[C@H](c1cn2ccc([C@H](NC(=O)CC3CC(F)(F)C3)C3CC3)nc2n1)C1CCC(F)(F)CC1]
;
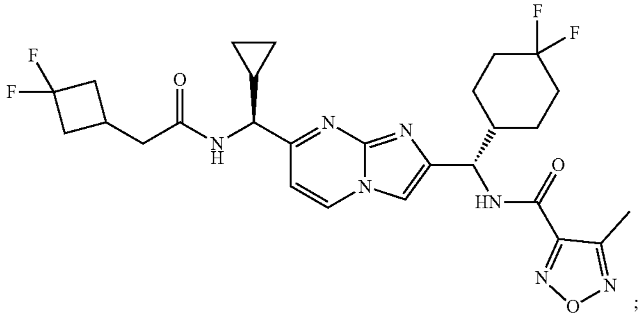 [SMILES: Cc1nonc1C(=O)N[C@H](c1cn2ccc([C@@H](NC(=O)CC3CC(F)(F)C3)C3CC3)nc2n1)C1CCC(F)(F)CC1]
;

TABLE 1A-continued
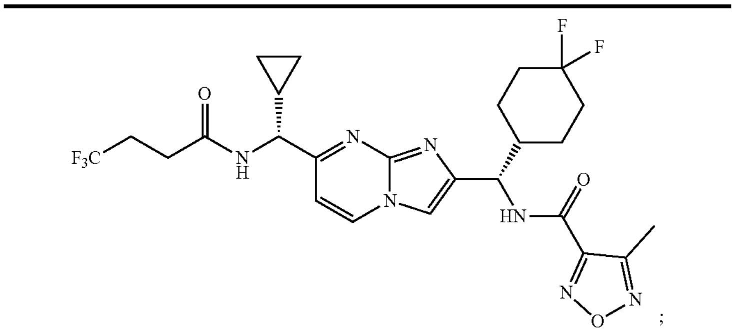
;
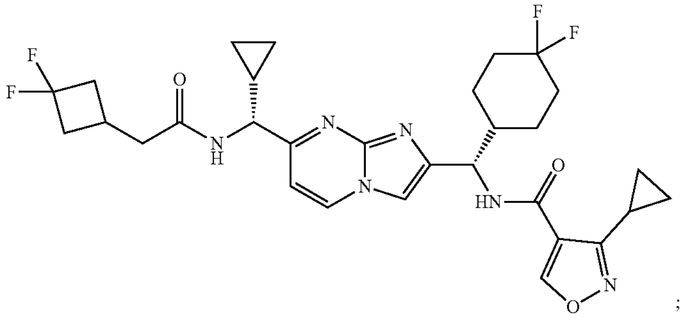 [SMILES: O=C(CC1CC(F)(F)C1)N[C@@H](c1ccn2cc([C@@H](NC(=O)c3conc3C3CC3)C3CCC(F)(F)CC3)nc2n1)C1CC1]
;
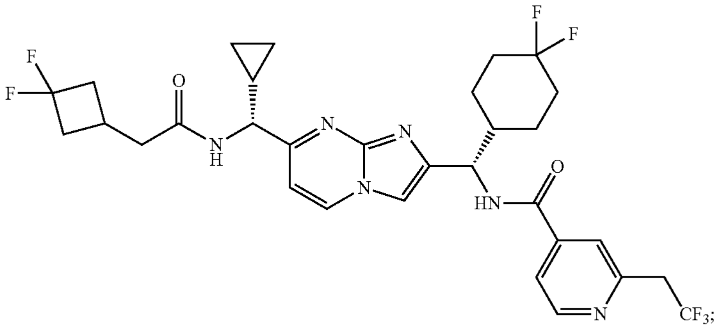 [SMILES: O=C(CC1CC(F)(F)C1)N[C@@H](c1ccn2cc([C@@H](NC(=O)c3ccnc(CC(F)(F)F)c3)C3CCC(F)(F)CC3)nc2n1)C1CC1]
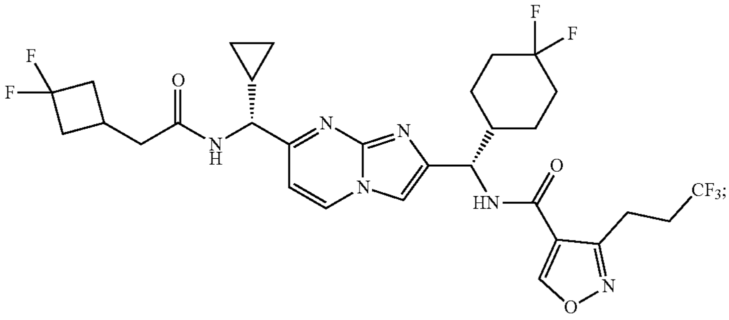 [SMILES: O=C(CC1CC(F)(F)C1)N[C@@H](c1ccn2cc([C@@H](NC(=O)c3conc3CCC(F)(F)F)C3CCC(F)(F)CC3)nc2n1)C1CC1]
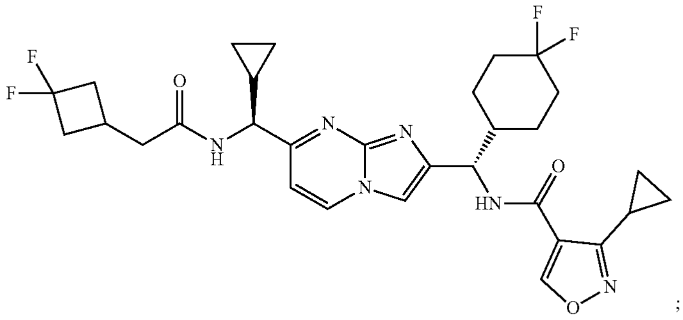 [SMILES: O=C(CC1CC(F)(F)C1)N[C@H](c1ccn2cc([C@@H](NC(=O)c3conc3C3CC3)C3CCC(F)(F)CC3)nc2n1)C1CC1]
;

TABLE 1A-continued
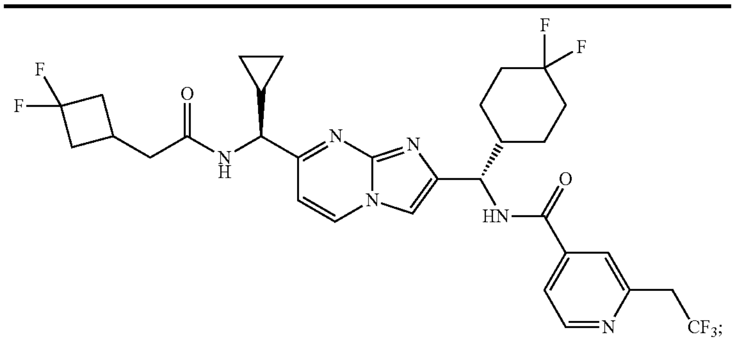
;
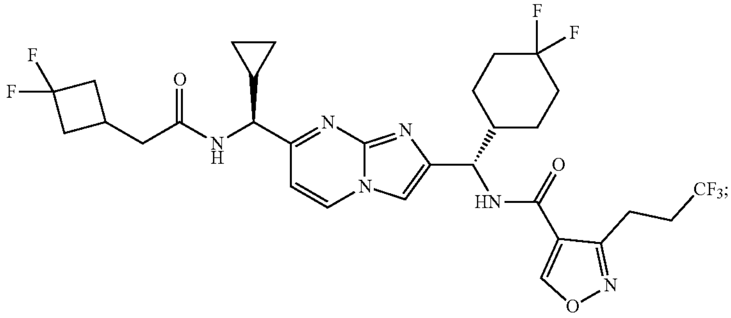 [SMILES: O=C(CC1CC(F)(F)C1)N[C@H](c1ccn2cc([C@@H](NC(=O)c3conc3CCC(F)(F)F)C3CCC(F)(F)CC3)nc2n1)C1CC1]
;
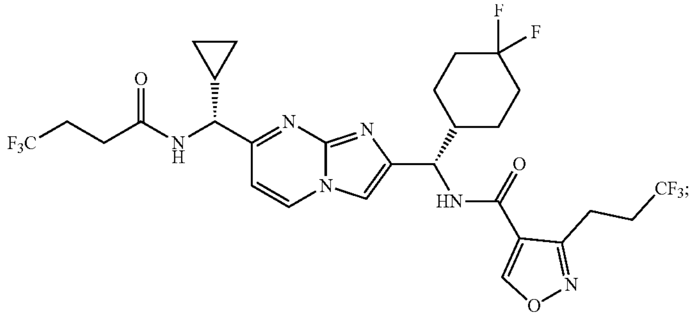 [SMILES: O=C(CCC(F)(F)F)N[C@@H](c1ccn2cc([C@@H](NC(=O)c3conc3CCC(F)(F)F)C3CCC(F)(F)CC3)nc2n1)C1CC1]
;
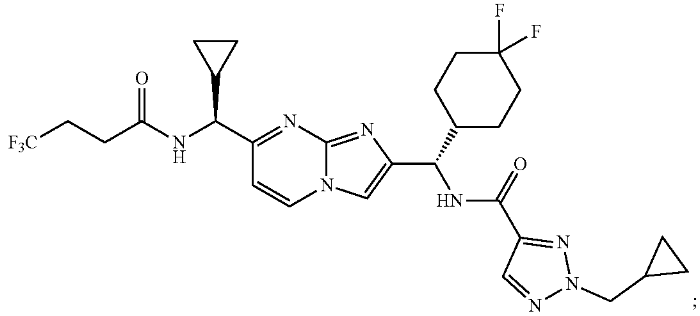
;
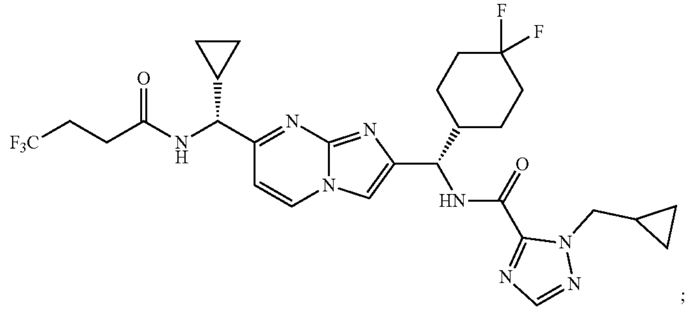 [SMILES: O=C(CCC(F)(F)F)N[C@@H](c1ccn2cc([C@@H](NC(=O)c3ncnn3CC3CC3)C3CCC(F)(F)CC3)nc2n1)C1CC1]
;

TABLE 1A-continued
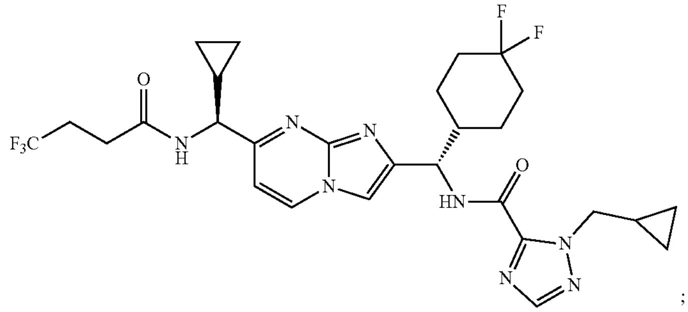 [SMILES: O=C(CCC(F)(F)F)N[C@H](c1ccn2cc([C@@H](NC(=O)c3ncnn3CC3CC3)C3CCC(F)(F)CC3)nc2n1)C1CC1]
;
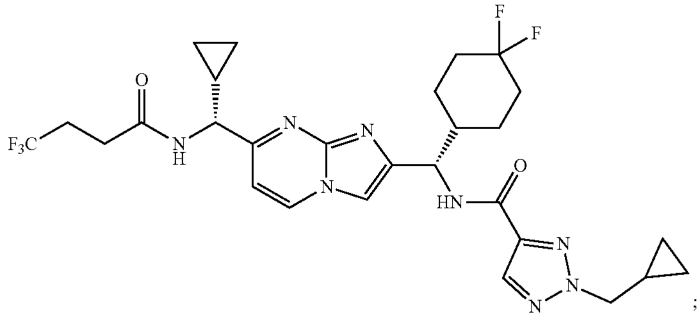 [SMILES: O=C(CCC(F)(F)F)N[C@@H](c1ccn2cc([C@@H](NC(=O)c3cnn(CC4CC4)n3)C3CCC(F)(F)CC3)nc2n1)C1CC1]
;
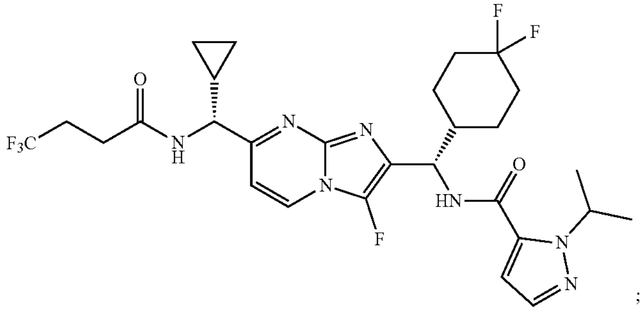 [SMILES: CC(C)n1nccc1C(=O)N[C@H](c1nc2nc([C@H](NC(=O)CCC(F)(F)F)C3CC3)ccn2c1F)C1CCC(F)(F)CC1]
;
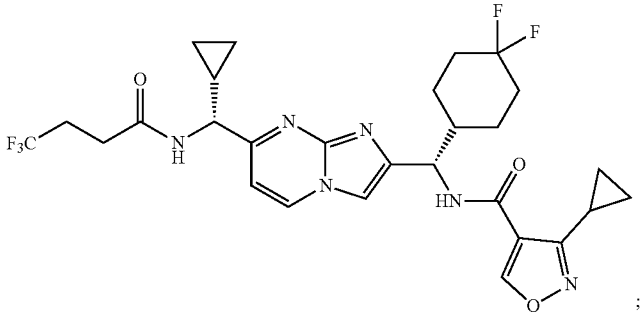 [SMILES: O=C(CCC(F)(F)F)N[C@@H](c1ccn2cc([C@@H](NC(=O)c3conc3C3CC3)C3CCC(F)(F)CC3)nc2n1)C1CC1]
;
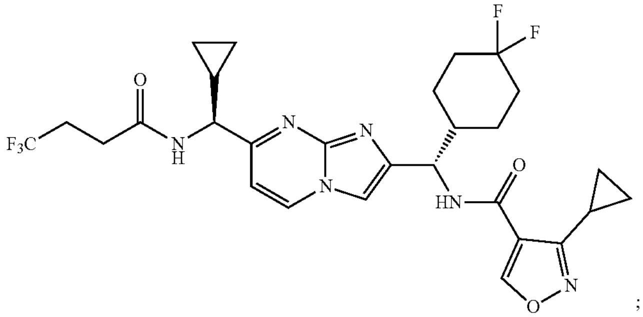 [SMILES: O=C(CCC(F)(F)F)N[C@H](c1ccn2cc([C@@H](NC(=O)c3conc3C3CC3)C3CCC(F)(F)CC3)nc2n1)C1CC1]
;

TABLE 1A-continued
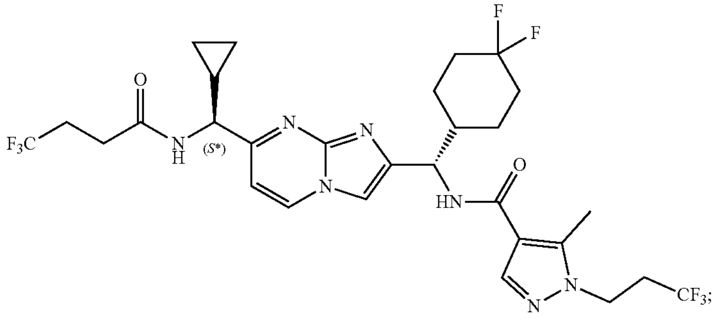 [SMILES: Cc1c(C(=O)N[C@H](c2cn3ccc([C@@H](NC(=O)CCC(F)(F)F)C4CC4)nc3n2)C2CCC(F)(F)CC2)cnn1CCC(F)(F)F]
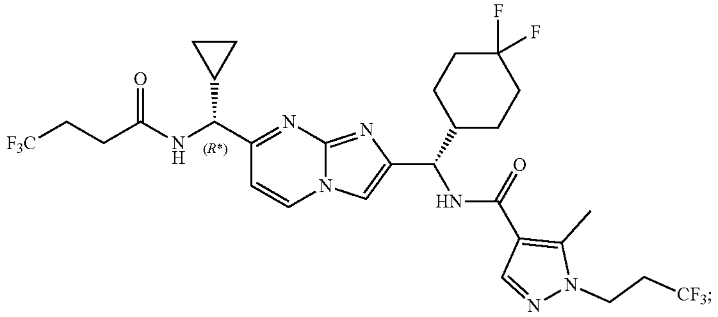 [SMILES: Cc1c(C(=O)N[C@H](c2cn3ccc([C@H](NC(=O)CCC(F)(F)F)C4CC4)nc3n2)C2CCC(F)(F)CC2)cnn1CCC(F)(F)F]
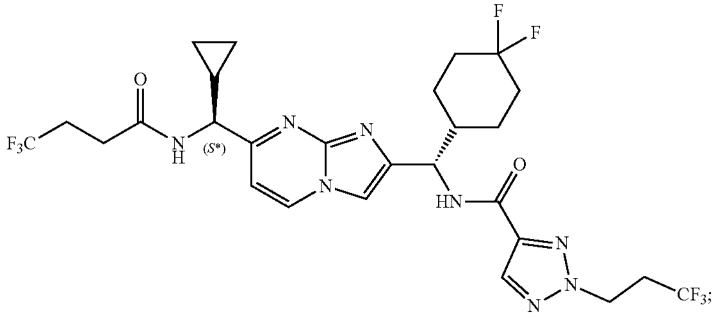
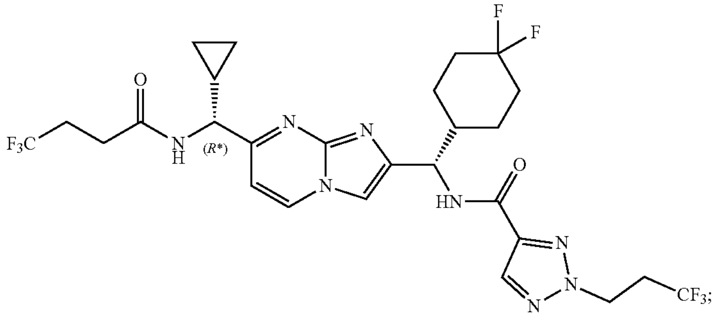 [SMILES: O=C(CCC(F)(F)F)N[C@@H](c1ccn2cc([C@@H](NC(=O)c3cnn(CCC(F)(F)F)n3)C3CCC(F)(F)CC3)nc2n1)C1CC1]
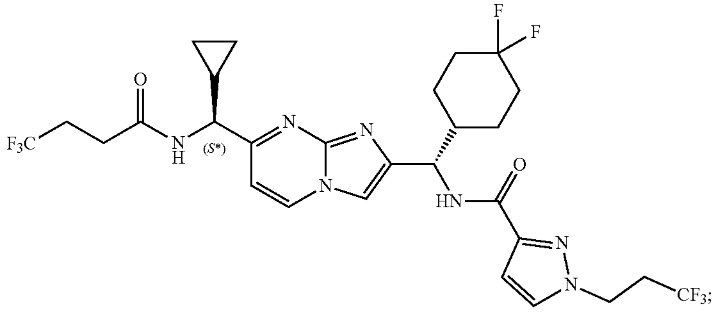 [SMILES: O=C(CCC(F)(F)F)N[C@H](c1ccn2cc([C@@H](NC(=O)c3ccn(CCC(F)(F)F)n3)C3CCC(F)(F)CC3)nc2n1)C1CC1]

TABLE 1A-continued
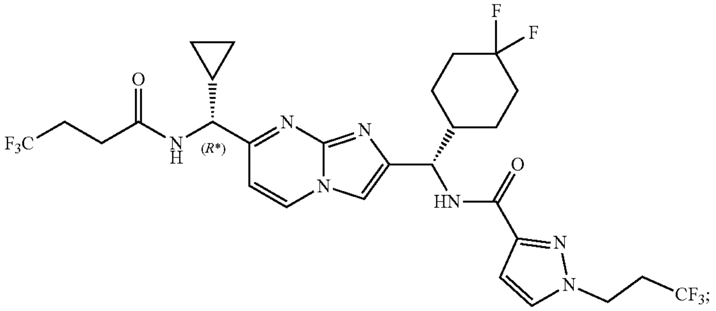 [SMILES: O=C(CCC(F)(F)F)N[C@@H](c1ccn2cc([C@@H](NC(=O)c3ccn(CCC(F)(F)F)n3)C3CCC(F)(F)CC3)nc2n1)C1CC1]
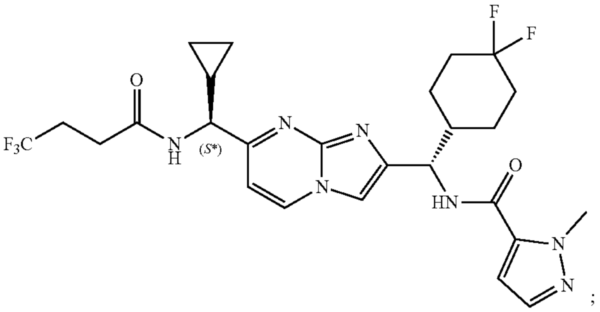 [SMILES: Cn1nccc1C(=O)N[C@H](c1cn2ccc([C@@H](NC(=O)CCC(F)(F)F)C3CC3)nc2n1)C1CCC(F)(F)CC1]
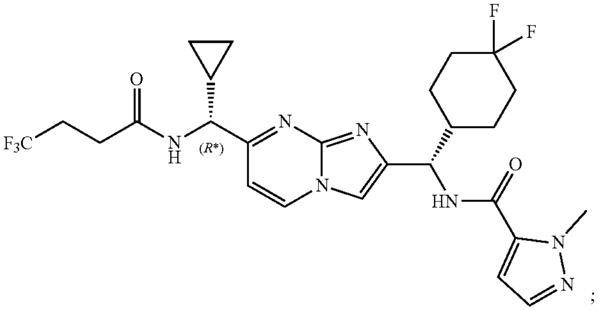 [SMILES: Cn1nccc1C(=O)N[C@H](c1cn2ccc([C@H](NC(=O)CCC(F)(F)F)C3CC3)nc2n1)C1CCC(F)(F)CC1]
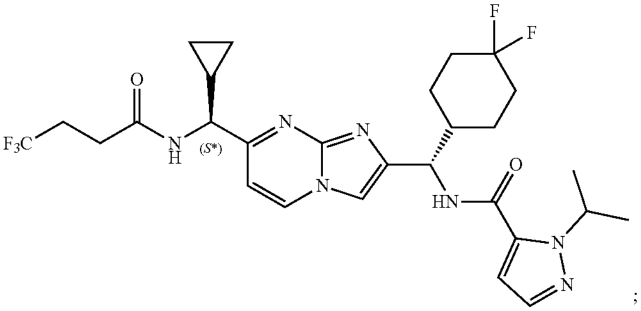 [SMILES: CC(C)n1nccc1C(=O)N[C@H](c1cn2ccc([C@@H](NC(=O)CCC(F)(F)F)C3CC3)nc2n1)C1CCC(F)(F)CC1]
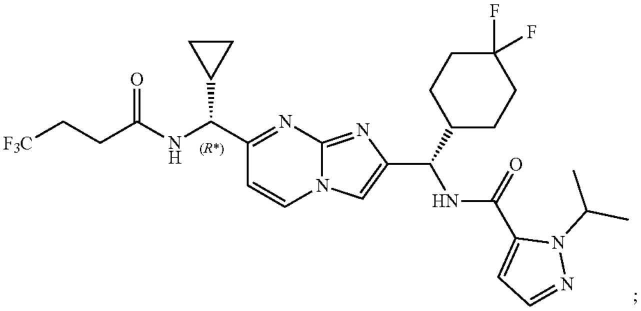 [SMILES: CC(C)n1nccc1C(=O)N[C@H](c1cn2ccc([C@H](NC(=O)CCC(F)(F)F)C3CC3)nc2n1)C1CCC(F)(F)CC1]

TABLE 1A-continued
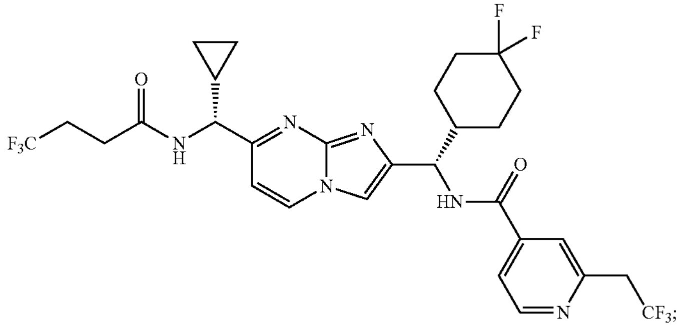 [SMILES: O=C(CCC(F)(F)F)N[C@@H](c1ccn2cc([C@@H](NC(=O)c3ccnc(CC(F)(F)F)c3)C3CCC(F)(F)CC3)nc2n1)C1CC1]
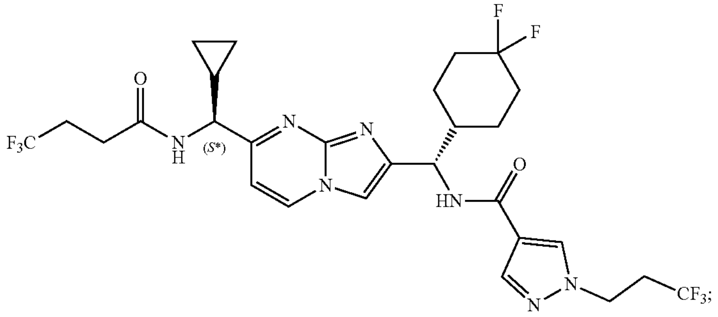 [SMILES: O=C(CCC(F)(F)F)N[C@H](c1ccn2cc([C@@H](NC(=O)c3cnn(CCC(F)(F)F)c3)C3CCC(F)(F)CC3)nc2n1)C1CC1]
and
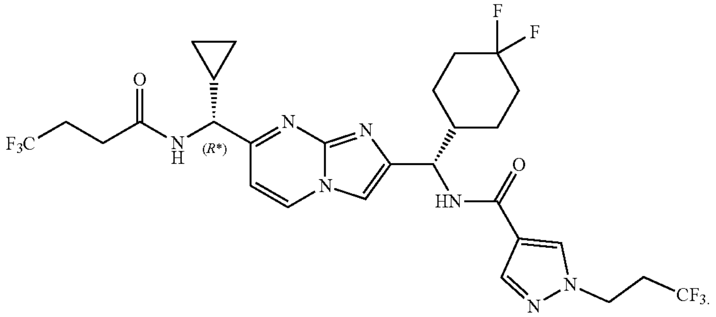 [SMILES: O=C(CCC(F)(F)F)N[C@@H](c1ccn2cc([C@@H](NC(=O)c3cnn(CCC(F)(F)F)c3)C3CCC(F)(F)CC3)nc2n1)C1CC1]
In some embodiments, disclosed herein is a compound of Formula I, or a pharmaceutically acceptable salt thereof wherein the compound is selected from the compounds below in Table 1AA.
TABLE 1AA
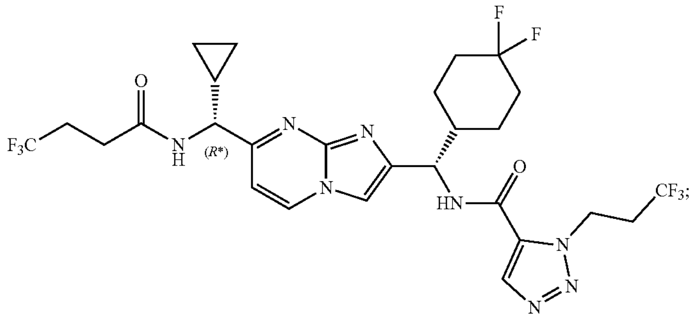 [SMILES: O=C(CCC(F)(F)F)N[C@@H](c1ccn2cc([C@@H](NC(=O)c3cnnn3CCC(F)(F)F)C3CCC(F)(F)CC3)nc2n1)C1CC1]

TABLE 1AA-continued
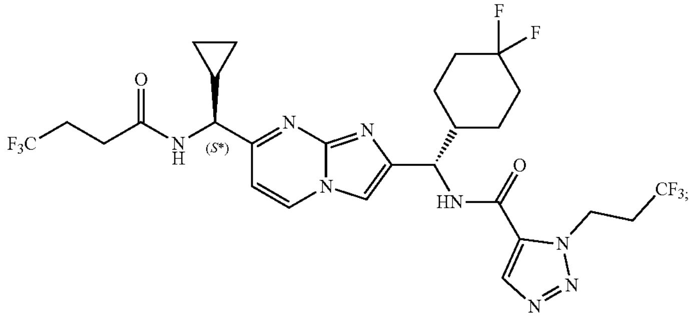 [SMILES: O=C(CCC(F)(F)F)N[C@H](c1ccn2cc([C@@H](NC(=O)c3cnnn3CCC(F)(F)F)C3CCC(F)(F)CC3)nc2n1)C1CC1]
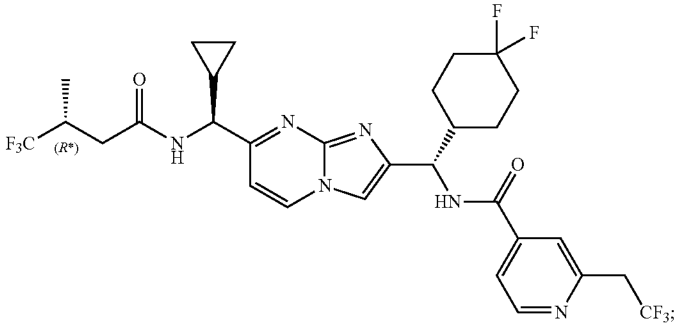 [SMILES: C[C@H](CC(=O)N[C@H](c1ccn2cc([C@@H](NC(=O)c3ccnc(CC(F)(F)F)c3)C3CCC(F)(F)CC3)nc2n1)C1CC1)C(F)(F)F]
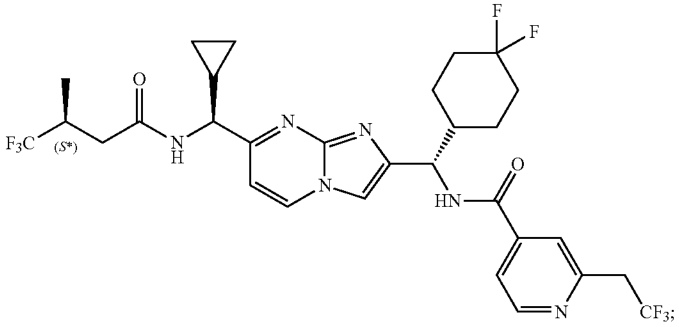 [SMILES: C[C@@H](CC(=O)N[C@H](c1ccn2cc([C@@H](NC(=O)c3ccnc(CC(F)(F)F)c3)C3CCC(F)(F)CC3)nc2n1)C1CC1)C(F)(F)F]
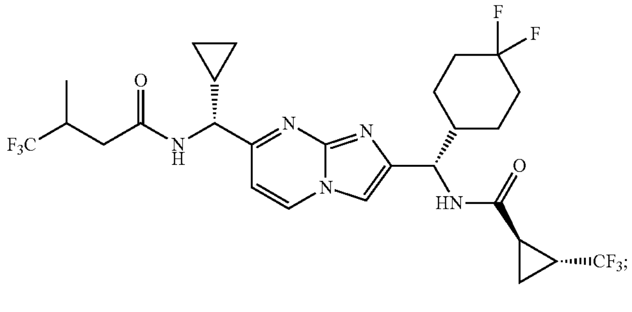 [SMILES: CC(CC(=O)N[C@@H](c1ccn2cc([C@@H](NC(=O)[C@@H]3C[C@H]3C(F)(F)F)C3CCC(F)(F)CC3)nc2n1)C1CC1)C(F)(F)F]
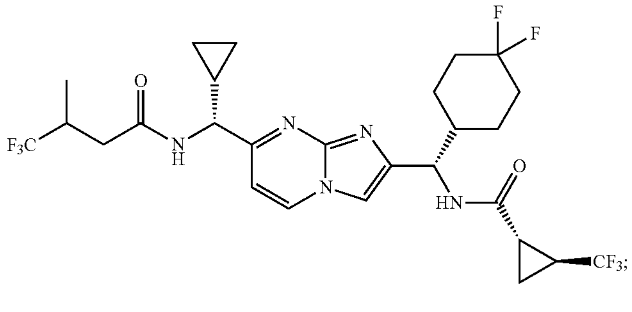 [SMILES: CC(CC(=O)N[C@@H](c1ccn2cc([C@@H](NC(=O)[C@H]3C[C@@H]3C(F)(F)F)C3CCC(F)(F)CC3)nc2n1)C1CC1)C(F)(F)F]

TABLE 1AA-continued
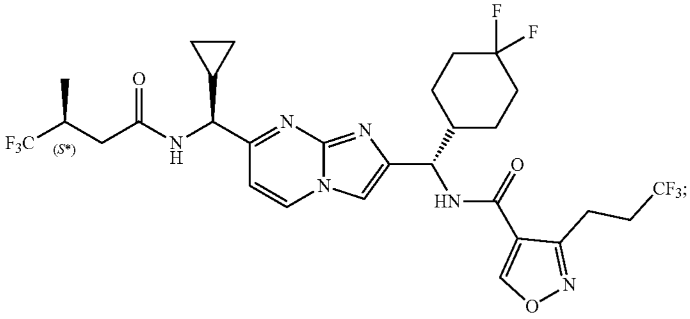 [SMILES: C[C@@H](CC(=O)N[C@H](c1ccn2cc([C@@H](NC(=O)c3conc3CCC(F)(F)F)C3CCC(F)(F)CC3)nc2n1)C1CC1)C(F)(F)F]
;
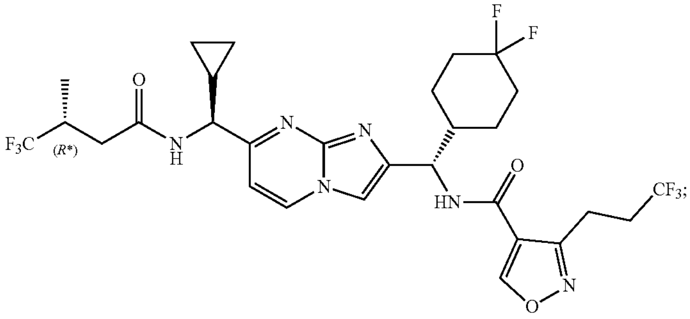 [SMILES: C[C@H](CC(=O)N[C@H](c1ccn2cc([C@@H](NC(=O)c3conc3CCC(F)(F)F)C3CCC(F)(F)CC3)nc2n1)C1CC1)C(F)(F)F]
;
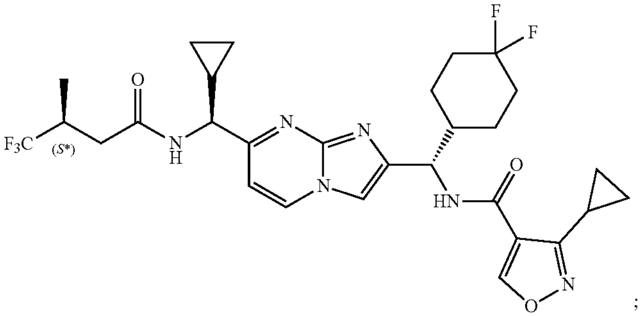 [SMILES: C[C@@H](CC(=O)N[C@H](c1ccn2cc([C@@H](NC(=O)c3conc3C3CC3)C3CCC(F)(F)CC3)nc2n1)C1CC1)C(F)(F)F]
;
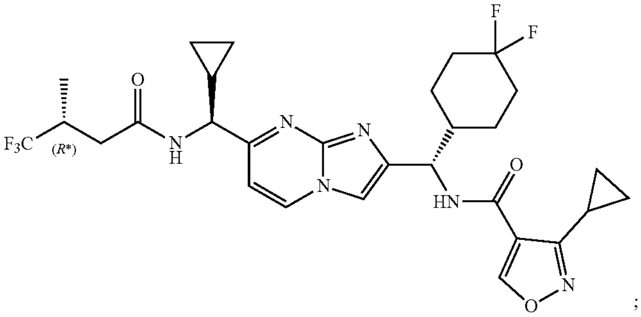 [SMILES: C[C@H](CC(=O)N[C@H](c1ccn2cc([C@@H](NC(=O)c3conc3C3CC3)C3CCC(F)(F)CC3)nc2n1)C1CC1)C(F)(F)F]
;
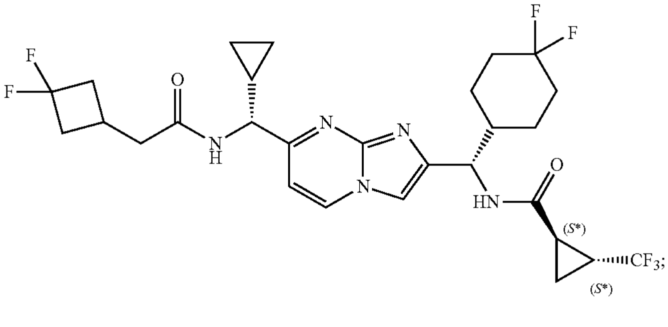 [SMILES: O=C(CC1CC(F)(F)C1)N[C@@H](c1ccn2cc([C@@H](NC(=O)[C@@H]3C[C@H]3C(F)(F)F)C3CCC(F)(F)CC3)nc2n1)C1CC1]
;

TABLE 1AA-continued
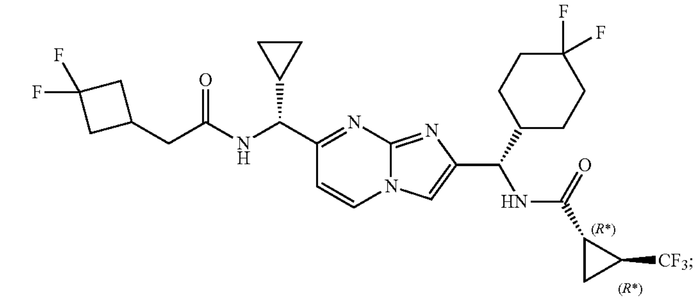 [SMILES: O=C(CC1CC(F)(F)C1)N[C@@H](c1ccn2cc([C@@H](NC(=O)[C@H]3C[C@@H]3C(F)(F)F)C3CCC(F)(F)CC3)nc2n1)C1CC1]
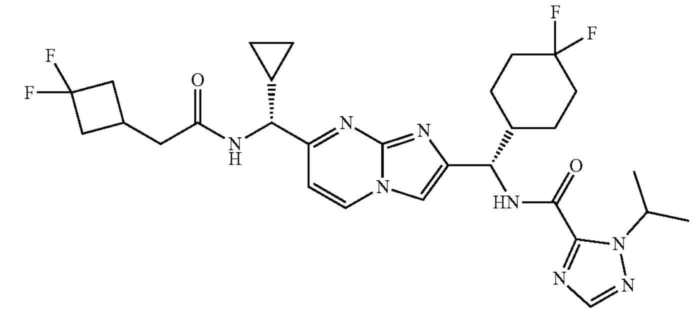
;
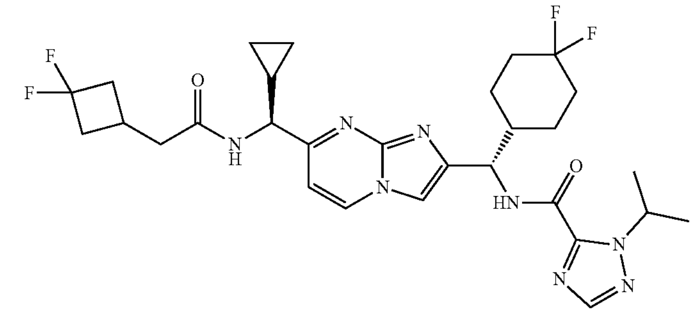
;
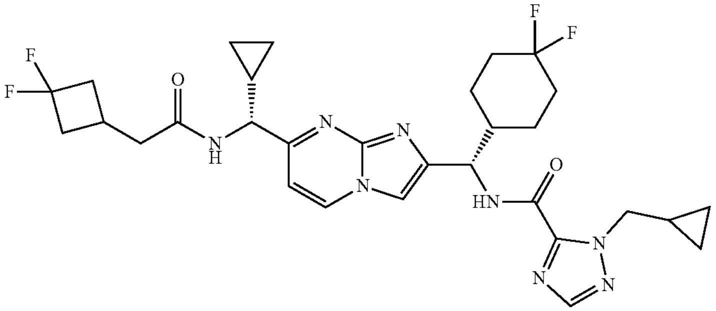
;
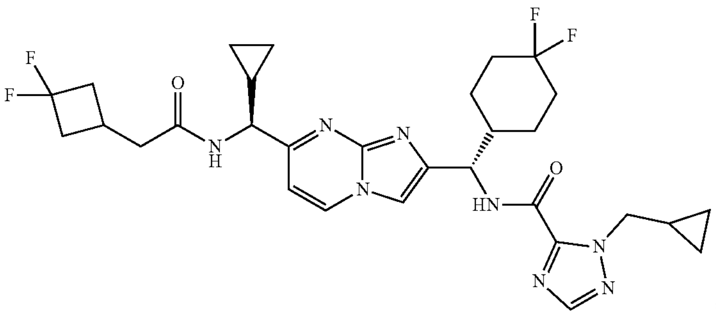
;

TABLE 1AA-continued
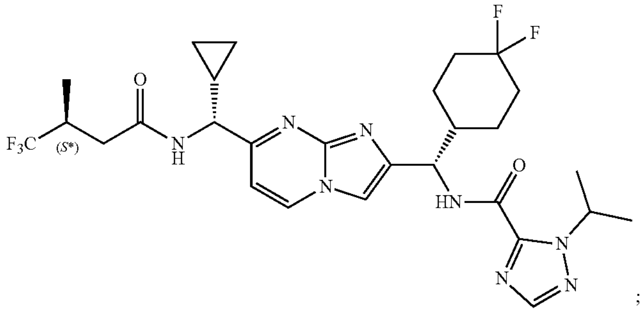 [SMILES: CC(C)n1ncnc1C(=O)N[C@H](c1cn2ccc([C@H](NC(=O)C[C@H](C)C(F)(F)F)C3CC3)nc2n1)C1CCC(F)(F)CC1]
;
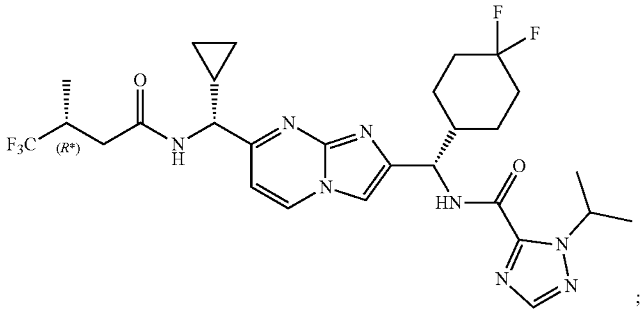 [SMILES: CC(C)n1ncnc1C(=O)N[C@H](c1cn2ccc([C@H](NC(=O)C[C@@H](C)C(F)(F)F)C3CC3)nc2n1)C1CCC(F)(F)CC1]
;
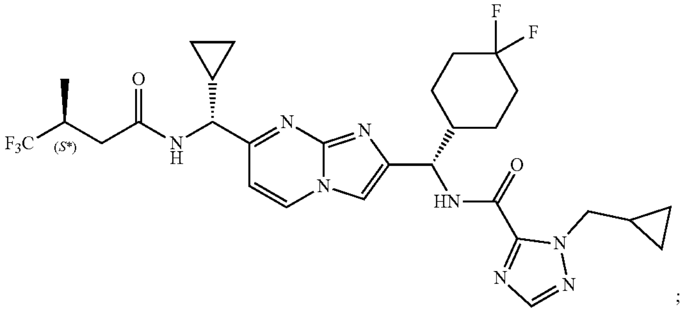 [SMILES: C[C@@H](CC(=O)N[C@@H](c1ccn2cc([C@@H](NC(=O)c3ncnn3CC3CC3)C3CCC(F)(F)CC3)nc2n1)C1CC1)C(F)(F)F]
;
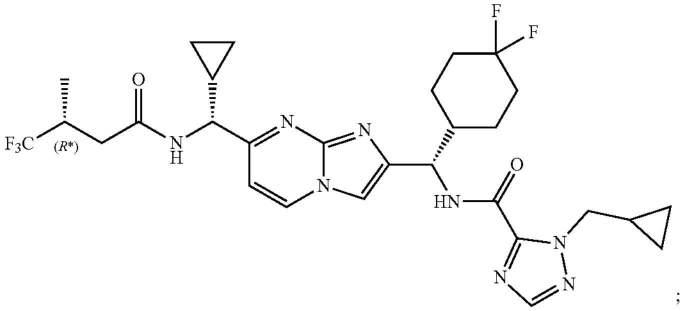 [SMILES: C[C@H](CC(=O)N[C@@H](c1ccn2cc([C@@H](NC(=O)c3ncnn3CC3CC3)C3CCC(F)(F)CC3)nc2n1)C1CC1)C(F)(F)F]
;
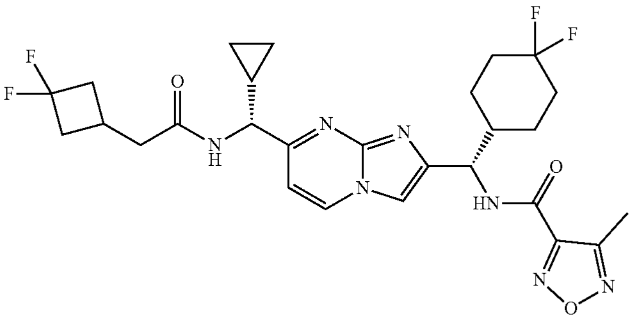
;

TABLE 1AA-continued
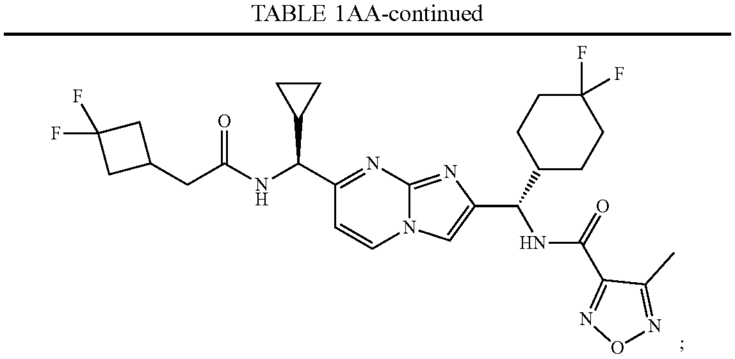
;
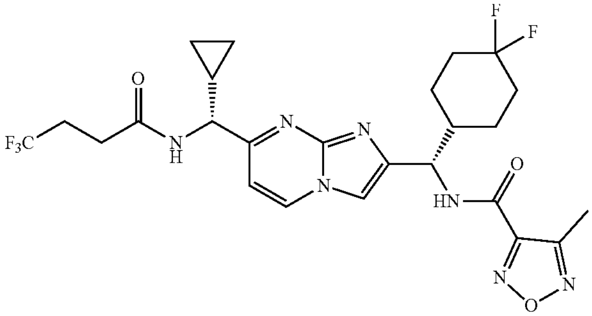
;
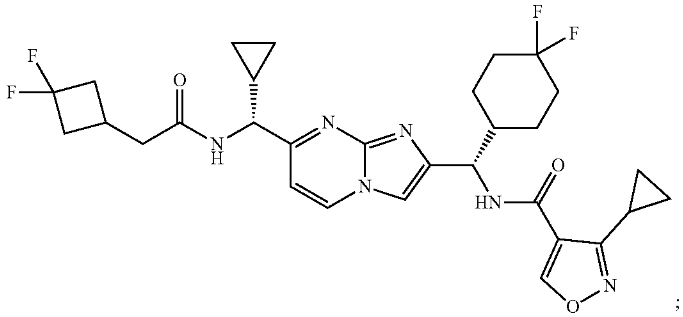 [SMILES: O=C(CC1CC(F)(F)C1)N[C@@H](c1ccn2cc([C@@H](NC(=O)c3conc3C3CC3)C3CCC(F)(F)CC3)nc2n1)C1CC1]
;
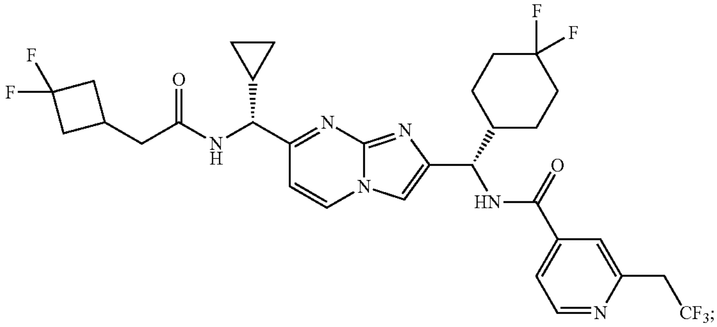 [SMILES: O=C(CC1CC(F)(F)C1)N[C@@H](c1ccn2cc([C@@H](NC(=O)c3ccnc(CC(F)(F)F)c3)C3CCC(F)(F)CC3)nc2n1)C1CC1]
;
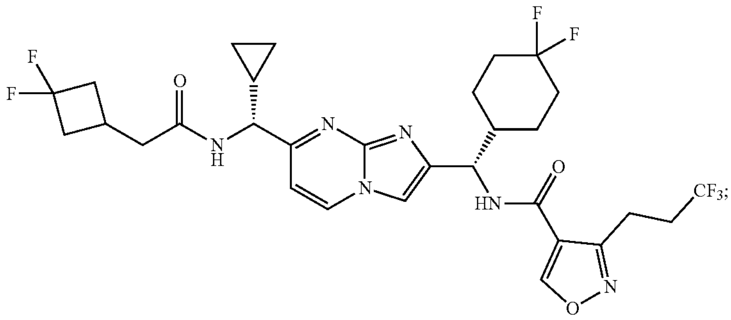 [SMILES: O=C(CC1CC(F)(F)C1)N[C@@H](c1ccn2cc([C@@H](NC(=O)c3conc3CCC(F)(F)F)C3CCC(F)(F)CC3)nc2n1)C1CC1]
;

TABLE 1AA-continued
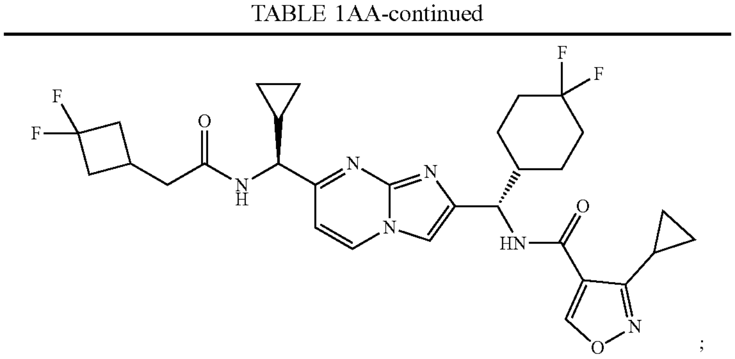
;
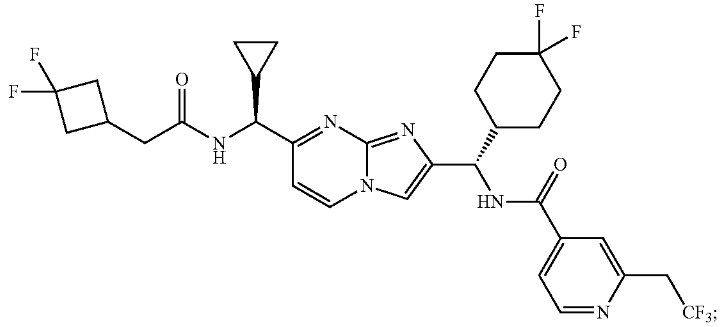
;
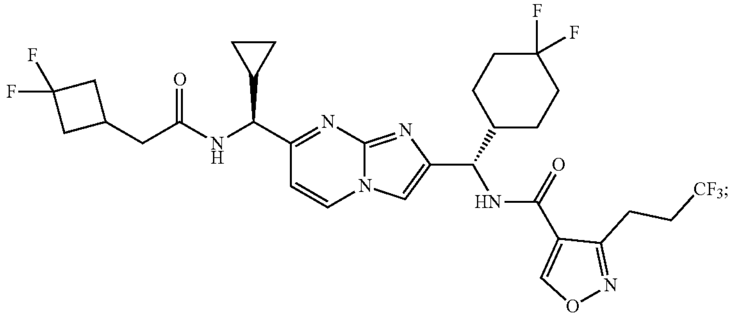 [SMILES: O=C(CC1CC(F)(F)C1)N[C@H](c1ccn2cc([C@@H](NC(=O)c3conc3CCC(F)(F)F)C3CCC(F)(F)CC3)nc2n1)C1CC1]
;
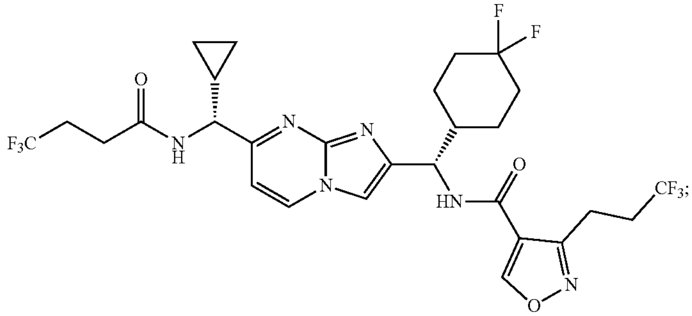 [SMILES: O=C(CCC(F)(F)F)N[C@@H](c1ccn2cc([C@@H](NC(=O)c3conc3CCC(F)(F)F)C3CCC(F)(F)CC3)nc2n1)C1CC1]
;
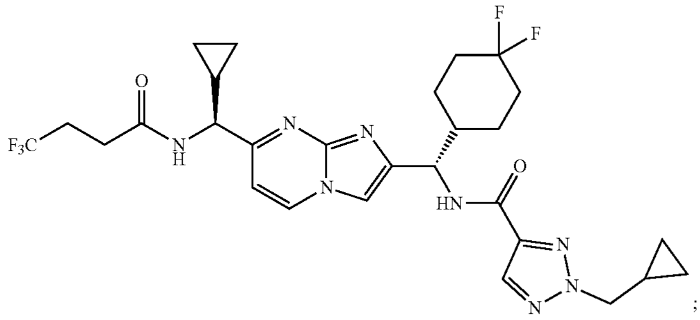 [SMILES: O=C(CCC(F)(F)F)N[C@H](c1ccn2cc([C@@H](NC(=O)c3cnn(CC4CC4)n3)C3CCC(F)(F)CC3)nc2n1)C1CC1]
;

TABLE 1AA-continued
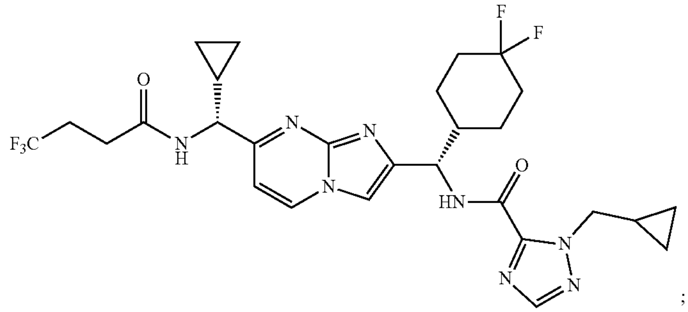 [SMILES: O=C(CCC(F)(F)F)N[C@@H](c1ccn2cc([C@@H](NC(=O)c3ncnn3CC3CC3)C3CCC(F)(F)CC3)nc2n1)C1CC1]
;
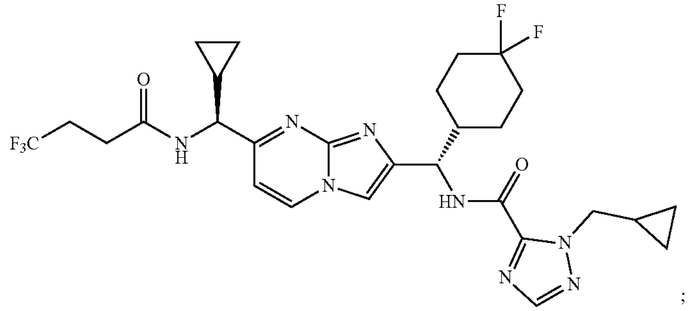 [SMILES: O=C(CCC(F)(F)F)N[C@H](c1ccn2cc([C@@H](NC(=O)c3ncnn3CC3CC3)C3CCC(F)(F)CC3)nc2n1)C1CC1]
;
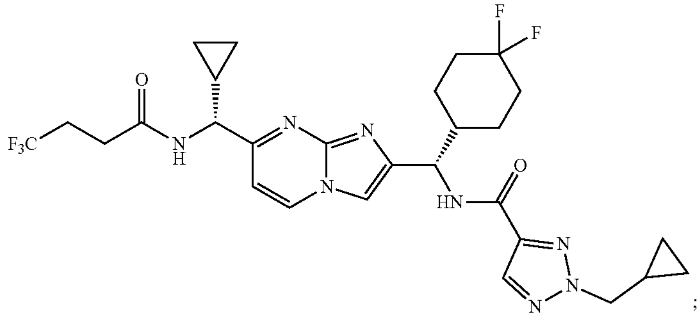 [SMILES: O=C(CCC(F)(F)F)N[C@@H](c1ccn2cc([C@@H](NC(=O)c3cnn(CC4CC4)n3)C3CCC(F)(F)CC3)nc2n1)C1CC1]
;
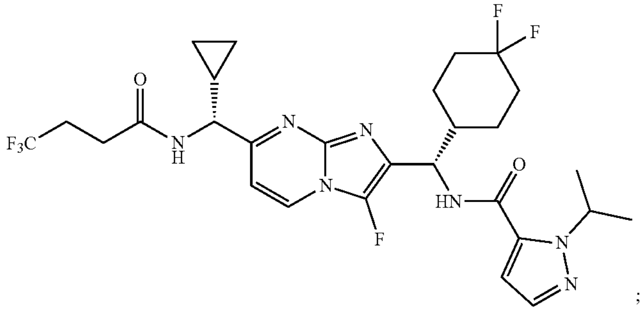 [SMILES: CC(C)n1nccc1C(=O)N[C@H](c1nc2nc([C@H](NC(=O)CCC(F)(F)F)C3CC3)ccn2c1F)C1CCC(F)(F)CC1]
;
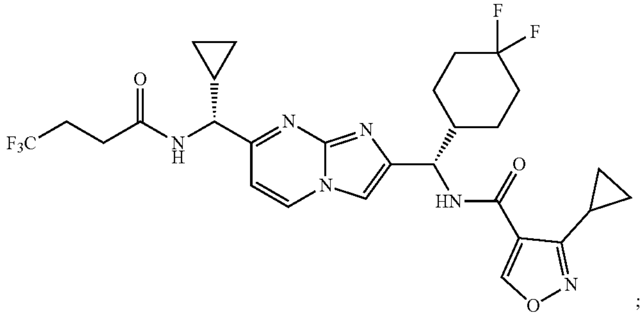 [SMILES: O=C(CCC(F)(F)F)N[C@@H](c1ccn2cc([C@@H](NC(=O)c3conc3C3CC3)C3CCC(F)(F)CC3)nc2n1)C1CC1]
;

TABLE 1AA-continued
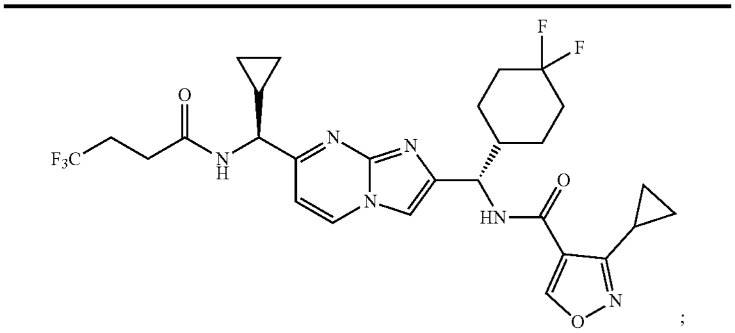
;
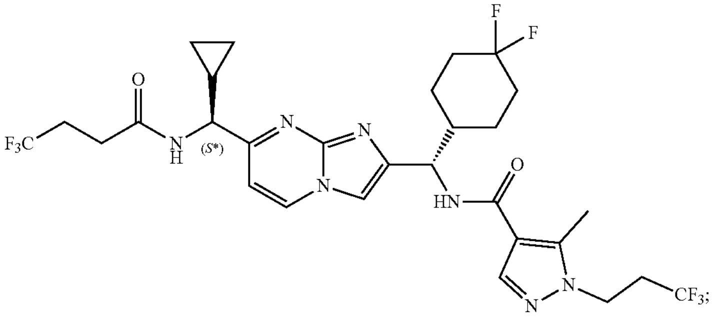 [SMILES: Cc1c(C(=O)N[C@H](c2cn3ccc([C@@H](NC(=O)CCC(F)(F)F)C4CC4)nc3n2)C2CCC(F)(F)CC2)cnn1CCC(F)(F)F]
;
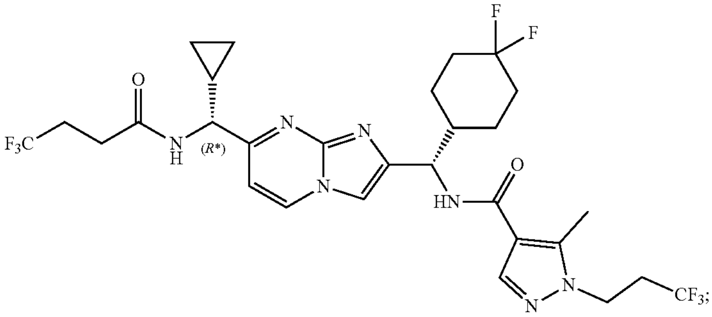
;
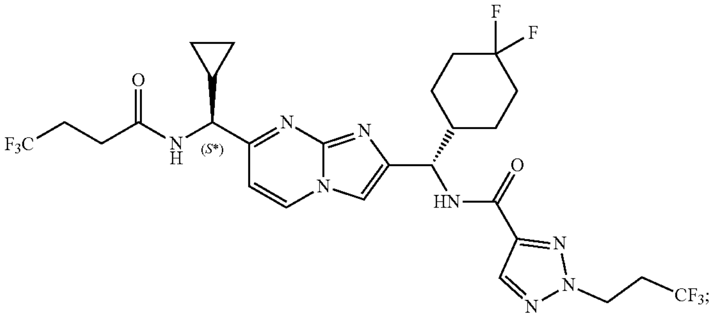 [SMILES: O=C(CCC(F)(F)F)N[C@H](c1ccn2cc([C@@H](NC(=O)c3cnn(CCC(F)(F)F)n3)C3CCC(F)(F)CC3)nc2n1)C1CC1]
;
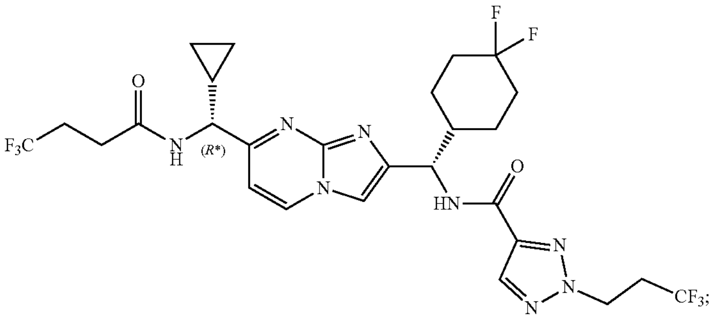
;

TABLE 1AA-continued
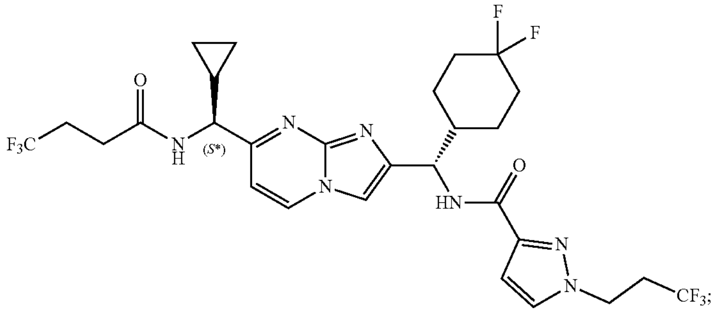 [SMILES: O=C(CCC(F)(F)F)N[C@H](c1ccn2cc([C@@H](NC(=O)c3ccn(CCC(F)(F)F)n3)C3CCC(F)(F)CC3)nc2n1)C1CC1]
;
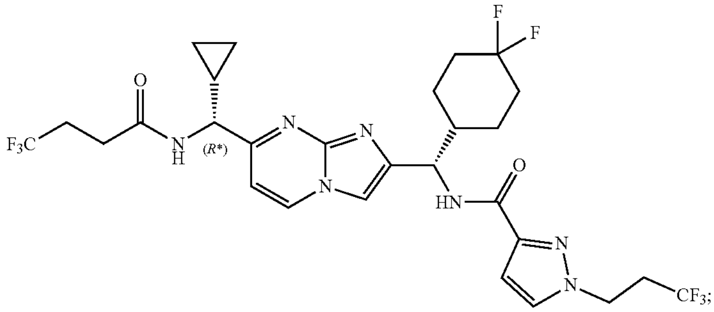 [SMILES: O=C(CCC(F)(F)F)N[C@@H](c1ccn2cc([C@@H](NC(=O)c3ccn(CCC(F)(F)F)n3)C3CCC(F)(F)CC3)nc2n1)C1CC1]
;
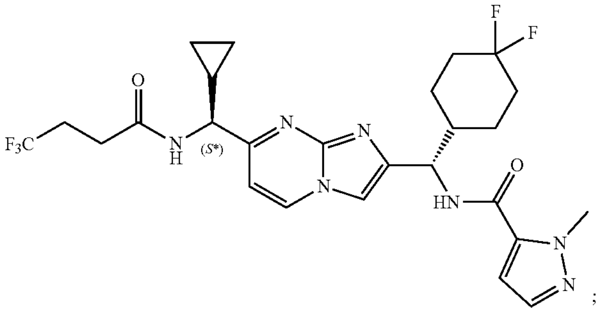 [SMILES: Cn1nccc1C(=O)N[C@H](c1cn2ccc([C@@H](NC(=O)CCC(F)(F)F)C3CC3)nc2n1)C1CCC(F)(F)CC1]
;
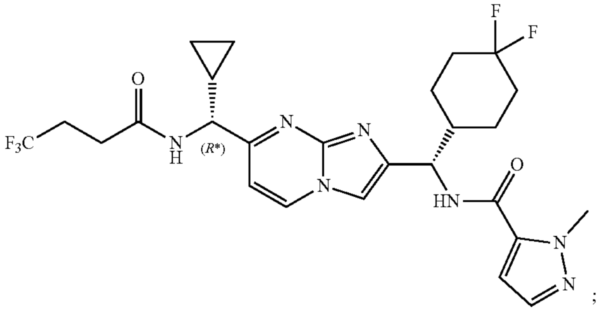 [SMILES: Cn1nccc1C(=O)N[C@H](c1cn2ccc([C@H](NC(=O)CCC(F)(F)F)C3CC3)nc2n1)C1CCC(F)(F)CC1]
;
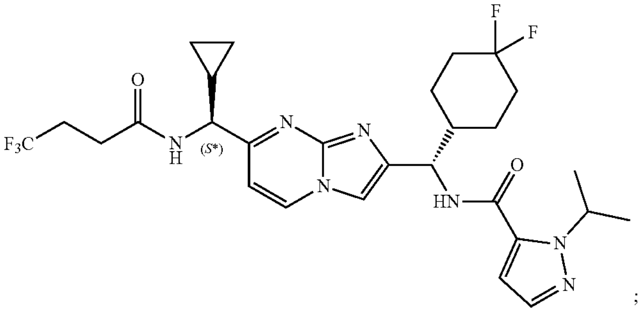 [SMILES: CC(C)n1nccc1C(=O)N[C@H](c1cn2ccc([C@@H](NC(=O)CCC(F)(F)F)C3CC3)nc2n1)C1CCC(F)(F)CC1]
;

TABLE 1AA-continued
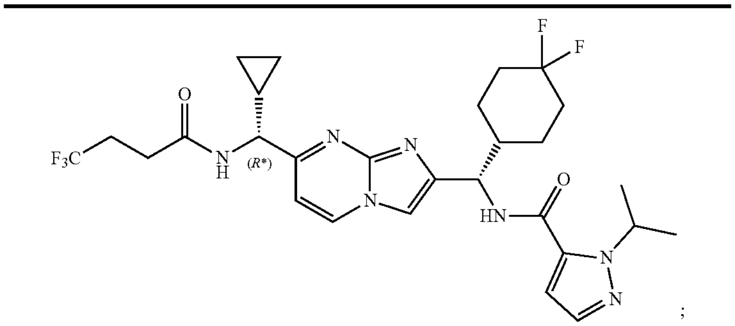
;
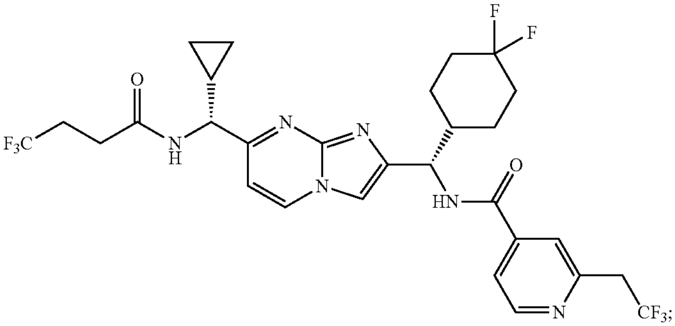 [SMILES: O=C(CCC(F)(F)F)N[C@@H](c1ccn2cc([C@@H](NC(=O)c3ccnc(CC(F)(F)F)c3)C3CCC(F)(F)CC3)nc2n1)C1CC1]
;
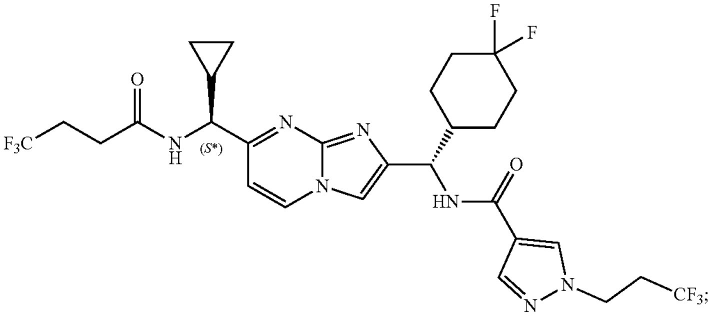 [SMILES: O=C(CCC(F)(F)F)N[C@H](c1ccn2cc([C@@H](NC(=O)c3cnn(CCC(F)(F)F)c3)C3CCC(F)(F)CC3)nc2n1)C1CC1]
;
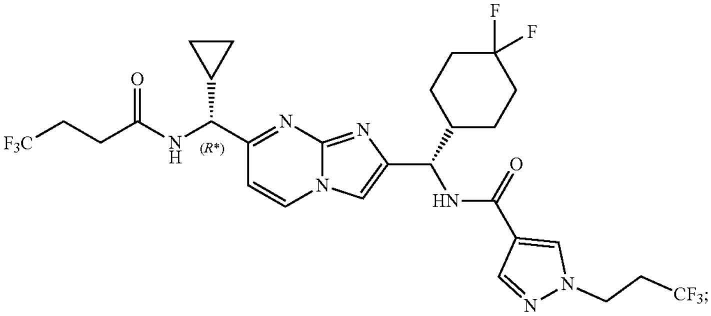 [SMILES: O=C(CCC(F)(F)F)N[C@@H](c1ccn2cc([C@@H](NC(=O)c3cnn(CCC(F)(F)F)c3)C3CCC(F)(F)CC3)nc2n1)C1CC1]
;
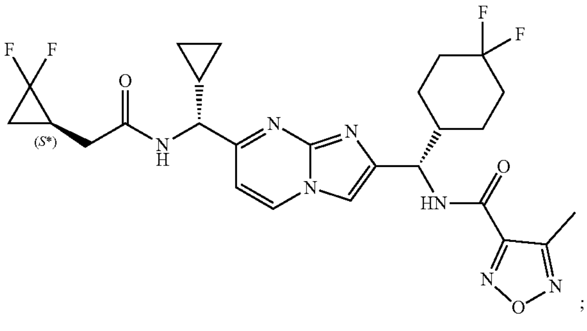 [SMILES: Cc1nonc1C(=O)N[C@H](c1cn2ccc([C@H](NC(=O)C[C@H]3CC3(F)F)C3CC3)nc2n1)C1CCC(F)(F)CC1]
;

TABLE 1AA-continued
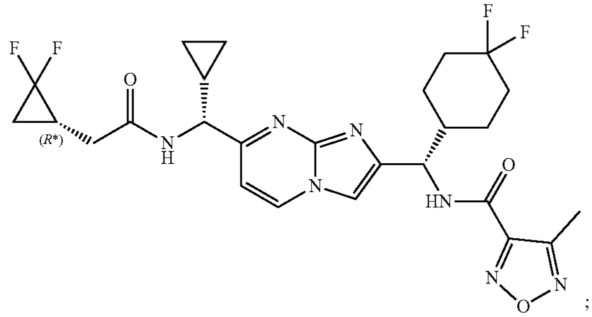 [SMILES: Cc1nonc1C(=O)N[C@H](c1cn2ccc([C@H](NC(=O)C[C@@H]3CC3(F)F)C3CC3)nc2n1)C1CCC(F)(F)CC1]
;
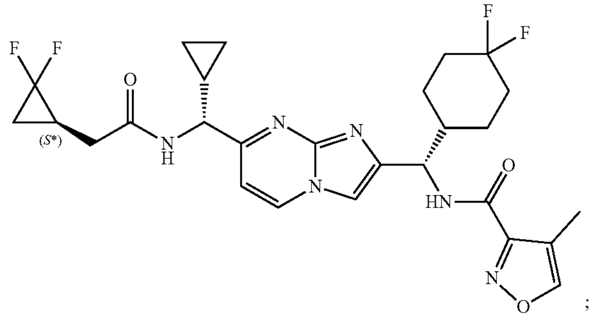
;
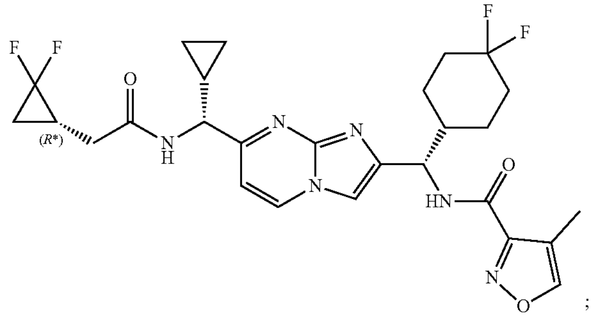 [SMILES: Cc1conc1C(=O)N[C@H](c1cn2ccc([C@H](NC(=O)C[C@@H]3CC3(F)F)C3CC3)nc2n1)C1CCC(F)(F)CC1]
;
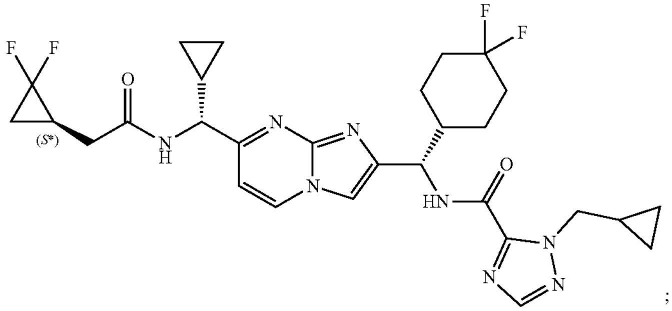 [SMILES: O=C(C[C@H]1CC1(F)F)N[C@@H](c1ccn2cc([C@@H](NC(=O)c3ncnn3CC3CC3)C3CCC(F)(F)CC3)nc2n1)C1CC1]
;
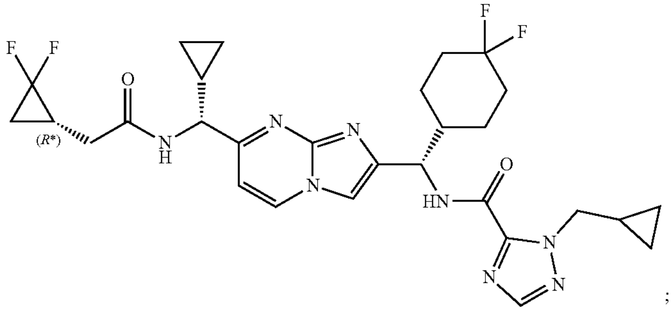 [SMILES: O=C(C[C@@H]1CC1(F)F)N[C@@H](c1ccn2cc([C@@H](NC(=O)c3ncnn3CC3CC3)C3CCC(F)(F)CC3)nc2n1)C1CC1]
;

TABLE 1AA-continued
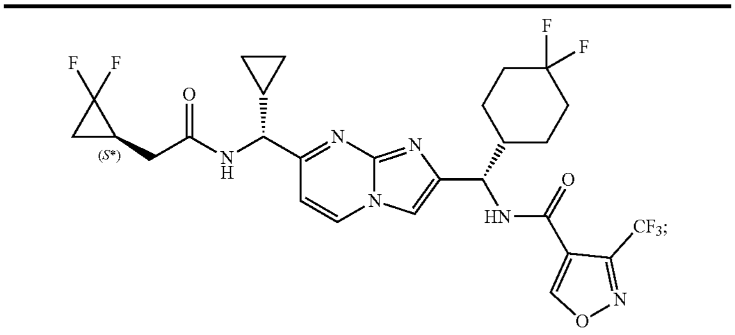
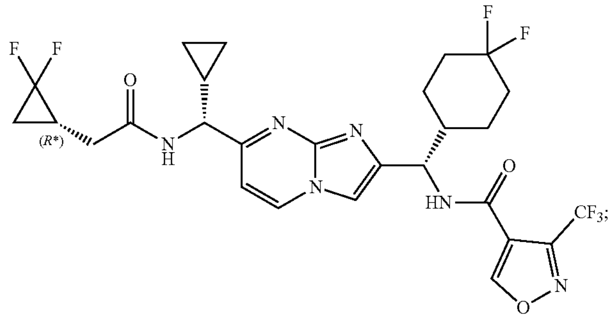 [SMILES: O=C(C[C@@H]1CC1(F)F)N[C@@H](c1ccn2cc([C@@H](NC(=O)c3conc3C(F)(F)F)C3CCC(F)(F)CC3)nc2n1)C1CC1]
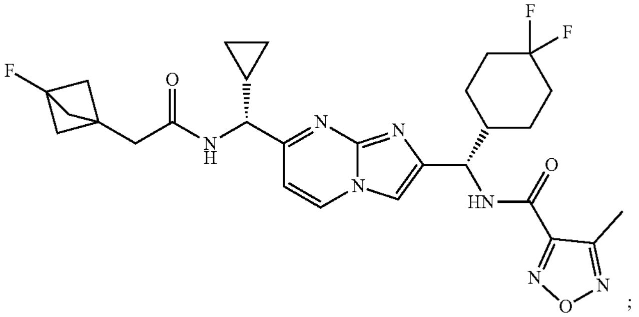 [SMILES: Cc1nonc1C(=O)N[C@H](c1cn2ccc([C@H](NC(=O)CC34CC(F)(C3)C4)C3CC3)nc2n1)C1CCC(F)(F)CC1]
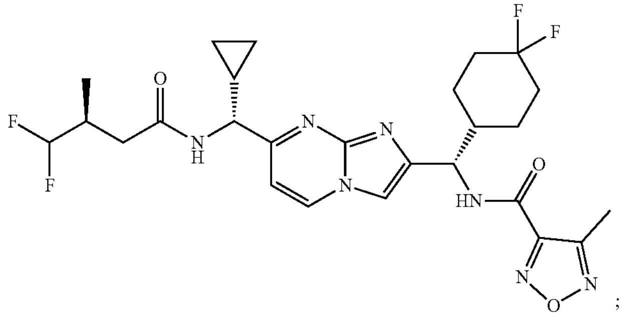 [SMILES: Cc1nonc1C(=O)N[C@H](c1cn2ccc([C@H](NC(=O)C[C@H](C)C(F)F)C3CC3)nc2n1)C1CCC(F)(F)CC1]
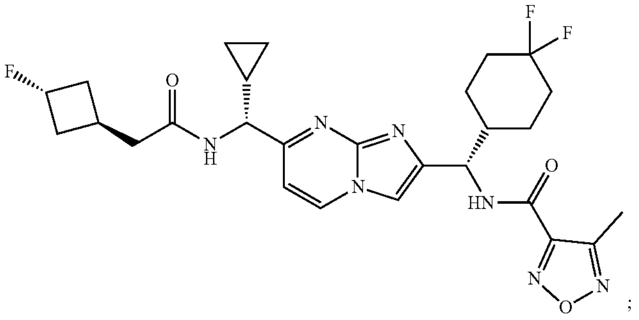 [SMILES: Cc1nonc1C(=O)N[C@H](c1cn2ccc([C@H](NC(=O)C[C@H]3C[C@H](F)C3)C3CC3)nc2n1)C1CCC(F)(F)CC1]

TABLE 1AA-continued
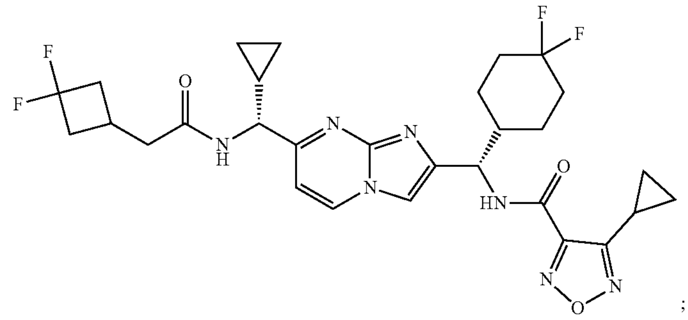 [SMILES: O=C(CC1CC(F)(F)C1)N[C@@H](c1ccn2cc([C@@H](NC(=O)c3nonc3C3CC3)C3CCC(F)(F)CC3)nc2n1)C1CC1]
;
and
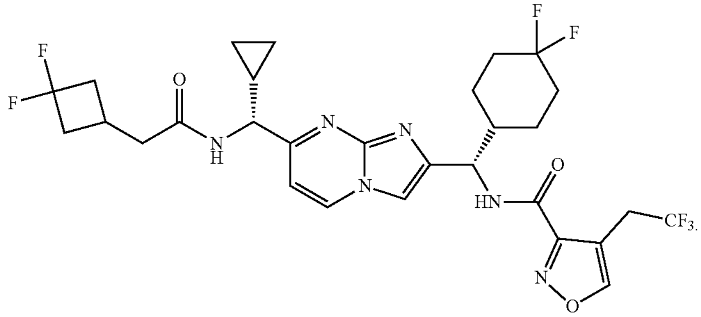 [SMILES: O=C(CC1CC(F)(F)C1)N[C@@H](c1ccn2cc([C@@H](NC(=O)c3nocc3CC(F)(F)F)C3CCC(F)(F)CC3)nc2n1)C1CC1]
In some embodiments, disclosed herein is a compound of Formula I, or a pharmaceutically acceptable salt thereof wherein the compound is selected from the compounds below in Table 1B.
TABLE IB
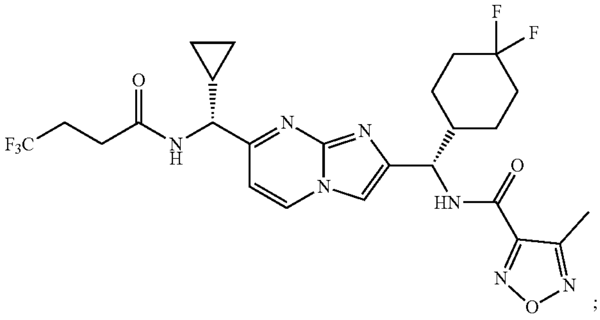 [SMILES: Cc1nonc1C(=O)N[C@H](c1cn2ccc([C@H](NC(=O)CCC(F)(F)F)C3CC3)nc2n1)C1CCC(F)(F)CC1]
;
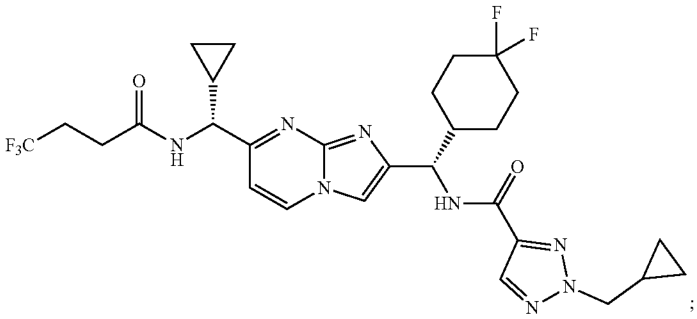 [SMILES: O=C(CCC(F)(F)F)N[C@@H](c1ccn2cc([C@@H](NC(=O)c3cnn(CC4CC4)n3)C3CCC(F)(F)CC3)nc2n1)C1CC1]
;

TABLE IB-continued

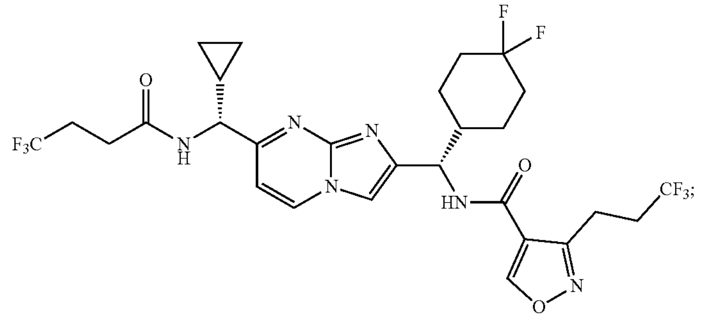 [SMILES: O=C(CCC(F)(F)F)N[C@@H](c1ccn2cc([C@@H](NC(=O)c3conc3CCC(F)(F)F)C3CCC(F)(F)CC3)nc2n1)C1CC1]

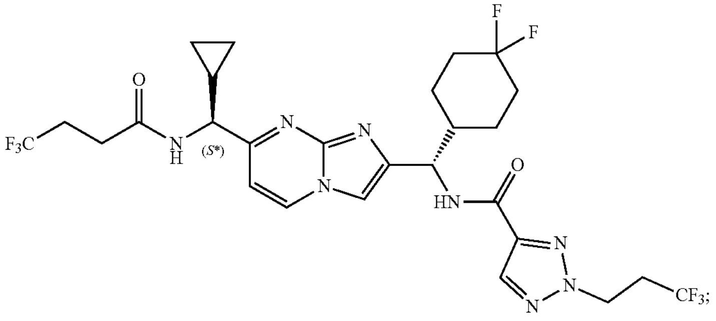 [SMILES: O=C(CCC(F)(F)F)N[C@H](c1ccn2cc([C@@H](NC(=O)c3cnn(CCC(F)(F)F)n3)C3CCC(F)(F)CC3)nc2n1)C1CC1]

and

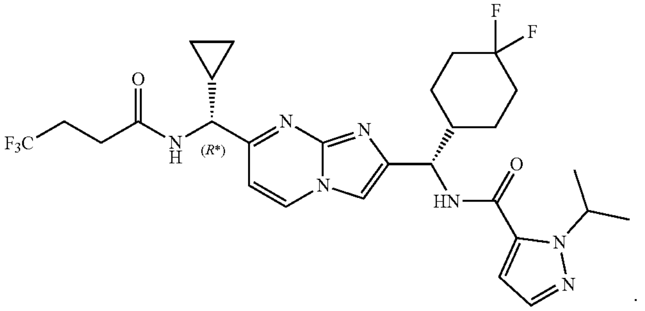 [SMILES: CC(C)n1nccc1C(=O)N[C@H](c1cn2ccc([C@H](NC(=O)CCC(F)(F)F)C3CC3)nc2n1)C1CCC(F)(F)CC1]

In some embodiments, disclosed herein is a compound of Formula I, wherein the compound is

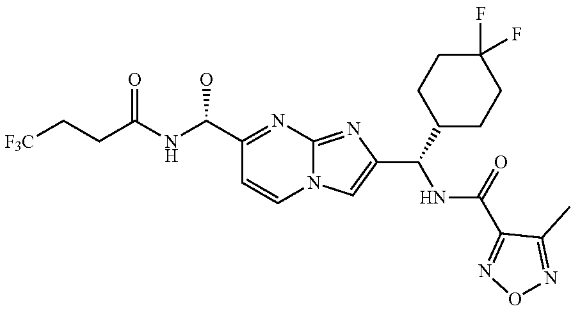

or a pharmaceutically acceptable salt thereof.

In some embodiments, disclosed herein is a compound of Formula I, wherein the compound is

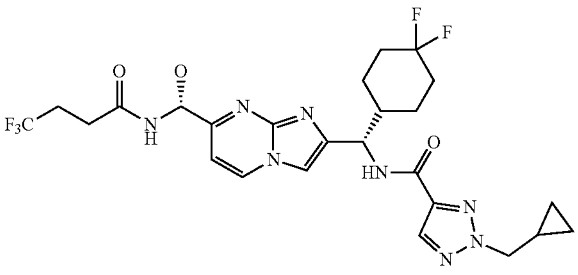

or a pharmaceutically acceptable salt thereof.

In some embodiments, disclosed herein is a compound of Formula I, wherein the compound is

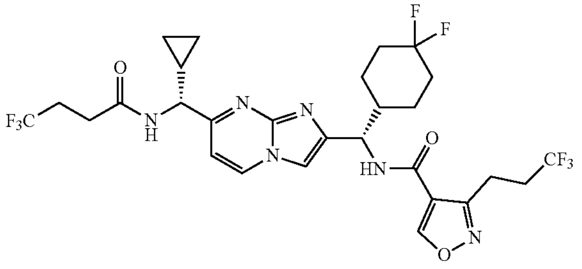 [SMILES: O=C(CCC(F)(F)F)N[C@@H](c1ccn2cc([C@@H](NC(=O)c3conc3CCC(F)(F)F)C3CCC(F)(F)CC3)nc2n1)C1CC1]

or a pharmaceutically acceptable salt thereof.

In some embodiments, disclosed herein is a compound of Formula I, wherein the compound is

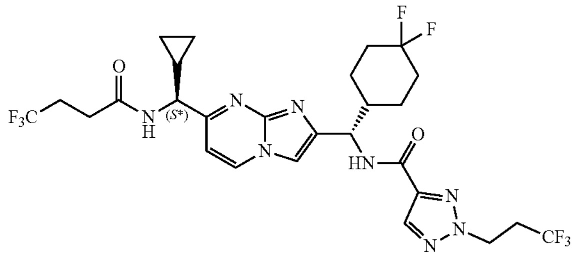 [SMILES: O=C(CCC(F)(F)F)N[C@H](c1ccn2cc([C@@H](NC(=O)c3cnn(CCC(F)(F)F)n3)C3CCC(F)(F)CC3)nc2n1)C1CC1]

or a pharmaceutically acceptable salt thereof.

In some embodiments, disclosed herein is a compound of Formula I, wherein the compound is

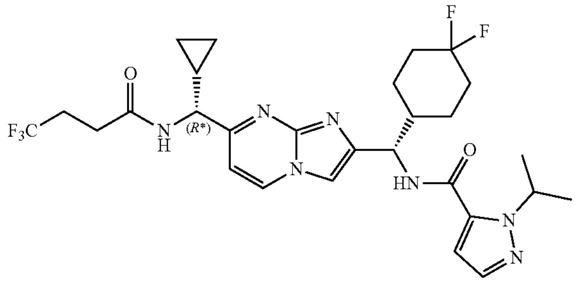 [SMILES: CC(C)n1nccc1C(=O)N[C@H](c1cn2ccc([C@H](NC(=O)CCC(F)(F)F)C3CC3)nc2n1)C1CCC(F)(F)CC1]

or a pharmaceutically acceptable salt thereof.

In some embodiments, disclosed herein is a pharmaceutical composition, comprising a compound of Formula I, or a pharmaceutically acceptable salt thereof, and a pharmaceutically acceptable carrier. In some embodiments, the pharmaceutical composition is formulated for oral administration (e.g., a tablet or capsule).

In some embodiments, disclosed herein is a pharmaceutical composition made by mixing a compound of Formula I, or a pharmaceutically acceptable salt thereof, and a pharmaceutically acceptable carrier.

In some embodiments, disclosed herein is a process for making a pharmaceutical composition comprising mixing a compound of Formula I, or a pharmaceutically acceptable salt thereof, and a pharmaceutically acceptable carrier.

III. Therapeutic Use

The present application is also directed to a method for treating and/or ameliorating a IL-17 mediated inflammatory syndrome, disorder or disease comprising administering to a subject in need thereof an effective amount of a compound of Formula I, or pharmaceutically acceptable salt thereof, composition thereof, or medicament thereof.

In some embodiments, disclosed herein is a method for treating or ameliorating an IL-17A mediated inflammatory syndrome, disorder, or disease comprising administering to a subject in need thereof a therapeutically effective amount of a compound of Formula I, or a pharmaceutically acceptable salt thereof.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is psoriasis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is psoriatic arthritis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is rheumatoid arthritis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is ankylosing spondylitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is hidradenitis suppurativa.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is bullous pemphigold.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is atopic dermatitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is vitiligo.

In some embodiments, disclosed herein is a method for treating or ameliorating and/an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is multiple sclerosis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is systemic lupus erythematosus.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is asthma.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is uveitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is chronic obstructive pulmonary disorder.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is multiple myeloma.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is systemic lupus erythematosus.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus, wherein the compound of Formula I or the pharmaceutically acceptable salt thereof is administered orally (e.g., as a tablet or capsule).

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus, wherein the therapeutically effective amount is a dose of about 10 mg to 300 mg QD. In some embodiments, the therapeutically effective amount is a dose of about 20 mg to 200 mg QD. In some embodiments, the therapeutically effective amount is a dose of about 50 mg to 100 mg QD.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus, wherein the therapeutically effective amount is a dose of about 20 mg to 200 mg BID. In some embodiments, the therapeutically effective amount is a dose of about 50 mg to 100 mg BID. In some embodiments, the therapeutically effective amount is a dose of about 5 mg to 150 mg BID.

In some embodiments, disclosed herein is the use of a therapeutically effective amount of compound of Formula I, or a pharmaceutically acceptable salt thereof, for treating and/or ameliorating an IL-17A mediated inflammatory syndrome, disorder, or disease selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus.

In some embodiments, disclosed herein is the use of a compound of Formula I, or pharmaceutically acceptable salt thereof, in the manufacture of a medicament for treating and/or ameliorating an IL-17A mediated inflammatory syndrome, disorder, or disease selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus.

In some embodiments, disclosed herein is a method for treating and/or ameliorating an IL-17 mediated inflammatory syndrome, disorder or disease comprising administering to a subject in need thereof a therapeutically effective amount of a compound of Formula I, or pharmaceutically acceptable salt thereof, a composition thereof, or a medicament thereof.

In some embodiments, disclosed herein is a method of treating and/or ameliorating an IL-17 mediated inflammatory syndrome, disorder or disease, wherein the syndrome, disorder or disease is selected from the group consisting of: psoriasis, psoriatic arthritis, rheumatoid arthritis, ankylosing spondylitis, hidradenitis suppurativa, atopic dermatitis, vitiligo, multiple sclerosis, asthma, allergic asthma, steroid resistant asthma, neutrophilic asthma, chronic obstructive pulmonary disease, uveitis, multiple myeloma, and systemic lupus erythematosus, comprising administering to a subject in need thereof a therapeutically effective amount of a compound of Formula I, or pharmaceutically acceptable salt thereof, a composition thereof, or a medicament thereof.

In some embodiments, disclosed herein is a method of treating or ameliorating an IL-17 mediated inflammatory syndrome, disorder or disease, wherein the syndrome, disorder or disease is selected from the group consisting of: psoriasis, psoriatic arthritis, and ankylosing spondylitis, comprising administering to a subject in need thereof a therapeutically effective amount of a compound of Formula I, or pharmaceutically acceptable salt thereof, a composition thereof, or a medicament thereof.

In some embodiments, disclosed herein are methods of modulating IL-17 activity in a mammal by administration of a therapeutically effective amount of at least one compound of Formula I, or pharmaceutically acceptable salt thereof.

Also disclosed herein is a method of inhibiting production of interleukin-17, comprising administering to a subject in need thereof a therapeutically effective amount of a compound of Formula I, or pharmaceutically acceptable salt thereof.

IV. Combination Therapy

A compound of Formula I, or pharmaceutically acceptable salt thereof, a composition thereof, or a medicament thereof may also be used in combination with one or more additional therapeutic agents.

In some embodiments, the one or more additional therapeutic agents is selected from the group consisting of anti-inflammatory agents, immunomodulatory agents, and immunosuppressive agents.

In some embodiments, the one or more additional therapeutic agents is selected from the group consisting of:

(a) anti-TNFalpha agents such as infliximab (Remicade®), adalimumab (Humira®), certolizumab pegol (Cimzia®), golimumab (Simponi®), etanercept (Enbrel®), thalidomide (Immunoprin®), lenalidomide (Revlimid®), and pomalidomide (Pomalyst®/Imnovid®);

(b) anti-p40 antibody agents such as ustekinumab (Stelara®); and (c) anti-p19 antibody agents such as guselkumab (Tremfya®), tildrakizumab (Ilumya™/Ilumetri), risankizumab (Skyrizi™), and mirikizumab.

In some embodiments, disclosed herein is a method of treating and/or ameliorating an IL-17 mediated inflammatory syndrome, disorder or disease, in a subject in need thereof comprising administering to the subject a therapeutically effective amount of the compound of Formula I, or pharmaceutically acceptable salt thereof, composition thereof, or medicament thereof in a combination therapy with one or more additional therapeutic agents, such as anti-inflammatory agents, immunomodulatory agents, or immunosuppressive agents, wherein said syndrome, disorder or disease is selected from the group consisting of psoriasis, psoriatic arthritis, rheumatoid arthritis, ankylosing spondylitis, hidradenitis suppurativa, atopic dermatitis, vitiligo, multiple sclerosis, asthma, allergic asthma, steroid resistant asthma, neutrophilic asthma, chronic obstructive pulmonary disease, uveitis, multiple myeloma, and systemic lupus erythematosus.

In some embodiments, disclosed herein is a method of treating and/or ameliorating an IL-17 mediated inflammatory syndrome, disorder or disease, in a subject in need thereof comprising administering to the subject a therapeutically effective amount of the compound of Formula I, or pharmaceutically acceptable salt thereof, composition thereof, or medicament thereof in a combination therapy with one or more additional therapeutic agents, such as anti-inflammatory agents, or immunosuppressive agents, wherein said syndrome, disorder or disease is psoriasis, psoriatic arthritis, ankylosing spondylitis. In some embodiments, the IL-17 mediated inflammatory syndrome, disorder or disease is psoriasis. In some embodiments, the IL-17 mediated inflammatory syndrome, disorder or disease is psoriatic arthritis. In some embodiments, the IL-17 mediated inflammatory syndrome, disorder or disease is ankylosing spondylitis.

V. Dosage Regimen

When employed as IL-17A modulators, the compounds disclosed herein may be administered in an effective amount within the dosage range of about 0.5 mg to about 1 g, preferably between about 0.5 mg to about 500 mg, in single or divided daily doses. In some embodiments, the dosage amount is about 5 mg to 400 mg. In some embodiments, the dosage amount is about 10 mg to 300 mg. In some embodiments, the dosage amount is about 0.5, 1, 5, 10, 15, 20, 25, 30, 35, 40, 45, 50, 55, 60, 65, 70, 75, 80, 85, 90, 95, or 100 mg of a compound of Formula I, or pharmaceutically acceptable salt thereof. In some embodiments, the dosage amount is about 100, 105, 110, 115, 120, 125, 130, 135, 140, 145, 150, 155, 160, 165, 170, 175, 180, 185, 190, 195, or 200 mg of a compound of Formula I, or pharmaceutically acceptable salt thereof. In some embodiments, the dosage amount is about 200, 205, 210, 215, 220, 225, 230, 235, 240, 245, 250, 255, 260, 265, 270, 275, 280, 285, 290, 295, or 300 mg of a compound of Formula I, or pharmaceutically acceptable salt thereof. In some embodiments, the dosage amount is about 300, 315, 320, 325, 330, 335, 340, 345, 350, 355, 360, 365, 370, 375, 380, 385, 390, 395, or 400 mg of a compound of Formula I, or pharmaceutically acceptable salt thereof. In some embodiments, the dosage amount is about 400, 405, 410, 415, 420, 425, 430, 435, 440, 445, 450, 455, 460, 465, 470, 475, 480, 485, 490, 495, or 500 mg of a compound of Formula I, or pharmaceutically acceptable salt thereof.

In some embodiments, a compound of Formula I, or pharmaceutically acceptable salt thereof, may be administered in an effective amount within the dosage range of about 10 mg to 300 mg QD. In some embodiments, a compound of Formula I, or pharmaceutically acceptable salt thereof, may be administered in an effective amount within the dosage range of about 20 mg to 200 mg QD. In some embodiments, a compound of Formula I, or pharmaceutically acceptable salt thereof, may be administered in an effective amount within the dosage range of about 50 mg to 100 mg QD.

In some embodiments, a compound of Formula I, or pharmaceutically acceptable salt thereof, may be administered in an effective amount within the dosage range of about 20 mg to 200 mg QD. In some embodiments, a compound of Formula I, or pharmaceutically acceptable salt thereof, may be administered in an effective amount within the dosage range of about 50 mg to 100 mg QD.

The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

VI. Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

VII. Pharmaceutical Compositions

The compounds of Formula I, or pharmaceutically acceptable salt thereof, may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I, or pharmaceutically acceptable salt thereof, include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, topical, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

Also disclosed herein is a method of making a pharmaceutical composition comprising mixing a pharmaceutically acceptable carrier with any of the compounds of Formula I, or pharmaceutically acceptable salt thereof. Additionally, the present application includes pharmaceutical compositions made by mixing a pharmaceutically acceptable carrier with any of the compounds of the present invention.

EXAMPLES

Abbreviations

Herein and throughout the application, the following abbreviations may be used.

Ac acetyl
ACN acetonitrile
Boc tert-butyloxycarbonyl
br broad
Bu butyl
Cbz benzyloxycarbonyl
CbzCl benzyl chloroformate
cod cyclooctadiene
δ NMR chemical shift in parts per million downfield from a standard
d doublet
d day(s)
DCM dichloromethane
DCE dichloroethane
DEA diethylamine
DIPEA N,N-diisopropylethylamine (Hunig's base)
DMF N,N-dimethylformamide
DMSO dimethyl sulfoxide
EDCI 1-ethyl-3-(3-dimethylaminopropyl) carbodiimide hydrochloride
ESI electrospray ionization Et ethyl
EtOAc ethyl acetate
FCC flash column chromatography
Fmoc fluorenylmethyloxycarbonyl
g gram(s)
h hour(s)
HATU N-[(dimethylamino)-1H-1,2,3-triazolo-[4,5-b]pyridin-1-ylmethylene]-N-methylmethanaminium hexafluorophosphate N-oxide
HOBt 1-hydroxybenzotriazole
HPLC high pressure liquid chromatography
Hz Hertz
i iso
IPA isopropanol
J coupling constant (NMR spectroscopy)
L liter(s)
LC liquid chromatography
m milli or multiplet
m/z mass-to-charge ratio
$M^+$ parent molecular ion
M molar (moles/liter) or mega
Me methyl
mCPBA 3-chloroperbenzoic acid
MeCN acetonitrile
min minute(s)
μ micro
MS mass spectrometry or molecular sieves
MTBE tert-butyl methyl ether
NCS N-chlorosuccinimide
n normal
n nano
N normal (equivalent concentration)
NMR nuclear magnetic resonance
Pd/C palladium on carbon
PPTS pyridinium p-toluenesulfonate
Pr propyl
q quartet
rt room temperature
s singlet
Selectfluor™ 1-Chloromethyl-4-fluoro-1,4-diazoniabicyclo[2.2.2]octane bis(tetrafluoroborate)
SFC supercritical fluid chromatography
t tert
t triplet
TCFH chloro-N,N,N',N'-tetramethylformamidinium hexafluorophosphate
Tf trifluoromethanesulfonate (triflate)
TFA trifluoroacetic acid
THF tetrahydrofuran
TMS trimethylsilyl
wt % weight percent In some embodiments, provided herein are processes and intermediates disclosed herein that are useful for preparing a compound of Formula I or pharmaceutically acceptable salts thereof.

General Schemes:

Compounds of Formula I are synthesized in accordance with synthetic methods described herein, which are only meant to represent synthetic examples and are in no way meant to be limitations.

Unless otherwise specified, the substituent groups in Schemes 1-11 are as defined above in reference to Formula I. If no temperature or temperature range is stated, it is to be understood that the reaction is run at room temperature.

SCHEME 1

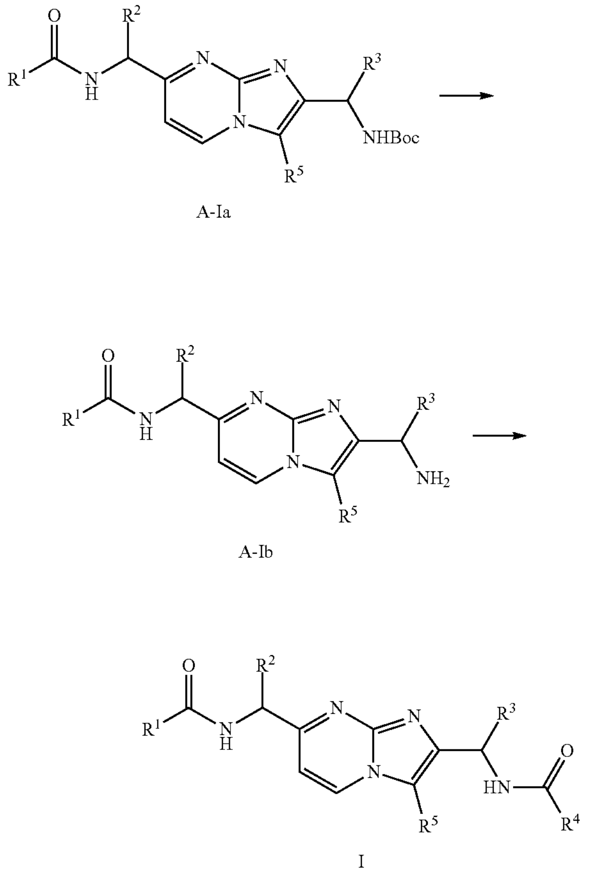

Compounds of Formula I can be prepared according to Scheme 1. Removal of the Boc group of A-Ia under acidic conditions, such as aqueous hydrochloric acid or TFA (neat) or TFA in DCM, yields the corresponding amine A-Ib. The above conditions to remove a Boc group are referred to as "Boc deprotection conditions". Amine A-Ib is subsequently coupled to a carboxylic acid ($R^4$—$CO_2H$ (A-Ic)) through amide bond forming techniques to yield compounds of Formula I. Examples of amide bond forming techniques include (i) reaction of amine A-Ib with carboxylic acid A-Ic where the carboxylic acid is activated with an appropriate activating reagent, for example a carbodiimide, such as DCC or EDCI optionally in the presence of HOBt and/or a catalyst such as DMAP; a halotrisaminophosphonium salt such as BOP, PyBOP, or PyBroP; a suitable pyridinium salt such as 2-chloro-1-methyl pyridinium chloride; or another suitable coupling agent such as HBTU, HATU, or 2,4,6-tripropyl-1,3,5,2,4,6-trioxatriphosphorinane-2,4,6-trioxide (T3P®). These coupling reactions are conducted in a suitable solvent such as DCM, THF, DMF and mixtures thereof, optionally in the presence of a tertiary amine such as N-methylmorpholine, diisopropylethyl amine, or triethylamine yielding compounds of Formula I; (ii) alternatively, reaction of amine A-Ib with a carboxylic acid chloride ($R^4$—COCl (A-Id)) or acid anhydride (($R^4$—C(O))$_2$O (A-Ie)) in a solvent such as THF or DCM in the presence of a base such as TEA, DIPEA, pyridine or NMO yields compounds of Formula I.

SCHEME 2

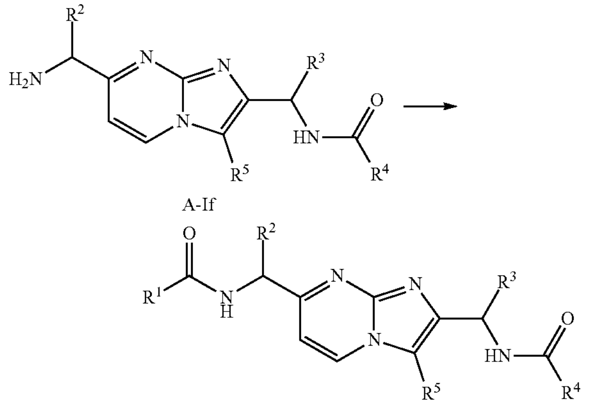

A-If

I

Alternatively, compounds of Formula I can be prepared according to Scheme 2. Amine A-If is subsequently coupled to a carboxylic acid ($R^1$—$CO_2H$ (A-Ig)) through amide bond forming techniques to yield compounds of Formula I. Examples of amide bond forming techniques include (i) reaction of amine A-If with carboxylic acid A-Ig where the carboxylic acid is activated with an appropriate activating reagent, for example a carbodiimide, such as DCC or EDCI optionally in the presence of HOBt and/or a catalyst such as DMAP; a halotrisaminophosphonium salt such as BOP, PyBOP, or PyBroP; a suitable pyridinium salt such as 2-chloro-1-methyl pyridinium chloride; or another suitable coupling agent such as HBTU, HATU, or 2,4,6-tripropyl-1,3,5,2,4,6-trioxatriphosphorinane-2,4,6-trioxide (T3P®). These coupling reactions are conducted in a suitable solvent such as DCM, THF, DMF and mixtures thereof, optionally in the presence of a tertiary amine such as N-methylmorpholine, diisopropylethyl amine, or triethylamine yielding compounds of Formula I; (ii) alternatively, reaction of amine A-If with a carboxylic acid chloride ($R^1$—COCl (A-Ih)) or acid anhydride (($R^1$—C(O))$^2$O (A-Ii)) in a solvent such as THF or DCM in the presence of a base such as TEA, DIPEA, pyridine or NMO yields compounds of Formula I.

SCHEME 3

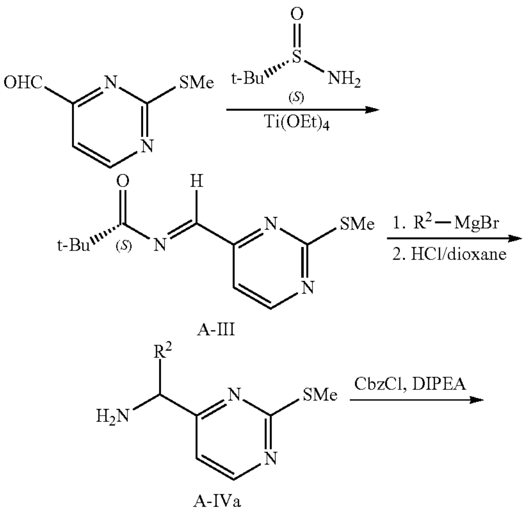

A-III

A-IVa

-continued

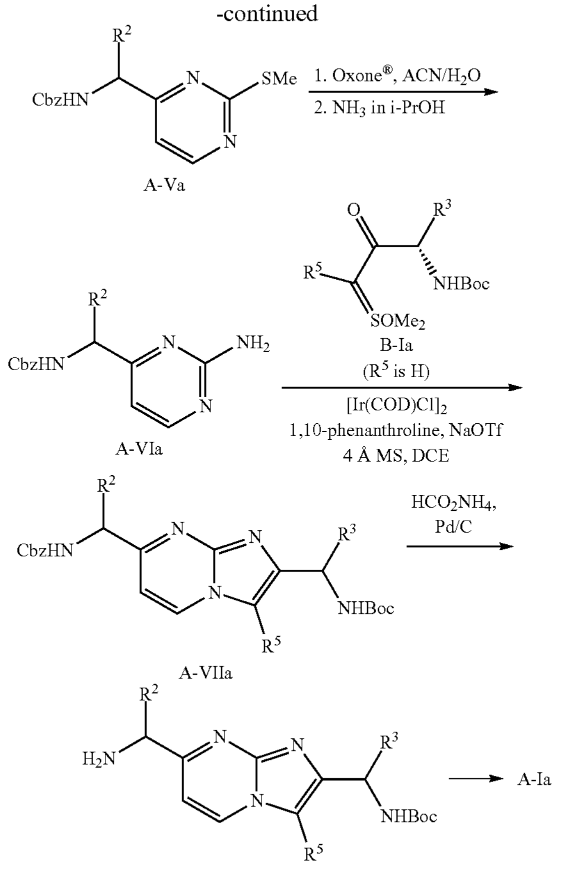

A-Va

A-VIa

A-VIIa

A-VIIIa

Compounds of the formula A-Ia can be prepared according to the sequence shown in Scheme 3. Condensation of 2-(methylthio)pyrimidine-4-carbaldehyde with (S)-(−)-2-methyl-2-propanesulfinamide yields the corresponding sulfinimide compound A-III. Addition of nucleophilic carbon-containing reagents, such as alkyl magnesium halides ($R^2$MgBr), to sulfinimide compound A-III yields the corresponding sulfinamide (structure not shown), and hydrolysis of the sulfinamide under acidic conditions, such as aqueous hydrochloric acid in dioxane, yields compound A-IVa. Subsequent protection of the amine within A-IVa using reagents such a CbzCl in the presence of a base, such as DIPEA, in a solvent, such as DCM, yields carbamate compound A-Va. The above conditions to protect an amine as a CBz group are referred to as “Cbz protection conditions” Oxidation of the methyl sulfide within compound A-Va using oxidizing reagents such as Oxone® in a solvent such as aqueous acetonitrile or mCPBA, yields the corresponding sulfone (structure not shown) that upon treatment with ammonia in a solvent, such as isopropanol, yields compound A-VIa. Cyclocondensation of compound A-VIa with ylide compound B-Ia, where $R^5$ is H, in the presence of a catalyst, such as di-μ-chlorobis[(1,2,5,6-η)-1,5-cyclooctadiene]diiridium, yields compound A-VIIa. Deprotection of the Cbz group using a reagent such as ammonium formate in the presence of palladium catalysis in a solvent such as aqueous methanol yields the corresponding amine that is separated into diastereomers using SFC to afford compounds A-VIIIa. The above conditions to remove a Cbz group are referred to as “Cbz deprotection conditions”. Subsequent amide bond formation using conditions described in Scheme 2 yields compounds of the general structure A-Ia.

SCHEME 4

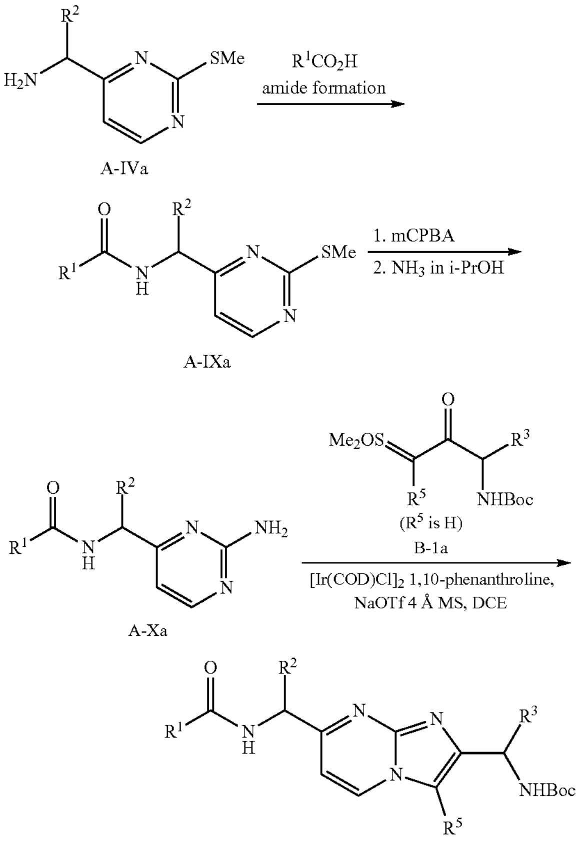

A-IVa

A-IXa

A-Xa

A-Ia
($R^5$ is H)

Alternatively, compound A-Ia can be prepared as shown in Scheme 4. Amine compound A-IVa is coupled with a carboxylic acid $R^1CO_2H$ (compound A-Ig) using amide bond coupling conditions as described in Scheme 2 yielding compound A-IXa. Oxidation of the methyl sulfide compounds A-IXa using oxidizing reagents such as mCPBA, yields the corresponding sulfone (structure not shown) that upon treatment with ammonia in a solvent, such as isopropanol, yields compounds A-Xa. Cyclocondensation of compounds A-Xa with an ylide compound B-1a, where $R^5$ is H, in the presence of a catalyst, such as di-μ-chlorobis[(1,2,5,6-η)-1,5-cyclooctadiene]diiridium, yields compounds A-Ia.

SCHEME 5

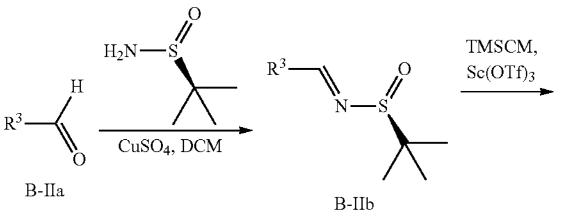

B-IIa

B-IIb

-continued

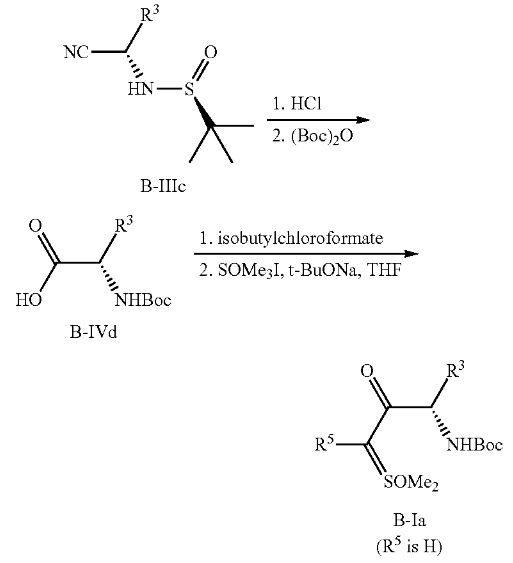

B-IIIc

B-IVd

B-Ia
($R^5$ is H)

Compound B-Ia can be prepared as shown in Scheme 5. Treatment of aldehydes B-IIa with (S)-(−)-2-methyl-2-propanesulfinamide in the presence of a dehydrating reagent, such as copper II sulfate, in a solvent such as DCM yields sulfinimine B-IIb. Cyanation of compounds B-IIb using TMSCN in the presence of a catalyst, such as $Sc(OTf)_3$, in a solvent such as DCM yields nitrile compounds B-IIIc. Concurrent hydrolysis of the nitrile and the sulfinamide groups of compound B-IIIc under acidic conditions such as aqueous hydrochloric acid yields the corresponding amino acids (structure not shown). The free $NH_2$ of the corresponding amino acid is protected as a t-butyl carbamate (Boc group) by reacting it with di-tert-butyl dicarbonate ($(Boc)_2O$) in a solvent such as DCM, THF or mixtures thereof yielding compounds B-IVd. Treatment of compounds B-IVd with isobutylchloroformate in the presence of a base such as $Et_3N$ in a solvent such as THF affords the corresponding mixed anhydride (structure not shown). This mixed anhydride is treated with (dimethyl(oxo)-$\lambda^6$-sulfanylidene)methane, which is made in situ by mixing trimethylsulfoxonium iodide with a base, such as sodium tert-butoxide, to yield ylide compounds B-Ia.

SCHEME 6

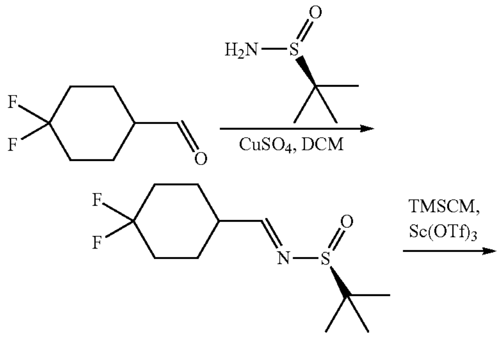

B-II

-continued

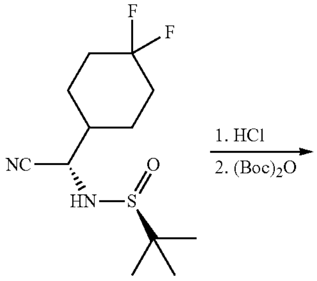

B-III

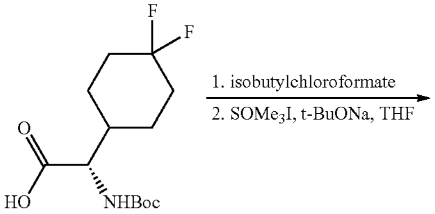

B-IV

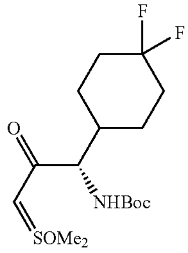

B-I

Ylide compound B-I can be prepared as shown in Scheme 6. Treatment of 4,4-difluorocyclohexanecarbaldehyde with (S)-(−)-2-methyl-2-propanesulfinamide in the presence of a dehydrating reagent, such as copper II sulfate, in a solvent such as DCM yields sulfinimine B-II. Cyanation of compound B-II using TMSCN in the presence of a catalyst such as, $Sc(OTf)_3$, in a solvent such as DCM yields nitrile compound B-III. Concurrent hydrolysis of the nitrile and the sulfinamide groups within compound B-III under acidic conditions such as aqueous hydrochloric acid yields the corresponding amino acid (structure not shown). The free $NH_2$ of the corresponding amino acid is protected as a t-butyl carbamate (Boc group) by reacting it with di-tert-butyl dicarbonate ($(Boc)_2O$) in a solvent such as DCM, THF or mixtures thereof yielding compound B-IV. Treatment of compound B-IV with isobutylchloroformate in the presence of a base such as $Et_3N$ in a solvent such as THF affords the corresponding mixed anhydride (structure not shown). This mixed anhydride is treated with (dimethyl(oxo)-$\lambda^6$-sulfanylidene)methane, which is made in situ by mixing trimethylsulfoxonium iodide with a base, such as sodium tert-butoxide, to yield ylide compound B-I.

SCHEME 7

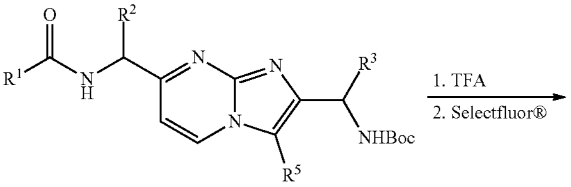

A-Ia
$R^5$ = H

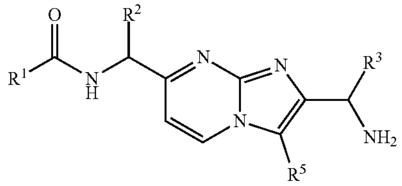

A-Ib
$R^5$ = F

Compounds of formula A-Ib where $R^5$ is F can be prepared from compounds of formula A-Ia where $R^5$ is H. Removal of the Boc protecting group within compound A-Ia using Boc deprotection conditions, followed by treatment with a fluorinating agent, such as Selectfluor®, in a solvent such as acetonitrile yields compound A-Ib.

SCHEME 8

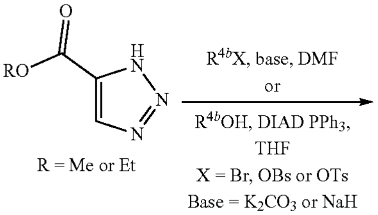

R = Me or Et

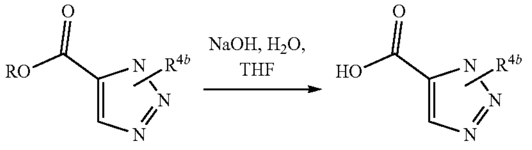

C-I
R = Me or Et
mixture of alkylation products at N1, N2 and N3

C-II

Substituted 1,2,3-triazole-5-carboxylic acid compounds C-II can be prepared as shown in Scheme 8. The 1H-1,2,3-triazole-5-carboxylate ester is alkylated by treatment with a base such as potassium carbonate and an alkylating agent, such as alkyl bromide ($R^{4b}Br$), in a solvent such as DMF to yield a mixture of N1, N2 or N3-1,2,3-triazole-5-carboxylate compounds C-I. These N1, N2 or N3-1,2,3-triazole-5-carboxylate compounds C-I are separated by FCC. Hydrolysis of the ester with aqueous base such as sodium hydroxide in a solvent such as THF yields carboxylic acids C-II.

SCHEME 9

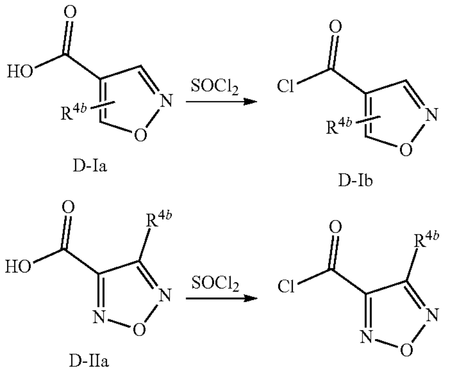

D-Ia D-Ib D-IIa D-IIb

Heteroaromatic carboxylic acid chlorides, D-Ib and D-IIb can be prepared as shown in Scheme 9. Isoxazole-4-carboxylic acid D-Ia is treated with excess thionyl chloride to yield acid chloride D-Ib. 4-Methyl-1,2,5-oxadiazole-3-carboxylic acid D-IIa is treated with excess thionyl chloride to yield acid chloride D-IIb.

SCHEME 10

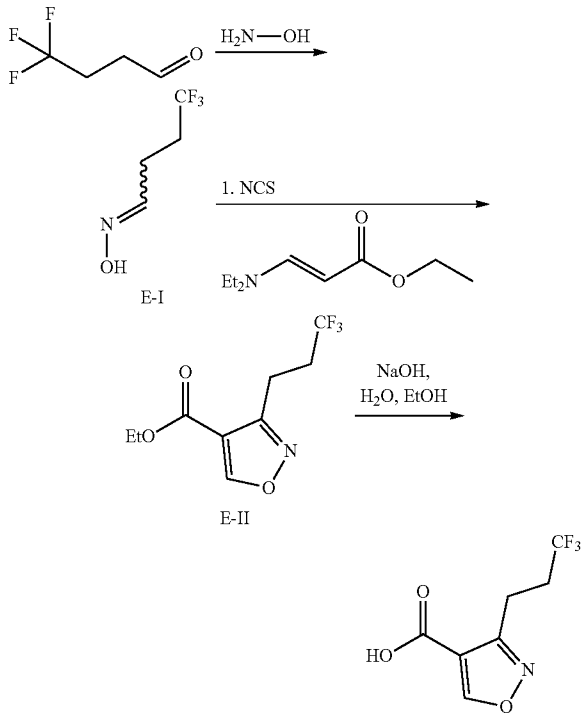

E-I E-II E-III

3-Substituted isoxazole 4-carboxylic acid E-III can be prepared as shown in Scheme 10. Condensation of 4,4,4-trifluorobutanal with hydroxylamine hydrochloride in a solvent such as ethanol yields the corresponding oxime E-I. Subsequent treatment with NCS and cycloaddition with ethyl-3-(diethylamino)acrylate in a solvent such as chloroform yields ester E-II. Saponification of the ester with sodium hydroxide in aqueous ethanol yields isoxazole 4-carboxylic acid E-III.

SCHEME 11

A-VIIIa

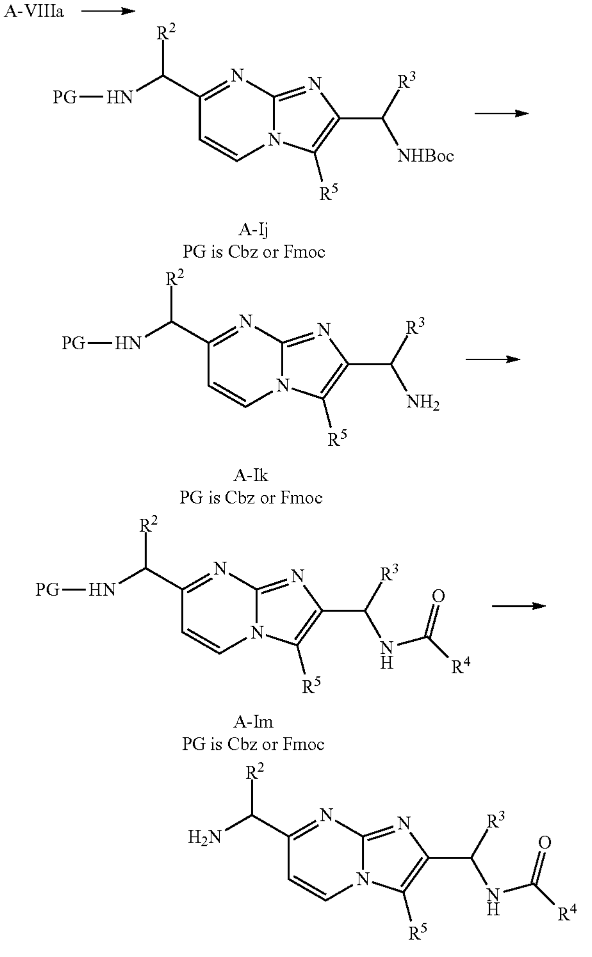

A-Ij
PG is Cbz or Fmoc

A-Ik
PG is Cbz or Fmoc

A-Im
PG is Cbz or Fmoc

A-If

Compounds A-If can be prepared as shown in Scheme 11. Compounds A-VIIIa are protected as a carbamate, such as a benzyloxy carbonyl (Cbz) or as a fluorenylmethyloxycarbonyl (Fmoc) to yield compound A-Ij. Compounds A-Ij where PG is Cbz are prepared by subjecting A-VIIIa to Cbz protection conditions. Compounds A-Ij where PG is Fmoc are prepared by treating A-VIIIa with Fmoc-Cl in a solvent such as DCM or THF in the presence of a base such as N-methylmorpholine, diisopropylethyl amine, or triethylamine. Compounds A-Ij are subjected to Boc deprotection conditions yielding compounds A-Ik. Compounds A-Ik are subjected to amide bond formation conditions, such as those described in Scheme 1 in the preparation of compounds of Formula I from compounds A-Tb, to yield compounds A-Im. When the carbamate compound A-Im is a Cbz group, it is removed using Cbz protecting group removal conditions yielding A-If. When the carbamate compound A-Im is an Fmoc group, it is removed by treating it with a base such as piperidine in solvent such as DMF to yield A-If.

In obtaining the compounds described in the examples below and the corresponding analytical data, the following experimental and analytical protocols were followed unless otherwise indicated.

Unless otherwise specified, reaction solutions were stirred at room temperature under a $N_{2(g)}$ or $Ar_{(g)}$ atmosphere.

When solutions were "concentrated to dryness", they were concentrated using a rotary evaporator under reduced pressure, when solutions were dried, they are typically dried over a drying agent such as $MgSO_4$ or $Na_2SO_4$.

Normal phase flash column chromatography (FCC) was performed on silica gel with prepackaged silica gel columns, such as RediSep®, using ethyl acetate (EtOAc)/hexanes, $CH_2Cl_2$/MeOH, or $CH_2Cl_2$/10% 2N $NH_3$ in MeOH, as eluent, unless otherwise indicated.

Thin-layer chromatography was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone. Mass spectra were obtained on an Agilent series 1100 MSD using electrospray ionization (ESI) in positive mode unless otherwise indicated. Calculated mass corresponds to the exact mass. NMR spectra were obtained on either a Bruker model DPX400 (400 MHz), DPX500 (500 MHz), DRX600 (600 MHz) spectrometer. The format of the $^1H$ NMR data below is as follows: Chemical shift in ppm down field of the tetramethylsilane reference (multiplicity, coupling constant J in Hz, integration).

Whenever a yield is given as a percentage, such yield refers to a mass of the entity for which the yield is given with respect to the maximum amount of the same entity that could be obtained under the particular stoichiometric conditions. Reagent concentrations that are given as percentages refer to mass ratios, unless indicated differently.

In general, chemical names were generated using ChemDraw Ultra 17.1 (CambridgeSoft Corp., Cambridge, MA) or OEMetaChem V1.4.0.4 (Open Eye).

INTERMEDIATES

Intermediate 1

(S,E)-2-Methyl-N-((2-(methylthio)pyrimidin-4-yl)methylene)propane-2-sulfinamide

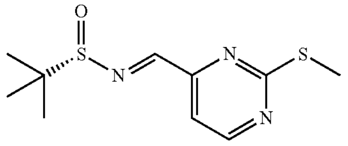 [SMILES: CSc1nccc(/C=N/[S@@](=O)C(C)(C)C)n1]

To a 500 mL three-necked flask equipped with an overhead stirrer were charged 2-(methylthio)pyrimidine-4-carbaldehyde (30 g, 194.7 mmol), (S)-t-$BuSONH_2$ (26.4 g, 214 mmol), $Ti(OEt)_4$ (8.9 g, 38.9 mmol) and THF (300 mL) under nitrogen at 20-30° C. The mixture was concentrated under vacuum. The residue was charged with saturated aqueous $NaHCO_3$ (60 mL), $H_2O$ (400 mL) and EtOAc (300 mL) and stirred for 15 min. The resulting mixture was filtered, and the cake was washed with EtOAc (60 mL). After phase separation, the aqueous phase was extracted with EtOAc (300 mL). The combined organic phases were concentrated under vacuum. The residue was purified by FCC (10:1 petroleum ether/ethyl acetate) to provide the title compound as a yellow solid.

Intermediate 2

(S)—N-(Cyclopropyl(2-(methylthio)pyrimidin-4-yl)methyl)-2-methylpropane-2-sulfinamide

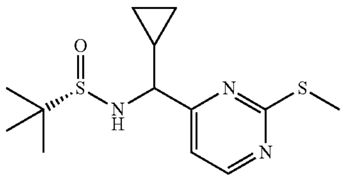 [SMILES: CSc1nccc(C(N[S@@](=O)C(C)(C)C)C2CC2)n1]

To a 2 L three-necked flask equipped with an overhead stirrer were charged (S)-2-methyl-N-((2-(methylthio)pyrimidin-4-yl)methylene)propane-2-sulfinamide (47.3 g, 183.8 mmol, Intermediate 1) and THF (710 mL) under nitrogen respectively. The resulting solution was cooled to −78° C., and cyclopropylmagnesium bromide (341 mL, 183.8 mmol, 0.6 M in THF) was added dropwise over 30 min at −78° C. The resulting reaction mixture was stirred at −78° C. for 1 h. After completion of the reaction, the mixture was quenched by 20 wt % aqueous citric acid (100 mL). Then, $H_2O$ (2 L) was added and the mixture was extracted with EtOAc (2×1 L). The combined organic phases were concentrated under vacuum to provide the title compound as a brown oil.

Intermediate 3

Cyclopropyl(2-(methylthio)pyrimidin-4-yl)methanamine

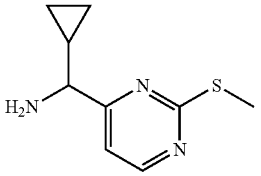

To a 2 L three-necked flask equipped with an overhead stirrer were charged (S)—N-(cyclopropyl(2-(methylthio)pyrimidin-4-yl)methyl)-2-methylpropane-2-sulfinamide (115 g, 295.7 mmol, Intermediate 2) and 1,4-dioxane (1150 mL) under nitrogen. After cooling to 15-20° C., HCl solution (380 mL, 1520 mmol, 4 M in 1,4-dioxane) was added dropwise over 30 min. The resulting mixture was stirred at 15-20° C. for 1 h. After completion of the reaction, the reacting mixture was concentrated under vacuum. The residue was dissolved in $H_2O$ (1150 mL) then extracted with MTBE (3×600 mL). After phase separation, the pH of the aqueous phase was adjusted to pH 8~9 by the addition of 0.1 N aqueous $K_2CO_3$. The resulting solution was extracted with EtOAc (6×600 mL). The combined EtOAc layers were concentrated under vacuum to provide the title compound as a yellow solid.

Intermediate 4

N-(Cyclopropyl(2-(methylthio)pyrimidin-4-yl)methyl)-4,4,4-trifluorobutanamide

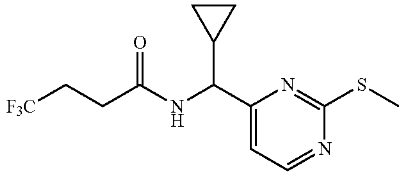 [SMILES: CSc1nccc(C(NC(=O)CCC(F)(F)F)C2CC2)n1]

To a mixture of cyclopropyl(2-(methylthio)pyrimidin-4-yl)methanamine (7.1 g, 36.4 mmol, Intermediate 3), 4,4,4-trifluorobutyric acid (5.86 g, 40 mmol), HOBt (5.16 g, 38.2 mmol) and ACN (150 mL) was added DIPEA (7.52 mL, 43.6 mmol) and the mixture was stirred for 10 min. Then, EDCI (7.32 g, 38.2 mmol) was added and the resulting mixture stirred at rt for 1 h followed by 60° C. for 1 min and was then allowed to cool to rt. The reaction was quenched by the addition of water (800 mL). A precipitate formed and the suspension was stirred at rt for 30 min. The solids were collected by filtration, washed with water and lyophilized to provide the title compound as a white solid.

Intermediate 5

N-(Cyclopropyl(2-(methylsulfonyl)pyrimidin-4-yl)methyl)-4,4,4-trifluorobutanamide

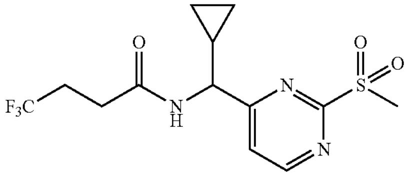 [SMILES: CS(=O)(=O)c1nccc(C(NC(=O)CCC(F)(F)F)C2CC2)n1]

A mixture of N-(cyclopropyl(2-(methylthio)pyrimidin-4-yl)methyl)-4,4,4-trifluorobutanamide (150 mg, 0.47 mmol, Intermediate 4) in DCM (5 mL) was cooled to 0° C. Then, mCPBA (243 mg, 1.41 mmol) was added and the resulting mixture was stirred at 0° C. for 1 h followed by warming to rt over an additional hour. The mixture was partitioned between saturated aqueous bicarbonate and DCM. The layers were separated and the organic layer was washed with water followed by brine, dried over anhydrous $MgSO_4$, filtered and concentrated. The residue was purified by FCC (0-100% EtOAc/hexanes) to provide the title compound as a white solid.

Intermediate 6

N-((2-Aminopyrimidin-4-yl)(cyclopropyl)methyl)-4,4-trifluorobutanamide

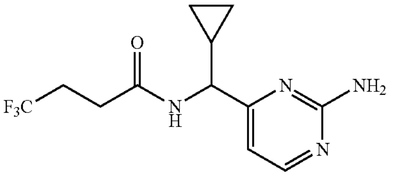 [SMILES: Nc1nccc(C(NC(=O)CCC(F)(F)F)C2CC2)n1]

To a sealed tube was added N-(cyclopropyl(2-(methylsulfonyl)pyrimidin-4-yl)methyl)-4,4,4-trifluorobutanamide (600 mg, 1.71 mmol, Intermediate 5) and ammonia solution (10 mL, 20 mmol, 2 M in 2-propanol). The tube was sealed and the mixture was stirred at 75° C. for 18 h. The mixture was allowed to cool to rt and was then concentrated to dryness. The residue was purified by FCC (0-100% (10% MeOH in EtOAc)/hexanes) to provide the title compound as a white solid.

Intermediate 7

(S,E)-N-((4,4-Difluorocyclohexyl)methylene)-2-methylpropane-2-sulfinamide

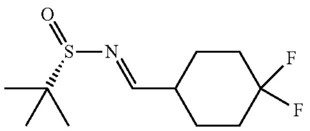 [SMILES: CC(C)(C)[S@](=O)/N=C/C1CCC(F)(F)CC1]

To a mixture of 4,4-difluorocyclohexanecarbaldehyde (3 mL, 21.6 mmol), (S)-(−)-2-methyl-2-propanesulfinamide (2.62 g, 21.6 mmol), copper (II) sulfate (10.75 g, 67.4 mmol) and DCM (65 mL) was added PPTS (574 mg, 2.29 mmol) and the resulting mixture was stirred at rt for 48 h. After that time, Celite® was added and the mixture was filtered. The filter cake was rinsed with EtOAc, and the combined filtrates were concentrated. The residue was purified by FCC (0-40% EtOAc/hexanes) to provide the title compound as a clear colorless oil.

Intermediate 8

(S)—N—((S)-Cyano(4,4-difluorocyclohexyl)methyl)-2-methylpropane-2-sulfinamide

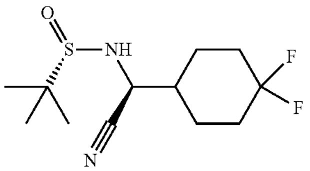 [SMILES: CC(C)(C)[S@](=O)N[C@H](C#N)C1CCC(F)(F)CC1]

To a solution of (S,E)-N-((4,4-difluorocyclohexyl)methylene)-2-methylpropane-2-sulfinamide (3.22 g, 12.8 mmol, Intermediate 7) and TMSCN (3.21 mL, 25.6 mmol) in DCM (85 mL) was added scandium trifluoromethanesulfonate (727 mg, 1.48 mmol) and the resulting suspension was stirred at rt for 72 h. After that time, the mixture was filtered through a pad of silica gel, rinsing with EtOAc, and the filtrate concentrated to dryness. The residue was purified twice by FCC (30-80% EtOAc/hexanes followed by 45-70% EtOAc/hexanes) to provide the title compound as a colorless crystalline solid.

Intermediate 9

(S)-2-((tert-Butoxycarbonyl)amino)-2-(4,4-difluorocyclohexyl)acetic acid

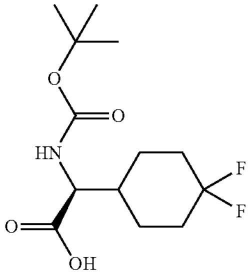 [SMILES: CC(C)(C)OC(=O)N[C@H](C(=O)O)C1CCC(F)(F)CC1]

A mixture of (S)—N—((S)-cyano(4,4-difluorocyclohexyl)methyl)-2-methylpropane-2-sulfinamide (1 g, 3.6 mmol, Intermediate 8) in HCl (9 mL, 107.5 mmol, 37% in water) was stirred at 80° C. for 24 h and then cooled to rt. Then, water was added to dissolve the solids which had formed upon cooling, and the mixture was washed with EtOAc twice and concentrated to dryness. The residue was diluted with 1 N aqueous NaOH (10 mL) and washed with EtOAc twice. Then, THF (10 mL) was added followed by di-tert-butyl dicarbonate (0.8 mL, 3.7 mmol) and the mixture stirred at rt for 45 h. After that time, the mixture was washed with $Et_2O$ and the aqueous layer made acidic by the addition of 1 N aqueous HCl. The aqueous layer was then extracted with EtOAc and the organics were combined, dried over anhydrous $MgSO_4$, filtered and concentrated to dryness to provide the title compound as a colorless foam.

Intermediate 10 tert-Butyl (S)-(1-(4,4-difluorocyclohexyl)-3-(dimethyl(oxo)-$\lambda^6$-sulfaneylidene)-2-oxopropyl)carbamate

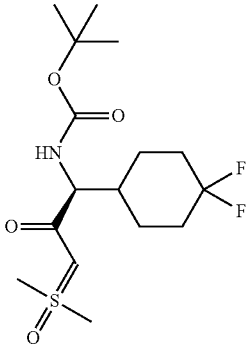 [SMILES: CC(C)(C)OC(=O)N[C@H](C(=O)C=S(C)(C)=O)C1CCC(F)(F)CC1]

Trimethylsulfoxonium iodide (2.64 g. 12 mmol) was added to a solution of potassium tert-butoxide (1.31 g, 11.7 mmol) in THF (42 mL), and the resulting mixture was stirred at reflux for 2 h. After that time, the solution was cooled to 0° C. To a separate flask was added (S)-2-((tert-butoxycarbonyl)amino)-2-(4,4-difluorocyclohexyl)acetic acid (2.4 g, 6.96 mmol, Intermediate 9), $Et_3N$ (0.96 mL, 6.96 mmol) and THF (9 mL), and that solution was then added dropwise to a 0° C. solution of isobutyl chloroformate (0.9 mL, 6.96 mmol) in THF (21 mL). The resulting mixture was stirred at 0° C. for 30 min. The suspension was then filtered and the solids washed with 0° C. THF (2 mL). The wash and the filtrate were combined and cooled to 0° C. and then added to the ylide solution dropwise. The resulting mixture was stirred at 0° C. for 2 h. After that time, the mixture was partitioned between water and EtOAc. The aqueous was further extracted with EtOAc (2×), then the organic layers were combined, washed with brine, dried over anhydrous $MgSO_4$, filtered and concentrated to dryness. The residue was purified by FCC (50-100% (10% MeOH in EtOAc)/hexanes) to provide the title compound as a colorless solid.

Intermediate 11 tert-Butyl ((1S)-(7-(cyclopropyl(4,4,4-trifluorobutanamido)methyl)imidazo[1,2-a]pyrimidin-2-yl)(4,4-difluorocyclohexyl)methyl)carbamate

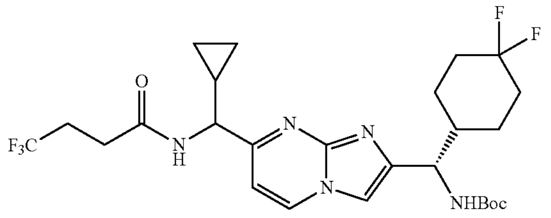 [SMILES: CC(C)(C)OC(=O)N[C@H](c1cn2ccc(C(NC(=O)CCC(F)(F)F)C3CC3)nc2n1)C1CCC(F)(F)CC1]

To a 50-mL three-necked flask equipped with a magnetic stirrer were charged N-((2-aminopyrimidin-4-yl)(cyclopropyl)methyl)-4,4,4-trifluorobutanamide (1.0 g, 3.47 mmol, Intermediate 6), tert-butyl (S)-(1-(4,4-difluorocyclohexyl)-3-(dimethyl(oxo)-$\lambda^6$-sulfaneylidene)-2-oxopropyl)carbamate (1.66 g, 4.51 mmol, Intermediate 10), $[Ir(COD)Cl]_2$ (47 mg, 0.07 mmol), 1,10-phenanthroline (40 mg, 0.14 mmol), NaOTf (40 mg, 0.14 mmol), 4 Å MS (3.0 g, 300% w/w) and DCE (15 mL). The resulting mixture was warmed to 80-85° C. and held at this temperature for 20 h. After this time, the mixture was filtered and the filtrate was concentrated under vacuum. The residue was purified by FCC (50% petroleum ether/EtOAc) to provide the title compound as a yellow solid.

Intermediate 12 tert-Butyl ((S)-(7-((S)-cyclopropyl(4,4,4-trifluorobutanamido)methyl)imidazo[1,2-a]pyrimidin-2-yl)(4,4-difluorocyclohexyl)methyl)carbamate

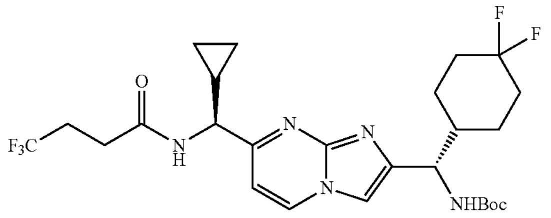 [SMILES: CC(C)(C)OC(=O)N[C@H](c1cn2ccc([C@@H](NC(=O)CCC(F)(F)F)C3CC3)nc2n1)C1CCC(F)(F)CC1]

Intermediate 13 tert-Butyl ((S)-(7-((R)-cyclopropyl(4,4,4-trifluorobutanamido)methyl)imidazo[1,2-a]pyrimidin-2-yl)(4,4-difluorocyclohexyl)methyl)carbamate

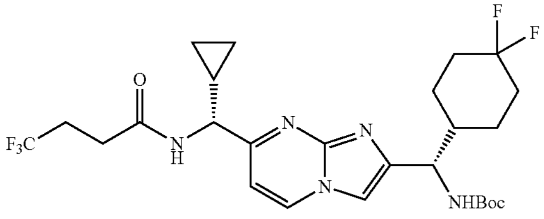 [SMILES: CC(C)(C)OC(=O)N[C@H](c1cn2ccc([C@H](NC(=O)CCC(F)(F)F)C3CC3)nc2n1)C1CCC(F)(F)CC1]

tert-Butyl ((1S)-(7-(cyclopropyl(4,4,4-trifluorobutanamido)methyl)imidazo[1,2-a]pyrimidin-2-yl)(4,4-difluorocyclohexyl)methyl)carbamate (Intermediate 11) was purified by SFC using a chiral stationary phase (CHIRALPAK IH, 50×250 mm; 20% i-PrOH (2 mM $NH_3$ in MeOH)/$CO_2$) to give a pair of diastereomers. The first eluting isomer was Intermediate 12, and the second eluting isomer was Intermediate 13.

Intermediate 14

N-((2-((S)-Amino(4,4-difluorocyclohexyl)methyl)imidazo[1,2-a]pyrimidin-7-yl)(cyclopropyl)methyl)-4,4,4-trifluorobutanamide

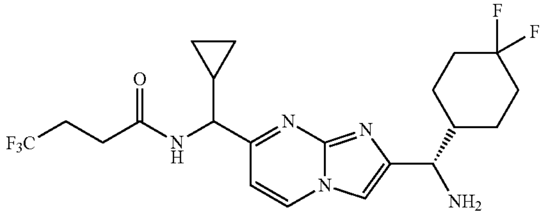 [SMILES: N[C@H](c1cn2ccc(C(NC(=O)CCC(F)(F)F)C3CC3)nc2n1)C1CCC(F)(F)CC1]

To a solution of tert-butyl ((1S)-(7-(cyclopropyl(4,4,4-trifluorobutanamido)methyl)imidazo[1,2-a]pyrimidin-2-yl)(4,4-difluorocyclohexyl)methyl)carbamate (215 mg, 0.38 mmol, Intermediate 11) in DCM (0.92 mL) was added HCl (0.38 mL, 1.54 mmol, 4 M in 1,4-dioxane) and the resulting suspension was stirred at rt for 4 h. The mixture was concentrated to dryness and the residue was partitioned between water and EtOAc. The aqueous layer was further washed with EtOAc and then the organic layers were discarded. The aqueous layer was made basic by the addition of 15% aqueous NaOH and then extracted with EtOAc (3×). The organic layers were combined, dried over anhydrous $MgSO_4$, filtered and concentrated to dryness to provide the title compound as a yellow film.

Intermediate 15

Methyl 2-(3,3,3-trifluoropropyl)-2H-1,2,3-triazole-4-carboxylate

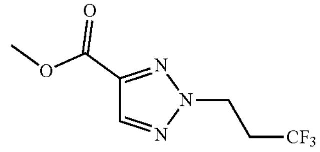

To a mixture of methyl 1H-1,2,3-triazole-4-carboxylate (5 g, 38.2 mmol), $K_2CO_3$ (5.27 g, 38.2 mmol) and DMF (49 mL) was added 3-bromo-1,1,1-trifluoropropane (4.07 mL, 38.2 mmol) and the resulting mixture was stirred at rt for 17 h. After that time the mixture was filtered through a pad of Celite®, rinsed with EtOAc and the filtrate was concentrated under vacuum. The residue was partitioned between EtOAc (50 mL) and water (50 mL). The layers were separated and the aqueous was further extracted with EtOAc (2×50 mL). The organic layers were combined, washed with brine (50 mL), dried over anhydrous $Na_2SO_4$, filtered and concentrated to dryness. The residue was purified by FCC (0 to 75% EtOAc/hexanes; second eluting isomer) to provide the title compound as a white solid.

Intermediate 16

Methyl 1-(3,3,3-trifluoropropyl)-1H-1,2,3-triazole-5-carboxylate

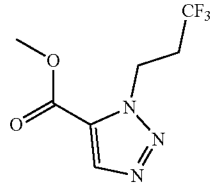

The title compound was prepared as described for the synthesis of Intermediate 15 and was the first eluting isomer isolated as a clear colorless oil.

Intermediate 17

2-(3,3,3-Trifluoropropyl)-2H-1,2,3-triazole-4-carboxylic acid

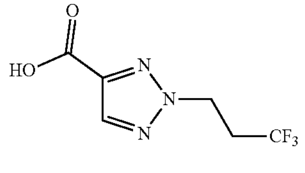

To a mixture of methyl 2-(3,3,3-trifluoropropyl)-2H-1,2,3-triazole-4-carboxylate (4.28 g, 19.2 mmol, Intermediate 15) in THF (58 mL) was added 2 M aqueous NaOH (58 mL, 115 mmol) and the mixture was stirred at rt for 15 h. After that time, the mixture was concentrated to remove the THF and then washed with EtOAc (2×50 mL). The aqueous layer was then acidified to pH 3 by the addition of 1 N aqueous HCl and extracted with 2-MeTHF (3×50 mL). The organic layers were combined, washed with brine (50 mL), dried over anhydrous $Na_2SO_4$, filtered and concentrated to dryness to provide the title compound as a white solid.

Intermediate 18

1-(3,3,3-Trifluoropropyl)-1H-1,2,3-triazole-5-carboxylic acid

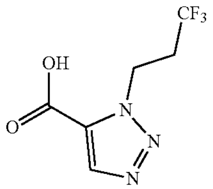 [SMILES: O=C(O)c1cnnn1CCC(F)(F)F]

The title compound was prepared as described for the synthesis of Intermediate 17, using methyl 1-(3,3,3-trifluoropropyl)-1H-1,2,3-triazole-5-carboxylate (Intermediate 16) in place of methyl 2-(3,3,3-trifluoropropyl)-2H-1,2,3-triazole-4-carboxylate, to provide the title compound as a white solid.

Intermediate 19

N-((1S)-(7-(Cyclopropyl(4,4,4-trifluorobutanamido)methyl)imidazo[1,2-a]pyrimidin-2-yl)(4,4-difluorocyclohexyl)methyl)-1-(3,3,3-trifluoropropyl)-1H-1,2,3-triazole-5-carboxamide

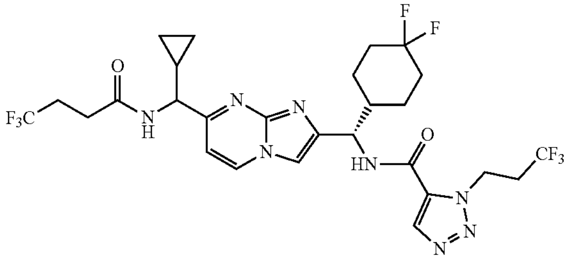 [SMILES: O=C(CCC(F)(F)F)NC(c1ccn2cc([C@@H](NC(=O)c3cnnn3CCC(F)(F)F)C3CCC(F)(F)CC3)nc2n1)C1CC1]

A mixture of N-((2-((S)-amino(4,4-difluorocyclohexyl)methyl)imidazo[1,2-a]pyrimidin-7-yl)(cyclopropyl)methyl)-4,4,4-trifluorobutanamide (80 mg, 0.16 mmol, Intermediate 14), 1-(3,3,3-trifluoropropyl)-1H-1,2,3-triazole-5-carboxylic acid (35 mg, 0.17 mmol, Intermediate 18) and HOBt (23 mg, 0.17 mmol) was diluted with MeCN (0.75 mL). DIPEA (0.069 mL, 0.4 mmol) and then EDCI (32.5 mg, 0.17 mmol) were added, and the resulting solution was heated to 45° C. for 18 h. After this time, the solution was cooled to rt and water and EtOAc were added. The layers were separated, and the aqueous layer was extracted twice with EtOAc. The organic layers were combined, washed with brine, dried over anhydrous $MgSO_4$, filtered and concentrated. The residue was purified by FCC (30-100% acetone/hexanes) to afford the title compound, a diastereomeric mixture, as a pale yellow film.

Intermediate 20

Benzyl (cyclopropyl(2-(methylthio)pyrimidin-4-yl)methyl)carbamate

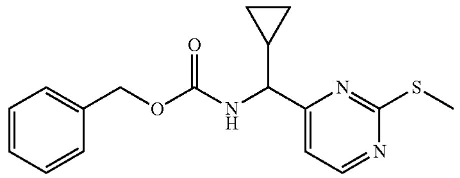 [SMILES: CSc1nccc(C(NC(=O)OCc2ccccc2)C2CC2)n1]

To a 1 L three-necked flask equipped with an overhead stirrer were charged cyclopropyl(2-(methylthio)pyrimidin-4-yl)methanamine (50 g, 256 mmol, Intermediate 3), DIPEA (49.6 g, 385 mmol) and DCM (500 mL). The resulting mixture was cooled to −5 to 5° C., and CbzCl (48 g, 282 mmol) was added dropwise over 30 min. The resulting mixture was stirred at −5 to 5° C. for 1 h. After that time, the reaction was quenched with $H_2O$ (100 mL) and the phases were separated. The organic phase was concentrated under vacuum to provide the title compound as a yellow solid.

Intermediate 21

Benzyl (cyclopropyl(2-(methylsulfonyl)pyrimidin-4-yl)methyl)carbamate

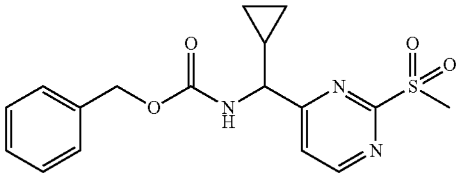 [SMILES: CS(=O)(=O)c1nccc(C(NC(=O)OCc2ccccc2)C2CC2)n1]

To a 3 L three-necked flask equipped with an overhead stirrer was charged benzyl (cyclopropyl(2-(methylthio)pyrimidin-4-yl)methyl)carbamate (95 g, 231 mmol, Intermediate 20), ACN (950 mL) and $H_2O$ (950 mL) under nitrogen. After cooling to 0-10° C., Oxone® (638 g, 1038 mmol) was added batchwise at 0-10° C. and the resulting mixture was stirred at the same temperature for 3 h. After that time, the mixture was filtered and the filter cake was washed with EtOAc (470 mL). The filtrate was collected and the pH adjusted to ~5-6 by the addition of 0.1 N aqueous $Na_2CO_3$. The phases were separated and the organic layer was concentrated to dryness. The residue was purified by FCC (15-50% EtOAc/petroleum ether) to provide the title compound as a brown oil.

Intermediate 22

Benzyl ((2-aminopyrimidin-4-yl)(cyclopropyl)methyl)carbamate

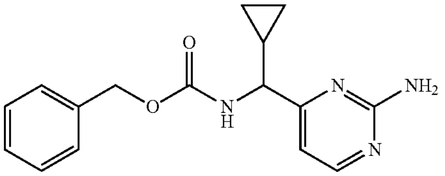 [SMILES: Nc1nccc(C(NC(=O)OCc2ccccc2)C2CC2)n1]

The title compound was prepared as described for the synthesis of Intermediate 6, using benzyl (cyclopropyl(2-(methylsulfonyl)pyrimidin-4-yl)methyl)carbamate (Intermediate 21) in place of N-(cyclopropyl(2-(methylsulfonyl)pyrimidin-4-yl)methyl)-4,4,4-trifluorobutanamide. The crude material was purified by FCC (35% EtOAc/petroleum ether) to provide the title compound as an off-white solid.

Intermediate 23 tert-Butyl ((1S)-(7-((((benzyloxy)carbonyl)amino)(cyclopropyl)methyl)imidazo[1,2-a]pyrimidin-2-yl)(4,4-difluorocyclohexyl)methyl)carbamate

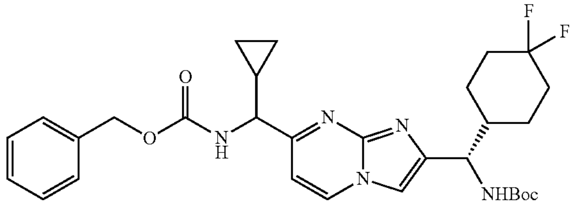 [SMILES: CC(C)(C)OC(=O)N[C@H](c1cn2ccc(C(NC(=O)OCc3ccccc3)C3CC3)nc2n1)C1CCC(F)(F)CC1]

To a 500 mL three-necked flask quipped with an overhead stirrer were charged benzyl ((2-aminopyrimidin-4-yl)(cyclopropyl)methyl)carbamate (11.0 g, 36.9 mmol, Intermediate 22), tert-butyl (S)-(1-(4,4-difluorocyclohexyl)-3-(dimethyl(oxo)-$\lambda^6$-sulfaneylidene)-2-oxopropyl)carbamate (20.0 g, 55.3 mmol, Intermediate 10), $[Ir(COD)Cl]_2$ (1.37 g, 1.84 mmol), 1,10-phenanthroline (0.73 g, 3.69 mmol), NaOTf (0.73 g, 3.69 mmol), 4 Å MS (22.0 g, 200% w/w) and toluene (165 mL) under nitrogen respectively. The resulting mixture was stirred at 80-85° C. for 40 h. After that time, the reaction mixture was cooled to rt and concentrated to dryness. The residue was purified by FCC (25-50% EtOAc/petroleum ether) to provide the title compound as a yellow solid.

Intermediate 24 tert-Butyl ((1S)-(7-(amino(cyclopropyl)methyl)imidazo[1,2-a]pyrimidin-2-yl)(4,4-difluorocyclohexyl)methyl)carbamate

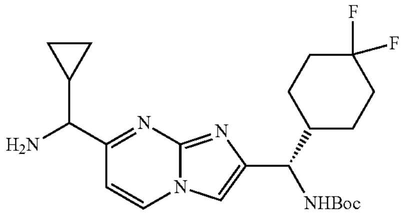 [SMILES: CC(C)(C)OC(=O)N[C@H](c1cn2ccc(C(N)C3CC3)nc2n1)C1CCC(F)(F)CC1]

To a 500 mL three-necked flask equipped with an overhead stirrer were charged tert-butyl ((1S)-(7-((((benzyloxy)carbonyl)amino)(cyclopropyl)methyl)imidazo[1,2-a]pyrimidin-2-yl)(4,4-difluorocyclohexyl)methyl)carbamate (11.0 g, 19.3 mmol, Intermediate 23), Pd/C (2.2 g, 20% w/w), $HCO_2NH_4$ (9.7 g, 154 mmol), MeOH (196 mL) and $H_2O$ (26.5 mL) under nitrogen respectively. After stirring at 25-35° C. for 3 h, the mixture was filtered, and the filtrate was concentrated under vacuum to remove MeOH. The resulting aqueous solution was extracted with 2-MeTHF (2×300 mL). The combined organic phases were concentrated to dryness to provide the title compound as an off-white solid.

Intermediate 25 tert-Butyl ((S)-(7-((S)-amino(cyclopropyl)methyl)imidazo[1,2-a]pyrimidin-2-yl)(4,4-difluorocyclohexyl)methyl)carbamate

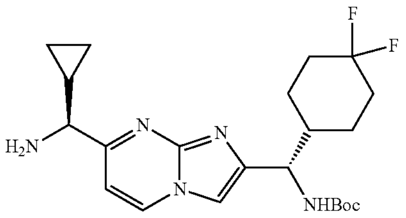 [SMILES: CC(C)(C)OC(=O)N[C@H](c1cn2ccc([C@@H](N)C3CC3)nc2n1)C1CCC(F)(F)CC1]

Intermediate 26 tert-Butyl ((S)-(7-((R)-amino(cyclopropyl)methyl)imidazo[1,2-a]pyrimidin-2-yl)(4,4-difluorocyclohexyl)methyl)carbamate

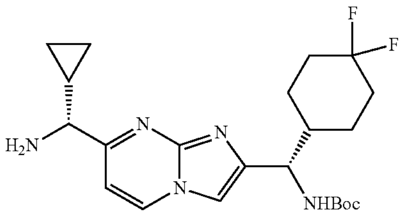 [SMILES: CC(C)(C)OC(=O)N[C@H](c1cn2ccc([C@H](N)C3CC3)nc2n1)C1CCC(F)(F)CC1]

tert-Butyl ((1S)-(7-(amino(cyclopropyl)methyl)imidazo[1,2-a]pyrimidin-2-yl)(4,4-difluorocyclohexyl)methyl)carbamate (Intermediate 24) was purified by SFC using a chiral stationary phase (CHIRALPAK IH, 50×250 mm; 30% MeOH (0.1% i-$PrNH_2$)/$CO_2$) to give a pair of diastereomers. The first eluting isomer was Intermediate 25, and the second eluting isomer was Intermediate 26.

Intermediate 27 tert-Butyl ((1S)-(7-((1S)-cyclopropyl(4,4,4-trifluoro-3-methylbutanamido)methyl)imidazo[1,2-a]pyrimidin-2-yl)(4,4-difluorocyclohexyl)methyl)carbamate

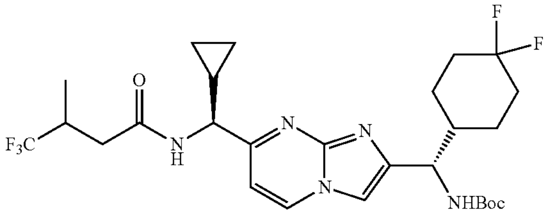 [SMILES: CC(CC(=O)N[C@H](c1ccn2cc([C@@H](NC(=O)OC(C)(C)C)C3CCC(F)(F)CC3)nc2n1)C1CC1)C(F)(F)F]

A mixture of tert-butyl ((S)-(7-((S)-amino(cyclopropyl)methyl)imidazo[1,2-a]pyrimidin-2-yl)(4,4-difluorocyclohexyl)methyl)carbamate (1.0 g, 2.3 mmol, Intermediate 25), 3-trifluoromethylbutyric acid (376 mg, 2.41 mmol), DIPEA (0.59 mL, 3.44 mmol) and HOBt (0.33 g, 2.41 mmol) was diluted with MeCN (50 mL). The mixture was stirred at 40° C. for 10 minutes and then EDCI (0.46 g, 2.41 mmol) was added. The resulting mixture was stirred at 40° C. for 1 h. After that time, the mixture was poured over water and extracted with EtOAc. The organic layers were combined, washed with brine, dried over anhydrous $MgSO_4$, filtered and concentrated to dryness to provide the title compound as a pale foam.

Intermediate 28

N—((S)-(2-((S)-Amino(4,4-difluorocyclohexyl)methyl)imidazo[1,2-a]pyrimidin-7-yl)(cyclopropyl)methyl)-4,4,4-trifluoro-3-methylbutanamide

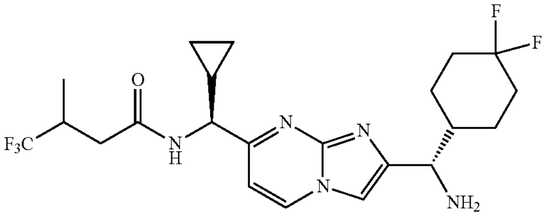 [SMILES: CC(CC(=O)N[C@H](c1ccn2cc([C@@H](N)C3CCC(F)(F)CC3)nc2n1)C1CC1)C(F)(F)F]

A mixture of tert-butyl ((1S)-(7-((1S)-cyclopropyl(4,4,4-trifluoro-3-methylbutanamido)methyl)imidazo[1,2-a]pyrimidin-2-yl)(4,4-difluorocyclohexyl)methyl)carbamate (1.3 g, 2.27 mmol, Intermediate 27) in TFA (10 mL, 131 mmol) was stirred at rt for 5 min and then concentrated to dryness. The residue was diluted with water and made basic by the addition of saturated aqueous $NaHCO_3$. The mixture was then extracted three times with EtOAc. The organic layers were combined, washed with brine, dried over anhydrous $MgSO_4$, filtered and concentrated to dryness to provide the title compound as a tan foam.

Intermediate 29

N-((1S)-(7-((1S)-Cyclopropyl(4,4,4-trifluoro-3-methylbutanamido)methyl)imidazo[1,2-a]pyrimidin-2-yl)(4,4-difluorocyclohexyl)methyl)-2-(2,2,2-trifluoroethyl)isonicotinamide

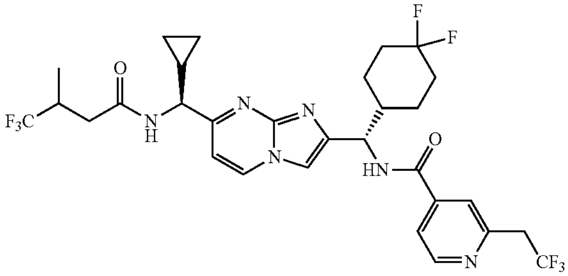 [SMILES: CC(CC(=O)N[C@H](c1ccn2cc([C@@H](NC(=O)c3ccnc(CC(F)(F)F)c3)C3CCC(F)(F)CC3)nc2n1)C1CC1)C(F)(F)F]

A mixture of N—((S)-(2-((S)-amino(4,4-difluorocyclohexyl)methyl)imidazo[1,2-a]pyrimidin-7-yl)(cyclopropyl)methyl)-4,4,4-trifluoro-3-methylbutanamide (100 mg, 0.21 mmol, Intermediate 28), 2-(2,2,2-trifluoroethyl)pyridine-4-carboxylic acid (45.5 mg, 0.22 mmol), DIPEA (0.055 mL, 0.32 mmol) and HOBt (30 mg, 0.22 mmol) was diluted with MeCN (5 mL). The mixture was stirred at 40° C. for 10 minutes and then EDCI (43 mg, 0.22 mmol) was added. The resulting mixture was stirred at 40° C. for 30 min. After that time, the mixture was poured over water and extracted with EtOAc. The organic layers were combined, washed with brine, dried over anhydrous $MgSO_4$ and concentrated to dryness. The residue was purified by FCC (0-100% (10% MeOH in EtOAc)/hexanes) to provide the title compound as a foam.

Intermediate 30

Methyl 2-(cyclopropylmethyl)-2H-1,2,3-triazole-4-carboxylate

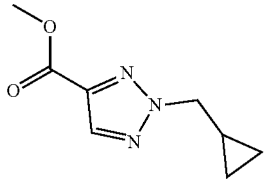

The title compound was prepared as described for the synthesis of Intermediate 15, using (bromomethyl)cyclopropane in place of 3-bromo-1,1,1-trifluoropropane, to provide the title compound as a clear colorless oil.

Intermediate 31

2-(Cyclopropylmethyl)-2H-1,2,3-triazole-4-carboxylic acid

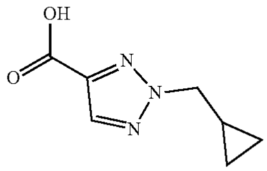 [SMILES: O=C(O)c1cnn(CC2CC2)n1]

The title compound was prepared as described for the synthesis of Intermediate 17, using methyl 2-(cyclopropylmethyl)-2H-1,2,3-triazole-4-carboxylate (Intermediate 30) in place of methyl 2-(3,3,3-trifluoropropyl)-2H-1,2,3-triazole-4-carboxylate to provide the title compound as a white solid.

Intermediate 32

(EZ)-4,4,4-Trifluorobutanal oxime

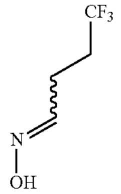

Potassium carbonate (3.29 g, 23.8 mmol) was added to a mixture of 4,4,4-trifluorobutanal (2 g, 15.9 mmol), hydroxylamine hydrochloride (1.21 g, 17.5 mmol) and EtOH (20 mL) and the resulting mixture was stirred at rt for 16 h. After that time, the mixture was concentrated to dryness, diluted with water (10 mL) and extracted with DCM (3×10 mL). The organic layers were combined, washed with brine (20 mL), dried over anhydrous $Na_2SO_4$, filtered and concentrated to dryness to provide the title compound as a colorless oil.

Intermediate 33

Ethyl 3-(3,3,3-trifluoropropyl)isoxazole-4-carboxylate

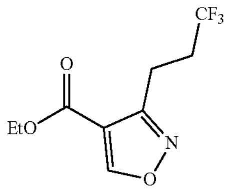 [SMILES: CCOC(=O)c1conc1CCC(F)(F)F]

NCS (392 mg, 2.93 mmol) was added to a solution of (EZ)-4,4,4-trifluorobutanal oxime (394 mg, 2.79 mmol, Intermediate 32) and chloroform (2 mL). The reaction mixture was stirred at room temperature for 3 h. Ethyl-3-(diethylamino)acrylate (400 mg, 2.79 mmol) was added and the reaction mixture was stirred at rt for 16 h. At this point, the mixture was concentrated under reduced pressure. Then, the residue was dissolved in EtOAc (10 mL) and washed with water (10 mL) followed by brine (10 mL), dried over anhydrous $Na_2SO_4$, filtered and concentrated to dryness under reduced pressure. Purification by preparative HPLC (Boston Green column, ODS 150×30 mm×5 μm (eluent: 50% to 80% (v/v) water/(0.2% formic acid)-ACN) and the resultant product was suspended in water (10 mL), frozen using dry ice/acetone, and then lyophilized to dryness to afford the title compound.

Intermediate 34

3-(3,3,3-Trifluoropropyl)isoxazole-4-carboxylic acid

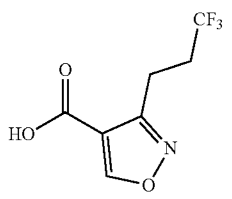 [SMILES: O=C(O)c1conc1CCC(F)(F)F]

Sodium hydroxide (84 mg, 2.1 mmol) was added to a mixture consisting of ethyl 3-(3,3,3-trifluoropropyl)isoxazole-4-carboxylate (100 mg, 0.42 mmol, Intermediate 33), $H_2O$ (0.5 mL) and EtOH (2.5 mL). The resultant mixture was stirred at room temperature for 3 h, then concentrated under reduced pressure and the residue was diluted with water (10 mL). The resultant mixture was acidified with 1 N aqueous HCl to pH 3, frozen using dry ice/acetone, and then lyophilized to dryness to afford the title compound as a white solid.

Intermediate 35 tert-Butyl ((S)-(7-((R)-cyclopropyl(2-(3,3-difluorocyclobutyl)acetamido)methyl)imidazo[1,2-a]pyrimidin-2-yl)(4,4-difluorocyclohexyl)methyl)carbamate

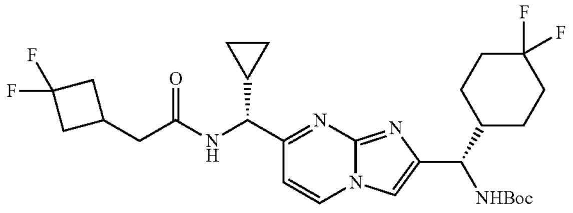 [SMILES: CC(C)(C)OC(=O)N[C@H](c1cn2ccc([C@H](NC(=O)CC3CC(F)(F)C3)C3CC3)nc2n1)C1CCC(F)(F)CC1]

A mixture of tert-butyl ((S)-(7-((R)-amino(cyclopropyl)methyl)imidazo[1,2-a]pyrimidin-2-yl)(4,4-difluorocyclohexyl)methyl)carbamate (750 mg, 1.72 mmol, Intermediate 26), 2-(3,3-difluorocyclobutyl)acetic acid (280 mg, 1.81 mmol) and HOBt (244 mg, 1.81 mmol) was diluted with MeCN (19 mL). Hunig's base (0.45 mL, 2.58 mmol) and then EDCI (347 mg, 1.81 mmol) were added, and the resulting solution was heated to 40° C. for 2 h. After this time, the solution was cooled to rt and water and EtOAc were added. The layers were separated, and the aqueous layer was extracted twice with EtOAc. The organic layers were combined, washed with brine, dried over anhydrous $Na_2SO_4$, filtered and concentrated to provide the title compound as a yellow foam.

Intermediate 36

N—((R)-(2-((S)-Amino(4,4-difluorocyclohexyl)methyl)imidazo[1,2-a]pyrimidin-7-yl)(cyclopropyl)methyl)-2-(3,3-difluorocyclobutyl)acetamide

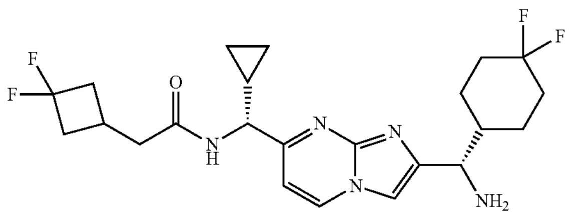 [SMILES: N[C@H](c1cn2ccc([C@H](NC(=O)CC3CC(F)(F)C3)C3CC3)nc2n1)C1CCC(F)(F)CC1]

The title compound was prepared as described in the synthesis of Intermediate 28 using tert-butyl ((S)-(7-((R)-cyclopropyl(2-(3,3-difluorocyclobutyl)acetamido)methyl)imidazo[1,2-a]pyrimidin-2-yl)(4,4-difluorocyclohexyl)methyl)carbamate (Intermediate 35) in place of tert-butyl ((1S)-(7-((1S)-cyclopropyl(4,4,4-trifluoro-3-methylbutanamido)methyl)imidazo[1,2-a]pyrimidin-2-yl)(4,4-difluorocyclohexyl)methyl)carbamate.

Intermediate 37 trans-(1,2)-N—((S)-(7-((R)-Cyclopropyl(2-(3,3-difluorocyclobutyl)acetamido)methyl)imidazo[1,2-a]pyrimidin-2-yl)(4,4-difluorocyclohexyl)methyl)-2-(trifluoromethyl)cyclopropane-1-carboxamide

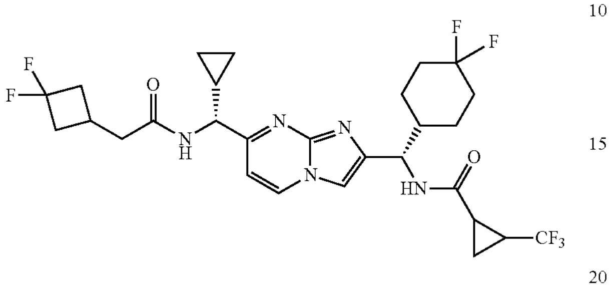

A mixture of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide (125 mg, 0.26 mmol, Intermediate 36), trans-2-(trifluoromethyl)cyclopropane-1-carboxylic acid (46 mg, 0.3 mmol) and HOBt (37 mg, 0.28 mmol) was diluted with MeCN (2.9 mL). Hunig's base (0.054 mL, 0.31 mmol) and then EDCI (53 mg, 0.28 mmol) were added, and the resulting solution was heated to 40° C. for 2 h. After this time, the solution was cooled to rt and water and EtOAc were added. The layers were separated, and the aqueous layer was extracted again with EtOAc. The organic layers were combined, washed with brine, dried over anhydrous $Na_2SO_4$, filtered and concentrated. The crude residue was purified by preparative HPLC (XBridge C18, 40% to 100% MeCN/aqueous $NH_4OH$ (20 mM)) to provide the title compound as a white solid.

Intermediate 38 tert-Butyl ((S)-(7-((S)-cyclopropyl(2-(3,3-difluorocyclobutyl)acetamido)methyl)imidazo[1,2-a]pyrimidin-2-yl)(4,4-difluorocyclohexyl)methyl)carbamate

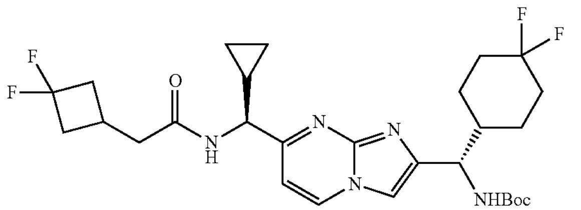 [SMILES: CC(C)(C)OC(=O)N[C@H](c1cn2ccc([C@@H](NC(=O)CC3CC(F)(F)C3)C3CC3)nc2n1)C1CCC(F)(F)CC1]

The title compound was prepared as described for the synthesis of Intermediate 35, using tert-butyl ((S)-(7-((S)-amino(cyclopropyl)methyl)imidazo[1,2-a]pyrimidin-2-yl)(4,4-difluorocyclohexyl)methyl)carbamate (Intermediate 25) in place of tert-butyl ((S)-(7-((R)-amino(cyclopropyl)methyl)imidazo[1,2-a]pyrimidin-2-yl)(4,4-difluorocyclohexyl)methyl)carbamate to provide the title compound as a light orange-brown foam.

Intermediate 39

N—((S)-(2-((S)-Amino(4,4-difluorocyclohexyl)methyl)imidazo[1,2-a]pyrimidin-7-yl)(cyclopropyl)methyl)-2-(3,3-difluorocyclobutyl)acetamide

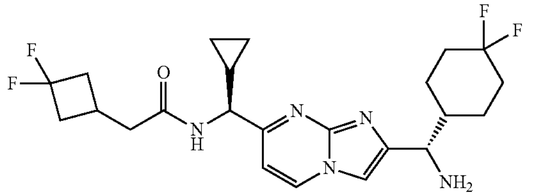 [SMILES: N[C@H](c1cn2ccc([C@@H](NC(=O)CC3CC(F)(F)C3)C3CC3)nc2n1)C1CCC(F)(F)CC1]

The title compound was prepared as described in the synthesis of Intermediate 28 using tert-butyl ((S)-(7-((S)-cyclopropyl(2-(3,3-difluorocyclobutyl)acetamido)methyl)imidazo[1,2-a]pyrimidin-2-yl)(4,4-difluorocyclohexyl)methyl)carbamate (Intermediate 38) in place of tert-butyl ((1S)-(7-((1S)-cyclopropyl(4,4,4-trifluoro-3-methylbutanamido)methyl)imidazo[1,2-a]pyrimidin-2-yl)(4,4-difluorocyclohexyl)methyl)carbamate.

Intermediate 40

4-Methyl-1,2,5-oxadiazole-3-carbonyl chloride

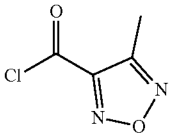

A mixture of 4-methyl-1,2,5-oxadiazole-3-carboxylic acid (135 mg, 1.05 mmol) and thionyl chloride (6.4 mL, 88 mmol) was stirred at 80° C. for 2 h and then concentrated to dryness.

Intermediate 41

N—((R)-(2-((S)-Amino(4,4-difluorocyclohexyl)methyl)imidazo[1,2-a]pyrimidin-7-yl)(cyclopropyl)methyl)-4,4,4-trifluorobutanamide

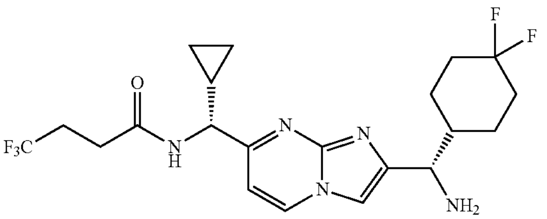

The title compound was prepared as described in the synthesis of Intermediate 28 using tert-butyl ((S)-(7-((R)-cyclopropyl(4,4,4-trifluorobutanamido)methyl)imidazo[1,2-a]pyrimidin-2-yl)(4,4-difluorocyclohexyl)methyl)carbamate (Intermediate 13) in place of tert-butyl ((1S)-(7-((1S)-cyclopropyl(4,4,4-trifluoro-3-methylbutanamido)

methyl)imidazo[1,2-a]pyrimidin-2-yl)(4,4-difluorocyclohexyl)methyl)carbamate. The crude residue was lyophilized to provide the title compound as an off-white solid.

Intermediate 42 trans-(1,2)-N—((S)-(7-((S)-Cyclopropyl(2-(3,3-difluorocyclobutyl)acetamido)methyl)imidazo[1,2-a]pyrimidin-2-yl)(4,4-difluorocyclohexyl)methyl)-2-(trifluoromethyl)cyclopropane-1-carboxamide

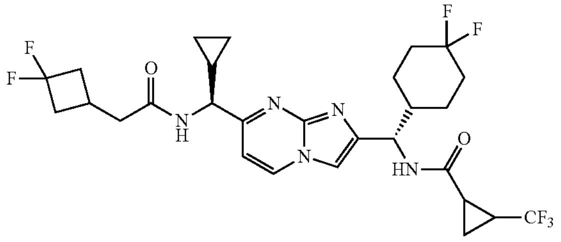 [SMILES: O=C(CC1CC(F)(F)C1)N[C@H](c1ccn2cc([C@@H](NC(=O)C3CC3C(F)(F)F)C3CCC(F)(F)CC3)nc2n1)C1CC1]

The title compound was prepared as described in the synthesis of Intermediate 37 using N—((S)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide (Intermediate 39) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide.

Intermediate 43

N-((1S)-(7-(Cyclopropyl(4,4,4-trifluorobutanamido)methyl)imidazo[1,2-a]pyrimidin-2-yl)(4,4-difluorocyclohexyl)methyl)-1-(3,3,3-trifluoropropyl)-1H-pyrazole-4-carboxamide

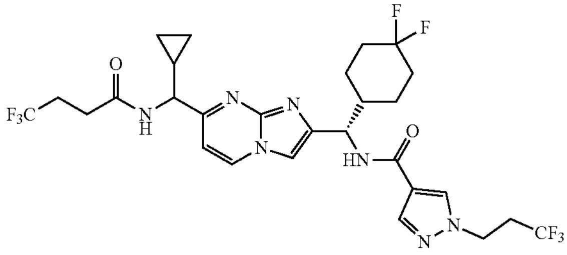 [SMILES: O=C(CCC(F)(F)F)NC(c1ccn2cc([C@@H](NC(=O)c3cnn(CCC(F)(F)F)c3)C3CCC(F)(F)CC3)nc2n1)C1CC1]

The title compound was prepared as described in the synthesis of Intermediate 19, using 1-(3,3,3-trifluoropropyl)-1H-pyrazole-4-carboxylic acid in place of 1-(3,3,3-trifluoropropyl)-1H-1,2,3-triazole-5-carboxylic acid.

Intermediate 44

N-((1S)-(7-(Cyclopropyl(4,4,4-trifluorobutanamido)methyl)imidazo[1,2-a]pyrimidin-2-yl)(4,4-difluorocyclohexyl)methyl)-1-isopropyl-1H-pyrazole-5-carboxamide

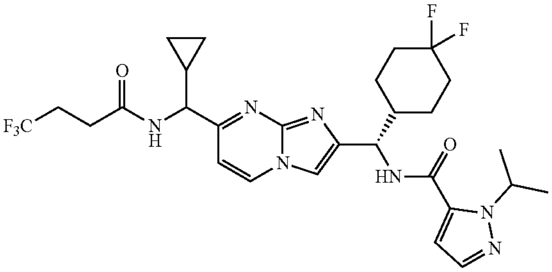 [SMILES: CC(C)n1nccc1C(=O)N[C@H](c1cn2ccc(C(NC(=O)CCC(F)(F)F)C3CC3)nc2n1)C1CCC(F)(F)CC1]

The title compound was prepared as described in the synthesis of Intermediate 19, using 1-isopropyl-1H-pyrazole-5-carboxylic acid in place of 1-(3,3,3-trifluoropropyl)-1H-1,2,3-triazole-5-carboxylic acid.

Intermediate 45

N-((1S)-(7-(Cyclopropyl(4,4,4-trifluorobutanamido)methyl)imidazo[1,2-a]pyrimidin-2-yl)(4,4-difluorocyclohexyl)methyl)-1-methyl-1H-pyrazole-5-carboxamide

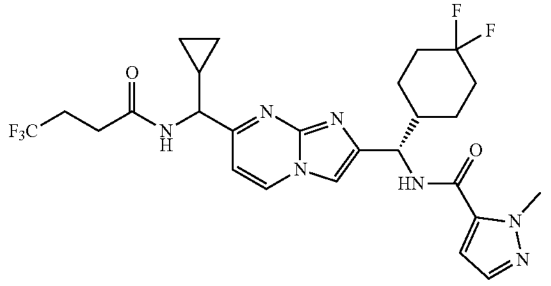 [SMILES: Cn1nccc1C(=O)N[C@H](c1cn2ccc(C(NC(=O)CCC(F)(F)F)C3CC3)nc2n1)C1CCC(F)(F)CC1]

The title compound was prepared as described in the synthesis of Intermediate 19, using 1-methyl-1H-pyrazole-5-carboxylic acid in place of 1-(3,3,3-trifluoropropyl)-1H-1,2,3-triazole-5-carboxylic acid.

Intermediate 46

N-((1S)-(7-(Cyclopropyl(4,4,4-trifluorobutanamido)methyl)imidazo[1,2-a]pyrimidin-2-yl)(4,4-difluorocyclohexyl)methyl)-1-(3,3,3-trifluoropropyl)-1H-pyrazole-3-carboxamide

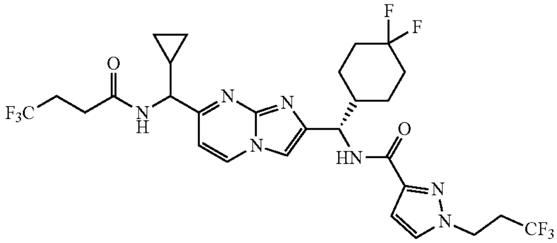 [SMILES: O=C(CCC(F)(F)F)NC(c1ccn2cc([C@@H](NC(=O)c3ccn(CCC(F)(F)F)n3)C3CCC(F)(F)CC3)nc2n1)C1CC1]

The title compound was prepared as described in the synthesis of Intermediate 19, using 1-(3,3,3-trifluoropropyl)-1H-pyrazole-3-carboxylic acid in place of 1-(3,3,3-trifluoropropyl)-1H-1,2,3-triazole-5-carboxylic acid.

Intermediate 47

N-((1S)-(7-(Cyclopropyl(4,4,4-trifluorobutanamido)methyl)imidazo[1,2-a]pyrimidin-2-yl)(4,4-difluorocyclohexyl)methyl)-2-(3,3,3-trifluoropropyl)-2H-1,2,3-triazole-4-carboxamide

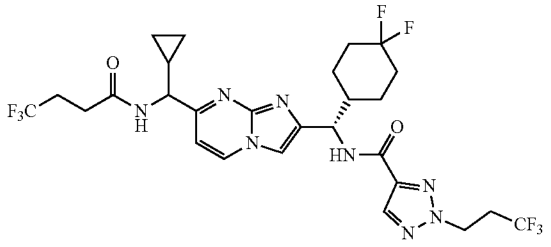 [SMILES: O=C(CCC(F)(F)F)NC(c1ccn2cc([C@@H](NC(=O)c3cnn(CCC(F)(F)F)n3)C3CCC(F)(F)CC3)nc2n1)C1CC1]

The title compound was prepared as described in the synthesis of Intermediate 19, using 2-(3,3,3-trifluoropropyl)-2H-1,2,3-triazole-4-carboxylic acid in place of 1-(3,3,3-trifluoropropyl)-1H-1,2,3-triazole-5-carboxylic acid.

Intermediate 48

N-((1S)-(7-(Cyclopropyl(4,4,4-trifluorobutanamido)methyl)imidazo[1,2-a]pyrimidin-2-yl)(4,4-difluorocyclohexyl)methyl)-5-methyl-1-(3,3,3-trifluoropropyl)-1H-pyrazole-4-carboxamide

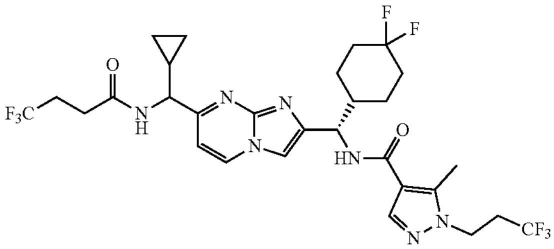 [SMILES: Cc1c(C(=O)N[C@H](c2cn3ccc(C(NC(=O)CCC(F)(F)F)C4CC4)nc3n2)C2CCC(F)(F)CC2)cnn1CCC(F)(F)F]

The title compound was prepared as described in the synthesis of Intermediate 19, using 5-methyl-1-(3,3,3-trifluoropropyl)-1H-pyrazole-4-carboxylic acid in place of 1-(3,3,3-trifluoropropyl)-1H-1,2,3-triazole-5-carboxylic acid.

Intermediate 49

N—((S)-(2-((S)-Amino(4,4-difluorocyclohexyl)methyl)imidazo[1,2-a]pyrimidin-7-yl)(cyclopropyl)methyl)-4,4,4-trifluorobutanamide

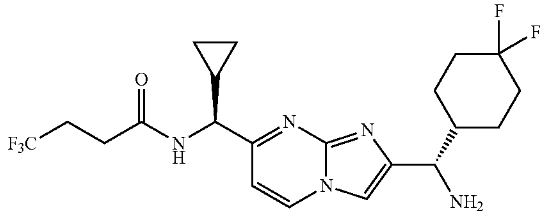

The title compound was prepared as described in the synthesis of Intermediate 28 using tert-butyl ((S)-(7-((S)-cyclopropyl(4,4,4-trifluorobutanamido)methyl)imidazo[1,2-a]pyrimidin-2-yl)(4,4-difluorocyclohexyl)methyl)carbamate (Intermediate 12) in place of tert-butyl ((1S)-(7-((1S)-cyclopropyl(4,4,4-trifluoro-3-methylbutanamido)methyl)imidazo[1,2-a]pyrimidin-2-yl)(4,4-difluorocyclohexyl)methyl)carbamate. The crude residue was lyophilized to provide the title compound as an off-white solid.

Intermediate 50

3-Cyclopropyl-N-((1S)-(7-((1S)-cyclopropyl(4,4,4-trifluoro-3-methylbutanamido)methyl)imidazo[1,2-a]pyrimidin-2-yl)(4,4-difluorocyclohexyl)methyl)isoxazole-4-carboxamide

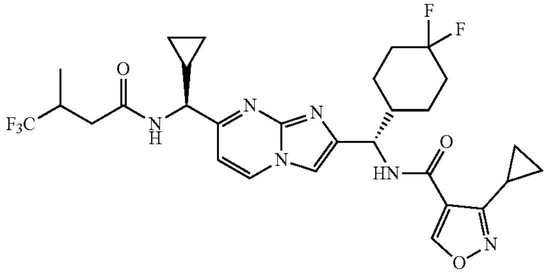 [SMILES: CC(CC(=O)N[C@H](c1ccn2cc([C@@H](NC(=O)c3conc3C3CC3)C3CCC(F)(F)CC3)nc2n1)C1CC1)C(F)(F)F]

The title compound was prepared as described for the synthesis of Intermediate 29, using 3-cyclopropylisoxazole-4-carboxylic acid in place of 2-(2,2,2-trifluoroethyl)pyridine-4-carboxylic acid.

Intermediate 51

N-((1S)-(7-((1S)-Cyclopropyl(4,4,4-trifluoro-3-methylbutanamido)methyl)imidazo[1,2-a]pyrimidin-2-yl)(4,4-difluorocyclohexyl)methyl)-3-(3,3,3-trifluoropropyl)isoxazole-4-carboxamide

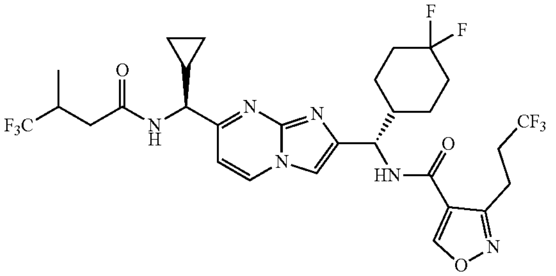 [SMILES: CC(CC(=O)N[C@H](c1ccn2cc([C@@H](NC(=O)c3conc3CCC(F)(F)F)C3CCC(F)(F)CC3)nc2n1)C1CC1)C(F)(F)F]

The title compound was prepared as described for the synthesis of Intermediate 29, using 3-(3,3,3-trifluoropropyl) isoxazole-4-carboxylic acid (Intermediate 34) in place of 2-(2,2,2-trifluoroethyl)pyridine-4-carboxylic acid.

Intermediate 52 tert-Butyl ((1S)-(7-((1R)-cyclopropyl(4,4,4-trifluoro-3-methylbutanamido)methyl)imidazo[1,2-a]pyrimidin-2-yl)(4,4-difluorocyclohexyl)methyl)carbamate

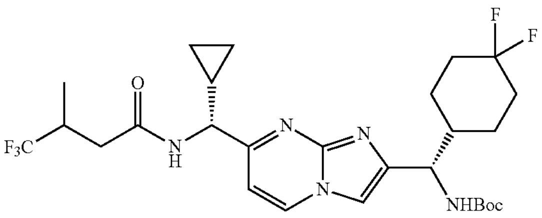 [SMILES: CC(CC(=O)N[C@@H](c1ccn2cc([C@@H](NC(=O)OC(C)(C)C)C3CCC(F)(F)CC3)nc2n1)C1CC1)C(F)(F)F]

The title compound was prepared as described for Intermediate 27 using tert-butyl ((S)-(7-((R)-amino(cyclopropyl)methyl)imidazo[1,2-a]pyrimidin-2-yl)(4,4-difluorocyclohexyl)methyl)carbamate (Intermediate 26) in place of tert-butyl ((S)-(7-((S)-amino(cyclopropyl)methyl)imidazo[1,2-a]pyrimidin-2-yl)(4,4-difluorocyclohexyl)methyl) carbamate.

Intermediate 53

N—((R)-(2-((S)-Amino(4,4-difluorocyclohexyl) methyl)imidazo[1,2-a]pyrimidin-7-yl)(cyclopropyl) methyl)-4,4,4-trifluoro-3-methylbutanamide

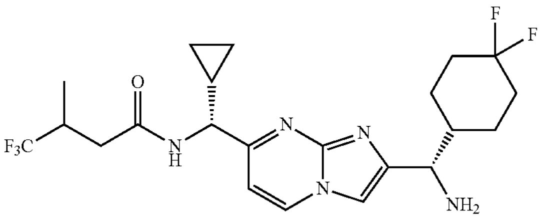 [SMILES: CC(CC(=O)N[C@@H](c1ccn2cc([C@@H](N)C3CCC(F)(F)CC3)nc2n1)C1CC1)C(F)(F)F]

The title compound was prepared as described for Intermediate 28 using tert-butyl ((1S)-(7-((1R)-cyclopropyl(4,4,4-trifluoro-3-methylbutanamido)methyl)imidazo[1,2-a]pyrimidin-2-yl)(4,4-difluorocyclohexyl)methyl)carbamate (Intermediate 52) in place of tert-butyl ((1S)-(7-((1S)-cyclopropyl(4,4,4-trifluoro-3-methylbutanamido)methyl)imidazo[1,2-a]pyrimidin-2-yl)(4,4-difluorocyclohexyl)methyl)carbamate.

Intermediate 54

N-((1S)-(7-((1R)-Cyclopropyl(4,4,4-trifluoro-3-methylbutanamido)methyl)imidazo[1,2-a]pyrimidin-2-yl)(4,4-difluorocyclohexyl)methyl)-1-(cyclopropylmethyl)-1H-1,2,4-triazole-5-carboxamide

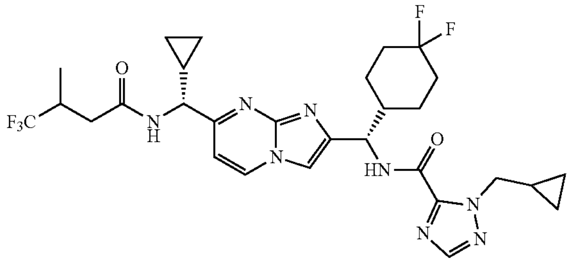 [SMILES: CC(CC(=O)N[C@@H](c1ccn2cc([C@@H](NC(=O)c3ncnn3CC3CC3)C3CCC(F)(F)CC3)nc2n1)C1CC1)C(F)(F)F]

The title compound was prepared as described for the synthesis of Intermediate 29, using N—((R)-(2-((S)-amino(4,4-difluorocyclohexyl)methyl)imidazo[1,2-a]pyrimidin-7-yl)(cyclopropyl)methyl)-4,4,4-trifluoro-3-methylbutanamide (Intermediate 53) in place of N—((S)-(2-((S)-amino(4,4-difluorocyclohexyl)methyl)imidazo[1,2-a]pyrimidin-7-yl)(cyclopropyl)methyl)-4,4,4-trifluoro-3-methylbutanamide and 1-(cyclopropylmethyl)-1H-1,2,4-triazole-5-carboxylic acid in place of 2-(2,2,2-trifluoroethyl) pyridine-4-carboxylic acid.

Intermediate 55

N-((1S)-(7-((1R)-Cyclopropyl(4,4,4-trifluoro-3-methylbutanamido)methyl)imidazo[1,2-a]pyrimidin-2-yl)(4,4-difluorocyclohexyl)methyl)-1-isopropyl-1H-1,2,4-triazole-5-carboxamide

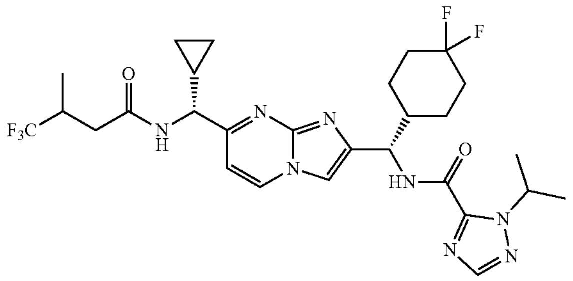 [SMILES: CC(C)n1ncnc1C(=O)N[C@H](c1cn2ccc([C@H](NC(=O)CC(C)C(F)(F)F)C3CC3)nc2n1)C1CCC(F)(F)CC1]

The title compound was prepared as described for the synthesis of Intermediate 29, using N—((R)-(2-((S)-amino(4,4-difluorocyclohexyl)methyl)imidazo[1,2-a]pyrimidin-7-yl)(cyclopropyl)methyl)-4,4,4-trifluoro-3-methylbutanamide (Intermediate 53) in place of N—((S)-(2-((S)-amino(4,4-difluorocyclohexyl)methyl)imidazo[1,2-a]pyrimidin-7- yl)(cyclopropyl)methyl)-4,4,4-trifluoro-3-methylbutanamide and 1-isopropyl-1H-1,2,4-triazole-5-carboxylic acid in place of 2-(2,2,2-trifluoroethyl)pyridine-4-carboxylic acid.

Intermediate 56 trans-(1,2)-N-((1S)-(7-((1R)-Cyclopropyl(4,4,4-trifluoro-3-methylbutanamido)methyl)imidazo[1,2-a]pyrimidin-2-yl)(4,4-difluorocyclohexyl)methyl)-2-(trifluoromethyl)cyclopropane-1-carboxamide

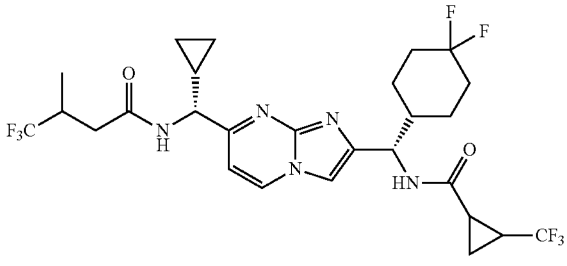 [SMILES: CC(CC(=O)N[C@@H](c1ccn2cc([C@@H](NC(=O)C3CC3C(F)(F)F)C3CCC(F)(F)CC3)nc2n1)C1CC1)C(F)(F)F]

The title compound was prepared as described for the synthesis of Intermediate 29, using N—((R)-(2-((S)-amino(4,4-difluorocyclohexyl)methyl)imidazo[1,2-a]pyrimidin-7-yl)(cyclopropyl)methyl)-4,4,4-trifluoro-3-methylbutanamide (Intermediate 53) in place of N—((S)-(2-((S)-amino(4,4-difluorocyclohexyl)methyl)imidazo[1,2-a]pyrimidin-7-yl)(cyclopropyl)methyl)-4,4,4-trifluoro-3-methylbutanamide and trans-2-(trifluoromethyl)cyclopropane-1-carboxylic acid in place of 2-(2,2,2-trifluoroethyl)pyridine-4-carboxylic acid. The above method produced four diastereomers which were separated into Examples 5 and 6.

Intermediate 57

N—((R)-(2-((S)-Amino(4,4-difluorocyclohexyl)methyl)-3-fluoroimidazo[1,2-a]pyrimidin-7-yl)(cyclopropyl)methyl)-4,4,4-trifluorobutanamide

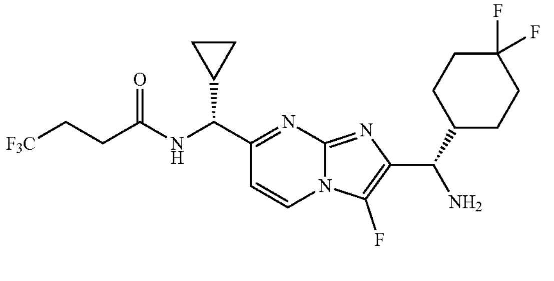 [SMILES: N[C@H](c1nc2nc([C@H](NC(=O)CCC(F)(F)F)C3CC3)ccn2c1F)C1CCC(F)(F)CC1]

A vial was charged with a stir bar, N—((R)-(2-((S)-amino(4,4-difluorocyclohexyl)methyl)imidazo[1,2-a]pyrimidin-7-yl)(cyclopropyl)methyl)-4,4,4-trifluorobutanamide (200 mg, 0.44 mmol, Intermediate 41), Selectfluor™ (386 mg, 1.09 mmol), and MeCN (8 mL). The reaction was stirred for an hour and had progressed to 60% conversion. The reaction was quenched by the addition of water and extracted with EtOAc (3×5 mL). The combined organics were washed with brine, dried over anhydrous $MgSO_4$, filtered and condensed. The crude material was purified by preparative HPLC (XBridge® Prep, 5 μM, C18 OBD™, 50×100 mm, 0-100% acetonitrile/water (with 20 mM $NH_4OH$). The product containing fractions were lyophilized to provide the title compound as a white solid.

Intermediate 58 tert-Butyl ((1S)-(7-((1R)-cyclopropyl(2-(2,2-difluorocyclopropyl)acetamido)methyl)imidazo[1,2-a]pyrimidin-2-yl)(4,4-difluorocyclohexyl)methyl)carbamate

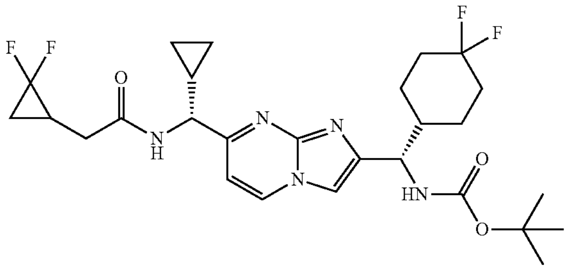 [SMILES: CC(C)(C)OC(=O)N[C@H](c1cn2ccc([C@H](NC(=O)CC3CC3(F)F)C3CC3)nc2n1)C1CCC(F)(F)CC1]

The title compound was prepared as described in the synthesis of Intermediate 27, using tert-butyl ((S)-(7-((R)-amino(cyclopropyl)methyl)imidazo[1,2-a]pyrimidin-2-yl)(4,4-difluorocyclohexyl)methyl)carbamate (Intermediate 26) in place of tert-butyl ((S)-(7-((S)-amino(cyclopropyl)methyl)imidazo[1,2-a]pyrimidin-2-yl)(4,4-difluorocyclohexyl)methyl)carbamate and (2,2-difluorocyclopropyl)acetic acid in place of 3-trifluoromethylbutyric acid. The crude material was purified by FCC (0-100% EtOAc/hexanes) to provide the title compound as a yellow foam.

Intermediate 59

N—((R)-(2-((S)-Amino(4,4-difluorocyclohexyl)methyl)imidazo[1,2-a]pyrimidin-7-yl)(cyclopropyl)methyl)-2-(2,2-difluorocyclopropyl)acetamide

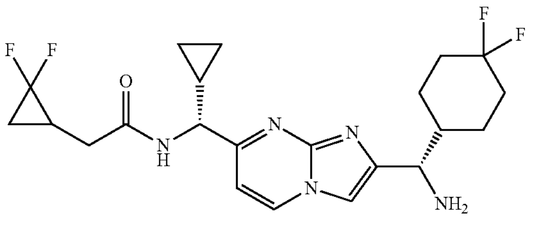 [SMILES: N[C@H](c1cn2ccc([C@H](NC(=O)CC3CC3(F)F)C3CC3)nc2n1)C1CCC(F)(F)CC1]

The title compound was prepared as described in the synthesis of Intermediate 28, using tert-butyl ((1S)-(7-((1R)-cyclopropyl(2-(2,2-difluorocyclopropyl)acetamido)methyl)imidazo[1,2-a]pyrimidin-2-yl)(4,4-difluorocyclohexyl)methyl)carbamate (Intermediate 58) in place of tert-butyl ((1S)-(7-((1S)-cyclopropyl(4,4,4-trifluoro-3-methylbutanamido)methyl)imidazo[1,2-a]pyrimidin-2-yl)(4,4-difluorocyclohexyl)methyl)carbamate to provide the title compound as a yellow amorphous solid.

Intermediate 60 tert-Butyl ((S)-(7-((R)-((((9H-fluoren-9-yl)methoxy)carbonyl)amino)(cyclopropyl)methyl)imidazo[1,2-a]pyrimidin-2-yl)(4,4-difluorocyclohexyl)methyl)carbamate

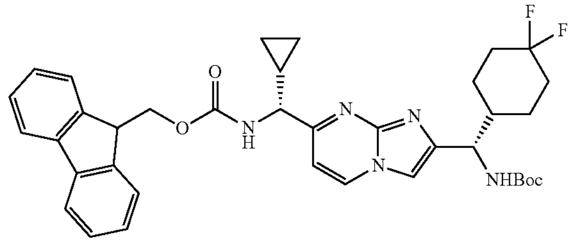 [SMILES: CC(C)(C)OC(=O)N[C@H](c1cn2ccc([C@H](NC(=O)OCC3c4ccccc4-c4ccccc43)C3CC3)nc2n1)C1CCC(F)(F)CC1]

To a mixture of tert-butyl ((S)-(7-((R)-amino(cyclopropyl)methyl)imidazo[1,2-a]pyrimidin-2-yl)(4,4-difluorocyclohexyl)methyl)carbamate (2 g, 4.6 mmol, Intermediate 26) in DCM (20 mL) were added DIPEA (1.37 mL, 8.27 mmol) and Fmoc-Cl (1.31 g, 5.05 mmol) and the resulting mixture stirred at rt for 2 h. The reaction was concentrated to dryness, then partitioned between water (20 mL) and EtOAc (20 mL). The aqueous layer was further extracted with EtOAc (2x20 mL) and the organic layers were combined, washed with brine (30 mL), dried over anhydrous $Na_2SO_4$, filtered and concentrated to dryness. The residue was purified by FCC (0-50% EtOAc/petroleum ether) to provide the title compound.

Intermediate 61

(9H-Fluoren-9-yl)methyl ((R)-(2-((S)-amino(4,4-difluorocyclohexyl)methyl)imidazo[1,2-a]pyrimidin-7-yl)(cyclopropyl)methyl)carbamate hydrochloride

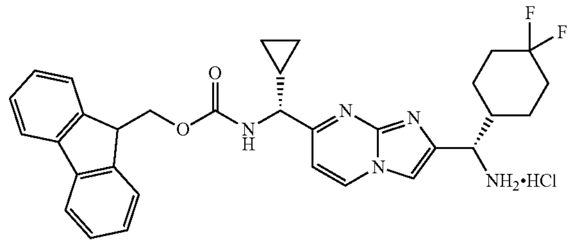

To a solution of tert-butyl ((S)-(7-((R)-((((9H-fluoren-9-yl)methoxy)carbonyl)amino)(cyclopropyl)methyl)imidazo[1,2-a]pyrimidin-2-yl)(4,4-difluorocyclohexyl)methyl)carbamate (3.0 g, 4.5 mmol, Intermediate 60) in DCM (4 mL) was added HCl (11 mL, 11 mmol, 1 M in EtOAc), and the resulting mixture was stirred at rt for 2 h. The mixture was concentrated to dryness to provide the title compound as a white solid.

Intermediate 62

(9H-Fluoren-9-yl)methyl ((R)-cyclopropyl(2-((S)-(4,4-difluorocyclohexyl)(4-methyl-1,2,5-oxadiazole-3-carboxamido)methyl)imidazo[1,2-a]pyrimidin-7-yl)methyl)carbamate

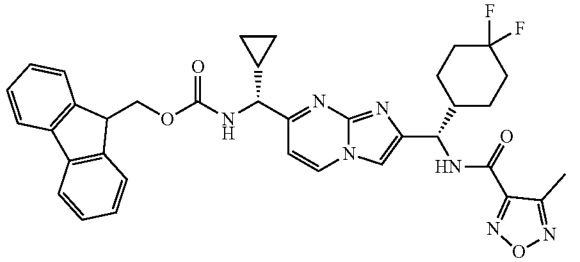 [SMILES: Cc1nonc1C(=O)N[C@H](c1cn2ccc([C@H](NC(=O)OCC3c4ccccc4-c4ccccc43)C3CC3)nc2n1)C1CCC(F)(F)CC1]

To a mixture of (9H-fluoren-9-yl)methyl ((R)-(2-((S)-amino(4,4-difluorocyclohexyl)methyl)imidazo[1,2-a]pyrimidin-7-yl)(cyclopropyl)methyl)carbamate hydrochloride (2.0 g, 3.6 mmol, Intermediate 61) and DIPEA (2.6 mL, 18 mmol) in DMF (5 mL) was added 4-methyl-1,2,5-oxadiazole-3-carboxylic acid (550 mg, 4.3 mmol) followed by HATU (1.6 g, 4.3 mmol), and the resulting mixture stirred at rt for 16 h. After that time, the reaction was quenched by the addition of saturated aqueous $NaHCO_3$ and extracted with EtOAc (3x25 mL). The organic layers were combined, dried over anhydrous $Na_2SO_4$, filtered and concentrated to dryness. The residue was purified by FCC (0-50% EtOAc/petroleum ether) to provide the title compound as a white solid.

Intermediate 63

N—((S)-(7-((R)-Amino(cyclopropyl)methyl)imidazo[1,2-a]pyrimidin-2-yl)(4,4-difluorocyclohexyl)methyl)-4-methyl-1,2,5-oxadiazole-3-carboxamide

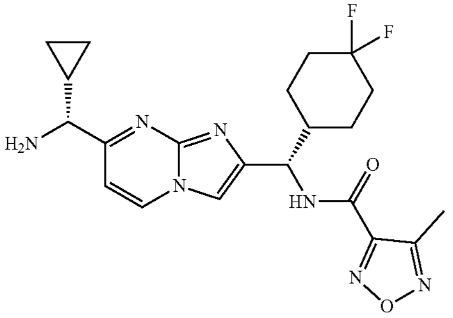 [SMILES: Cc1nonc1C(=O)N[C@H](c1cn2ccc([C@H](N)C3CC3)nc2n1)C1CCC(F)(F)CC1]

Piperidine (0.58 g, 6.8 mmol) was added to a mixture of (9H-fluoren-9-yl)methyl ((R)-cyclopropyl(2-((S)-(4,4-difluorocyclohexyl)(4-methyl-1,2,5-oxadiazole-3-carboxamido)methyl)imidazo[1,2-a]pyrimidin-7-yl)methyl)carbamate (1.6 g, 2.3 mmol, Intermediate 62) in DCM (15 mL), and the resulting mixture was stirred at rt for 2 h. The mixture was concentrated to dryness and purified by FCC twice (0-100% EtOAc/$Et_2O$ followed by 0-15% MeOH/EtOAc) followed by SFC (DAICEL CHIRALPAK AD, 30×250 mm, 10 μm, 60% EtOH (0.1% $NH_4OH$)/$CO_2$) to provide the title compound as a white solid.

Intermediate 64

3-Fluorobicyclo[1.1.1]pentane-1-carbonyl chloride

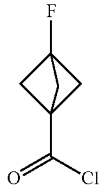

To a solution of 3-fluorobicyclo[1.1.1]pentane-1-carboxylic acid (0.3 g, 2.30 mmol) in DCM (5 mL) and DMF (0.02 ml) was added oxalyl chloride (438 mg, 3.45 mmol) in DCM (1 mL), and the resulting solution was stirred at rt for 2 h. After that time, the solvent was removed under reduced pressure to provide the title compound as a yellow oil.

Intermediate 65

2-Diazo-1-(3-fluorobicyclo[1.1.1]pentan-1-yl)ethan-1-one

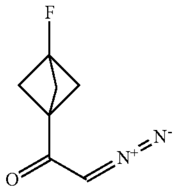 [SMILES: [N-]=[N+]=CC(=O)C12CC(F)(C1)C2]

To a solution of 3-fluorobicyclo[1.1.1]pentane-1-carbonyl chloride (330 mg, 2.22 mmol, Intermediate 64) in ACN (2 mL) and THF (2 mL) at 0° C. was added (diazomethyl) trimethylsilane (2.22 mL, 4.44 mmol), and the resulting mixture was stirred at rt for 3 h. The reaction was concentrated to dryness and then dissolved in $Et_2O$ and washed with 0.5 M aqueous citric acid followed by saturated aqueous $NaHCO_3$ (5 mL). The organic layer was concentrated to dryness to provide the title compound as a yellow oil.

Intermediate 66

Ethyl 5-(pyrrolidin-1-yl)-4-(2,2,2-trifluoroethyl)-4,5-dihydroisoxazole-3-carboxylate

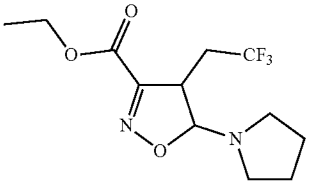 [SMILES: CCOC(=O)C1=NOC(N2CCCC2)C1CC(F)(F)F]

4,4,4-Trifluorobutyraldehyde (0.28 mL, 2.6 mmol) was added to a solution of pyrrolidine (0.12 mL, 1.5 mmol) and triethylamine (0.092 mL, 0.66 mmol) in DCM (1.3 mL) at 0° C. A solution of ethyl 2-chloro-2-(hydroxyamino)acetate (100 mg, 0.66 mmol) in DCM (6.6 mL) was added in 5 portions over 5 min intervals. After 10 min, the ice bath was removed and the reaction was allowed to stir at rt for 1.5 h. The solution was then concentrated under reduced pressure and carried on crude without further purification.

Intermediate 67

Ethyl 4-(2,2,2-trifluoroethyl)isoxazole-3-carboxylate

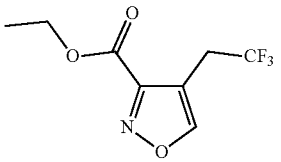

mCPBA (180 mg, 1.1 mmol) was added to a solution of ethyl 5-(pyrrolidin-1-yl)-4-(2,2,2-trifluoroethyl)-4,5-dihydroisoxazole-3-carboxylate (190 mg, 0.66 mmol, Intermediate 66) in DCM (2.5 mL) at rt. The reaction was stirred at rt for 2 h and was subsequently quenched with a saturated aqueous solution of $NaHCO_3$. The biphasic mixture was transferred to a separatory funnel and extracted with EtOAc (3×20 mL). The combined organic layers were washed with a saturated aqueous solution of $NaHCO_3$ and brine, dried over anhydrous $MgSO_4$, filtered, and concentrated under reduced pressure. Purification by FCC (0-45% EtOAc/hexanes) yielded the title compound.

Intermediate 68

4-(2,2,2-Trifluoroethyl)isoxazole-3-carboxylic acid

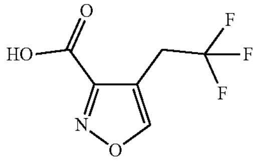 [SMILES: O=C(O)c1nocc1CC(F)(F)F]

Ethyl 4-(2,2,2-trifluoroethyl)isoxazole-3-carboxylate (110 mg, 0.49 mmol, Intermediate 67) was dissolved in THF (0.29 mL) and a solution of LiOH (24 mg, 0.99 mmol) in water (0.49 mL) was added dropwise. The mixture stirred until full consumption of starting material (about 1 h), at which time the reaction was acidified with 1 N aqueous HCl and diluted with water (10 mL). The mixture was extracted with 20% IPA in $CHCl_3$ (15 mL×3). The combined organic layers were washed with brine, dried over anhydrous $MgSO_4$, filtered, and concentrated to afford the title compound as an off-white solid that was used without further purification.

EXAMPLES

Example 1

N—((S)-(7-((R*)-Cyclopropyl(4,4,4-trifluorobutanamido)methyl)imidazo[1,2-a]pyrimidin-2-yl)(4,4-difluorocyclohexyl)methyl)-1-(3,3,3-trifluoropropyl)-1H-1,2,3-triazole-5-carboxamide

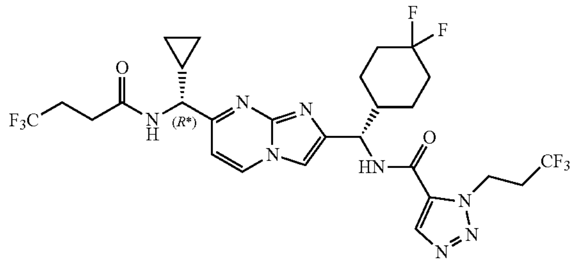 [SMILES: O=C(CCC(F)(F)F)N[C@@H](c1ccn2cc([C@@H](NC(=O)c3cnnn3CCC(F)(F)F)C3CCC(F)(F)CC3)nc2n1)C1CC1]

Example 2

N—((S)-(7-((S*)-Cyclopropyl(4,4,4-trifluorobutanamido)methyl)imidazo[1,2-a]pyrimidin-2-yl)(4,4-difluorocyclohexyl)methyl)-1-(3,3,3-trifluoropropyl)-1H-1,2,3-triazole-5-carboxamide

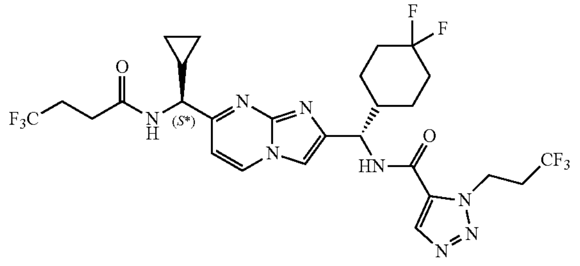 [SMILES: O=C(CCC(F)(F)F)N[C@H](c1ccn2cc([C@@H](NC(=O)c3cnnn3CCC(F)(F)F)C3CCC(F)(F)CC3)nc2n1)C1CC1]

N-((1S)-(7-(Cyclopropyl(4,4,4-trifluorobutanamido)methyl)imidazo[1,2-a]pyrimidin-2-yl)(4,4-difluorocyclohexyl)methyl)-1-(3,3,3-trifluoropropyl)-1H-1,2,3-triazole-5-carboxamide (Intermediate 19) was purified by SFC using a chiral stationary phase (Whelk-01 (S,S), 25:75 MeOH/$CO_2$) to give a pair of diastereomers. The first-eluting isomer was re-purified by preparative HPLC (XBridge C18, 10-100% MeCN/aqueous $NH_4OH$ (20 mM)) to give Example 1 as a colorless solid. The second-eluting isomer was re-purified by preparative HPLC (XBridge C18, 10% to 100% MeCN/aqueous $NH_4OH$ (20 mM)) to give Example 2 as a colorless solid. Example 1: $^1H$ NMR (500 MHz, DMSO-$d_6$) δ 9.20 (d, J=9.0 Hz, 1H), 8.87 (d, J=6.9 Hz, 1H), 8.72 (d, J=7.5 Hz, 1H), 8.45 (s, 1H), 7.83 (s, 1H), 7.04 (d, J=7.0 Hz, 1H), 5.14 (t, J=8.7 Hz, 1H), 4.99-4.84 (m, 2H), 4.25 (t, J=8.3 Hz, 1H), 2.99-2.85 (m, 2H), 2.52-2.38 (m, 4H), 2.28-2.17 (m, 1H), 2.11-1.87 (m, 3H), 1.87-1.68 (m, 2H), 1.68-1.57 (m, 1H), 1.45-1.14 (m, 3H), 0.60-0.35 (m, 4H). MS (ESI) m/z: $[M+H]^+$ Found 651.3. Example 2: $^1H$ NMR (400 MHz, DMSO-$d_6$) δ 9.19 (d, J=8.9 Hz, 1H), 8.88 (d, J=6.9 Hz, 1H), 8.72 (d, J=7.6 Hz, 1H), 8.46 (s, 1H), 7.84 (s, 1H), 7.05 (d, J=7.0 Hz, 1H), 5.15 (t, J=8.6 Hz, 1H), 4.98-4.86 (m, 2H), 4.31-4.25 (m, 1H), 3.00-2.86 (m, 2H), 2.55-2.39 (m, 4H), 2.29-2.16 (m, 1H), 2.13-1.60 (m, 6H), 1.47-1.17 (m, 3H), 0.59-0.37 (m, 4H). MS (ESI) m/z: $[M+H]^+$ Found 651.3.

Example 3

N—((S)-(7-((S)-Cyclopropyl((R*)-4,4,4-trifluoro-3-methylbutanamido)methyl)imidazo[1,2-a]pyrimidin-2-yl)(4,4-difluorocyclohexyl)methyl)-2-(2,2,2-trifluoroethyl)isonicotinamide

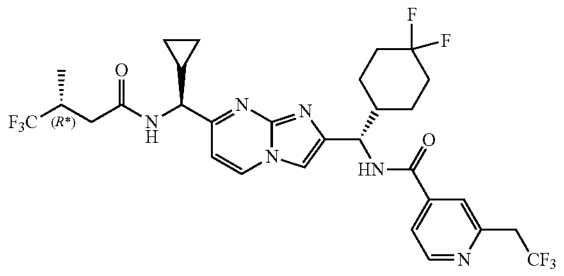 [SMILES: C[C@H](CC(=O)N[C@H](c1ccn2cc([C@@H](NC(=O)c3ccnc(CC(F)(F)F)c3)C3CCC(F)(F)CC3)nc2n1)C1CC1)C(F)(F)F]

Example 4

N—((S)-(7-((S)-Cyclopropyl((S*)-4,4,4-trifluoro-3-methylbutanamido)methyl)imidazo[1,2-a]pyrimidin-2-yl)(4,4-difluorocyclohexyl)methyl)-2-(2,2,2-trifluoroethyl)isonicotinamide

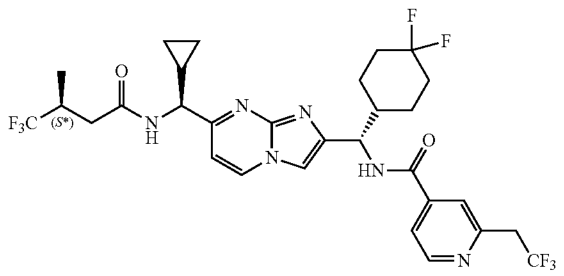 [SMILES: C[C@@H](CC(=O)N[C@H](c1ccn2cc([C@@H](NC(=O)c3ccnc(CC(F)(F)F)c3)C3CCC(F)(F)CC3)nc2n1)C1CC1)C(F)(F)F]

N-((1S)-(7-((1S)-Cyclopropyl(4,4,4-trifluoro-3-methylbutanamido)methyl)imidazo[1,2-a]pyrimidin-2-yl)(4,4-difluorocyclohexyl)methyl)-2-(2,2,2-trifluoroethyl)isonicotinamide (Intermediate 29) was purified twice by SFC using a chiral stationary phase (Whelk-O1 (S,S), 21.2×250 mm, 30:70 i-PrOH/$CO_2$ followed by CHIRALCEL OD-H, 30×250 mm, 9:91 i-PrOH (0.3% i-$PrNH_2$)/$CO_2$) to give a pair of diastereomers. The first-eluting isomer was Example 3 and the second eluting isomer was Example 4. Example 3: $^1H$ NMR (600 MHz, DMSO-$d_6$) δ 9.09 (d, J=9.0 Hz, 1H), 8.87 (d, J=6.9 Hz, 1H), 8.76 (d, J=7.6 Hz, 1H), 8.74-8.70 (m, 1H), 7.85 (s, 1H), 7.83 (s, 1H), 7.81 (dd, J=1.5, 5.1 Hz, 1H), 7.04 (d, J=6.9 Hz, 1H), 5.17 (t, J=8.6 Hz, 1H), 4.36-4.18 (m, 1H), 3.89 (q, J=11.4 Hz, 2H), 2.85-2.68 (m, 1H), 2.49-2.45 (m, 1H), 2.35-2.27 (m, 1H), 2.27-2.18 (m, 1H), 2.10-1.96 (m, 2H), 1.95-1.88 (m, 1H), 1.86-1.72 (m, 2H), 1.71-1.64 (m, 1H), 1.46-1.36 (m, 1H), 1.34-1.27 (m, 1H), 1.26-1.21 (m, 1H), 1.07 (d, J=6.9 Hz, 3H), 0.58-0.45 (m, 3H), 0.44-0.37 (m, 1H). MS (ESI) m/z: $[M+H]^+$ Found 661.3. Example 4: $^1H$ NMR (600 MHz, DMSO-$d_6$) δ 9.09 (d, J=8.8 Hz, 1H), 8.87 (d, J=7.1 Hz, 1H), 8.77 (d, J=7.6 Hz, 1H), 8.72 (d, J=5.1

Hz, 1H), 7.85 (s, 1H), 7.83 (s, 1H), 7.81 (dd, J=1.7, 5.1 Hz, 1H), 7.05 (d, J=6.9 Hz, 1H), 5.17 (t, J=8.6 Hz, 1H), 4.33-4.16 (m, 1H), 3.89 (q, J=11.4 Hz, 2H), 2.82-2.68 (m, 1H), 2.56-2.52 (m, 1H), 2.32-2.25 (m, 1H), 2.25-2.18 (m, 1H), 2.10-1.96 (m, 2H), 1.94-1.87 (m, 1H), 1.86-1.72 (m, 2H), 1.71-1.64 (m, 1H), 1.47-1.37 (m, 1H), 1.34-1.26 (m, 1H), 1.25-1.19 (m, 1H), 1.02 (d, J=6.9 Hz, 3H), 0.58-0.52 (m, 1H), 0.52-0.44 (m, 2H), 0.43-0.35 (m, 1H). MS (ESI) m/z: $[M+H]^+$ Found 661.2.

Example 5 trans-(1,2)-N—((S)-(7-((R)-Cyclopropyl-4,4,4-trifluoro-3-methylbutanamido)methyl)imidazo[1,2-a]pyrimidin-2-yl)(4,4-difluorocyclohexyl)methyl)-2-(trifluoromethyl)cyclopropane-1-carboxamide

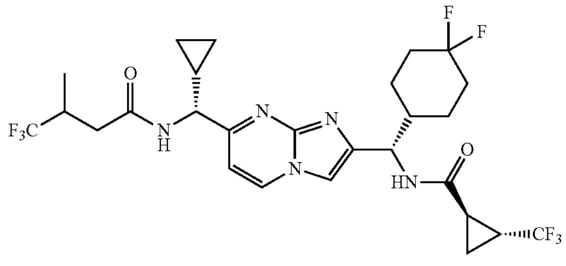 [SMILES: CC(CC(=O)N[C@@H](c1ccn2cc([C@@H](NC(=O)[C@@H]3C[C@H]3C(F)(F)F)C3CCC(F)(F)CC3)nc2n1)C1CC1)C(F)(F)F]

Example 6 trans-(1,2)-N-((1S)-(7-((1R)-Cyclopropyl-(4,4,4-trifluoro-3-methylbutanamido)methyl)imidazo[1,2-a]pyrimidin-2-yl)(4,4-difluorocyclohexyl)methyl)-2-(trifluoromethyl)cyclopropane-1-carboxamide

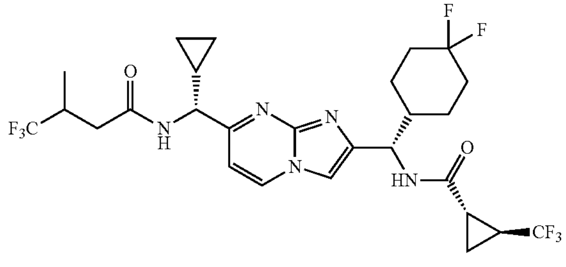 [SMILES: CC(CC(=O)N[C@@H](c1ccn2cc([C@@H](NC(=O)[C@H]3C[C@@H]3C(F)(F)F)C3CCC(F)(F)CC3)nc2n1)C1CC1)C(F)(F)F]

trans-(1,2)-N-((1S)-(7-((1R)-Cyclopropyl(4,4,4-trifluoro-3-methylbutanamido)methyl)imidazo[1,2-a]pyrimidin-2-yl)(4,4-difluorocyclohexyl)methyl)-2-(trifluoromethyl)cyclopropane-1-carboxamide (Intermediate 56, four diastereomers) was purified by SFC using a chiral stationary phase (OD-H 2×25 cm/15% (2:1) heptane:IPA/$CO_2$, 100 bar 70 mL/min) to provide two products (Examples 5 and 6) which are each a 1:1 mixture of two diastereomers. The first eluting material was Example 5 and the second eluting material was Example 6. Example 5: $^1$H NMR (600 MHz, DMSO-$d_6$) δ 8.89 (dd, J=1.0, 7.1 Hz, 1H), 8.81 (d, J=9.3 Hz, 1H), 8.77 (dd, J=5.2, 7.7 Hz, 1H), 7.72 (d, J=1.1 Hz, 1H), 7.05 (dd, J=1.2, 7.0 Hz, 1H), 5.07-4.82 (m, 1H), 4.35-4.16 (m, 1H), 2.80-2.71 (m, 1H), 2.57-2.52 (m, 1H), 2.38-2.23 (m, 2H), 2.11-1.91 (m, 4H), 1.84-1.68 (m, 3H), 1.62-1.53 (m, 1H), 1.39-1.28 (m, 1H), 1.27-1.14 (m, 4H), 1.11-0.98 (m, 3H), 0.58-0.45 (m, 3H), 0.44-0.35 (m, 1H). MS (ESI) m/z: $[M+H]^+$ Found 610.3. Example 6: $^1$H NMR (600 MHz, DMSO-$d_6$) δ 8.87 (d, J=6.9 Hz, 1H), 8.81-8.73 (m, 2H), 7.71 (d, J=0.8 Hz, 1H), 7.05 (dd, J=1.3, 7.1 Hz, 1H), 5.05-4.93 (m, 1H), 4.33-4.22 (m, 1H), 4.14-4.01 (m, 1H), 2.82-2.69 (m, 1H), 2.56-2.52 (m, 1H), 2.37-2.23 (m, 2H), 2.17-2.10 (m, 1H), 2.10-1.92 (m, 3H), 1.86-1.69 (m, 3H), 1.64-1.57 (m, 1H), 1.43-1.31 (m, 1H), 1.27-1.17 (m, 2H), 1.14-1.10 (m, 1H), 1.09-0.98 (m, 3H), 0.59-0.44 (m, 3H), 0.44-0.36 (m, 1H). MS (ESI) m/z: $[M+H]^+$ Found 610.3.

Example 7

N—((S)-(7-((S)-Cyclopropyl((S*)-4,4,4-trifluoro-3-methylbutanamido)methyl)imidazo[1,2-a]pyrimidin-2-yl)(4,4-difluorocyclohexyl)methyl)-3-(3,3,3-trifluoropropyl)isoxazole-4-carboxamide

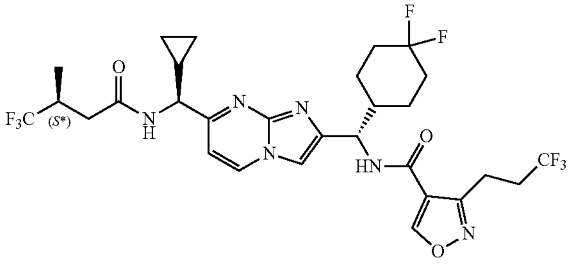 [SMILES: C[C@@H](CC(=O)N[C@H](c1ccn2cc([C@@H](NC(=O)c3conc3CCC(F)(F)F)C3CCC(F)(F)CC3)nc2n1)C1CC1)C(F)(F)F]

Example 8

N—((S)-(7-((S)-Cyclopropyl((R*)-4,4,4-trifluoro-3-methylbutanamido)methyl)imidazo[1,2-a]pyrimidin-2-yl)(4,4-difluorocyclohexyl)methyl)-3-(3,3,3-trifluoropropyl)isoxazole-4-carboxamide

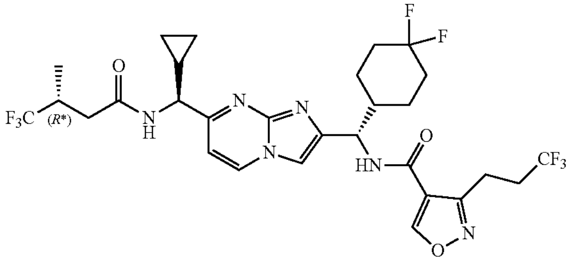 [SMILES: C[C@H](CC(=O)N[C@H](c1ccn2cc([C@@H](NC(=O)c3conc3CCC(F)(F)F)C3CCC(F)(F)CC3)nc2n1)C1CC1)C(F)(F)F]

N-((1S)-(7-((1S)-Cyclopropyl(4,4,4-trifluoro-3-methylbutanamido)methyl)imidazo[1,2-a]pyrimidin-2-yl)(4,4-difluorocyclohexyl)methyl)-3-(3,3,3-trifluoropropyl)isoxazole-4-carboxamide (Intermediate 51) was purified by SFC using a chiral stationary phase (CHIRALCEL OD-H, 5 μm, 250×30 mm, 91% $CO_2$, 9% IPA (with 0.3% $iPrNH_2$)) to give a pair of diastereomers. The first eluting isomer was Example 8 and the second eluting isomer was Example 7. Both isomers were further purified by preparative HPLC (XBridge® Prep, 5 μM, C18 OBD™, 50×100 mm, 0-100% acetonitrile/water (with 20 mM $NH_4OH$). The product containing fractions were lyophilized into white powders. Example 7: $^1$H NMR (500 MHz, DMSO-$d_6$) δ 9.51 (s, 1H), 8.86 (d, J=7.0 Hz, 1H), 8.82-8.73 (m, 2H), 7.80 (s, 1H), 7.04

(d, J=7.0 Hz, 1H), 5.14 (t, J=8.5 Hz, 1H), 4.33-4.16 (m, 1H), 3.15-3.01 (m, 2H), 2.80-2.61 (m, 3H), 2.57-2.52 (m, 1H), 2.33-2.22 (m, 1H), 2.21-2.10 (m, 1H), 2.10-1.94 (m, 2H), 1.92-1.70 (m, 3H), 1.69-1.59 (m, 1H), 1.45-1.17 (m, 3H), 1.02 (d, J=6.9 Hz, 3H), 0.60-0.53 (m, 1H), 0.51-0.44 (m, 2H), 0.43-0.35 (m, 1H). MS (ESI) m/z: $[M+H]^+$ Found 665.3. Example 8: $^1H$ NMR (500 MHz, DMSO-$d_6$) δ 9.51 (s, 1H), 8.87 (d, J=6.9 Hz, 1H), 8.82-8.72 (m, 2H), 7.81 (s, 1H), 7.04 (d, J=6.9 Hz, 1H), 5.21-5.07 (m, 1H), 4.32-4.20 (m, 1H), 3.13-2.97 (m, 2H), 2.81-2.62 (m, 3H), 2.49-2.45 (m, 1H), 2.35-2.27 (m, 1H), 2.22-2.13 (m, 1H), 2.10-1.94 (m, 2H), 1.93-1.70 (m, 3H), 1.68-1.60 (m, 1H), 1.47-1.18 (m, 3H), 1.07 (d, J=6.9 Hz, 3H), 0.60-0.44 (m, 3H), 0.44-0.34 (m, 1H). MS (ESI) m/z: $[M+H]^+$ Found 665.3.

Example 9

3-Cyclopropyl-N—((S)-(7-((S)-cyclopropyl((S*)-4,4,4-trifluoro-3-methylbutanamido)methyl)imidazo[1,2-a]pyrimidin-2-yl)(4,4-difluorocyclohexyl)methyl) isoxazole-4-carboxamide

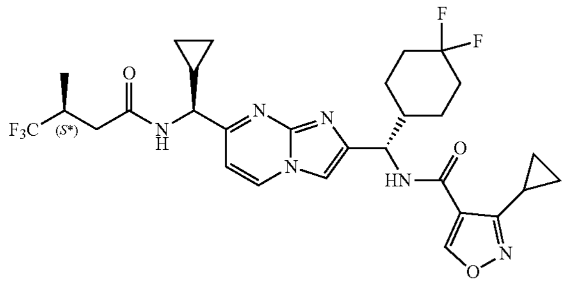 [SMILES: C[C@@H](CC(=O)N[C@H](c1ccn2cc([C@@H](NC(=O)c3conc3C3CC3)C3CCC(F)(F)CC3)nc2n1)C1CC1)C(F)(F)F]

Example 10

3-Cyclopropyl-N—((S)-(7-((S)-cyclopropyl((R*)-4,4,4-trifluoro-3-methylbutanamido)methyl)imidazo[1,2-a]pyrimidin-2-yl)(4,4-difluorocyclohexyl)methyl) isoxazole-4-carboxamide

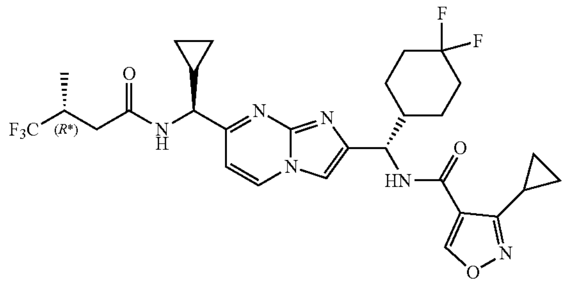 [SMILES: C[C@H](CC(=O)N[C@H](c1ccn2cc([C@@H](NC(=O)c3conc3C3CC3)C3CCC(F)(F)CC3)nc2n1)C1CC1)C(F)(F)F]

3-Cyclopropyl-N-((1S)-(7-((1S)-cyclopropyl(4,4,4-trifluoro-3-methylbutanamido)methyl)imidazo[1,2-a]pyrimidin-2-yl)(4,4-difluorocyclohexyl)methyl)isoxazole-4-carboxamide (Intermediate 50) was purified by SFC using a chiral stationary phase (CHIRALCEL OD-H, 5 μm, 250×30 mm, Mobile phase: 91% $CO_2$, 9% IPA (0.3% $iPrNH_2$)) to give a pair of diastereomers. The first eluting isomer was Example 10 and the second eluting isomer was Example 9. Example 9: $^1H$ NMR (500 MHz, DMSO-$d_6$) δ 9.36 (s, 1H), 8.87 (d, J=7.0 Hz, 1H), 8.77 (d, J=7.5 Hz, 1H), 8.66 (d, J=8.9 Hz, 1H), 7.80 (s, 1H), 7.05 (d, J=7.0 Hz, 1H), 5.23-5.06 (m, 1H), 4.37-4.15 (m, 1H), 2.84-2.67 (m, 1H), 2.56-2.54 (m, 1H), 2.48-2.41 (m, 1H), 2.32-2.24 (m, 1H), 2.21-2.13 (m, 1H), 2.10-1.95 (m, 2H), 1.93-1.71 (m, 3H), 1.70-1.62 (m, 1H), 1.47-1.35 (m, 1H), 1.35-1.18 (m, 2H), 1.10-0.96 (m, 5H), 0.94-0.81 (m, 2H), 0.60-0.52 (m, 1H), 0.52-0.43 (m, 2H), 0.43-0.37 (m, 1H). MS (ESI) m/z: $[M+H]^+$ Found 609.3. Example 10: $^1H$ NMR (500 MHz, DMSO-$d_6$) δ 9.36 (s, 1H), 8.87 (d, J=6.9 Hz, 1H), 8.76 (d, J=7.8 Hz, 1H), 8.66 (d, J=9.0 Hz, 1H), 7.81 (s, 1H), 7.04 (d, J=7.0 Hz, 1H), 5.15 (t, J=8.4 Hz, 1H), 4.35-4.22 (m, 1H), 2.83-2.70 (m, 1H), 2.49-2.42 (m, 2H), 2.34-2.27 (m, 1H), 2.22-2.13 (m, 1H), 2.10-1.94 (m, 2H), 1.94-1.71 (m, 3H), 1.69-1.62 (m, 1H), 1.45-1.35 (m, 1H), 1.34-1.19 (m, 2H), 1.08 (d, J=6.9 Hz, 3H), 1.04-0.95 (m, 2H), 0.94-0.82 (m, 2H), 0.59-0.44 (m, 3H), 0.44-0.36 (m, 1H). MS (ESI) m/z: $[M+H]^+$ Found 609.3.

Example 11 trans-(1S*,2S*)—N—((S)-(7-((R)-Cyclopropyl(2-(3,3-difluorocyclobutyl)acetamido)methyl)imidazo[1,2-a]pyrimidin-2-yl)(4,4-difluorocyclohexyl)methyl)-2-(trifluoromethyl)cyclopropane-1-carboxamide

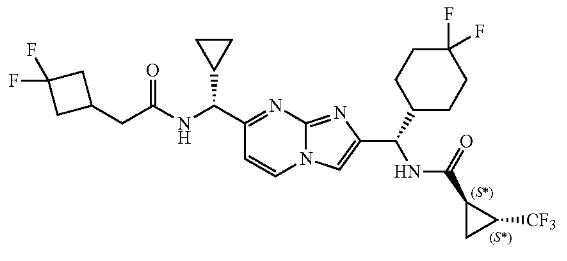 [SMILES: O=C(CC1CC(F)(F)C1)N[C@@H](c1ccn2cc([C@@H](NC(=O)[C@@H]3C[C@H]3C(F)(F)F)C3CCC(F)(F)CC3)nc2n1)C1CC1]

Example 12 trans-(1R*,2R*)—N—((S)-(7-((R)-Cyclopropyl(2-(3,3-difluorocyclobutyl)acetamido)methyl)imidazo[1,2-a]pyrimidin-2-yl)(4,4-difluorocyclohexyl)methyl)-2-(trifluoromethyl)cyclopropane-1-carboxamide

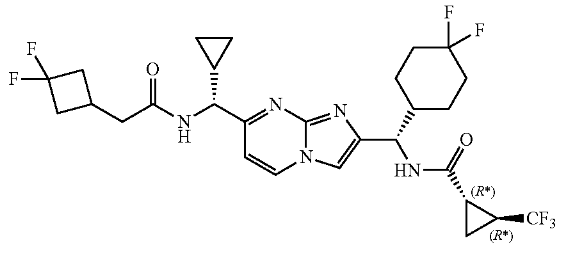 [SMILES: O=C(CC1CC(F)(F)C1)N[C@@H](c1ccn2cc([C@@H](NC(=O)[C@H]3C[C@@H]3C(F)(F)F)C3CCC(F)(F)CC3)nc2n1)C1CC1]

trans-(1,2)-N—((S)-(7-((R)-Cyclopropyl(2-(3,3-difluorocyclobutyl)acetamido)methyl)imidazo[1,2-a]pyrimidin-2-yl)(4,4-difluorocyclohexyl)methyl)-2-(trifluoromethyl)cyclopropane-1-carboxamide (Intermediate 37) was purified by SFC using a chiral stationary phase (Whelk-O1 (S,S), 21.2×250 mm, 5 μm, 20:80 i-PrOH/$CO_2$) to give a pair of diastereomers. The first-eluting isomer was Example 11 and the second eluting isomer was Example 12. Example 11: $^1$H NMR (500 MHz, $CDCl_3$) δ 8.35 (d, J=6.9 Hz, 1H), 7.41 (s, 1H), 6.90 (d, J=6.9 Hz, 1H), 6.85-6.78 (m, 2H), 5.09 (dd, J=8.7, 7.3 Hz, 1H), 4.62 (t, J=8.3 Hz, 1H), 2.82-2.69 (m, 2H), 2.61-2.50 (m, 1H), 2.47 (d, J=7.5 Hz, 2H), 2.34-2.22 (m, 2H), 2.16-2.07 (m, 2H), 2.04-2.01 (m, 1H), 1.97-1.90 (m, 1H), 1.83-1.79 (m, 1H), 1.77-1.62 (m, 3H), 1.49-1.17 (m, 6H), 0.63-0.57 (m, 3H), 0.53-0.47 (m, 1H). MS (ESI) m/z: $[M+H]^+$ Found 604.2. Example 12: $^1$H NMR (500 MHz, $CDCl_3$) δ 8.35 (d, J=6.9 Hz, 1H), 7.43 (s, 1H), 7.30 (d, J=8.8 Hz, 1H), 7.04 (d, J=7.9 Hz, 1H), 6.91 (d, J=6.9 Hz, 1H), 5.01 (t, J=8.4 Hz, 1H), 4.56 (t, J=8.4 Hz, 1H), 2.81-2.69 (m, 2H), 2.60-2.45 (m, 3H), 2.36-2.25 (m, 2H), 2.19-2.11 (m, 2H), 2.07-1.97 (m, 3H), 1.92-1.84 (m, 1H), 1.78-1.56 (m, 3H), 1.30-1.24 (m, 3H), 1.21-1.17 (m, 1H), 1.15-1.10 (m, 1H), 0.63-0.56 (m, 3H), 0.53-0.49 (m, 1H). MS (ESI) m/z: $[M+H]^+$ Found 604.2.

Example 13

N—((S)-(7-((R)-Cyclopropyl(2-(3,3-difluorocyclobutyl)acetamido)methyl)imidazo[1,2-a]pyrimidin-2-yl)(4,4-difluorocyclohexyl)methyl)-1-isopropyl-1H-1,2,4-triazole-5-carboxamide

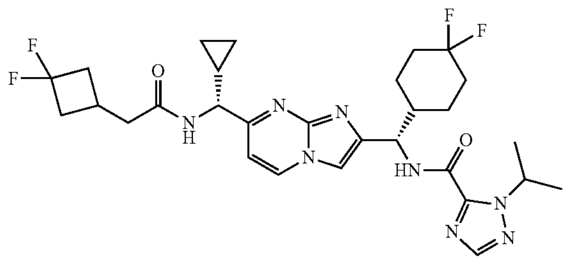 [SMILES: CC(C)n1ncnc1C(=O)N[C@H](c1cn2ccc([C@H](NC(=O)CC3CC(F)(F)C3)C3CC3)nc2n1)C1CCC(F)(F)CC1]

The title compound was prepared as described in the synthesis of Intermediate 37 using 1-isopropyl-1H-1,2,4-triazole-5-carboxylic acid in place of trans-2-(trifluoromethyl)cyclopropane-1-carboxylic acid. The mixture was stirred at 40° C. for 23 h instead of 2 h, and the crude residue was purified by preparative HPLC (XBridge C18, 40% to 100% MeCN/aqueous $NH_4OH$ (20 mM)) followed by SFC using a chiral stationary phase (CHIRALCEL OD-H, 21.2×250 mm, 5 μm, 20:80 MeOH/$CO_2$) to provide the title compound as a white solid. $^1$H NMR (500 MHz, $CDCl_3$) δ 8.33 (d, J=6.9 Hz, 1H), 8.14 (d, J=9.3 Hz, 1H), 7.85 (s, 1H), 7.48 (s, 1H), 6.91-6.84 (m, 2H), 5.78-5.68 (m, 1H), 5.21-5.14 (m, 1H), 4.62 (t, J=8.3 Hz, 1H), 2.79-2.70 (m, 2H), 2.62-2.50 (m, 1H), 2.50-2.46 (m, 2H), 2.34-2.24 (m, 3H), 2.17-1.99 (m, 3H), 1.74-1.70 (m, 2H), 1.52 (d, J=6.6 Hz, 3H), 1.46 (d, J=6.7 Hz, 3H), 1.43-1.39 (m, 1H), 1.26-1.16 (m, 3H), 0.63-0.56 (m, 3H), 0.52-0.46 (m, 1H). MS (ESI) m/z: $[M+H]^+$ Found 605.2.

Example 14

N—((S)-(7-((S)-Cyclopropyl(2-(3,3-difluorocyclobutyl)acetamido)methyl)imidazo[1,2-a]pyrimidin-2-yl)(4,4-difluorocyclohexyl)methyl)-1-isopropyl-1H-1,2,4-triazole-5-carboxamide

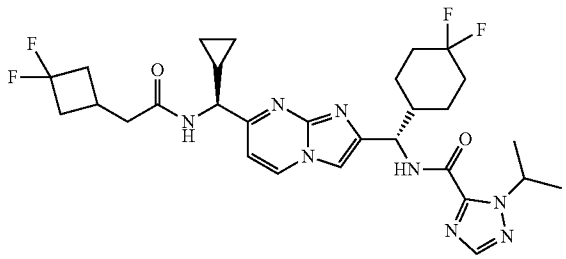 [SMILES: CC(C)n1ncnc1C(=O)N[C@H](c1cn2ccc([C@@H](NC(=O)CC3CC(F)(F)C3)C3CC3)nc2n1)C1CCC(F)(F)CC1]

The title compound was prepared as described in the synthesis of Intermediate 37 using N—((S)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide (Intermediate 39) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide and 1-isopropyl-1H-1,2,4-triazole-5-carboxylic acid in place of trans-2-(trifluoromethyl)cyclopropane-1-carboxylic acid. The mixture was stirred at 40° C. for 21 h instead of 2 h, and the crude residue was purified by preparative HPLC (XBridge C18, 40% to 100% MeCN/aqueous $NH_4OH$ (20 mM)) followed by SFC using a chiral stationary phase (CHIRALCEL OD-H, 21.2×250 mm, 5 μm, 15:85 MeOH/$CO_2$) to provide the title compound as a cream-colored solid. $^1$H NMR (500 MHz, $CDCl_3$) 8.33 (d, J=6.9 Hz, 1H), 8.12 (d, J=9.3 Hz, 1H), 7.86-7.82 (m, 1H), 7.48 (s, 1H), 6.88 (dd, J=7.3, 2.1 Hz, 2H), 5.73 (hept, J=6.7 Hz, 1H), 5.21-5.14 (m, 1H), 4.62 (t, J=8.3 Hz, 1H), 2.81-2.68 (m, 2H), 2.62-2.51 (m, 1H), 2.50-2.46 (m, 2H), 2.35-2.25 (m, 3H), 2.04-1.99 (m, 1H), 1.81-1.67 (m, 4H), 1.55-1.49 (m, 4H), 1.46 (d, J=6.7 Hz, 3H), 1.44-1.38 (m, 1H), 1.27-1.24 (m, 1H), 1.18-1.12 (m, 1H), 0.60-0.53 (m, 3H), 0.49-0.43 (m, 1H). MS (ESI) m/z: $[M+H]^+$ Found 605.3.

Example 15

N—((S)-(7-((R)-Cyclopropyl(2-(3,3-difluorocyclobutyl)acetamido)methyl)imidazo[1,2-a]pyrimidin-2-yl)(4,4-difluorocyclohexyl)methyl)-1-(cyclopropylmethyl)-1H-1,2,4-triazole-5-carboxamide

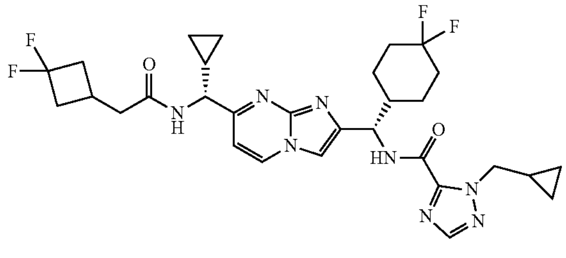 [SMILES: O=C(CC1CC(F)(F)C1)N[C@@H](c1ccn2cc([C@@H](NC(=O)c3ncnn3CC3CC3)C3CCC(F)(F)CC3)nc2n1)C1CC1]

The title compound was prepared as described in the synthesis of Intermediate 37 using 1-(cyclopropylmethyl)-

1H-1,2,4-triazole-5-carboxylic acid in place of trans-2-(trifluoromethyl)cyclopropane-1-carboxylic acid. The mixture was stirred at 40° C. for 21 h instead of 2 h, and an additional aliquot of 1-(cyclopropylmethyl)-1H-1,2,4-triazole-5-carboxylic acid (12 mg, 0.07 mmol) pre-stirred with EDCI (13 mg, 0.07 mmol), HOBt (9 mg, 0.07 mmol), DIPEA (13 L, 0.08 mmol) and ACN (0.2 mL) was added after 3 h. $^1$H NMR (400 MHz, $CDCl_3$) δ 8.33 (d, J=6.9 Hz, 1H), 8.14 (d, J=9.3 Hz, 1H), 7.86 (s, 1H), 7.48 (s, 1H), 6.95-6.84 (m, 2H), 5.17 (dd, J=9.3, 7.8 Hz, 1H), 4.62 (t, J=8.3 Hz, 1H), 4.53 (d, J=2.5 Hz, 1H), 2.82-2.69 (m, 2H), 2.62-2.51 (m, 1H), 2.51-2.45 (m, 2H), 2.35-2.23 (m, 3H), 2.20-2.10 (m, 1H), 2.08-1.98 (m, 2H), 1.85-1.79 (m, 1H), 1.60-1.13 (m, 7H), 0.60-0.42 (m, 8H). MS (ESI) m/z: [M+H]$^+$ Found 617.3.

Example 16

N—((S)-(7-((S)-Cyclopropyl(2-(3,3-difluorocyclobutyl)acetamido)methyl)imidazo[1,2-a]pyrimidin-2-yl)(4,4-difluorocyclohexyl)methyl)-1-(cyclopropylmethyl)-1H-1,2,4-triazole-5-carboxamide

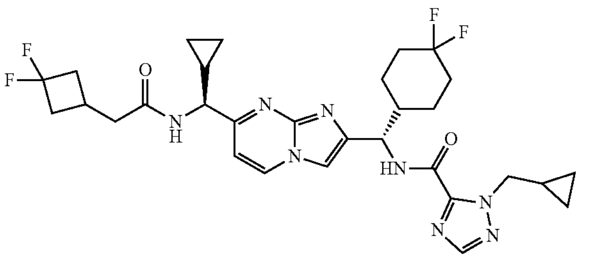 [SMILES: O=C(CC1CC(F)(F)C1)N[C@H](c1ccn2cc([C@@H](NC(=O)c3ncnn3CC3CC3)C3CCC(F)(F)CC3)nc2n1)C1CC1]

The title compound was prepared as described in the synthesis of Intermediate 37 using N—((S)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide (Intermediate 39) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl) acetamide and 1-(cyclopropylmethyl)-1H-1,2,4-triazole-5-carboxylic acid in place of trans-2-(trifluoromethyl) cyclopropane-1-carboxylic acid. The mixture was stirred at 40° C. for 21 h instead of 2 h, and an additional aliquot of 1-(cyclopropylmethyl)-1H-1,2,4-triazole-5-carboxylic acid (12 mg, 0.07 mmol) pre-stirred with EDCI (13 mg, 0.07 mmol), HOBt (9 mg, 0.07 mmol), DIPEA (13 μL, 0.08 mmol) and ACN (0.2 mL) was added after 3 h. $^1$H NMR (400 MHz, $CDCl_3$) δ 8.33 (d, J=6.9 Hz, 1H), 8.12 (d, J=9.4 Hz, 1H), 7.85 (s, 1H), 7.48 (s, 1H), 6.92-6.83 (m, 2H), 5.22-5.12 (m, 1H), 4.62 (t, J=8.3 Hz, 1H), 4.56-4.49 (m, 2H), 2.84-2.67 (m, 2H), 2.62-2.51 (m, 1H), 2.51-2.47 (m, 2H), 2.38-2.22 (m, 3H), 2.17-1.98 (m, 3H), 1.82-1.70 (m, 2H), 1.56-1.48 (m, 1H), 1.43-1.34 (m, 2H), 1.27-1.24 (m, 1H), 1.18-1.12 (m, 1H), 0.62-0.41 (m, 8H). MS (ESI) m/z: [M+H]$^+$ Found 617.2.

Example 17

N—((S)-(7-((R)-Cyclopropyl((S*)-4,4,4-trifluoro-3-methylbutanamido)methyl)imidazo[1,2-a]pyrimidin-2-yl)(4,4-difluorocyclohexyl)methyl)-1-isopropyl-1H-1,2,4-triazole-5-carboxamide

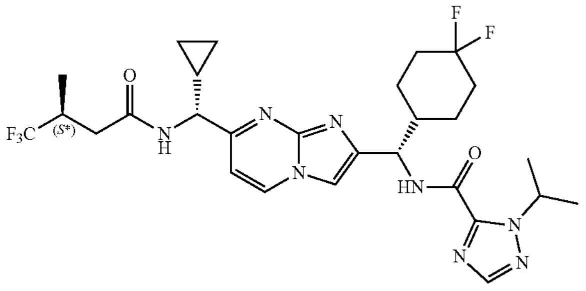 [SMILES: CC(C)n1ncnc1C(=O)N[C@H](c1cn2ccc([C@H](NC(=O)C[C@H](C)C(F)(F)F)C3CC3)nc2n1)C1CCC(F)(F)CC1]

Example 18

N—((S)-(7-((R)-Cyclopropyl((R*)-4,4,4-trifluoro-3-methylbutanamido)methyl)imidazo[1,2-a]pyrimidin-2-yl)(4,4-difluorocyclohexyl)methyl)-1-isopropyl-1H-1,2,4-triazole-5-carboxamide

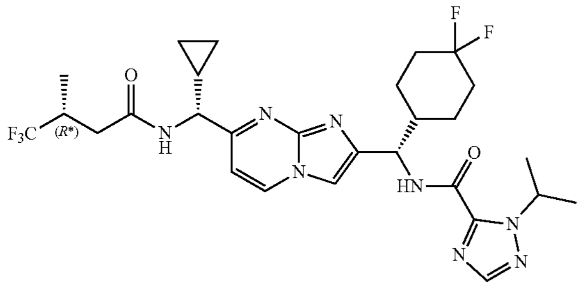 [SMILES: CC(C)n1ncnc1C(=O)N[C@H](c1cn2ccc([C@H](NC(=O)C[C@@H](C)C(F)(F)F)C3CC3)nc2n1)C1CCC(F)(F)CC1]

N-((1S)-(7-((1R)-Cyclopropyl(4,4,4-trifluoro-3-methylbutanamido)methyl)imidazo[1,2-a]pyrimidin-2-yl)(4,4-difluorocyclohexyl)methyl)-1-isopropyl-1H-1,2,4-triazole-5-carboxamide (Intermediate 55) was separated via SFC with a chiral stationary phase (IC 2×15 cm, 12% IPA (with 0.3% NPA) in $CO_2$, 100 bar, 65 mL/min) to give a pair of diastereomers. The first eluting isomer was Example 18, and the second eluting isomer was Example 17. Example 17: $^1$H NMR (400 MHz, DMSO-$d_6$) δ 8.90 (d, J=7.0 Hz, 1H), 8.86-8.67 (m, 2H), 8.10 (s, 1H), 7.85 (s, 1H), 7.06 (d, J=6.9 Hz, 1H), 5.68-5.42 (m, 1H), 5.12 (t, J=8.5 Hz, 1H), 4.37-4.26 (m, 1H), 2.84-2.68 (m, 1H), 2.36-2.28 (m, 1H), 2.21-2.10 (m, 1H), 2.09-1.96 (m, 2H), 1.96-1.87 (m, 1H), 1.85-1.69 (m, 2H), 1.68-1.60 (m, 1H), 1.47-1.34 (m, 7H), 1.31-1.19 (m, 3H), 1.08 (d, J=6.9 Hz, 3H), 0.59-0.45 (m, 3H), 0.45-0.37 (m, 1H). MS (ESI) m/z: [M+H]$^+$ Found 611.3. Example 18: $^1$H NMR (400 MHz, DMSO-$d_6$) δ 8.89 (d, J=6.9 Hz, 1H), 8.80 (dd, J=8.4, 16.0 Hz, 2H), 8.09 (d, J=0.6 Hz, 1H), 7.85 (s, 1H), 7.06 (d, J=7.0 Hz, 1H), 5.63-5.44 (m, 1H), 5.11 (t, J=8.4 Hz, 1H), 4.35-4.19 (m, 1H), 2.81-2.69 (m, 1H), 2.32-2.24 (m, 1H), 2.20-2.10 (m, 1H), 2.09-1.96 (m, 2H), 1.95-1.87 (m, 1H), 1.85-1.69 (m, 2H), 1.68-1.60 (m, 1H), 1.45-1.35 (m, 7H), 1.33-1.17 (m, 3H), 1.02 (d, J=6.9 Hz, 3H), 0.58-0.45 (m, 3H), 0.44-0.37 (m, 1H). MS (ESI) m/z: $[M+H]^+$ Found 611.3.

Example 19

N—((S)-(7-((R)-Cyclopropyl((S*)-4,4,4-trifluoro-3-methylbutanamido)methyl)imidazo[1,2-a]pyrimidin-2-yl)(4,4-difluorocyclohexyl)methyl)-1-(cyclopropylmethyl)-1H-1,2,4-triazole-5-carboxamide

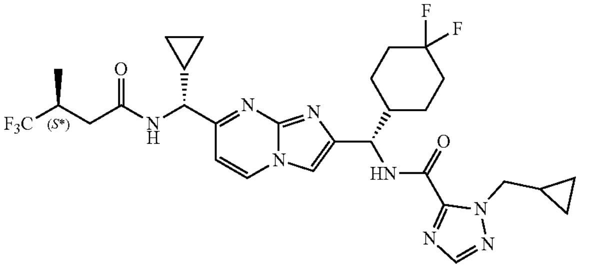 [SMILES: C[C@@H](CC(=O)N[C@@H](c1ccn2cc([C@@H](NC(=O)c3ncnn3CC3CC3)C3CCC(F)(F)CC3)nc2n1)C1CC1)C(F)(F)F]

Example 20

N—((S)-(7-((R)-Cyclopropyl((R*)-4,4,4-trifluoro-3-methylbutanamido)methyl)imidazo[1,2-a]pyrimidin-2-yl)(4,4-difluorocyclohexyl)methyl)-1-(cyclopropylmethyl)-1H-1,2,4-triazole-5-carboxamide

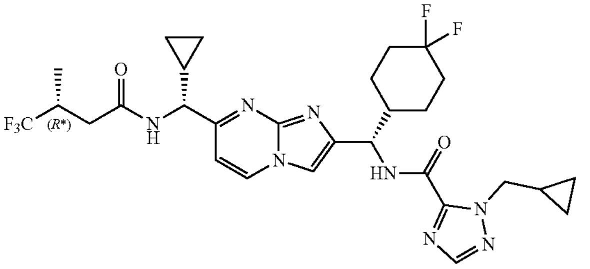 [SMILES: C[C@H](CC(=O)N[C@@H](c1ccn2cc([C@@H](NC(=O)c3ncnn3CC3CC3)C3CCC(F)(F)CC3)nc2n1)C1CC1)C(F)(F)F]

N-((1S)-(7-((1R)-Cyclopropyl(4,4,4-trifluoro-3-methylbutanamido)methyl)imidazo[1,2-a]pyrimidin-2-yl)(4,4-difluorocyclohexyl)methyl)-1-(cyclopropylmethyl)-1H-1,2,4-triazole-5-carboxamide (Intermediate 54) was purified by SFC with a chiral stationary phase (IC 2×15 cm, 13% IPA in $CO_2$, 100 bar, 65 mL/min) to give a pair of diastereomers. The first eluting isomer was Example 20 and the second eluting isomer was Example 19. Example 20: $^1$H NMR (500 MHz, DMSO-$d_6$) δ 8.90 (d, J=7.0 Hz, 1H), 8.87 (d, J=9.1 Hz, 1H), 8.78 (d, J=7.6 Hz, 1H), 8.10 (s, 1H), 7.85 (s, 1H), 7.06 (d, J=7.0 Hz, 1H), 5.11 (t, J=8.5 Hz, 1H), 4.51-4.36 (m, 2H), 4.33-4.21 (m, 1H), 2.79-2.69 (m, 1H), 2.33-2.25 (m, 1H), 2.22-2.12 (m, 1H), 2.09-1.94 (m, 2H), 1.93-1.87 (m, 1H), 1.86-1.70 (m, 2H), 1.69-1.61 (m, 1H), 1.43-1.31 (m, 1H), 1.31-1.17 (m, 4H), 1.02 (d, J=6.9 Hz, 3H), 0.59-0.52 (m, 1H), 0.52-0.44 (m, 4H), 0.44-0.33 (m, 3H). MS (ESI) m/z: $[M+H]^+$ Found 623.3. Example 19: $^1$H NMR (500 MHz, DMSO-$d_6$) δ 8.90 (d, J=7.0 Hz, 1H), 8.87 (d, J=9.1 Hz, 1H), 8.78 (d, J=7.8 Hz, 1H), 8.11 (s, 1H), 7.85 (s, 1H), 7.06 (d, J=7.0 Hz, 1H), 5.11 (t, J=8.5 Hz, 1H), 4.50-4.39 (m, 2H), 4.37-4.28 (m, 1H), 2.82-2.71 (m, 1H), 2.36-2.28 (m, 1H), 2.21-2.10 (m, 1H), 2.09-1.94 (m, 2H), 1.93-1.87 (m, 1H), 1.86-1.69 (m, 2H), 1.69-1.59 (m, 1H), 1.42-1.31 (m, 1H), 1.31-1.18 (m, 4H), 1.08 (d, J=6.9 Hz, 3H), 0.58-0.44 (m, 5H), 0.44-0.33 (m, 3H). MS (ESI) m/z: $[M+H]^+$ Found 623.3.

Example 21

N—((S)-(7-((R)-Cyclopropyl(2-(3,3-difluorocyclobutyl)acetamido)methyl)imidazo[1,2-a]pyrimidin-2-yl)(4,4-difluorocyclohexyl)methyl)-4-methyl-1,2,5-oxadiazole-3-carboxamide

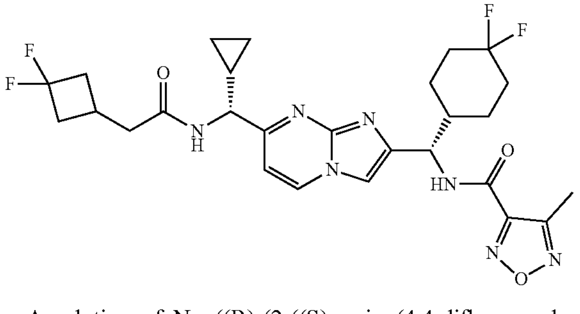

A solution of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide (65 mg, 0.14 mmol, Intermediate 36) in DCM (2.6 mL) was cooled to 0° C. in an ice bath and then DIPEA (84 µL, 0.49 mmol) was added followed by 4-methyl-1,2,5-oxadiazole-3-carbonyl chloride (51 mg, 0.35 mmol, Intermediate 40). The resulting mixture was stirred at 0° C. for 45 minutes, then removed from the ice bath and allowed to warm to rt over 19 h. After that time, the mixture was cooled to 0° C. and quenched with water. Then, EtOAc (20 mL) was added and the layers separated. The aqueous layer was further extracted with EtOAc (25 mL), and the organic layers combined, dried over anhydrous $Na_2SO_4$, filtered and concentrated to dryness. The residue was purified by preparative HPLC (XBridge C18, 40% to 100% MeCN/aqueous $NH_4OH$ (20 mM)) to provide the title compound as a cream-colored solid. $^1$H NMR (400 MHz, $CDCl_3$) δ 8.35 (d, J=6.9 Hz, 1H), 7.70 (d, J=8.9 Hz, 1H), 7.47 (s, 1H), 6.90 (d, J=6.9 Hz, 1H), 6.84 (d, J=8.0 Hz, 1H), 5.22 (dd, J=9.0, 7.7 Hz, 1H), 4.61 (t, J=8.3 Hz, 1H), 2.80-2.69 (m, 2H), 2.60 (s, 3H), 2.58-2.51 (m, 1H), 2.51-2.45 (m, 2H), 2.35-2.12 (m, 4H), 2.08-1.98 (m, 2H), 1.84-1.63 (m, 3H), 1.54-1.35 (m, 2H), 1.24-1.13 (m, 1H), 0.65-0.56 (m, 3H), 0.54-0.44 (m, 1H). MS (ESI) m/z: $[M+H]^+$ Found 578.2.

Example 22

N—((S)-(7-((S)-Cyclopropyl(2-(3,3-difluorocyclobutyl)acetamido)methyl)imidazo[1,2-a]pyrimidin-2-yl)(4,4-difluorocyclohexyl)methyl)-4-methyl-1,2,5-oxadiazole-3-carboxamide

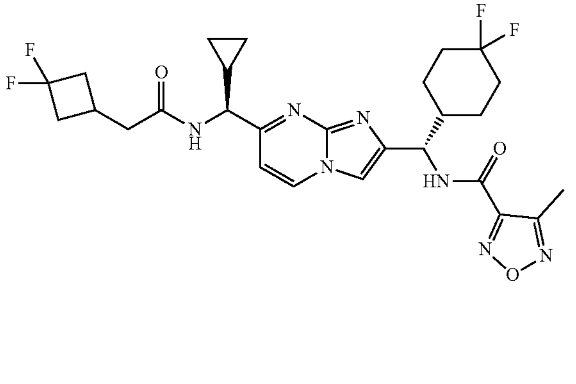 [SMILES: Cc1nonc1C(=O)N[C@H](c1cn2ccc([C@@H](NC(=O)CC3CC(F)(F)C3)C3CC3)nc2n1)C1CCC(F)(F)CC1]

The title compound was prepared as described in the synthesis of Example 21 using N—((S)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide (Intermediate 39) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide. $^{1}$H NMR (400 MHz, $CDCl_3$) δ 8.35 (d, J=6.9 Hz, 1H), 7.68 (d, J=9.0 Hz, 1H), 7.48 (s, 1H), 6.90 (d, J=6.9 Hz, 1H), 6.82 (d, J=8.0 Hz, 1H), 5.26-5.18 (m, 1H), 4.62 (t, J=8.3 Hz, 1H), 2.82-2.67 (m, 2H), 2.60 (s, 3H), 2.59-2.52 (m, 1H), 2.52-2.47 (m, 2H), 2.38-2.11 (m, 4H), 2.10-1.99 (m, 2H), 1.82-1.62 (m, 3H), 1.55-1.33 (m, 2H), 1.21-1.11 (m, 1H), 0.61-0.53 (m, 3H), 0.53-0.44 (m, 1H). MS (ESI) m/z: $[M+H]^+$ Found 578.2.

Example 23

N—((S)-(7-((R)-Cyclopropyl(4,4,4-trifluorobutanamido)methyl)imidazo[1,2-a]pyrimidin-2-yl)(4,4-difluorocyclohexyl)methyl)-4-methyl-1,2,5-oxadiazole-3-carboxamide

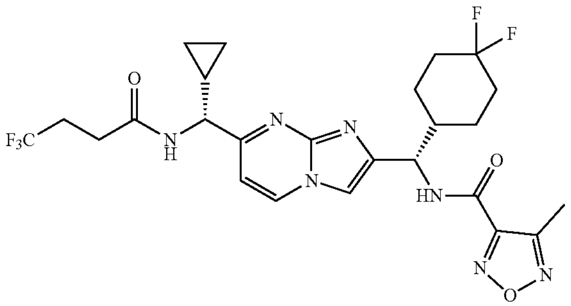 [SMILES: Cc1nonc1C(=O)N[C@H](c1cn2ccc([C@H](NC(=O)CCC(F)(F)F)C3CC3)nc2n1)C1CCC(F)(F)CC1]

The title compound was prepared as described in the synthesis of Example 21 using N—((R)-(2-((S)-amino(4,4-difluorocyclohexyl)methyl)imidazo[1,2-a]pyrimidin-7-yl)(cyclopropyl)methyl)-4,4,4-trifluorobutanamide (Intermediate 41) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide. $^{1}$H NMR (400 MHz, $CDCl_3$) δ 8.35 (d, J=6.9 Hz, 1H), 7.69 (d, J=9.0 Hz, 1H), 7.48 (s, 1H), 6.94-6.87 (m, 2H), 5.22 (dd, J=9.0, 7.7 Hz, 1H), 4.62 (t, J=8.3 Hz, 1H), 2.60 (s, 3H), 2.57-2.43 (m, 4H), 2.27-2.12 (m, 2H), 2.09-1.99 (m, 2H), 1.82-1.63 (m, 3H), 1.55-1.32 (m, 2H), 1.25-1.16 (m, 1H), 0.66-0.57 (m, 3H), 0.55-0.47 (m, 1H). MS (ESI) m/z: $[M+H]^+$ Found 570.1.

Example 24

3-Cyclopropyl-N—((S)-(7-((R)-cyclopropyl(2-(3,3-difluorocyclobutyl)acetamido)methyl)imidazo[1,2-a]pyrimidin-2-yl)(4,4-difluorocyclohexyl)methyl)isoxazole-4-carboxamide

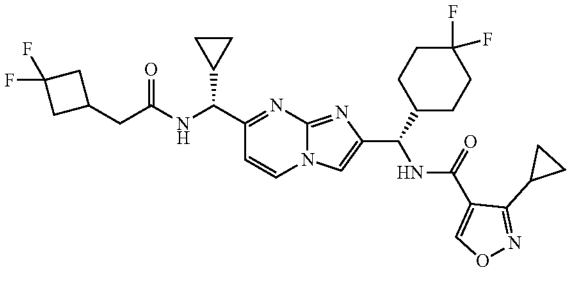 [SMILES: O=C(CC1CC(F)(F)C1)N[C@@H](c1ccn2cc([C@@H](NC(=O)c3conc3C3CC3)C3CCC(F)(F)CC3)nc2n1)C1CC1]

The title compound was prepared as described in the synthesis of Intermediate 37 using 3-cyclopropyl-1,2-oxazole-4-carboxylic acid in place of trans-2-(trifluoromethyl)cyclopropane-1-carboxylic acid. $^{1}$H NMR (500 MHz, $CDCl_3$) δ 8.76 (s, 1H), 8.35 (d, J=6.9 Hz, 1H), 7.46 (s, 1H), 7.18 (d, J=8.5 Hz, 1H), 6.91 (d, J=6.9 Hz, 1H), 6.79 (d, J=7.9 Hz, 1H), 5.28-5.23 (m, 1H), 4.59 (t, J=8.3 Hz, 1H), 2.81-2.67 (m, 2H), 2.60-2.50 (m, 1H), 2.49-2.46 (m, 2H), 2.34-2.24 (m, 2H), 2.23-2.12 (m, 3H), 2.09-1.98 (m, 2H), 1.81-1.64 (m, 3H), 1.57-1.48 (m, 1H), 1.42-1.34 (m, 1H), 1.20-1.05 (m, 5H), 0.63-0.58 (m, 3H), 0.54-0.48 (m, 1H). MS (ESI) m/z: $[M+H]^+$ Found 603.2.

Example 25

N—((S)-(7-((R)-Cyclopropyl(2-(3,3-difluorocyclobutyl)acetamido)methyl)imidazo[1,2-a]pyrimidin-2-yl)(4,4-difluorocyclohexyl)methyl)-2-(2,2,2-trifluoroethyl)isonicotinamide

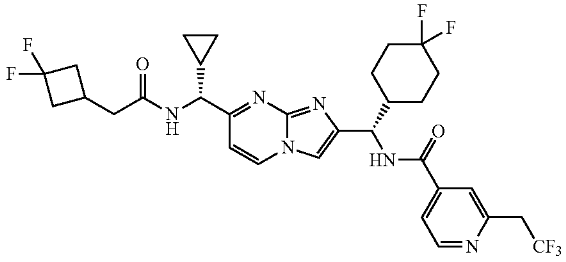 [SMILES: O=C(CC1CC(F)(F)C1)N[C@@H](c1ccn2cc([C@@H](NC(=O)c3ccnc(CC(F)(F)F)c3)C3CCC(F)(F)CC3)nc2n1)C1CC1]

The title compound was prepared as described in the synthesis of Intermediate 37 using 2-(2,2,2-trifluoroethyl)pyridine-4-carboxylic acid in place of trans-2-(trifluoromethyl)cyclopropane-1-carboxylic acid, and the mixture was stirred at 40° C. for 23 h instead of 2 h. $^{1}$H NMR (500 MHz, $CDCl_3$) δ 8.73 (dd, J=5.1, 0.8 Hz, 1H), 8.36 (d, J=6.9 Hz, 1H), 7.72-7.68 (m, 1H), 7.60 (dd, J=5.1, 1.7 Hz, 1H), 7.48 (s, 1H), 7.33 (d, J=8.6 Hz, 1H), 6.92 (d, J=6.9 Hz, 1H), 6.77 (d, J=7.9 Hz, 1H), 5.32-5.24 (m, 1H), 4.59 (t, J=8.3 Hz, 1H), 3.67 (q, J=10.6 Hz, 2H), 2.81-2.67 (m, 2H), 2.61-2.49 (m, 1H), 2.49-2.44 (m, 2H), 2.34-2.24 (m, 2H), 2.20-2.12 (m, 2H), 2.08-1.98 (m, 2H), 1.79-1.60 (m, 3H), 1.55-1.31 (m, 2H), 1.22-1.16 (m, 1H), 0.64-0.58 (m, 3H), 0.54-0.48 (m, 1H). MS (ESI) m/z: $[M+H]^+$ Found 655.2.

Example 26

N—((S)-(7-((R)-Cyclopropyl(2-(3,3-difluorocyclobutyl)acetamido)methyl)imidazo[1,2-a]pyrimidin-2-yl)(4,4-difluorocyclohexyl)methyl)-3-(3,3,3-trifluoropropyl)isoxazole-4-carboxamide

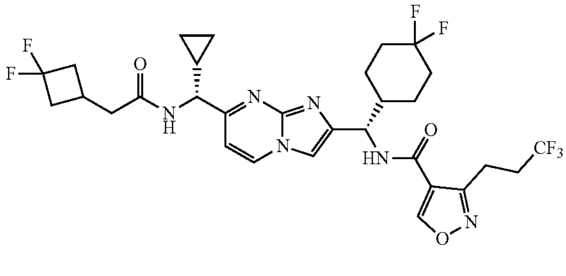 [SMILES: O=C(CC1CC(F)(F)C1)N[C@@H](c1ccn2cc([C@@H](NC(=O)c3conc3CCC(F)(F)F)C3CCC(F)(F)CC3)nc2n1)C1CC1]

The title compound was prepared as described in the synthesis of Intermediate 37 using 3-(3,3,3-trifluoropropyl) isoxazole-4-carboxylic acid (Intermediate 34) in place of trans-2-(trifluoromethyl)cyclopropane-1-carboxylic acid. $^1$H NMR (500 MHz, $CDCl_3$) δ 8.76 (s, 1H), 8.36 (d, J=6.9 Hz, 1H), 7.45 (s, 1H), 6.99 (d, J=8.4 Hz, 1H), 6.92 (d, J=6.9 Hz, 1H), 6.75 (d, J=7.8 Hz, 1H), 5.21 (dd, J=8.5, 7.3 Hz, 1H), 4.58 (dd, J=8.7, 7.9 Hz, 1H), 3.24-3.17 (m, 2H), 2.81-2.69 (m, 2H), 2.67-2.53 (m, 3H), 2.49-2.45 (m, 2H), 2.33-2.24 (m, 2H), 2.19-1.97 (m, 4H), 1.84-1.63 (m, 3H), 1.55-1.47 (m, 1H), 1.37-1.29 (m, 1H), 1.22-1.15 (m, 1H), 0.64-0.58 (m, 3H), 0.54-0.48 (m, 1H). MS (ESI) m/z: [M+H]$^+$ Found 659.2.

Example 27

3-Cyclopropyl-N—((S)-(7-((S)-cyclopropyl(2-(3,3-difluorocyclobutyl)acetamido)methyl)imidazo[1,2-a]pyrimidin-2-yl)(4,4-difluorocyclohexyl)methyl)isoxazole-4-carboxamide

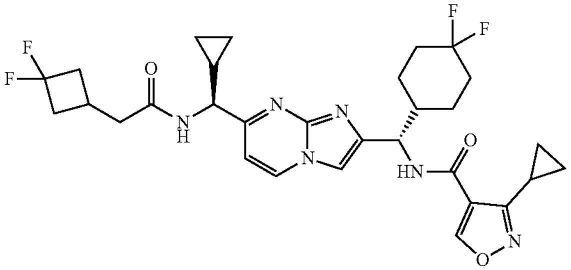 [SMILES: O=C(CC1CC(F)(F)C1)N[C@H](c1ccn2cc([C@@H](NC(=O)c3conc3C3CC3)C3CCC(F)(F)CC3)nc2n1)C1CC1]

The title compound was prepared as described in the synthesis of Intermediate 37 using N—((S)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide (Intermediate 39) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide and 3-cyclopropyl-1,2-oxazole-4-carboxylic acid in place of trans-2-(trifluoromethyl)cyclopropane-1-carboxylic acid. $^1$H NMR (500 MHz, $CDCl_3$) δ 8.75 (s, 1H), 8.35 (d, J=6.9 Hz, 1H), 7.47 (s, 1H), 7.13 (d, J=8.6 Hz, 1H), 6.90 (d, J=6.9 Hz, 1H), 6.77 (d, J=7.9 Hz, 1H), 5.29-5.23 (m, 1H), 4.60 (t, J=8.3 Hz, 1H), 2.83-2.70 (m, 2H), 2.61-2.51 (m, 1H), 2.50-2.46 (m, 2H), 2.36-2.25 (m, 2H), 2.25-2.19 (m, 1H), 2.18-1.99 (m, 4H), 1.80-1.64 (m, 3H), 1.56-1.34 (m, 2H), 1.20-1.06 (m, 5H), 0.61-0.54 (m, 3H), 0.52-0.45 (m, 1H). MS (ESI) m/z: [M+H]$^+$ Found 603.2.

Example 28

N—((S)-(7-((S)-Cyclopropyl(2-(3,3-difluorocyclobutyl)acetamido)methyl)imidazo[1,2-a]pyrimidin-2-yl)(4,4-difluorocyclohexyl)methyl)-2-(2,2,2-trifluoroethyl)isonicotinamide

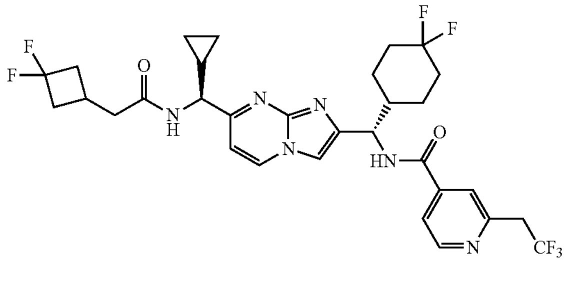

The title compound was prepared as described in the synthesis of Intermediate 37 using N—((S)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide (Intermediate 39) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide and 2-(2,2,2-trifluoroethyl)pyridine-4-carboxylic acid in place of trans-2-(trifluoromethyl)cyclopropane-1-carboxylic acid. $^1$H NMR (500 MHz, $CDCl_3$) δ 8.73 (dd, J=5.1, 0.9 Hz, 1H), 8.36 (d, J=6.9 Hz, 1H), 7.72-7.67 (m, 1H), 7.60 (dd, J=5.1, 1.6 Hz, 1H), 7.48 (s, 1H), 7.28 (d, J=8.5 Hz, 1H), 6.91 (d, J=6.9 Hz, 1H), 6.76 (d, J=8.0 Hz, 1H), 5.30-5.27 (m, 1H), 4.61 (t, J=8.3 Hz, 1H), 3.67 (q, J=10.6 Hz, 2H), 2.80-2.71 (m, 2H), 2.61-2.51 (m, 1H), 2.50-2.47 (m, 2H), 2.36-2.24 (m, 2H), 2.20-2.00 (m, 4H), 1.80-1.62 (m, 3H), 1.56-1.49 (m, 1H), 1.42-1.34 (m, 1H), 1.21-1.13 (m, 1H), 0.61-0.55 (m, 3H), 0.51-0.44 (m, 1H). MS (ESI) m/z: [M+H]$^+$ Found 655.2.

Example 29

N—((S)-(7-((S)-Cyclopropyl(2-(3,3-difluorocyclobutyl)acetamido)methyl)imidazo[1,2-a]pyrimidin-2-yl)(4,4-difluorocyclohexyl)methyl)-3-(3,3,3-trifluoropropyl)isoxazole-4-carboxamide

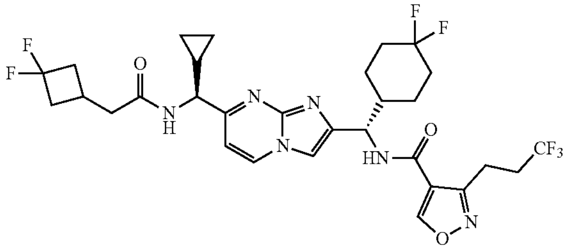 [SMILES: O=C(CC1CC(F)(F)C1)N[C@H](c1ccn2cc([C@@H](NC(=O)c3conc3CCC(F)(F)F)C3CCC(F)(F)CC3)nc2n1)C1CC1]

The title compound was prepared as described in the synthesis of Intermediate 37 using N—((S)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide (Intermediate 39) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide and 3-(3,3,3-trifluoropropyl)isoxazole-4-carboxylic acid (Intermediate 34) in place trans-2-(trifluoromethyl)cyclopropane-1-carboxylic acid. $^1$H NMR (500 MHz, $CDCl_3$) δ 8.76 (s, 1H), 8.36 (d, J=6.9 Hz, 1H), 7.46 (s, 1H), 6.96 (d, J=8.6 Hz, 1H), 6.92 (d, J=6.9 Hz, 1H), 6.74 (d, J=7.9 Hz, 1H), 5.21 (dd, J=8.6, 7.5 Hz, 1H), 4.60 (t, J=8.3 Hz, 1H), 3.24-3.16 (m, 2H), 2.81-2.71 (m, 2H), 2.65-2.55 (m, 3H), 2.50-2.46 (m, 2H), 2.36-2.25 (m, 2H), 2.20-2.11 (m, 1H), 2.10-1.97 (m, 3H), 1.81-1.64 (m, 3H), 1.55-1.45 (m, 1H), 1.39-1.29 (m, 1H), 1.21-1.12 (m, 1H), 0.61-0.54 (m, 3H), 0.50-0.45 (m, 1H). MS (ESI) m/z: [M+H]$^+$ Found 659.2.

Example 30

N—((S)-(7-((R)-Cyclopropyl(4,4,4-trifluorobutanamido)methyl)imidazo[1,2-a]pyrimidin-2-yl)(4,4-difluorocyclohexyl)methyl)-3-(3,3,3-trifluoropropyl)isoxazole-4-carboxamide

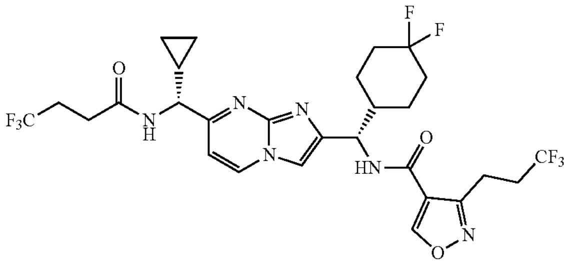 [SMILES: O=C(CCC(F)(F)F)N[C@@H](c1ccn2cc([C@@H](NC(=O)c3conc3CCC(F)(F)F)C3CCC(F)(F)CC3)nc2n1)C1CC1]

The title compound was prepared as described in the synthesis of Intermediate 37 using N—((R)-(2-((S)-amino(4,4-difluorocyclohexyl)methyl)imidazo[1,2-a]pyrimidin-7-yl)(cyclopropyl)methyl)-4,4,4-trifluorobutanamide (Intermediate 41) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide and 3-(3,3,3-trifluoropropyl)isoxazole-4-carboxylic acid (Intermediate 34) in place of trans-2-(trifluoromethyl)cyclopropane-1-carboxylic acid and the mixture was stirred at 40° C. for 4.5 h instead of 2 h. $^1$H NMR (500 MHz, $CDCl_3$) δ 8.77 (s, 1H), 8.37 (d, J=6.9 Hz, 1H), 7.46 (s, 1H), 7.05 (d, J=8.4 Hz, 1H), 6.93 (d, J=7.0 Hz, 1H), 6.82 (d, J=7.8 Hz, 1H), 5.21 (dd, J=8.5, 7.4 Hz, 1H), 4.58 (dd, J=8.8, 7.8 Hz, 1H), 3.23-3.17 (m, 2H), 2.65-2.42 (m, 6H), 2.12-1.98 (m, 3H), 1.79-1.62 (m, 4H), 1.54-1.45 (m, 1H), 1.37-1.28 (m, 1H), 1.24-1.15 (m, 1H), 0.65-0.59 (m, 3H), 0.56-0.50 (m, 1H). MS (ESI) m/z: $[M+H]^+$ Found 651.2.

Example 31

N—((S)-(7-((S)-Cyclopropyl(4,4,4-trifluorobutanamido)methyl)imidazo[1,2-a]pyrimidin-2-yl)(4,4-difluorocyclohexyl)methyl)-2-(cyclopropylmethyl)-2H-1,2,3-triazole-4-carboxamide

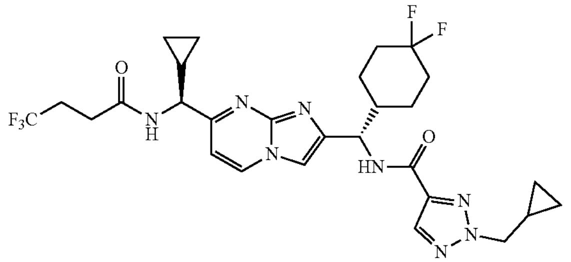 [SMILES: O=C(CCC(F)(F)F)N[C@H](c1ccn2cc([C@@H](NC(=O)c3cnn(CC4CC4)n3)C3CCC(F)(F)CC3)nc2n1)C1CC1]

A vial was charged with a stir bar, N—((S)-(2-((S)-amino(4,4-difluorocyclohexyl)methyl)imidazo[1,2-a]pyrimidin-7-yl)(cyclopropyl)methyl)-4,4,4-trifluorobutanamide (75 mg, 0.16 mmol, Intermediate 49), MeCN (2 mL), HOBt (23 mg, 0.17 mmol) and 2-(cyclopropylmethyl)-2H-1,2,3-triazole-4-carboxylic acid (29 mg, 0.17 mmol, Intermediate 31). The reaction was stirred for 5 min then EDCI (33 mg, 0.17 mmol) and Hünig's base (0.042 mL, 0.25 mmol) were added and the reaction was stirred for 30 min at 40° C. The reaction was cooled to rt and poured over water and diluted with EtOAc. The layers were separated, and the aqueous phase was further extracted with EtOAc (2×5 mL). The combined organics were washed with brine, dried over anhydrous $MgSO_4$, filtered and condensed into a glassy solid. The crude material was purified by FCC (0-100% (10% MeOH in EtOAc)/hexanes). The product containing fractions were condensed, taken up in minimal MeCN:water and lyophilized to afford the title compound as a white powder. $^1$H NMR (500 MHz, DMSO-$d_6$) δ 8.88 (d, J=7.0 Hz, 1H), 8.71 (d, J=7.6 Hz, 1H), 8.41 (d, J=9.0 Hz, 1H), 8.19 (s, 1H), 7.83 (s, 1H), 7.05 (d, J=7.0 Hz, 1H), 5.15 (t, J=8.6 Hz, 1H), 4.36 (d, J=7.4 Hz, 2H), 4.28 (dd, J=7.9, 8.8 Hz, 1H), 2.49-2.41 (m, 4H), 2.20-2.10 (m, 1H), 2.09-1.93 (m, 2H), 1.93-1.86 (m, 1H), 1.85-1.67 (m, 2H), 1.67-1.56 (m, 1H), 1.44-1.32 (m, 2H), 1.31-1.18 (m, 2H), 0.60-0.51 (m, 3H), 0.51-0.37 (m, 5H). MS (ESI) m/z: $[M+H]^+$ Found 609.3.

Example 32

N—((S)-(7-((R)-Cyclopropyl(4,4,4-trifluorobutanamido)methyl)imidazo[1,2-a]pyrimidin-2-yl)(4,4-difluorocyclohexyl)methyl)-1-(cyclopropylmethyl)-1H-1,2,4-triazole-5-carboxamide

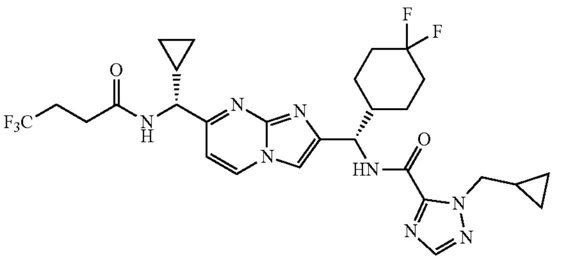 [SMILES: O=C(CCC(F)(F)F)N[C@@H](c1ccn2cc([C@@H](NC(=O)c3ncnn3CC3CC3)C3CCC(F)(F)CC3)nc2n1)C1CC1]

The title compound was prepared as described in the synthesis of Example 31 using N—((R)-(2-((S)-amino(4,4-difluorocyclohexyl)methyl)imidazo[1,2-a]pyrimidin-7-yl)(cyclopropyl)methyl)-4,4,4-trifluorobutanamide (Intermediate 41) in place of N—((S)-(2-((S)-amino(4,4-difluorocyclohexyl)methyl)imidazo[1,2-a]pyrimidin-7-yl)(cyclopropyl)methyl)-4,4,4-trifluorobutanamide and 1-(cyclopropylmethyl)-1H-1,2,4-triazole-5-carboxylic acid in place of 2-(cyclopropylmethyl)-2H-1,2,3-triazole-4-carboxylic acid. The material was further purified by preparative HPLC (XBridge® Prep, 5 μM, C18 OBD™, 50×100 mm, 0-100% acetonitrile/water (with 20 mM $NH_4OH$)) to provide the title compound. $^1$H NMR (400 MHz, DMSO-$d_6$) δ 8.97-8.81 (m, 2H), 8.72 (d, J=7.8 Hz, 1H), 8.10 (s, 1H), 7.84 (s, 1H), 7.06 (d, J=7.0 Hz, 1H), 5.10 (t, J=8.6 Hz, 1H), 4.52-4.37 (m, 2H), 4.28 (dd, J=7.8, 8.8 Hz, 1H), 2.48-2.39 (m, 4H), 2.22-2.09 (m, 1H), 2.09-1.94 (m, 2H), 1.94-1.85 (m, 1H), 1.85-1.68 (m, 2H), 1.68-1.59 (m, 1H), 1.41-1.30 (m, 1H), 1.29-1.15 (m, 3H), 0.59-0.34 (m, 8H). MS (ESI) m/z: $[M+H]^+$ Found 609.2.

Example 33

N—((S)-(7-((S)-Cyclopropyl(4,4,4-trifluorobutanamido)methyl)imidazo[1,2-a]pyrimidin-2-yl)(4,4-difluorocyclohexyl)methyl)-1-(cyclopropylmethyl)-1H-1,2,4-triazole-5-carboxamide

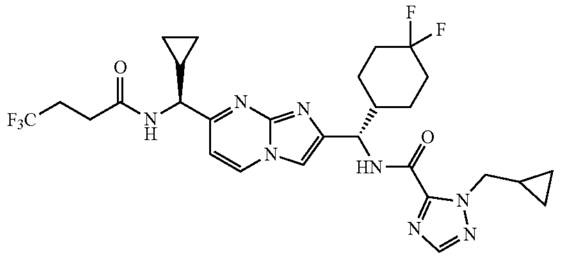 [SMILES: O=C(CCC(F)(F)F)N[C@H](c1ccn2cc([C@@H](NC(=O)c3ncnn3CC3CC3)C3CCC(F)(F)CC3)nc2n1)C1CC1]

The title compound was prepared as described in the synthesis of Example 31 using 1-(cyclopropylmethyl)-1H-1,2,4-triazole-5-carboxylic acid in place of 2-(cyclopropylmethyl)-2H-1,2,3-triazole-4-carboxylic acid. The material was further purified by preparative HPLC (XBridge® Prep, 5 μM, C18 OBD™, 50×100 mm, 0-100% acetonitrile/water (with 20 mM $NH_4OH$)) to provide the title compound. $^1H$ NMR (400 MHz, DMSO-$d_6$) δ 8.94-8.83 (m, 2H), 8.72 (d, J=7.8 Hz, 1H), 8.10 (s, 1H), 7.84 (s, 1H), 7.06 (d, J=7.0 Hz, 1H), 5.10 (t, J=8.5 Hz, 1H), 4.51-4.36 (m, 2H), 4.30 (dd, J=8.0, 8.6 Hz, 1H), 2.56-2.52 (m, 1H), 2.48-2.40 (m, 3H), 2.22-2.10 (m, 1H), 2.09-1.93 (m, 2H), 1.93-1.68 (m, 3H), 1.67-1.60 (m, 1H), 1.44-1.30 (m, 1H), 1.30-1.16 (m, 3H), 0.57-0.32 (m, 8H). MS (ESI) m/z: $[M+H]^+$ Found 609.3.

Example 34

N—((S)-(7-((R)-Cyclopropyl(4,4,4-trifluorobutanamido)methyl)imidazo[1,2-a]pyrimidin-2-yl)(4,4-difluorocyclohexyl)methyl)-2-(cyclopropylmethyl)-2H-1,2,3-triazole-4-carboxamide

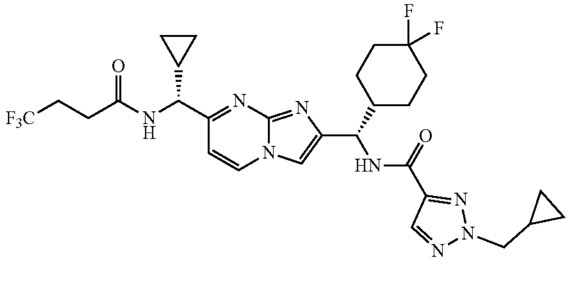 [SMILES: O=C(CCC(F)(F)F)N[C@@H](c1ccn2cc([C@@H](NC(=O)c3cnn(CC4CC4)n3)C3CCC(F)(F)CC3)nc2n1)C1CC1]

The title compound was prepared as described in the synthesis of Example 31 using N—((R)-(2-((S)-amino(4,4-difluorocyclohexyl)methyl)imidazo[1,2-a]pyrimidin-7-yl)(cyclopropyl)methyl)-4,4,4-trifluorobutanamide (Intermediate 41) in place of N—((S)-(2-((S)-amino(4,4-difluorocyclohexyl)methyl)imidazo[1,2-a]pyrimidin-7-yl)(cyclopropyl)methyl)-4,4,4-trifluorobutanamide. $^1H$ NMR (500 MHz, DMSO-$d_6$) δ 8.88 (d, J=7.0 Hz, 1H), 8.72 (d, J=7.6 Hz, 1H), 8.41 (d, J=9.1 Hz, 1H), 8.19 (s, 1H), 7.83 (s, 1H), 7.05 (d, J=6.9 Hz, 1H), 5.15 (t, J=8.6 Hz, 1H), 4.35 (d, J=7.3 Hz, 2H), 4.27 (dd, J=7.8, 8.8 Hz, 1H), 2.49-2.40 (m, 4H), 2.21-2.10 (m, 1H), 2.08-1.94 (m, 2H), 1.93-1.86 (m, 1H), 1.86-1.66 (m, 2H), 1.66-1.58 (m, 1H), 1.41-1.31 (m, 2H), 1.31-1.17 (m, 2H), 0.60-0.50 (m, 3H), 0.50-0.36 (m, 5H). MS (ESI) m/z: $[M+H]^+$ Found 609.3.

Example 35

N—((S)-(7-((R)-Cyclopropyl(4,4,4-trifluorobutanamido)methyl)-3-fluoroimidazo[1,2-a]pyrimidin-2-yl)(4,4-difluorocyclohexyl)methyl)-1-isopropyl-1H-pyrazole-5-carboxamide

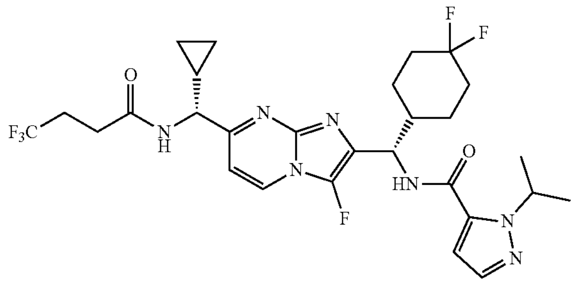 [SMILES: CC(C)n1nccc1C(=O)N[C@H](c1nc2nc([C@H](NC(=O)CCC(F)(F)F)C3CC3)ccn2c1F)C1CCC(F)(F)CC1]

The title compound was prepared as described in the synthesis of Example 31 using N—((R)-(2-((S)-amino(4,4-difluorocyclohexyl)methyl)-3-fluoroimidazo[1,2-a]pyrimidin-7-yl)(cyclopropyl)methyl)-4,4,4-trifluorobutanamide (Intermediate 57) in place of N—((S)-(2-((S)-amino(4,4-difluorocyclohexyl)methyl)imidazo[1,2-a]pyrimidin-7-yl)(cyclopropyl)methyl)-4,4,4-trifluorobutanamide and 1-isopropyl-1H-pyrazole-5-carboxylic acid in place of 2-(cyclopropylmethyl)-2H-1,2,3-triazole-4-carboxylic acid. $^1H$ NMR (500 MHz, DMSO-$d_6$) δ 8.81 (d, J=8.5 Hz, 1H), 8.75-8.67 (m, 2H), 7.47 (d, J=1.9 Hz, 1H), 7.13 (d, J=7.1 Hz, 1H), 6.92 (d, J=2.0 Hz, 1H), 5.38 (spt, J=6.6 Hz, 1H), 5.10 (t, J=8.9 Hz, 1H), 4.25 (dd, J=7.6, 8.9 Hz, 1H), 2.48-2.39 (m, 3H), 2.30-2.18 (m, 1H), 2.13-2.04 (m, 1H), 2.04-1.92 (m, 2H), 1.87-1.67 (m, 2H), 1.65-1.57 (m, 1H), 1.42-1.27 (m, 8H), 1.27-1.13 (m, 2H), 0.58-0.51 (m, 1H), 0.50-0.43 (m, 2H), 0.43-0.36 (m, 1H). MS (ESI) m/z: $[M+H]^+$ Found 614.3.

Example 36

3-Cyclopropyl-N—((S)-(7-((R)-cyclopropyl(4,4,4-trifluorobutanamido)methyl)imidazo[1,2-a]pyrimidin-2-yl)(4,4-difluorocyclohexyl)methyl)isoxazole-4-carboxamide

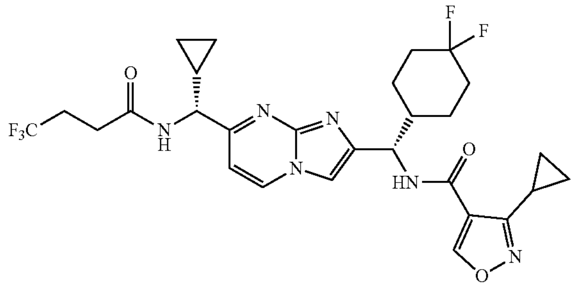 [SMILES: O=C(CCC(F)(F)F)N[C@@H](c1ccn2cc([C@@H](NC(=O)c3conc3C3CC3)C3CCC(F)(F)CC3)nc2n1)C1CC1]

The title compound was prepared as described in the synthesis of Example 31 using N—((R)-(2-((S)-amino(4,4- difluorocyclohexyl)methyl)imidazo[1,2-a]pyrimidin-7-yl)(cyclopropyl)methyl)-4,4,4-trifluorobutanamide (Intermediate 41) in place of N—((S)-(2-((S)-amino(4,4-difluorocyclohexyl)methyl)imidazo[1,2-a]pyrimidin-7-yl)(cyclopropyl)methyl)-4,4,4-trifluorobutanamide and 3-cyclopropylisoxazole-4-carboxylic acid in place of 2-(cyclopropylmethyl)-2H-1,2,3-triazole-4-carboxylic acid. $^{1}$H NMR (500 MHz, DMSO-$d_6$) δ 9.36 (s, 1H), 8.86 (d, J=7.0 Hz, 1H), 8.72 (d, J=7.6 Hz, 1H), 8.67 (d, J=9.0 Hz, 1H), 7.80 (s, 1H), 7.04 (d, J=7.0 Hz, 1H), 5.13 (t, J=8.5 Hz, 1H), 4.26 (dd, J=7.7, 8.8 Hz, 1H), 2.49-2.40 (m, 5H), 2.23-2.11 (m, 1H), 2.10-1.94 (m, 2H), 1.94-1.86 (m, 1H), 1.85-1.69 (m, 2H), 1.86-1.56 (m, 1H), 1.46-1.34 (m, 1H), 1.34-1.24 (m, 1H), 1.24-1.14 (m, 1H), 1.04-0.94 (m, 2H), 0.93-0.81 (m, 2H), 0.59-0.43 (m, 3H), 0.43-0.36 (m, 1H). MS (ESI) m/z: $[M+H]^+$ Found 595.2.

Example 37

3-Cyclopropyl-N—((S)-(7-((S)-cyclopropyl(4,4,4-trifluorobutanamido)methyl)imidazo[1,2-a]pyrimidin-2-yl)(4,4-difluorocyclohexyl)methyl)isoxazole-4-carboxamide

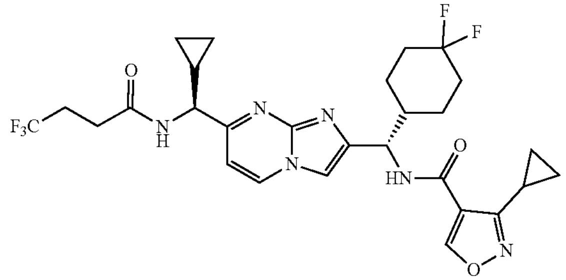 [SMILES: O=C(CCC(F)(F)F)N[C@H](c1ccn2cc([C@@H](NC(=O)c3conc3C3CC3)C3CCC(F)(F)CC3)nc2n1)C1CC1]

The title compound was prepared as described in the synthesis of Example 31 using 3-cyclopropylisoxazole-4-carboxylic acid in place of 2-(cyclopropylmethyl)-2H-1,2,3-triazole-4-carboxylic acid. $^{1}$H NMR (500 MHz, DMSO-$d_6$) δ 9.35 (s, 1H), 8.86 (d, J=6.9 Hz, 1H), 8.71 (d, J=7.6 Hz, 1H), 8.65 (d, J=9.0 Hz, 1H), 7.80 (s, 1H), 7.04 (d, J=7.0 Hz, 1H), 5.14 (t, J=8.4 Hz, 1H), 4.27 (dd, J=7.8, 8.7 Hz, 1H), 2.48-2.39 (m, 5H), 2.22-2.11 (m, 1H), 2.10-1.94 (m, 2H), 1.92-1.85 (m, 1H), 1.85-1.70 (m, 2H), 1.70-1.58 (m, 1H), 1.47-1.35 (m, 1H), 1.34-1.26 (m, 1H), 1.26-1.19 (m, 1H), 1.04-0.94 (m, 2H), 0.93-0.82 (m, 2H), 0.57-0.50 (m, 1H), 0.50-0.42 (m, 2H), 0.42-0.37 (m, 1H). MS (ESI) m/z: $[M+H]^+$ Found 595.3.

Example 38

N—((S)-(7-((S*)-Cyclopropyl(4,4,4-trifluorobutanamido)methyl)imidazo[1,2-a]pyrimidin-2-yl)(4,4-difluorocyclohexyl)methyl)-5-methyl-1-(3,3,3-trifluoropropyl)-1H-pyrazole-4-carboxamide

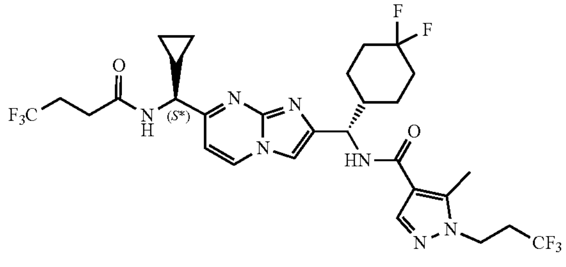 [SMILES: Cc1c(C(=O)N[C@H](c2cn3ccc([C@@H](NC(=O)CCC(F)(F)F)C4CC4)nc3n2)C2CCC(F)(F)CC2)cnn1CCC(F)(F)F]

Example 39

N—((S)-(7-((R*)-Cyclopropyl(4,4,4-trifluorobutanamido)methyl)imidazo[1,2-a]pyrimidin-2-yl)(4,4-difluorocyclohexyl)methyl)-5-methyl-1-(3,3,3-trifluoropropyl)-1H-pyrazole-4-carboxamide

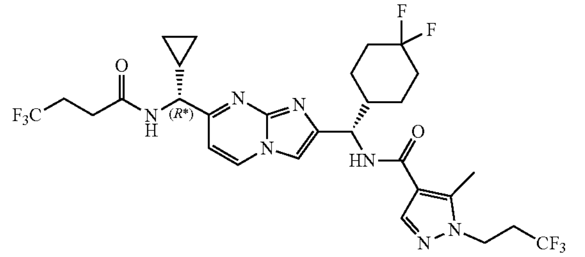

N-((1S)-(7-(Cyclopropyl(4,4,4-trifluorobutanamido)methyl)imidazo[1,2-a]pyrimidin-2-yl)(4,4-difluorocyclohexyl)methyl)-5-methyl-1-(3,3,3-trifluoropropyl)-1H-pyrazole-4-carboxamide (Intermediate 48) was purified by SFC using a chiral stationary phase (Whelk-01 (R,R), 25×2 cm; 25:75 EtOH (0.1% DEA)/$CO_2$) to give a pair of diastereomers. The first-eluting isomer was Example 39, and the second-eluting isomer was Example 38. Example 38: $^{1}$H NMR (400 MHz, DMSO-$d_6$) δ 8.87 (d, J=7.0 Hz, 1H), 8.72 (d, J=7.7 Hz, 1H), 8.18 (d, J=9.1 Hz, 1H), 8.12 (s, 1H), 7.77 (s, 1H), 7.04 (d, J=7.0 Hz, 1H), 5.14 (t, J=8.6 Hz, 1H), 4.37-4.21 (m, 3H), 2.91-2.75 (m, 2H), 2.53-2.39 (m, 7H), 2.24-2.13 (m, 1H), 2.11-1.93 (m, 2H), 1.92-1.60 (m, 4H), 1.47-1.14 (m, 3H), 0.61-0.35 (m, 4H). MS (ESI) m/z: $[M+H]^+$ Found 664.0. Example 39: $^{1}$H NMR (500 MHz, DMSO-$d_6$) δ 8.86 (d, J=6.9 Hz, 1H), 8.70 (d, J=7.7 Hz, 1H), 8.15 (d, J=9.1 Hz, 1H), 8.11 (s, 1H), 7.76 (s, 1H), 7.02 (d, J=7.0 Hz, 1H), 5.14 (t, J=8.5 Hz, 1H), 4.32-4.25 (m, 3H), 2.88-2.76 (m, 2H), 2.49 (s, 3H), 2.49-2.39 (m, 4H), 2.21-2.11 (m, 1H), 2.09-1.93 (m, 2H), 1.89-1.62 (m, 4H), 1.44-1.34 (m, 1H), 1.32-1.17 (m, 2H), 0.57-0.36 (m, 4H). MS (ESI) m/z: $[M+H]^+$ Found 664.2.

Example 40

N—((S)-(7-((S*)-Cyclopropyl(4,4,4-trifluorobutanamido)methyl)imidazo[1,2-a]pyrimidin-2-yl)(4,4-difluorocyclohexyl)methyl)-2-(3,3,3-trifluoropropyl)-2H-1,2,3-triazole-4-carboxamide

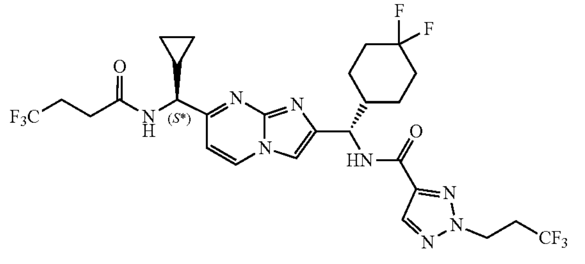 [SMILES: O=C(CCC(F)(F)F)N[C@H](c1ccn2cc([C@@H](NC(=O)c3cnn(CCC(F)(F)F)n3)C3CCC(F)(F)CC3)nc2n1)C1CC1]

Example 41

N—((S)-(7-((R*)-Cyclopropyl(4,4,4-trifluorobutanamido)methyl)imidazo[1,2-a]pyrimidin-2-yl)(4,4-difluorocyclohexyl)methyl)-2-(3,3,3-trifluoropropyl)-2H-1,2,3-triazole-4-carboxamide

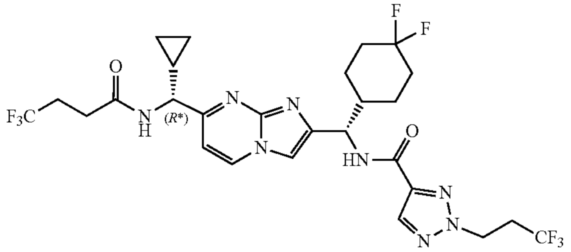 [SMILES: O=C(CCC(F)(F)F)N[C@@H](c1ccn2cc([C@@H](NC(=O)c3cnn(CCC(F)(F)F)n3)C3CCC(F)(F)CC3)nc2n1)C1CC1]

N-((1S)-(7-(Cyclopropyl(4,4,4-trifluorobutanamido)methyl)imidazo[1,2-a]pyrimidin-2-yl)(4,4-difluorocyclohexyl)methyl)-2-(3,3,3-trifluoropropyl)-2H-1,2,3-triazole-4-carboxamide (Intermediate 47) was purified by SFC using a chiral stationary phase (CHIRALPAK IA, 25×2 cm; 40:60 EtOH (0.1% DEA)/$CO_2$) to give a pair of diastereomers. The first-eluting isomer was Example 41, and the second-eluting isomer was Example 40. Example 40: $^1$H NMR (500 MHz, DMSO-$d_6$) δ 8.88 (d, J=6.9 Hz, 1H), 8.72 (d, J=7.6 Hz, 1H), 8.47 (d, J=9.0 Hz, 1H), 8.24 (s, 1H), 7.83 (s, 1H), 7.05 (d, J=7.0 Hz, 1H), 5.15 (t, J=8.6 Hz, 1H), 4.77 (t, J=6.7 Hz, 2H), 4.27 (t, J=8.2 Hz, 1H), 3.12-2.98 (m, 2H), 2.53-2.38 (m, 4H), 2.22-2.10 (m, 1H), 2.10-1.86 (m, 3H), 1.86-1.66 (m, 2H), 1.66-1.56 (m, 1H), 1.43-1.16 (m, 3H), 0.60-0.35 (m, 4H). MS (ESI) m/z: $[M+H]^+$ Found 651.1. Example 41: $^1$H NMR (500 MHz, DMSO-$d_6$) δ 8.87 (d, J=6.9 Hz, 1H), 8.71 (d, J=7.5 Hz, 1H), 8.46 (d, J=9.0 Hz, 1H), 8.24 (s, 1H), 7.82 (s, 1H), 7.05 (d, J=6.9 Hz, 1H), 5.15 (t, J=8.6 Hz, 1H), 4.76 (t, J=6.7 Hz, 2H), 4.31-4.25 (m, 1H), 3.10-2.99 (m, 2H), 2.51-2.40 (m, 4H), 2.20-2.10 (m, 1H), 2.09-1.93 (m, 2H), 1.93-1.85 (m, 1H), 1.85-1.67 (m, 2H), 1.66-1.58 (m, 1H), 1.42-1.31 (m, 1H), 1.31-1.17 (m, 2H), 0.57-0.37 (m, 4H). MS (ESI) m/z: $[M+H]^+$ Found 651.1.

Example 42

N—((S)-(7-((S*)-Cyclopropyl(4,4,4-trifluorobutanamido)methyl)imidazo[1,2-a]pyrimidin-2-yl)(4,4-difluorocyclohexyl)methyl)-1-(3,3,3-trifluoropropyl)-1H-pyrazole-3-carboxamide

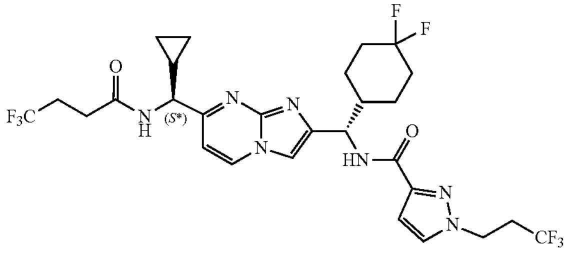 [SMILES: O=C(CCC(F)(F)F)N[C@H](c1ccn2cc([C@@H](NC(=O)c3ccn(CCC(F)(F)F)n3)C3CCC(F)(F)CC3)nc2n1)C1CC1]

Example 43

N—((S)-(7-((R*)-Cyclopropyl(4,4,4-trifluorobutanamido)methyl)imidazo[1,2-a]pyrimidin-2-yl)(4,4-difluorocyclohexyl)methyl)-1-(3,3,3-trifluoropropyl)-1H-pyrazole-3-carboxamide

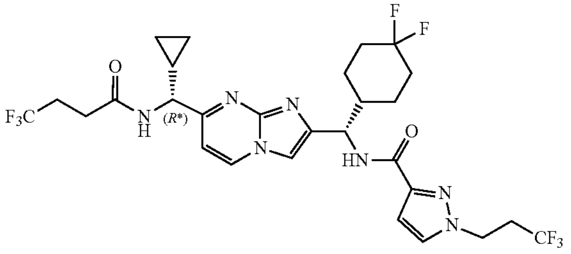 [SMILES: O=C(CCC(F)(F)F)N[C@@H](c1ccn2cc([C@@H](NC(=O)c3ccn(CCC(F)(F)F)n3)C3CCC(F)(F)CC3)nc2n1)C1CC1]

N-((1S)-(7-(Cyclopropyl(4,4,4-trifluorobutanamido)methyl)imidazo[1,2-a]pyrimidin-2-yl)(4,4-difluorocyclohexyl)methyl)-1-(3,3,3-trifluoropropyl)-1H-pyrazole-3-carboxamide (Intermediate 46) was purified by SFC using a chiral stationary phase (CHIRALPAK AD-H, 25×2 cm; 15:85 MeOH (0.1% DEA)/$CO_2$) to give a pair of diastereomers. The first-eluting isomer was Example 43, and the second-eluting isomer was Example 42. Example 42: $^1$H NMR (500 MHz, DMSO-$d_6$) δ 8.88 (d, J=6.9 Hz, 1H), 8.73 (d, J=7.6 Hz, 1H), 7.99 (d, J=9.2 Hz, 1H), 7.91 (d, J=2.4 Hz, 1H), 7.82 (s, 1H), 7.06 (d, J=7.0 Hz, 1H), 6.67 (d, J=2.3 Hz, 1H), 5.16-5.11 (m, 1H), 4.47 (t, J=7.0 Hz, 2H), 4.28 (dd, J=8.9, 7.6 Hz, 1H), 2.99-2.88 (m, 2H), 2.52-2.41 (m, 4H), 2.15-1.66 (m, 6H), 1.65-1.57 (m, 1H), 1.39-1.18 (m, 3H), 0.57-0.38 (m, 4H). MS (ESI) m/z: $[M+H]^+$ Found 650.3. Example 43: $^1$H NMR (500 MHz, DMSO-$d_6$) δ 8.88 (d, J=6.9 Hz, 1H), 8.71 (d, J=7.7 Hz, 1H), 7.99 (d, J=9.2 Hz, 1H), 7.90 (d, J=2.3 Hz, 1H), 7.82 (s, 1H), 7.05 (d, J=7.0 Hz, 1H), 6.67 (d, J=2.4 Hz, 1H), 5.13 (t, J=8.5 Hz, 1H), 4.46 (t, J=7.0 Hz, 2H), 4.32-4.27 (m, 1H), 2.99-2.88 (m, 2H), 2.55-2.40 (m, 4H), 2.15-1.92 (m, 3H), 1.92-1.65 (m, 3H), 1.65-1.57 (m, 1H), 1.39-1.30 (m, 1H), 1.30-1.17 (m, 2H), 0.57-0.37 (m, 4H). MS (ESI) m/z: $[M+H]^+$ Found 650.3.

Example 44

N—((S)-(7-((S*)-Cyclopropyl(4,4,4-trifluorobutanamido)methyl)imidazo[1,2-a]pyrimidin-2-yl)(4,4-difluorocyclohexyl)methyl)-1-methyl-1H-pyrazole-5-carboxamide

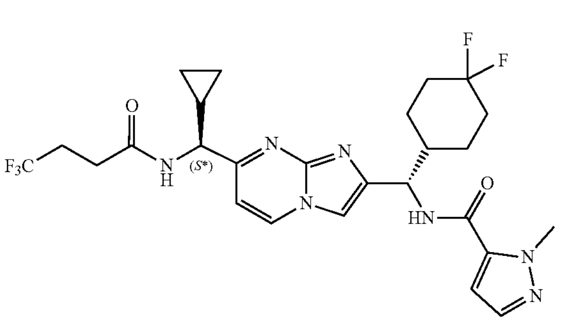 [SMILES: Cn1nccc1C(=O)N[C@H](c1cn2ccc([C@@H](NC(=O)CCC(F)(F)F)C3CC3)nc2n1)C1CCC(F)(F)CC1]

Example 45

N—((S)-(7-((R*)-Cyclopropyl(4,4,4-trifluorobutanamido)methyl)imidazo[1,2-a]pyrimidin-2-yl)(4,4-difluorocyclohexyl)methyl)-1-methyl-1H-pyrazole-5-carboxamide

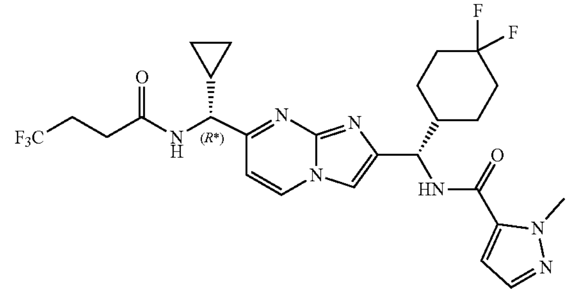 [SMILES: Cn1nccc1C(=O)N[C@H](c1cn2ccc([C@H](NC(=O)CCC(F)(F)F)C3CC3)nc2n1)C1CCC(F)(F)CC1]

N-((1S)-(7-(Cyclopropyl(4,4,4-trifluorobutanamido)methyl)imidazo[1,2-a]pyrimidin-2-yl)(4,4-difluorocyclohexyl)methyl)-1-methyl-1H-pyrazole-5-carboxamide (Intermediate 45) was purified by SFC using a chiral stationary phase (CHIRALPAK AD-H, 25×2 cm; 20:80 MeOH (0.1% DEA)/$CO_2$) to give a pair of diastereomers. The first-eluting isomer was Example 45, and the second-eluting isomer was Example 44. Example 44: $^1$H NMR (400 MHz, DMSO-$d_6$) δ 8.86 (d, J=6.9 Hz, 1H), 8.77-8.66 (m, 2H), 7.80 (s, 1H), 7.45 (d, J=2.1 Hz, 1H), 7.08-6.99 (m, 2H), 5.11 (t, J=8.6 Hz, 1H), 4.30-4.22 (m, 1H), 4.02 (s, 3H), 2.57-2.37 (m, 4H), 2.27-2.14 (m, 1H), 2.12-1.59 (m, 6H), 1.46-1.14 (m, 3H), 0.59-0.35 (m, 4H). MS (ESI) m/z: $[M+H]^+$ Found 568.3. Example 45: $^1$H NMR (500 MHz, DMSO-$d_6$) δ 8.86 (d, J=6.9 Hz, 1H), 8.71 (d, J=8.4 Hz, 2H), 7.79 (s, 1H), 7.45 (d, J=2.0 Hz, 1H), 7.05-7.01 (m, 2H), 5.11 (t, J=8.6 Hz, 1H), 4.29-4.24 (m, 1H), 4.01 (s, 3H), 2.53-2.40 (m, 4H), 2.24-2.15 (m, 1H), 2.10-1.94 (m, 2H), 1.92-1.85 (m, 1H), 1.85-1.63 (m, 3H), 1.44-1.34 (m, 1H), 1.32-1.17 (m, 2H), 0.57-0.37 (m, 4H). MS (ESI) m/z: $[M+H]^+$ Found 568.3.

Example 46

N—((S)-(7-((S*)-Cyclopropyl(4,4,4-trifluorobutanamido)methyl)imidazo[1,2-a]pyrimidin-2-yl)(4,4-difluorocyclohexyl)methyl)-1-isopropyl-1H-pyrazole-5-carboxamide

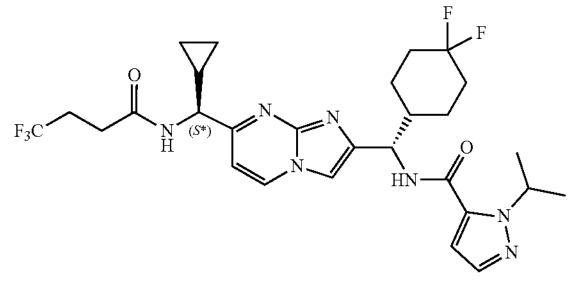 [SMILES: CC(C)n1nccc1C(=O)N[C@H](c1cn2ccc([C@@H](NC(=O)CCC(F)(F)F)C3CC3)nc2n1)C1CCC(F)(F)CC1]

Example 47

N—((S)-(7-((R*)-Cyclopropyl(4,4,4-trifluorobutanamido)methyl)imidazo[1,2-a]pyrimidin-2-yl)(4,4-difluorocyclohexyl)methyl)-1-isopropyl-1H-pyrazole-5-carboxamide

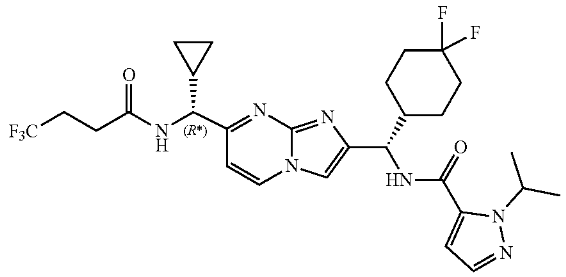 [SMILES: CC(C)n1nccc1C(=O)N[C@H](c1cn2ccc([C@H](NC(=O)CCC(F)(F)F)C3CC3)nc2n1)C1CCC(F)(F)CC1]

N-((1S)-(7-(Cyclopropyl(4,4,4-trifluorobutanamido)methyl)imidazo[1,2-a]pyrimidin-2-yl)(4,4-difluorocyclohexyl)methyl)-1-isopropyl-1H-pyrazole-5-carboxamide (Intermediate 44) was purified by SFC using a chiral stationary phase (Whelk-01 (S,S), 25×2 cm; 25:75 MeOH/$CO_2$) to give a pair of diastereomers. The first-eluting isomer was Example 47, and the second-eluting isomer was Example 46. Example 46: $^1$H NMR (600 MHz, DMSO-$d_6$) δ 8.88 (d, J=6.9 Hz, 1H), 8.74-8.70 (m, 2H), 7.81 (s, 1H), 7.50 (d, J=2.0 Hz, 1H), 7.05 (d, J=7.0 Hz, 1H), 6.93 (d, J=2.0 Hz, 1H), 5.43-5.36 (m, 1H), 5.14 (t, J=8.5 Hz, 1H), 4.31-4.26 (m, 1H), 2.54-2.41 (m, 4H), 2.24-2.16 (m, 1H), 2.10-1.95 (m, 2H), 1.92-1.85 (m, 1H), 1.84-1.64 (m, 3H), 1.46-1.19 (m, 9H), 0.57-0.51 (m, 1H), 0.51-0.44 (m, 2H), 0.43-0.38 (m, 1H). MS (ESI) m/z: $[M+H]^+$ Found 596.3. Example 47: $^1$H NMR (500 MHz, DMSO-$d_6$) δ 8.87 (d, J=6.9 Hz, 1H), 8.78-8.67 (m, 2H), 7.80 (s, 1H), 7.48 (s, 1H), 7.04 (d, J=6.9 Hz, 1H), 6.93 (d, J=2.0 Hz, 1H), 5.44-5.34 (m, 1H), 5.12 (t, J=8.7 Hz, 1H), 4.27 (t, J=8.3 Hz, 1H), 2.56-2.40 (m, 4H), 2.25-2.16 (m, 1H), 2.11-1.93 (m, 2H), 1.93-1.61 (m, 4H), 1.46-1.16 (m, 9H), 0.57-0.36 (m, 4H). MS (ESI) m/z: $[M+H]^+$ Found 596.3.

Example 48

N—((S)-(7-((R)-Cyclopropyl(4,4,4-trifluorobutanamido)methyl)imidazo[1,2-a]pyrimidin-2-yl)(4,4-difluorocyclohexyl)methyl)-2-(2,2,2-trifluoroethyl)isonicotinamide

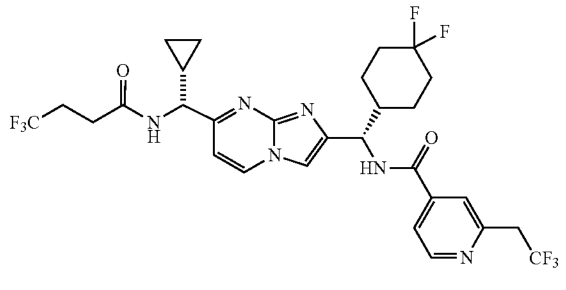 [SMILES: O=C(CCC(F)(F)F)N[C@@H](c1ccn2cc([C@@H](NC(=O)c3ccnc(CC(F)(F)F)c3)C3CCC(F)(F)CC3)nc2n1)C1CC1]

The title compound was prepared as described in the synthesis of Intermediate 37 using N—((R)-(2-((S)-amino (4,4-difluorocyclohexyl)methyl)imidazo[1,2-a]pyrimidin-7-yl)(cyclopropyl)methyl)-4,4,4-trifluorobutanamide (Intermediate 41) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide and 2-(2,2,2-trifluoroethyl)pyridine-4-carboxylic acid in place of trans-2-(trifluoromethyl)cyclopropane-1-carboxylic acid and the mixture was stirred at 40° C. for 21 h instead of 2 h. $^1$H NMR (500 MHz, $CDCl_3$) δ 8.76-8.70 (m, 1H), 8.37 (d, J=6.9 Hz, 1H), 7.71 (s, 1H), 7.61 (d, J=5.1 Hz, 1H), 7.48 (s, 1H), 7.34 (br s, 1H), 6.93 (d, J=6.9 Hz, 1H), 6.84 (d, J=7.8 Hz, 1H), 5.29 (t, J=8.0 Hz, 1H), 4.62-4.56 (m, 1H), 3.67 (q, J=10.6 Hz, 2H), 2.57-2.42 (m, 4H), 2.22-2.11 (m, 2H), 2.09-1.98 (m, 2H), 1.82-1.63 (m, 3H), 1.55-1.49 (m, 1H), 1.41-1.32 (m, 1H), 1.24-1.18 (m, 1H), 0.65-0.59 (m, 3H), 0.56-0.50 (m, 1H). MS (ESI) m/z: $[M+H]^+$ Found 647.2.

Example 49

N—((S)-(7-((S*)-Cyclopropyl(4,4,4-trifluorobutanamido)methyl)imidazo[1,2-a]pyrimidin-2-yl)(4,4-difluorocyclohexyl)methyl)-1-(3,3,3-trifluoropropyl)-1H-pyrazole-4-carboxamide

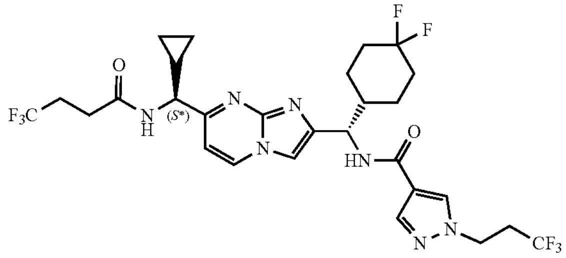

Example 50

N—((S)-(7-((R*)-Cyclopropyl(4,4,4-trifluorobutanamido)methyl)imidazo[1,2-a]pyrimidin-2-yl)(4,4-difluorocyclohexyl)methyl)-1-(3,3,3-trifluoropropyl)-1H-pyrazole-4-carboxamide

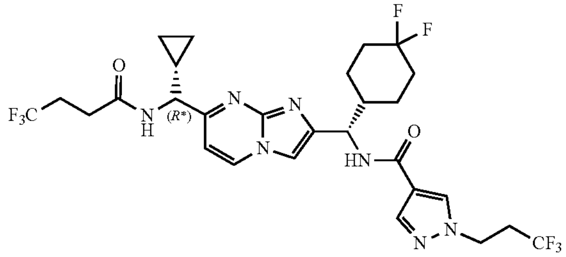

N-((1S)-(7-(Cyclopropyl(4,4,4-trifluorobutanamido)methyl)imidazo[1,2-a]pyrimidin-2-yl)(4,4-difluorocyclohexyl)methyl)-1-(3,3,3-trifluoropropyl)-1H-pyrazole-4-carboxamide (Intermediate 43) was purified by SFC using a chiral stationary phase (CHIRALPAK AD-H, 25×3 cm; 45:55 EtOH/$CO_2$) to give a pair of diastereomers. The first-eluting isomer was Example 50, and the second-eluting isomer was Example 49. Example 49: $^1$H NMR (400 MHz, DMSO-$d_6$) δ 8.86 (d, J=6.8 Hz, 1H), 8.73 (d, J=7.7 Hz, 1H), 8.40-8.28 (m, 2H), 8.01 (s, 1H), 7.76 (s, 1H), 7.03 (d, J=6.8 Hz, 1H), 5.12 (t, J=8.5 Hz, 1H), 4.39 (t, J=6.7 Hz, 2H), 4.25 (t, J=8.3 Hz, 1H), 2.97-2.80 (m, 2H), 2.54-2.37 (m, 4H), 2.24-2.11 (m, 1H), 2.11-1.92 (m, 2H), 1.92-1.58 (m, 4H), 1.45-1.13 (m, 3H), 0.58-0.34 (m, 4H). MS (ESI) m/z: $[M+H]^+$ Found 650.3. Example 50: $^1$H NMR (400 MHz, DMSO-$d_6$) δ 8.86 (d, J=6.7 Hz, 1H), 8.72 (d, J=7.7 Hz, 1H), 8.40-8.27 (m, 2H), 8.02 (s, 1H), 7.76 (s, 1H), 7.03 (d, J=6.9 Hz, 1H), 5.13 (t, J=8.5 Hz, 1H), 4.39 (t, J=6.8 Hz, 2H), 4.27 (t, J=8.3 Hz, 1H), 2.96-2.81 (m, 2H), 2.53-2.40 (m, 4H), 2.23-2.11 (m, 1H), 2.11-1.93 (m, 2H), 1.93-1.61 (m, 4H), 1.49-1.15 (m, 3H), 0.60-0.35 (m, 4H). MS (ESI) m/z: $[M+H]^+$ Found 650.3.

Example 51

N—((S)-(7-((R)-Cyclopropyl(2-((S*)-2,2-difluorocyclopropyl)acetamido)methyl)imidazo[1,2-a]pyrimidin-2-yl)(4,4-difluorocyclohexyl)methyl)-4-methyl-1,2,5-oxadiazole-3-carboxamide

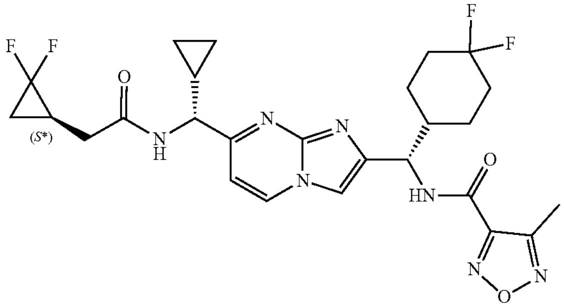 [SMILES: Cc1nonc1C(=O)N[C@H](c1cn2ccc([C@H](NC(=O)C[C@H]3CC3(F)F)C3CC3)nc2n1)C1CCC(F)(F)CC1]

Example 52

N—((S)-(7-((R)-Cyclopropyl(2-((R*)-2,2-difluorocyclopropyl)acetamido)methyl)imidazo[1,2-a]pyrimidin-2-yl)(4,4-difluorocyclohexyl)methyl)-4-methyl-1,2,5-oxadiazole-3-carboxamide

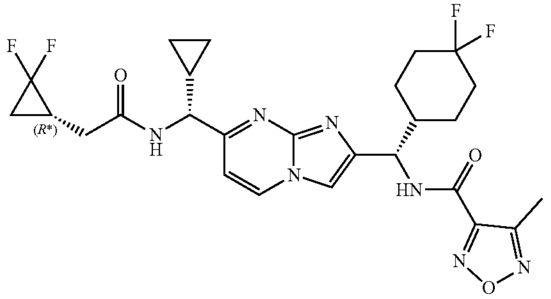 [SMILES: Cc1nonc1C(=O)N[C@H](c1cn2ccc([C@H](NC(=O)C[C@@H]3CC3(F)F)C3CC3)nc2n1)C1CCC(F)(F)CC1]

To a solution of N—((R)-(2-((S)-amino(4,4-difluorocyclohexyl)methyl)imidazo[1,2-a]pyrimidin-7-yl)(cyclopropyl)methyl)-2-(2,2-difluorocyclopropyl)acetamide (125 mg, 0.28 mmol, Intermediate 59) in ACN (5.8 mL) were added TCFH (80 mg, 0.28 mmol), 4-methyl-1,2,5-oxadiazole-3-carboxylic acid (30 mg, 0.24 mmol) and 1-methylimidazole (0.1 mL, 1.25 mmol) and the resulting mixture was stirred at rt for 30 min. After that time, the mixture was poured over water (20 mL) and extracted with EtOAc (3×15 mL). The organic layers were combined, washed with brine, dried over anhydrous $Na_2SO_4$, filtered and concentrated to dryness. The residue was purified by preparative basic HPLC followed by preparative HPLC (irregular bare silica, 0.2%/98%/2% $NH_4OH$/DCM/MeOH). This material was further purified by achiral SFC (AMINO 6 μm, 250×21.2 mm, 12:88 MeOH (0.3% i-$PrNH_2$)/$CO_2$) followed by SFC using a chiral stationary phase (Whelk-O1 (S,S), 21.2×250 mm, 5 μm, 25:75 i-PrOH (0.3% i-$PrNH_2$)/$CO_2$) to give a pair of diastereomers. The first-eluting isomer was Example 52 and the second-eluting isomer was Example 51. Example 51: $^1$H NMR (500 MHz, $CDCl_3$) δ 8.35 (d, J=6.9 Hz, 1H), 7.70 (d, J=9.0 Hz, 1H), 7.47 (s, 1H), 6.91 (d, J=6.9 Hz, 1H), 6.87 (d, J=7.8 Hz, 1H), 5.21 (dd, J=9.0, 7.8 Hz, 1H), 4.62 (t, J=8.2 Hz, 1H), 2.60 (s, 3H), 2.54-2.35 (m, 2H), 2.26-2.12 (m, 2H), 2.08-1.99 (m, 2H), 1.94-1.87 (m, 1H), 1.82-1.65 (m, 3H), 1.55-1.50 (m, 2H), 1.46-1.35 (m, 1H), 1.27-1.22 (m, 1H), 1.13-1.06 (m, 1H), 0.65-0.58 (m, 3H), 0.54-0.47 (m, 1H). MS (ESI) m/z: $[M+H]^+$ Found 564.2. Example 52: $^1$H NMR (500 MHz, $CDCl_3$) δ 8.34 (d, J=6.9 Hz, 1H), 7.70 (d, J=9.0 Hz, 1H), 7.47 (s, 1H), 6.91 (d, J=6.9 Hz, 1H), 6.84 (d, J=7.9 Hz, 1H), 5.21 (dd, J=8.9, 7.8 Hz, 1H), 4.63 (t, J=8.3 Hz, 1H), 2.60 (s, 3H), 2.52-2.36 (m, 2H), 2.26-2.13 (m, 2H), 2.08-2.00 (m, 2H), 1.95-1.86 (m, 1H), 1.80-1.67 (m, 3H), 1.55-1.48 (m, 3H), 1.41-1.35 (m, 1H), 1.10-1.04 (m, 1H), 0.64-0.58 (m, 3H), 0.54-0.48 (m, 1H). MS (ESI) m/z: $[M+H]^+$ Found 564.2.

Example 53

N—((S)-(7-((R)-Cyclopropyl(2-((S*)-2,2-difluorocyclopropyl)acetamido)methyl)imidazo[1,2-a]pyrimidin-2-yl)(4,4-difluorocyclohexyl)methyl)-4-methylisoxazole-3-carboxamide

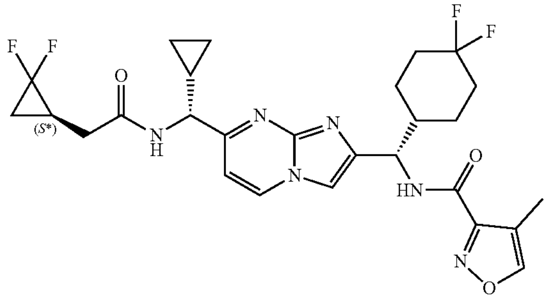 [SMILES: Cc1conc1C(=O)N[C@H](c1cn2ccc([C@H](NC(=O)C[C@H]3CC3(F)F)C3CC3)nc2n1)C1CCC(F)(F)CC1]

Example 54

N—((S)-(7-((R)-Cyclopropyl(2-((R*)-2,2-difluorocyclopropyl)acetamido)methyl)imidazo[1,2-a]pyrimidin-2-yl)(4,4-difluorocyclohexyl)methyl)-4-methylisoxazole-3-carboxamide

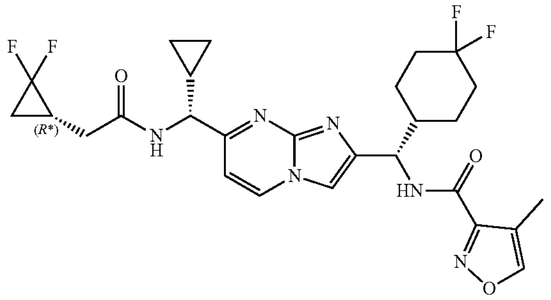 [SMILES: Cc1conc1C(=O)N[C@H](c1cn2ccc([C@H](NC(=O)C[C@@H]3CC3(F)F)C3CC3)nc2n1)C1CCC(F)(F)CC1]

Examples 53 and 54 were prepared as described in the synthesis of Intermediate 37, using N—((R)-(2-((S)-amino(4,4-difluorocyclohexyl)methyl)imidazo[1,2-a]pyrimidin-7-yl)(cyclopropyl)methyl)-2-(2,2-difluorocyclopropyl)acetamide (Intermediate 59) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide and 4-methylisoxazole-3-carboxylic acid in place of trans-2-(trifluoromethyl)cyclopropane-1-carboxylic acid. The pure mixture of diastereomers (Example 53 and 54) were separated by SFC using a chiral stationary phase (Whelk-O1 (S,S), 21.2×250 mm, 5 μm, 25:75 i-PrOH (0.3% i-$PrNH_2$)/$CO_2$). The first-eluting isomer was Example 54 and the second-eluting isomer was Example 53. Example 53: $^1$H NMR (400 MHz, $CDCl_3$) δ 8.33 (d, J=6.9 Hz, 1H), 8.24-8.20 (m, 1H), 7.59 (d, J=9.1 Hz, 1H), 7.47 (s, 1H), 6.90 (dd, J=16.5, 7.4 Hz, 2H), 5.23 (dd, J=9.2, 7.8 Hz, 1H), 4.64 (t, J=8.2 Hz, 1H), 3.76-3.45 (m, 2H), 2.53 (dd, J=15.8, 6.8 Hz, 1H), 2.41-2.32 (m, 1H), 2.25-2.23 (m, 3H), 2.18-2.11 (m, 1H), 2.08-1.99 (m, 2H), 1.96-1.85 (m, 1H), 1.78-1.65 (m, 3H), 1.44-1.34 (m, 1H), 1.26-1.07 (m, 3H), 0.65-0.46 (m, 4H). MS (ESI) m/z: $[M+H]^+$ Found 563.2. Example 54: $^1$H NMR (400 MHz, $CDCl_3$) δ 8.33 (d, J=6.9 Hz, 1H), 8.25-8.19 (m, 1H), 7.60 (d, J=9.1 Hz, 1H), 7.47 (s, 1H), 6.89 (d, J=6.9 Hz, 2H), 5.23 (dd, J=9.2, 7.7 Hz, 1H), 4.65 (t, J=8.2 Hz, 1H), 3.76-3.47 (m, 2H), 2.54-2.46 (m, 1H), 2.42-2.35 (m, 1H), 2.25-2.24 (m, 3H), 2.07-1.98 (m, 2H), 1.95-1.85 (m, 1H), 1.75-1.67 (m, 2H), 1.55-1.47 (m, 2H), 1.43-1.35 (m, 1H), 1.26-1.19 (m, 2H), 1.11-1.03 (m, 1H), 0.65-0.45 (m, 4H). MS (ESI) m/z: $[M+H]^+$ Found 563.2.

Example 55

N—((S)-(7-((R)-Cyclopropyl(2-((S*)-2,2-difluorocyclopropyl)acetamido)methyl)imidazo[1,2-a]pyrimidin-2-yl)(4,4-difluorocyclohexyl)methyl)-1-(cyclopropylmethyl)-1H-1,2,4-triazole-5-carboxamide

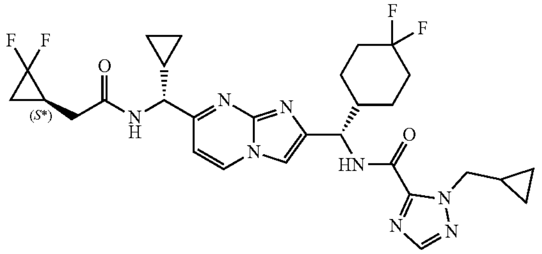 [SMILES: O=C(C[C@H]1CC1(F)F)N[C@@H](c1ccn2cc([C@@H](NC(=O)c3ncnn3CC3CC3)C3CCC(F)(F)CC3)nc2n1)C1CC1]

Example 56

N—((S)-(7-((R)-Cyclopropyl(2-((R*)-2,2-difluorocyclopropyl)acetamido)methyl)imidazo[1,2-a]pyrimidin-2-yl)(4,4-difluorocyclohexyl)methyl)-1-(cyclopropylmethyl)-1H-1,2,4-triazole-5-carboxamide

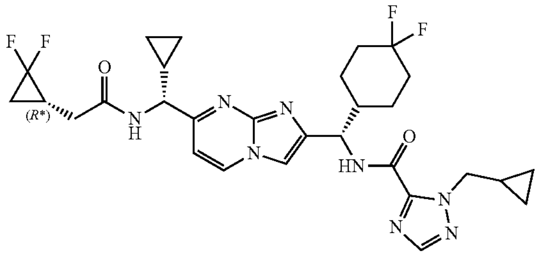 [SMILES: O=C(C[C@@H]1CC1(F)F)N[C@@H](c1ccn2cc([C@@H](NC(=O)c3ncnn3CC3CC3)C3CCC(F)(F)CC3)nc2n1)C1CC1]

Examples 55 and 56 were prepared as described in the synthesis of Intermediate 37, using N—((R)-(2-((S)-amino(4,4-difluorocyclohexyl)methyl)imidazo[1,2-a]pyrimidin-7-yl)(cyclopropyl)methyl)-2-(2,2-difluorocyclopropyl)acetamide (Intermediate 59) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl) acetamide and 1-(cyclopropylmethyl)-1H-1,2,4-triazole-5-carboxylic acid in place of trans-2-(trifluoromethyl) cyclopropane-1-carboxylic acid. The mixture was stirred at 40° C. for 24 h instead of 2 h, and an additional aliquot of EDCI (43 mg, 0.26 mmol) was added after 2 h. Examples 55 and 56 were separated by SFC using a chiral stationary phase (Whelk-O1 (S,S), 21.2×250 mm, 5 μm, 25:75 i-PrOH (0.3% i-$PrNH_2$)/$CO_2$). The first-eluting isomer was Example 56 and the second-eluting isomer was Example 55. Example 55: $^1$H NMR (400 MHz, $CDCl_3$) δ 8.33 (d, J=6.9 Hz, 1H), 8.13 (d, J=9.3 Hz, 1H), 7.85 (s, 1H), 7.47 (s, 1H), 6.90 (dd, J=15.5, 7.4 Hz, 2H), 5.17 (dd, J=9.3, 7.8 Hz, 1H), 4.63 (t, J=8.2 Hz, 1H), 4.58-4.47 (m, 2H), 2.57-2.48 (m, 1H), 2.41-2.33 (m, 1H), 2.31-2.23 (m, 1H), 2.20-2.10 (m, 1H), 1.96-1.86 (m, 1H), 1.81-1.62 (m, 4H), 1.59-1.50 (m, 2H), 1.43-1.34 (m, 2H), 1.26-1.19 (m, 2H), 1.14-1.07 (m, 1H), 0.66-0.41 (m, 8H). MS (ESI) m/z: $[M+H]^+$ Found 603.3. Example 56: $^1$H NMR (400 MHz, $CDCl_3$) δ 8.33 (d, J=6.9 Hz, 1H), 8.12 (d, J=9.3 Hz, 1H), 7.85 (s, 1H), 7.47 (s, 1H), 6.89 (d, J=6.9 Hz, 2H), 5.17 (dd, J=9.3, 7.8 Hz, 1H), 4.64 (t, J=8.2 Hz, 1H), 4.57-4.45 (m, 2H), 2.55-2.46 (m, 1H), 2.42-2.34 (m, 1H), 2.32-2.22 (m, 1H), 2.19-2.10 (m, 1H), 1.96-1.87 (m, 1H), 1.79-1.63 (m, 4H), 1.57-1.48 (m, 2H), 1.43-1.33 (m, 2H), 1.27-1.18 (m, 2H), 1.11-1.04 (m, 1H), 0.64-0.41 (m, 8H). MS (ESI) m/z: $[M+H]^+$ Found 603.2.

Example 57

N—((S)-(7-((R)-Cyclopropyl(2-((S*)-2,2-difluorocyclopropyl)acetamido)methyl)imidazo[1,2-a]pyrimidin-2-yl)(4,4-difluorocyclohexyl)methyl)-3-(trifluoromethyl)isoxazole-4-carboxamide

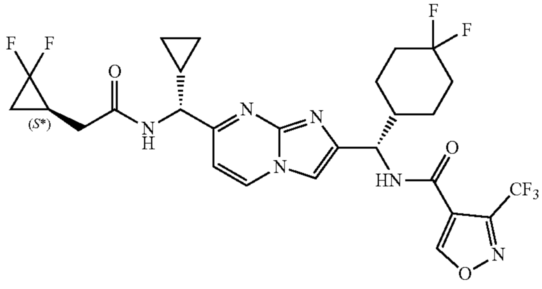 [SMILES: O=C(C[C@H]1CC1(F)F)N[C@@H](c1ccn2cc([C@@H](NC(=O)c3conc3C(F)(F)F)C3CCC(F)(F)CC3)nc2n1)C1CC1]

Example 58

N—((S)-(7-((R)-Cyclopropyl(2-((R*)-2,2-difluorocyclopropyl)acetamido)methyl)imidazo[1,2-a]pyrimidin-2-yl)(4,4-difluorocyclohexyl)methyl)-3-(trifluoromethyl)isoxazole-4-carboxamide

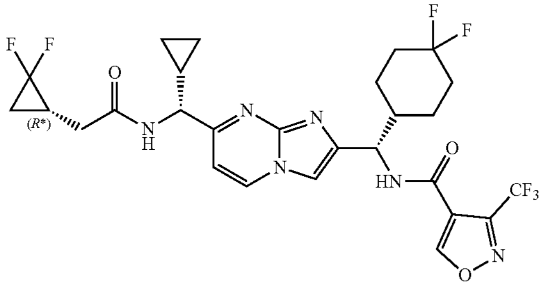 [SMILES: O=C(C[C@@H]1CC1(F)F)N[C@@H](c1ccn2cc([C@@H](NC(=O)c3conc3C(F)(F)F)C3CCC(F)(F)CC3)nc2n1)C1CC1]

Examples 57 and 58 were prepared as described in the synthesis of Intermediate 37, using N—((R)-(2-((S)-amino(4,4-difluorocyclohexyl)methyl)imidazo[1,2-a]pyrimidin-7-yl)(cyclopropyl)methyl)-2-(2,2-difluorocyclopropyl)acetamide (Intermediate 59) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl) acetamide and 3-(trifluoromethyl)isoxazole-4-carboxylic acid in place of trans-2-(trifluoromethyl)cyclopropane-1-carboxylic acid. Examples 57 and 58 was separated by SFC using a chiral stationary phase (Whelk-O1 (S,S), 21.2×250 mm, 5 μm, 15:85 EtOH/$CO_2$). The second-eluting diastereomer (Example 57) was repurified by SFC using a chiral stationary phase (Whelk-O1 (S,S), 21.2×250 mm, 5 μm, 15:85 EtOH/$CO_2$). The first-eluting isomer was Example 58 and the second-eluting isomer was Example 57. Example 57: $^1$H NMR (400 MHz, $CDCl_3$) δ 9.03-8.96 (m, 1H), 8.36 (d, J=6.9 Hz, 1H), 7.46 (s, 1H), 7.19 (d, J=8.4 Hz, 1H), 6.92 (d, J=6.9 Hz, 1H), 6.85 (d, J=7.7 Hz, 1H), 5.22 (t, J=8.0 Hz, 1H), 4.58 (t, J=8.2 Hz, 1H), 2.52-2.37 (m, 2H), 2.18-2.11 (m, 2H), 2.05-1.86 (m, 3H), 1.70-1.64 (m, 2H), 1.61-1.50 (m, 2H), 1.36-1.25 (m, 2H), 1.23-1.17 (m, 1H), 1.14-1.06 (m, 1H), 0.64-0.48 (m, 4H). MS (ESI) m/z: $[M+H]^+$ Found 617.2. Example 58: $^1$H NMR (400 MHz, $CDCl_3$) δ 9.01-8.95 (m, 1H), 8.36 (d, J=6.9 Hz, 1H), 7.46 (s, 1H), 7.17 (d, J=8.5 Hz, 1H), 6.93 (d, J=6.9 Hz, 1H), 6.80 (d, J=7.8 Hz, 1H), 5.22 (t, J=7.9 Hz, 1H), 4.60 (t, J=8.2 Hz, 1H), 2.53-2.36 (m, 2H), 2.20-2.09 (m, 2H), 2.06-1.86 (m, 3H), 1.81-1.74 (m, 1H), 1.67-1.64 (m, 1H), 1.58-1.47 (m, 2H), 1.38-1.18 (m, 3H), 1.12-1.04 (m, 1H), 0.66-0.48 (m, 4H). MS (ESI) m/z: $[M+H]^+$ Found 617.2.

Example 59

N—((S)-(7-((R)-Cyclopropyl(2-(3-fluorobicyclo[1.1.1]pentan-1-yl)acetamido)methyl)imidazo[1,2-a]pyrimidin-2-yl)(4,4-difluorocyclohexyl)methyl)-4-methyl-1,2,5-oxadiazole-3-carboxamide

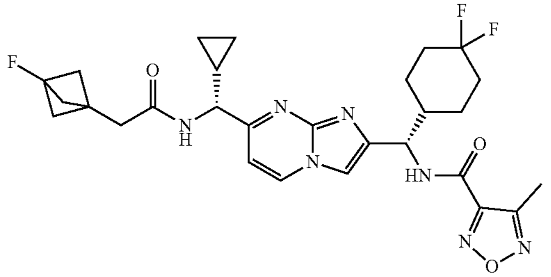 [SMILES: Cc1nonc1C(=O)N[C@H](c1cn2ccc([C@H](NC(=O)CC34CC(F)(C3)C4)C3CC3)nc2n1)C1CCC(F)(F)CC1]

To a solution of 2-diazo-1-(3-fluorobicyclo[1.1.1]pentan-1-yl)ethan-1-one (50 mg, 0.32 mmol, Intermediate 65), N—((S)-(7-((R)-amino(cyclopropyl)methyl)imidazo[1,2-a]pyrimidin-2-yl)(4,4-difluorocyclohexyl)methyl)-4-methyl-1,2,5-oxadiazole-3-carboxamide (75 mg, 0.16 mmol, Intermediate 63) and DIPEA (0.17 mL, 0.98 mmol) in ACN (3 mL) was added silver(I) benzoate (7 mg, 0.03 mmol). The resulting mixture was stirred at 45° C. for 2 h and then concentrated to dryness. The residue was purified by preparative HPLC (Phenomenex Gemini-NX C18, 30×75 mm, 3 μm, 40-70% ACN/water (0.05% $NH_4OH$+10 mM $NH_4HCO_3$)) to provide the title compound. $^1$H NMR (400 MHz, $CDCl_3$) δ 8.34 (d, J=6.8 Hz, 1H), 7.73 (d, J=9.0 Hz, 1H), 7.46 (s, 1H), 6.89 (d, J=6.8 Hz, 1H), 6.83 (d, J=8.1 Hz, 1H), 5.20 (t, J=8.4 Hz, 1H), 4.60 (t, J=8.4 Hz, 1H), 2.65-2.53 (m, 5H), 2.04 (d, J=2.4 Hz, 10H), 1.83-1.66 (m, 3H), 1.57-1.29 (m, 2H), 1.23-1.10 (m, 1H), 0.67-0.45 (m, 4H). MS (ESI) m/z: $[M+H]^+$ Found 572.2.

Example 60

N—((S)-(7-((R)-Cyclopropyl((S)-4,4-difluoro-3-methylbutanamido)methyl)imidazo[1,2-a]pyrimidin-2-yl)(4,4-difluorocyclohexyl)methyl)-4-methyl-1,2,5-oxadiazole-3-carboxamide

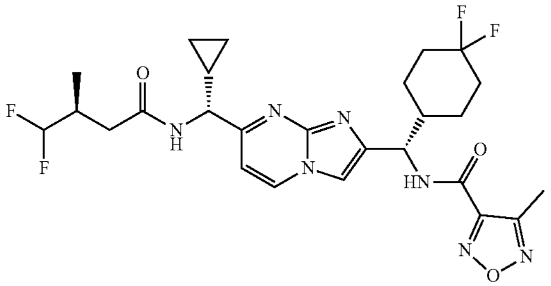 [SMILES: Cc1nonc1C(=O)N[C@H](c1cn2ccc([C@H](NC(=O)C[C@H](C)C(F)F)C3CC3)nc2n1)C1CCC(F)(F)CC1]

The title compound was prepared as described in the synthesis of Intermediate 37, using N—((S)-(7-((R)-amino(cyclopropyl)methyl)imidazo[1,2-a]pyrimidin-2-yl)(4,4-difluorocyclohexyl)methyl)-4-methyl-1,2,5-oxadiazole-3-carboxamide (Intermediate 63) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide and (S)-4,4-difluoro-3-methylbutanamide in place of trans-2-(trifluoromethyl)cyclopropane-1-carboxylic acid. The reaction was run at rt for 30 min instead of 40° C. for 2 h, and after that time the mixture was concentrated to dryness and purified by preparative HPLC (Phenomenex Gemini-NX C18, 30×75 mm, 3 μm, 40-70% ACN/water (0.05% $NH_4OH$+10 mM $NH_4HCO_3$)) to provide the title compound. $^1H$ NMR (400 MHz, $CDCl_3$) δ 8.37 (d, J=6.8 Hz, 1H), 7.75 (d, J=9.2 Hz, 1H), 7.50 (s, 1H), 6.93 (d, J=6.8 Hz, 2H), 5.98-5.59 (m, 1H), 5.23 (t, J=8.4 Hz, 1H), 4.64 (t, J=8.4 Hz, 1H), 2.62 (s, 3H), 2.58-2.46 (m, 2H), 2.32-1.98 (m, 5H), 1.87-1.67 (m, 3H), 1.60-1.33 (m, 2H), 1.30-1.17 (m, 1H), 1.07 (dd, J=19.6, 6.8 Hz, 3H), 0.74-0.45 (m, 4H). MS (ESI) m/z: $[M+H]^+$ Found 566.4.

Example 61

N—((S)-(7-((R)-Cyclopropyl(2-((1r,3S)-3-fluorocyclobutyl)acetamido)methyl)imidazo[1,2-a]pyrimidin-2-yl)(4,4-difluorocyclohexyl)methyl)-4-methyl-1,2,5-oxadiazole-3-carboxamide

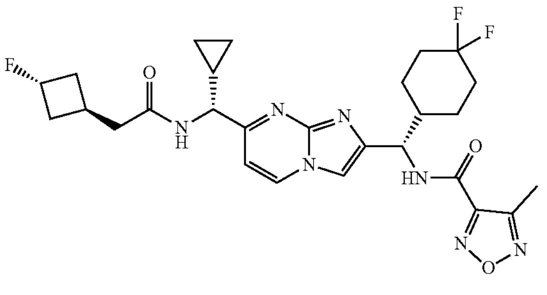 [SMILES: Cc1nonc1C(=O)N[C@H](c1cn2ccc([C@H](NC(=O)C[C@H]3C[C@H](F)C3)C3CC3)nc2n1)C1CCC(F)(F)CC1]

The title compound was prepared as described in the synthesis of Intermediate 37, using N—((S)-(7-((R)-amino(cyclopropyl)methyl)imidazo[1,2-a]pyrimidin-2-yl)(4,4-difluorocyclohexyl)methyl)-4-methyl-1,2,5-oxadiazole-3-carboxamide (Intermediate 63) in place of N—((R)-(2-((S)-amino(4,4-difluorocyclohexyl)methyl)imidazo[1,2-a]pyrimidin-7-yl)(cyclopropyl)methyl)-2-(3,3-difluorocyclobutyl)acetamide and 2-((1r,3s)-3-fluorocyclobutyl)acetic acid in place of trans-2-(trifluoromethyl)cyclopropane-1-carboxylic acid. The reaction was run at rt for 30 min instead of 40° C. for 2 h, and after that time the mixture was concentrated to dryness and purified by preparative HPLC (Phenomenex Gemini-NX C18, 30×75 mm, 3 μm, 35-65% ACN/water (0.05% $NH_4OH$+10 mM $NH_4HCO_3$)) to provide the title compound. $^1H$ NMR (400 MHz, $CDCl_3$) δ 8.37 (d, J=7.0 Hz, 1H), 7.80 (d, J=8.8 Hz, 1H), 7.50 (s, 1H), 6.96-6.82 (m, 2H), 5.30-5.01 (m, 2H), 4.64 (t, J=8.3 Hz, 1H), 2.88-2.71 (m, 1H), 2.67-2.56 (m, 3H), 2.54-2.36 (m, 4H), 2.32-2.00 (m, 6H), 1.88-1.69 (m, 3H), 1.60-1.15 (m, 3H), 0.68-0.45 (m, 4H). MS (ESI) m/z: $[M+H]^+$ Found 560.4.

Example 62

4-Cyclopropyl-N—((S)-(7-((R)-cyclopropyl(2-(3,3-difluorocyclobutyl)acetamido)methyl)imidazo[1,2-a]pyrimidin-2-yl)(4,4-difluorocyclohexyl)methyl)-1,2,5-oxadiazole-3-carboxamide

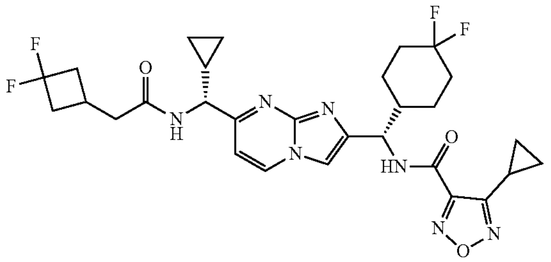 [SMILES: O=C(CC1CC(F)(F)C1)N[C@@H](c1ccn2cc([C@@H](NC(=O)c3nonc3C3CC3)C3CCC(F)(F)CC3)nc2n1)C1CC1]

The title compound was prepared as described for the synthesis of Intermediate 37, using 4-cyclopropyl-1,2,5-oxadiazole-3-carboxylic acid (CAS 1083246-26-7) in place of trans-2-(trifluoromethyl)cyclopropane-1-carboxylic acid, and stirring the solution for 30 min at rt instead of 40° C. for 2 h. The crude material was purified by preparative HPLC (Boston Green ODS, 150×30 mm, 5 μm, 10-40% ACN/water (0.05% $NH_4OH$)) to provide the title compound. $^1H$ NMR (400 MHz, DMSO-$d_6$) δ 9.50 (d, J=8.8 Hz, 1H), 8.90 (d, J=7.0 Hz, 1H), 8.63 (d, J=7.5 Hz, 1H), 7.82 (s, 1H), 7.05 (d, J=7.0 Hz, 1H), 5.16 (t, J=8.4 Hz, 1H), 4.25-4.17 (m, 1H), 2.70-2.56 (m, 2H), 2.40 (br s, 2H), 2.35 (d, J=13.6 Hz, 2H), 2.31-2.23 (m, 2H), 2.19 (d, J=8.5 Hz, 1H), 2.02 (d, J=10.3 Hz, 2H), 1.94-1.60 (m, 4H), 1.47-1.34 (m, 1H), 1.34-1.24 (m, 1H), 1.23-1.16 (m, 1H), 1.16-1.08 (m, 2H), 0.99-0.93 (m, 2H), 0.57-0.43 (m, 3H), 0.43-0.35 (m, 1H). MS (ESI) m/z: $[M+H]^+$ Found 604.2.

Example 63

N—((S)-(7-((R)-Cyclopropyl(2-(3,3-difluorocyclobutyl)acetamido)methyl)imidazo[1,2-a]pyrimidin-2-yl)(4,4-difluorocyclohexyl)methyl)-4-(2,2,2-trifluoroethyl)isoxazole-3-carboxamide

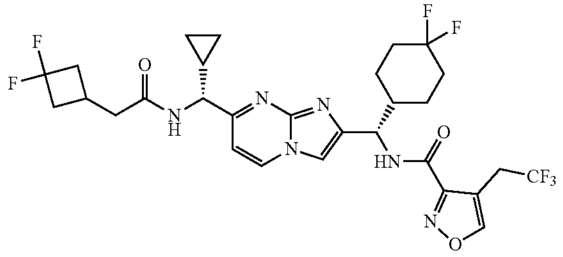 [SMILES: O=C(CC1CC(F)(F)C1)N[C@@H](c1ccn2cc([C@@H](NC(=O)c3nocc3CC(F)(F)F)C3CCC(F)(F)CC3)nc2n1)C1CC1]

The title compound was prepared as described for the synthesis of Intermediate 37, using 4-(2,2,2-trifluoroethyl) isoxazole-3-carboxylic acid (Intermediate 68) in place of trans-2-(trifluoromethyl)cyclopropane-1-carboxylic acid and DCM in place of ACN, and stirring the solution for 30 min at rt instead of 40° C. for 2 h. The crude material was purified by preparative HPLC (Boston Green ODS, 150×30 mm, 5 μm, 10-40% ACN/water (0.05% $NH_4OH$)) to provide the title compound. $^1H$ NMR (400 MHz, DMSO-$d_6$) δ 9.20-9.11 (m, 2H), 8.90 (d, J=7.0 Hz, 1H), 8.63 (d, J=7.8 Hz, 1H), 7.80 (s, 1H), 7.04 (d, J=7.0 Hz, 1H), 5.13 (t, J=8.7 Hz, 1H), 4.23 (t, J=8.3 Hz, 1H), 3.77 (q, J=11.2 Hz, 2H), 2.66-2.58 (m, 1H), 2.40 (br s, 2H), 2.34 (d, J=11.8 Hz, 2H), 2.31-2.23 (m, 1H), 2.17 (d, J=8.0 Hz, 1H), 2.00 (d, J=7.8 Hz, 2H), 1.91-1.58 (m, 4H), 1.44-1.28 (m, 2H), 1.28-1.16 (m, 2H), 0.57-0.43 (m, 3H), 0.42-0.34 (m, 1H). MS (ESI) m/z: $[M+H]^+$ Found 645.4.

In Vitro Biological Data

IL-17A(FLAG-Tagged): IL-17RA(His-Tagged) Binding Disruption Eu-HTRF Assay

An antibody directed against the FLAG tag of IL-17A (SEQ ID NO: 1) is labeled with the HTRF donor chromophore (Europium-cryptate). IL-17A is present as a dimer that is "locked into" this quaternary structure due to the formation of loop-spanning intramolecular disulfide bridges. The construct of IL-17RA used in the assay excludes the outer-membrane portion of the receptor and is fused to a C-terminal 10×His tag (SEQ ID NO:2). An antibody directed against the His tag of the IL-17RA chimera is labeled with the HTRF acceptor chromophore ("D2"). The fluorescence-resonance energy transfer (FRET) depends on the vicinity of the donor chromophore to the acceptor, and interruption of the binding between the IL-17A and IL-17RA causes the reduction/loss of FRET. Therefore, this assay allows to evaluate the compound effect on the binding IL-17A and IL-17RA by monitoring the fluorescence intensity of donor vs acceptor. The assay is run as described below.

40 nL of 2-fold serial diluted compound solution for total 22 dilution points is added into each well of a 1536-well, white, low-volume, non-binding plate (Greiner #782904), then 2 μL of FLAG tagged IL-17A at 2× final concentration (2.5 nM) in solution of PBS+0.01% Triton-X100 is added to each well. The assay plate is briefly centrifuged then incubated for 1 h at rt. A mixed solution is prepared containing 2×5 nM 10HIS×IL-17RA, 2×2.5 nM Eu-anti-FLAG (CISBIO), 2×5 nM D2-anti-HIS (CISBIO) in PBS+0.01% Triton-X100+200 mM Potassium Fluoride (Sigma 60238) and 2 μL of mix is added to each well of the assay plate. The plate is briefly centrifuged then incubated for 2 h at rt. The HTRF intensities at the wavelength of donor (620 nm) and acceptor (665 nm) are measured using BMG Pherastar. The ratio between intensities at two wavelengths is calculated and plotted against the compound concentration and the data is fitted to a one-site competition model to yield $IC_{50}$ of the compound.

IL-17A acts directly on keratinocytes through binding to dimeric receptor IL-17RA/RC and drives the production of a number of inflammatory mediators known to be elevated in psoriasis lesional tissue. IL-17A small molecule inhibitors that block the IL-17A to interact with IL-17R would inhibit the IL-17A signaling in its targeted cells such as keratinocytes. The compound functional activity is evaluated for its impact on IL-17A-induced G-CSF production in human normal keratinocytes (NHK).

NHK Assay

Adult normal human keratinocytes are cultured in keratinocyte growth medium (Lonza) in a flask till reaching ~ 90% confluence, then cells are transferred to a 384-well plate at density of 3000-4000 cell/well. Recombinant human IL-17A (Gibco PHC9174) is pre-incubated with titrated compound or DMSO for 1 h at rt then added to the cell culture plate. The final concentration of IL-17A is 5 ng/mL and DMSO is 0.2%, in the culture containing 5% FBS. Cells are cultured/treated for 24 h at 37° C. Supernatants are collected and G-CSF production is measured through HTRF technology using Human G-CSF Kit (CisBio). G-CSF concentration was extrapolated from the standard curve and $IC_{50}$ is determined using GraphPad Prism. Cell viability is also evaluated using CellTiter-Glo kit (Promega) and effect of compound on cell viability is compared to DMSO control.

In cases where the compound was tested more than once, the $IC_{50}$ value shown is a simple average of the measured values.

| Example | HTRF $IC_{50}$ (μM) | NHK $IC_{50}$ (μM) |
|---|---|---|
| 1 | 0.29 | 0.39 |
| 2 | 3.7 | 6.2 |
| 3 | 3.1 | 0.64 |
| 4 | 1.8 | 1.2 |
| 5 | 0.70 | 0.96 |
| 6 | 2.7 | 2.1 |
| 7 | 0.52 | 0.88 |
| 8 | 1.1 | 6.0 |
| 9 | 1.8 | 0.61 |
| 10 | 4.1 | 5.8 |
| 11 | 0.66 | 0.54 |
| 12 | 6.0 | >20 |
| 13 | 0.34 | 0.50 |
| 14 | 17 | >20 |
| 15 | 0.29 | 1.4 |
| 16 | 12 | >20 |
| 17 | 0.22 | 1.1 |
| 18 | 0.58 | 2.0 |
| 19 | 0.26 | 1.2 |
| 20 | 0.47 | 2.8 |
| 21 | 0.099 | 0.59 |
| 22 | 6.2 | >20 |
| 23 | 0.13 | 0.52 |
| 24 | 0.18 | 0.18 |
| 25 | 0.31 | 0.21 |
| 26 | 0.13 | 0.11 |
| 27 | 3.8 | 2.6 |
| 28 | 5.4 | 1.2 |
| 29 | 2.3 | 2.6 |
| 30 | 0.11 | 0.074 |
| 31 | 3.0 | >20 |

-continued

| Example | HTRF $IC_{50}$ (μM) | NHK $IC_{50}$ (μM) |
|---|---|---|
| 32 | 0.17 | 0.52 |
| 33 | 8.7 | >20 |
| 34 | 0.24 | 0.58 |
| 35 | 0.81 | 0.95 |
| 36 | 0.22 | 0.19 |
| 37 | 1.4 | >20 |
| 38 | 0.89 | 0.93 |
| 39 | 13 | ~20 |
| 40 | 0.31 | 0.36 |
| 41 | 2.4 | 2.5 |
| 42 | 0.48 | 0.52 |
| 43 | 5.7 | ~20 |
| 44 | 0.22 | 0.17 |
| 45 | 2.9 | 2.1 |
| 46 | 2.6 | 2.6 |
| 47 | 0.41 | 0.12 |
| 48 | 0.16 | 0.17 |
| 49 | 0.50 | 0.74 |
| 50 | 6.8 | >20 |
| 51 | 0.36 | 2.0 |
| 52 | 0.68 | 2.8 |
| 53 | 0.49 | 2.3 |
| 54 | 0.46 | 4.5 |
| 55 | 0.57 | 1.1 |
| 56 | 0.73 | 1.8 |
| 57 | 0.22 | 0.93 |
| 58 | 0.34 | 2.2 |
| 59 | 0.39 | 0.99 |
| 60 | 0.38 | 0.76 |
| 61 | 0.46 | 2.3 |
| 62 | 0.091 | 0.12 |
| 63 | 0.22 | 0.64 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

Name: IL-17A-Flag

SEQ ID NO: 1

MATGSRTSLLLAFGLLCLPWLQEGSAGSDYKDDDDKGSGSGSLEVLFQG

PGITIPRNPGCPNSEDKNFPRTVMVNLNIHNRNTNTNPKRSSDYYNRST

SPWNLHRNEDPERYPSVIWEAQCRHLGCINADGNVDYHMNSVPIQQEIL

VLRREPPHCPNSFRLEKILVSVGCTCVTPIVHHVQ

Name: IL-17RA

SEQ ID NO: 2

MKFLVNVALVFMVVYISYIYALRLLDHRALVCSQPGLNCTVKNSTCLDD

SWIHPRNLTPSSPKDLQIQLHFAHTQQGDLFPVAHIEWTLQTDASILYL

EGAELSVLQLNTNERLCVRFEFLSKLRHHHRRWRFTFSHFVVDPDQEYE

VTVHHLPKPIPDGDPNHQSKNFLVPDCEHARMKVTTPCMSSGSLWDPNI

TVETLEAHQLRVSFTLWNESTHYQILLTSFPHMENHSCFEHMHHIPAPR

PEEFHQRSNVTLTLRNLKGCCRHQVQIQPFFSSCLNDCLRHSATVSCPE

MPDTPEPIPDYMPLWGSGGHHHHHHHHHH*

We claim:

1. A compound of Formula I:

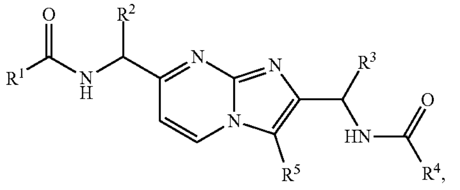

I or a pharmaceutically acceptable salt thereof, wherein:

$R^1$ is —$C_{(1-6)}$alkyl or —$C_{(0-3)}$alkyl$C_{(3-6)}$cycloalkyl; wherein the —$C_{(1-6)}$alkyl and the —$C_{(0-3)}$alkyl$C_{(3-6)}$cycloalkyl are unsubstituted or substituted with one to six fluorine atoms;

$R^2$ is —$C_{(3-5)}$cycloalkyl;

$R^3$ is-$C_{(0-1)}$alkyl$C_{(3-6)}$cycloalkyl, wherein the —$C_{(0-1)}$alkyl$C_{(3-6)}$cycloalkyl is unsubstituted or substituted with one to five fluorine atoms;

$R^4$ is-$C_{(3-4)}$cycloalkyl or a 5- to 6-membered heteroaryl having 1 to 4 heteroatoms selected from N, O, and S;

wherein the $C_{(3-4)}$cycloalkyl is unsubstituted or substituted with one to three $R^{4a}$ groups; and wherein the 5- to 6-membered heteroaryl is unsubstituted or substituted with one or two $R^{4b}$ groups;

each $R^{4a}$ group is independently selected from-$C_{(1-4)}$alkyl that is unsubstituted or substituted with one to six fluorine atoms; and each $R^{4b}$ group is independently selected from-$C_{(0-2)}$alkyl$C_{(3-4)}$cycloalkyl or —$C_{(1-5)}$alkyl, wherein the —$C_{(0-2)}$alkyl$C_{(3-4)}$cycloalkyl and —$C_{(1-5)}$alkyl are unsubstituted or substituted with one to six fluorine atoms;

$R^5$ is H or F;

wherein when $R^4$ is —$C_{(3-4)}$cycloalkyl then the compound of Formula I is a compound of Formula Ia:

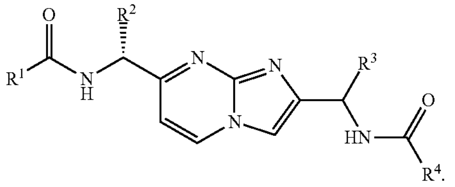

Ia

2. The compound of claim 1, or a pharmaceutically acceptable salt thereof, wherein:

$R^1$ is —$C_{(1-6)}$alkyl or —$C_{(0-3)}$alkyl$C_{(3-6)}$cycloalkyl;

wherein the —$C_{(1-6)}$alkyl and the —$C_{(0-3)}$alkyl$C_{(3-6)}$cycloalkyl are unsubstituted or substituted with one to six fluorine atoms;

$R^2$ is —$C_{(3-5)}$cycloalkyl;

$R^3$ is —$C_{(0-1)}$alkyl$C_{(3-6)}$cycloalkyl, wherein the —$C_{(0-1)}$alkyl$C_{(3-6)}$cycloalkyl is unsubstituted or substituted with one to five fluorine atoms;

$R^4$ is a 5- to 6-membered heteroaryl having 1 to 4 heteroatoms selected from N, O, and S;

wherein the 5- to 6-membered heteroaryl is unsubstituted or substituted with one or two $R^{4b}$ groups;

each $R^{4b}$ group is independently selected from —$C_{(0-2)}$alkyl$C_{(3-4)}$cycloalkyl or —$C_{(1-5)}$alkyl, wherein the —$C_{(0-2)}$alkyl$C_{(3-4)}$cycloalkyl and —$C_{(1-5)}$alkyl are unsubstituted or substituted with one to six fluorine atoms; and $R^5$ is H or F.

3. The compound of claim 1, or a pharmaceutically acceptable salt thereof, wherein:

$R^5$ is H.

4. The compound of claim 1, or a pharmaceutically acceptable salt thereof, wherein:

$R^1$ is-$C_{(1-4)}$alkyl, wherein the —$C_{(1-4)}$alkyl is unsubstituted or substituted with one to six fluorine atoms.

5. The compound of claim 1, or a pharmaceutically acceptable salt thereof, wherein:

$R^1$ is $C_{(1-2)}$alkyl$C_{(3-5)}$cycloalkyl, wherein the —$C_{(1-2)}$alkyl$C_{(3-5)}$cycloalkyl is unsubstituted or substituted with one to three fluorine atoms.

6. The compound of claim 1, or a pharmaceutically acceptable salt thereof, wherein $R^1$ is:

is:

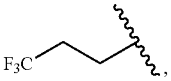, 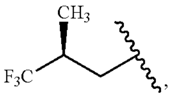, 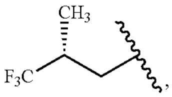, 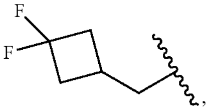, 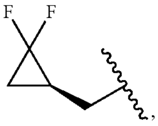, 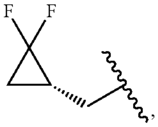, 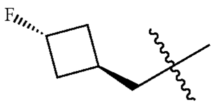, 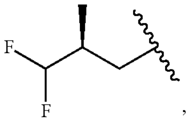, or 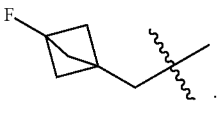.

7. The compound of claim 1, or a pharmaceutically acceptable salt thereof, wherein $R^2$ is cyclopropyl.

8. The compound of claim 1, or a pharmaceutically acceptable salt thereof, wherein $R^3$ is

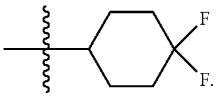 [SMILES: *C1CCC(F)(F)CC1]

9. The compound of claim 1, or a pharmaceutically acceptable salt thereof, wherein $R^4$ is pyridinyl that is unsubstituted or substituted with $C_{(1-2)}$alkyl that is unsubstituted or substituted with one to three fluorine atoms.

10. The compound of claim 1, or a pharmaceutically acceptable salt thereof, wherein $R^4$ is pyrazolyl, triazolyl, isoxazolyl, or oxadiazolyl that is unsubstituted or substituted with one or two $R^{4b}$ groups, each $R^{4b}$ group is independently selected from-$C_{(0-1)}$alkyl$C_{(3)}$cycloalkyl or —$C_{(1-3)}$alkyl, wherein the —$C_{(0-1)}$alkyl$C_{(3)}$cycloalkyl and —$C_{(1-3)}$alkyl are unsubstituted or substituted with one to four fluorine atoms.

11. The compound of claim 1 or a pharmaceutically acceptable salt thereof, wherein $R^4$ is 1H-pyrazolyl, 1H-1,2,3-triazolyl, 2H-1,2,3-triazolyl, 1H-1,2,4-triazolyl, isoxazole-4-yl, or 1,2,5-oxadiazolyl that is unsubstituted or substituted with one or two $R^{4b}$ groups.

12. The compound of claim 1, or a pharmaceutically acceptable salt thereof, wherein $R^4$ is:

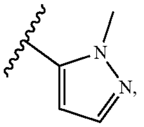
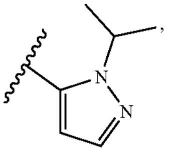
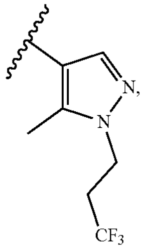
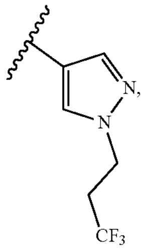
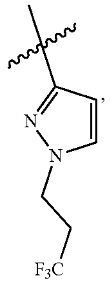
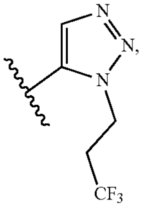
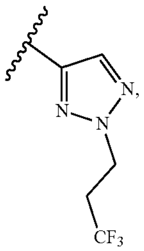
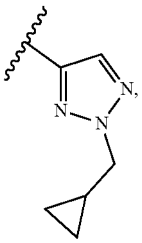
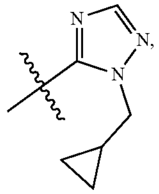

-continued

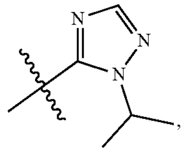
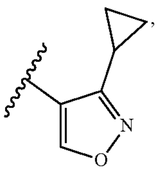
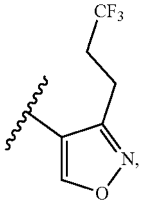
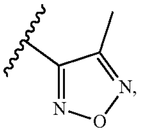
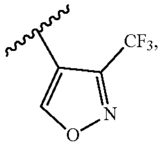
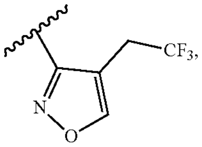
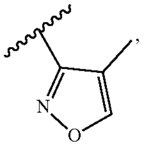
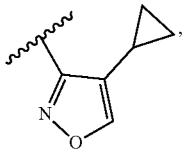
or
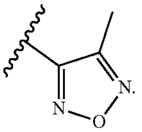

13. The compound of claim 12, or a pharmaceutically acceptable salt thereof, wherein $R^4$ is:

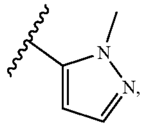
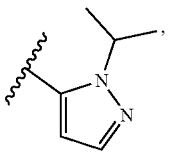
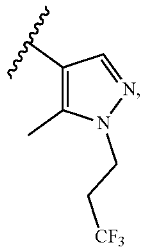
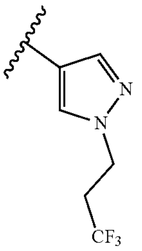
or
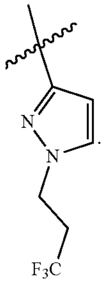

14. The compound of claim 12, or a pharmaceutically acceptable salt thereof, wherein $R^4$ is:

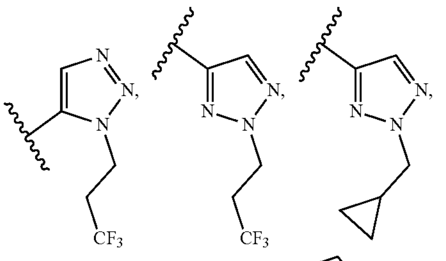

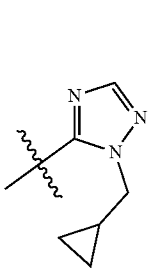

or

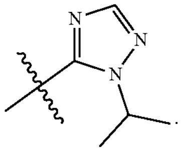

15. The compound of claim 12, or a pharmaceutically acceptable salt thereof, wherein $R^4$ is:

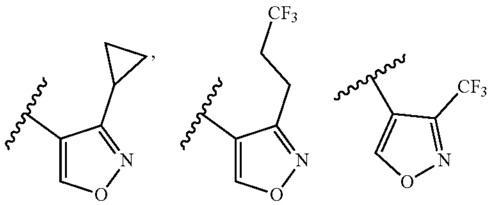

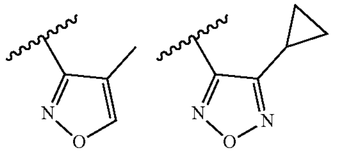

or

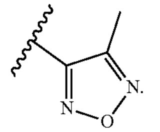

16. The compound of claim 1, or a pharmaceutically acceptable salt thereof, wherein:

$R^4$ is —$C_{(3)}$cycloalkyl;

wherein the $C_{(3)}$cycloalkyl is unsubstituted or substituted with one to three $R^{4a}$ groups; and each $R^{4a}$ group is independently selected from —$C_{(1-2)}$alkyl that is unsubstituted or substituted with one to three fluorine atoms; and wherein the compound of Formula I is a compound of Formula Ia:

Ia

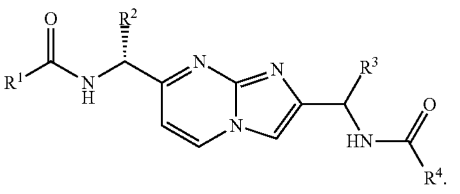

17. The compound of claim 1, or a pharmaceutically acceptable salt thereof, wherein the compound is selected from

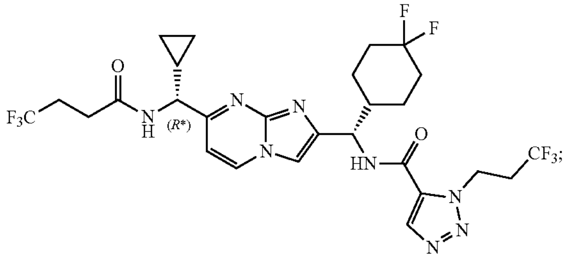

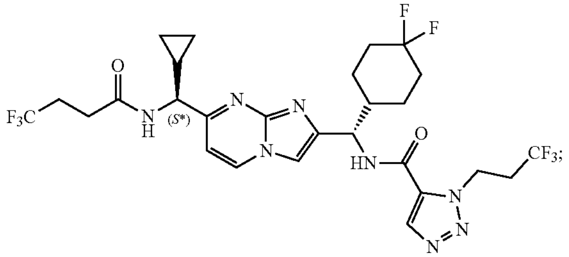

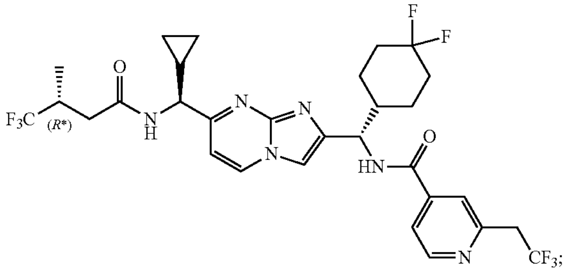

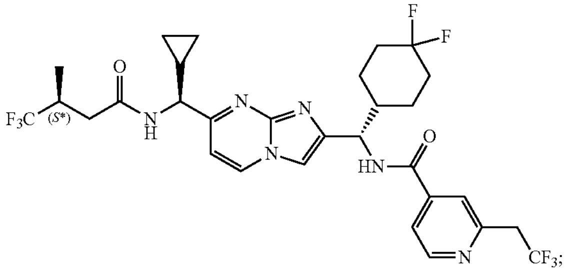

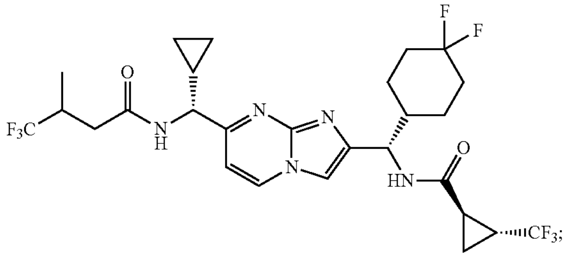

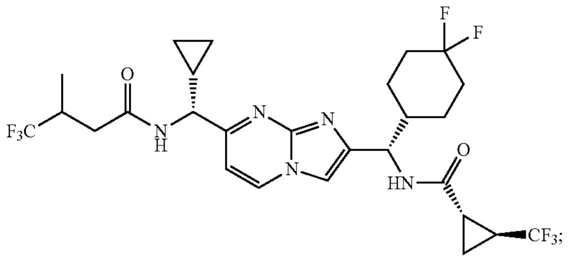

-continued
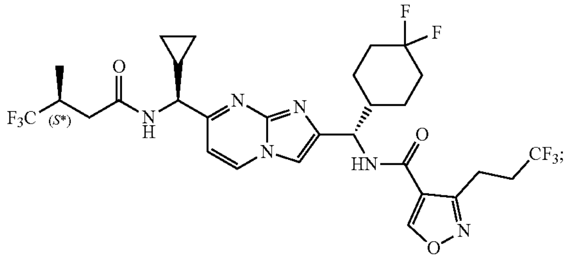
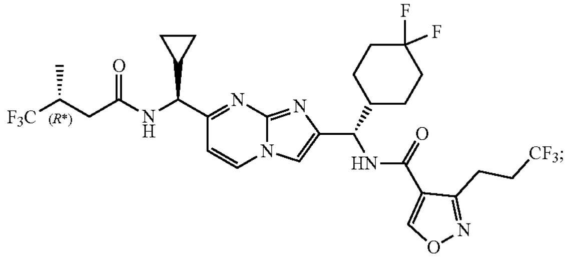
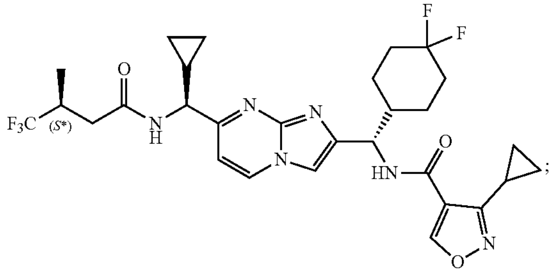
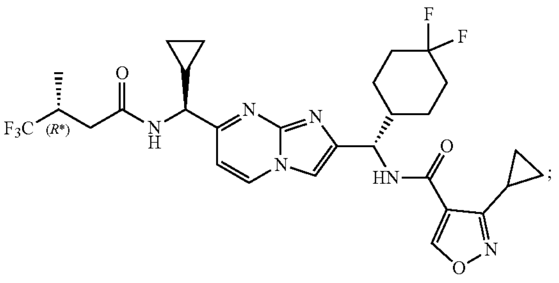
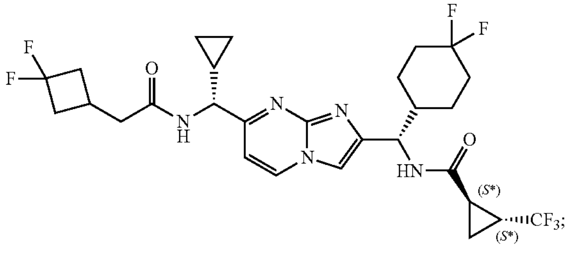
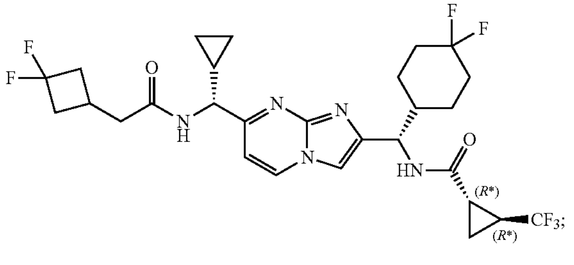
-continued
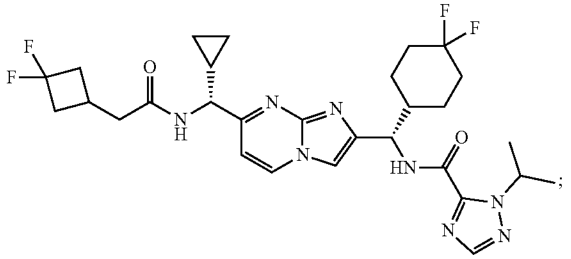
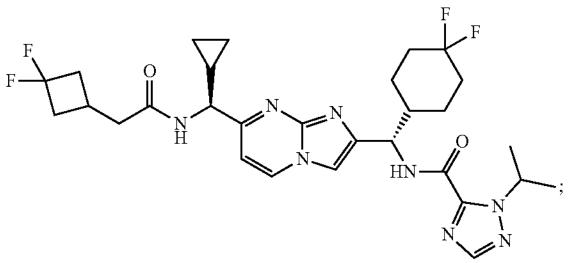
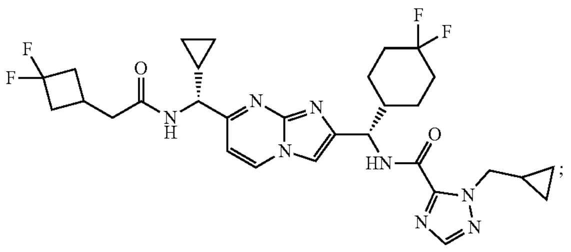
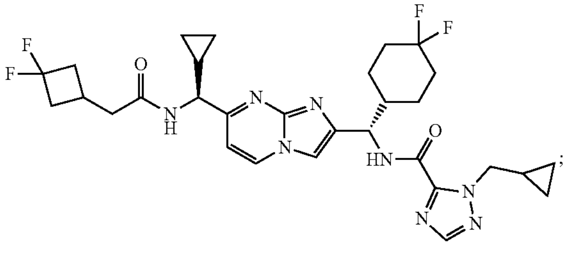
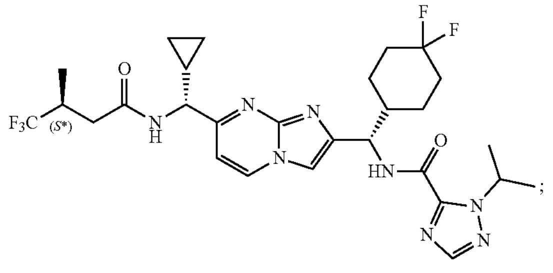
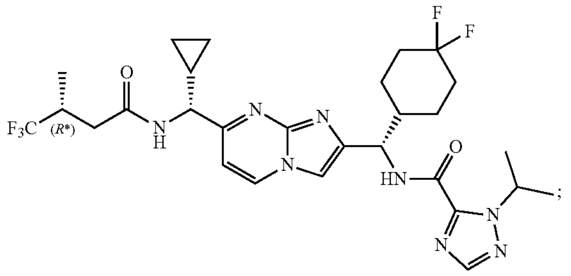

-continued
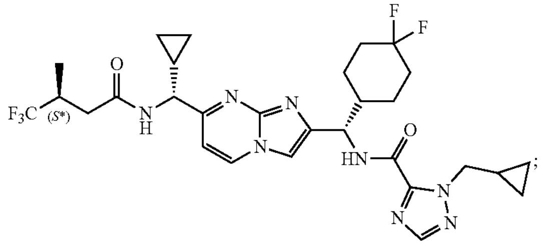
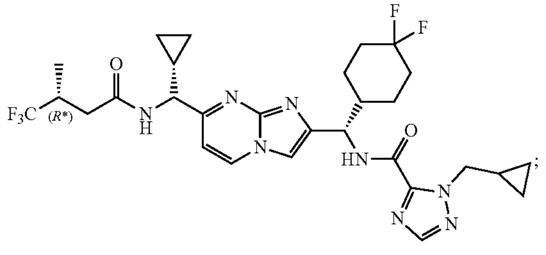
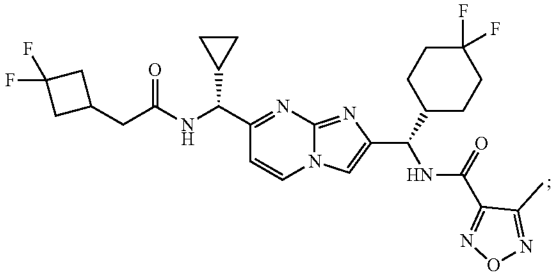
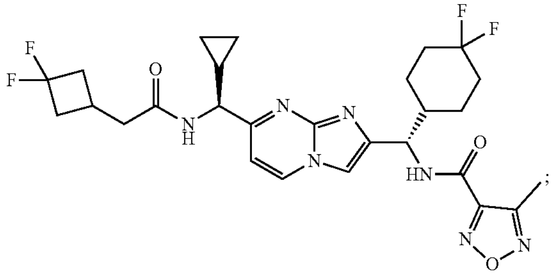
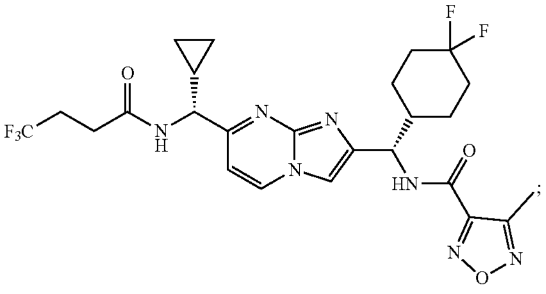 [SMILES: Cc1nonc1C(=O)N[C@H](c1cn2ccc([C@H](NC(=O)CCC(F)(F)F)C3CC3)nc2n1)C1CCC(F)(F)CC1]
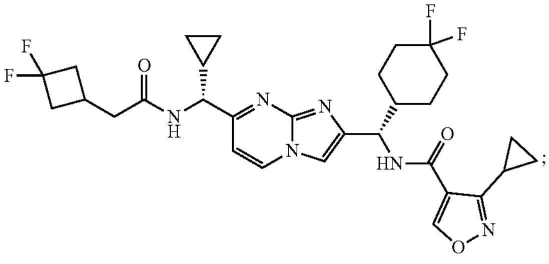
-continued
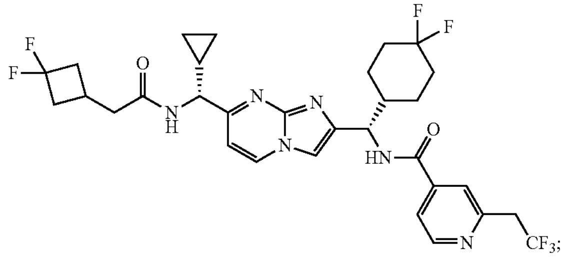
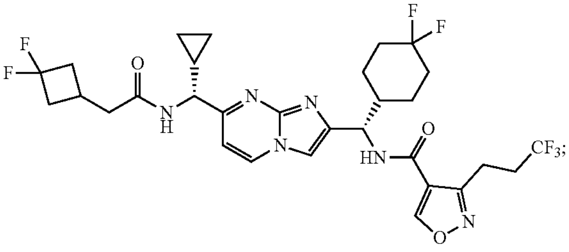
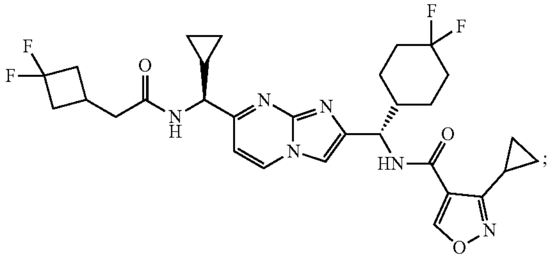
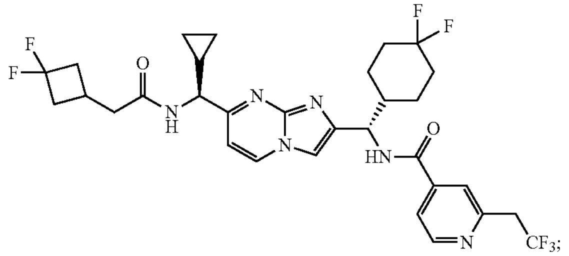
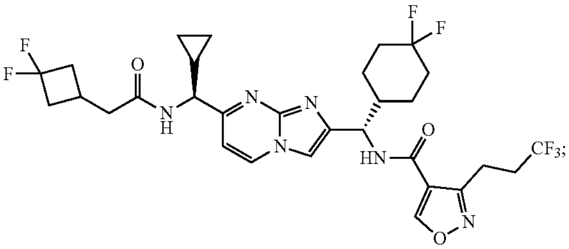
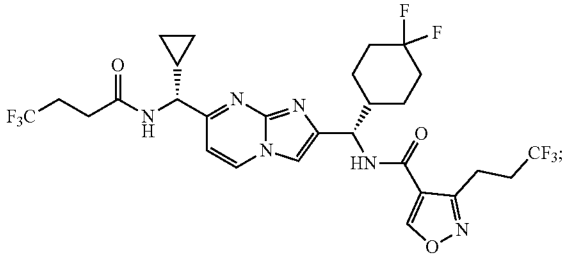

-continued
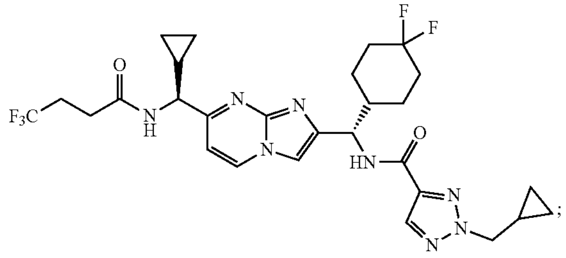
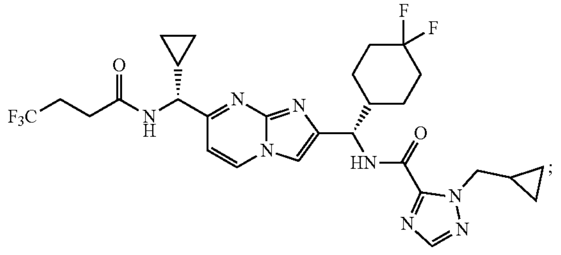
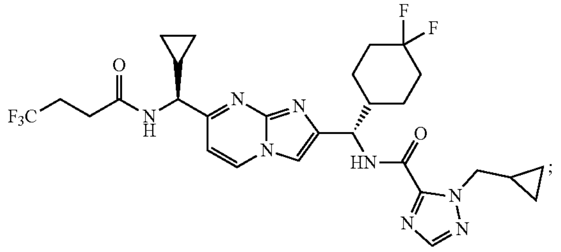
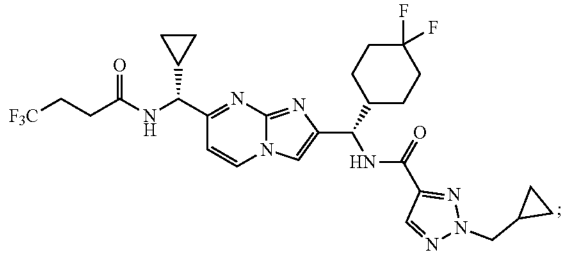
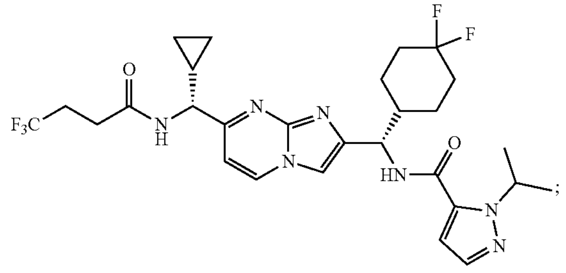
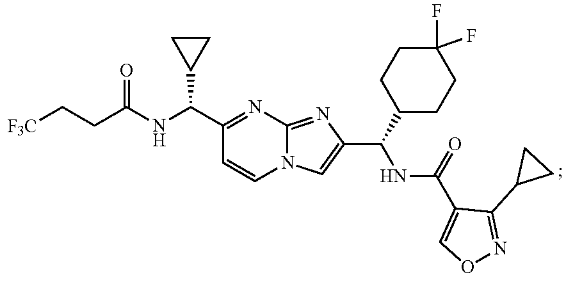
-continued
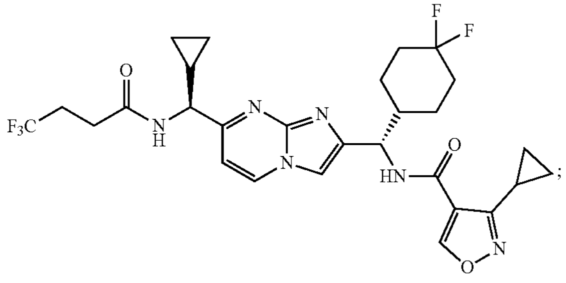
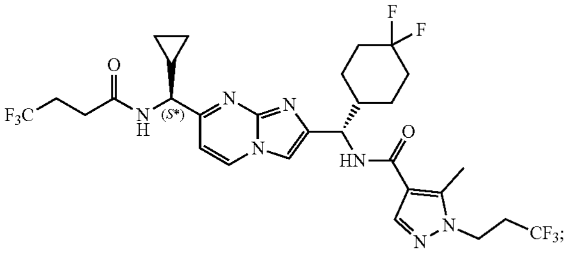
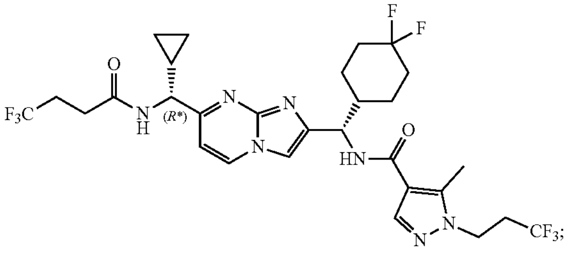
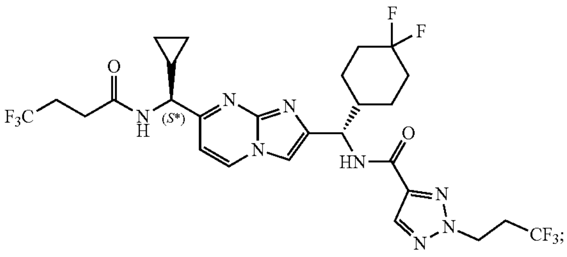
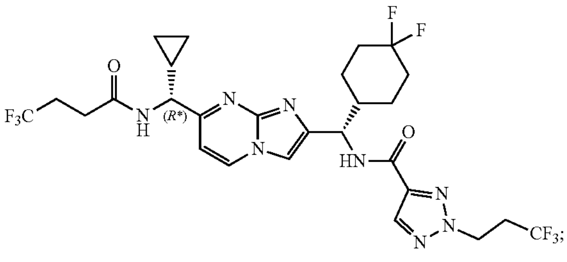
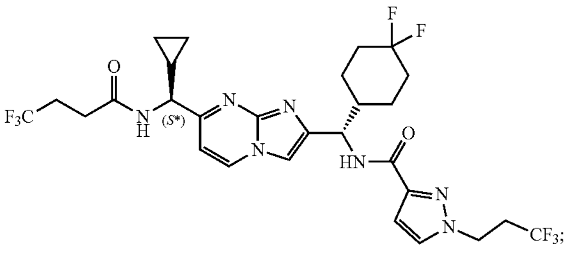

-continued
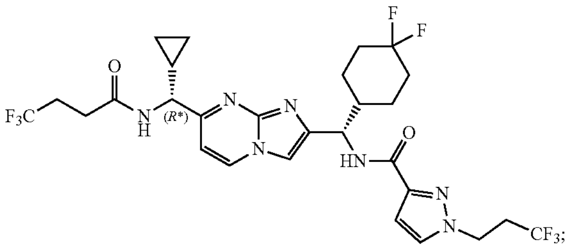
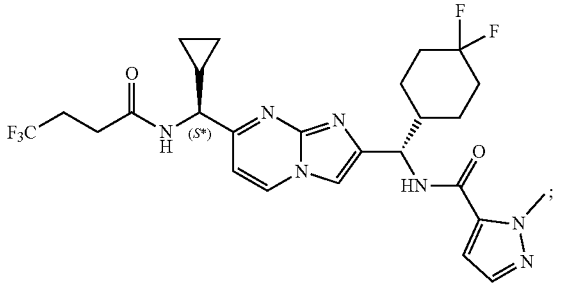
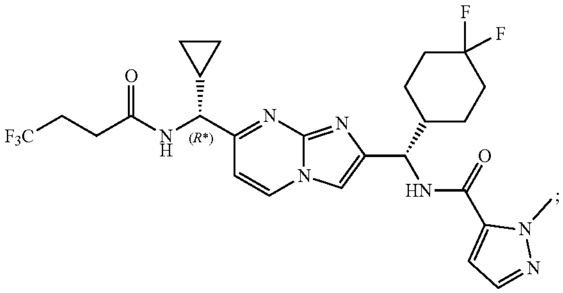
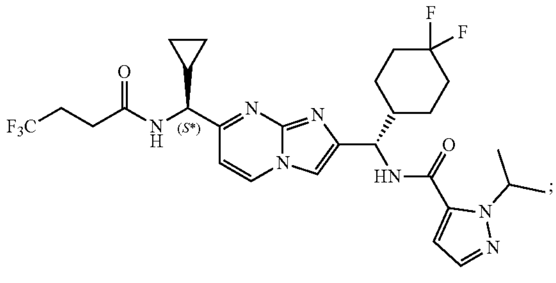
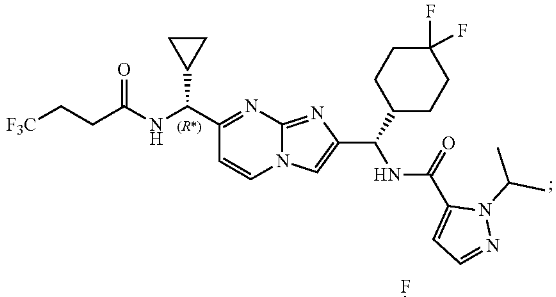
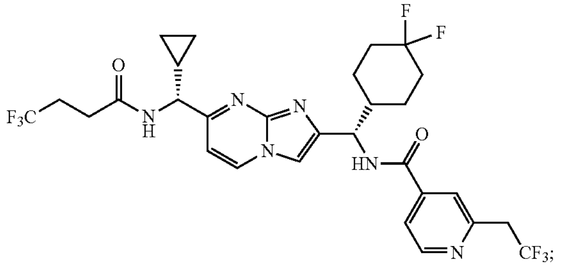
-continued
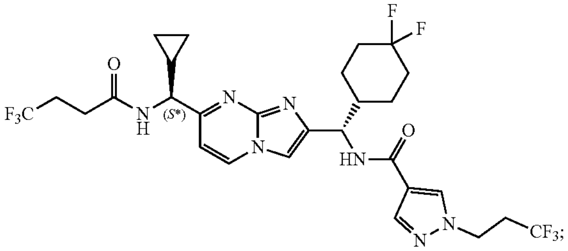
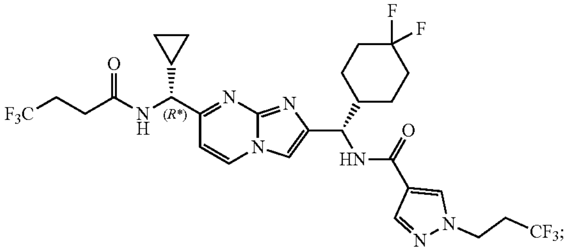
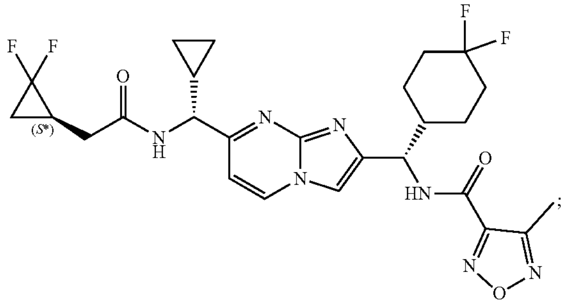
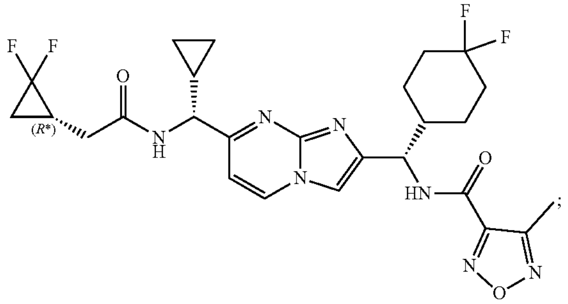
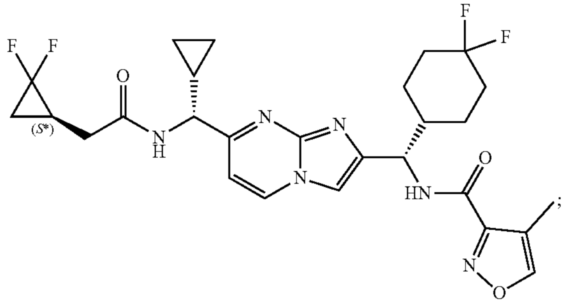
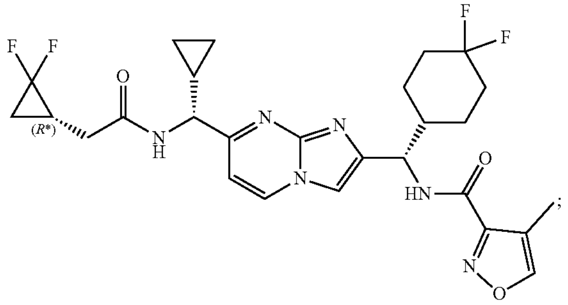

-continued
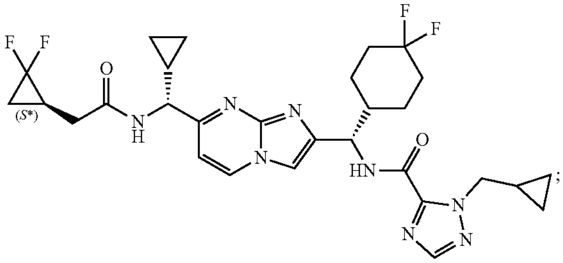
;
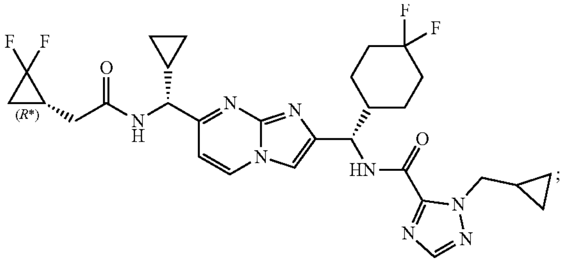
;
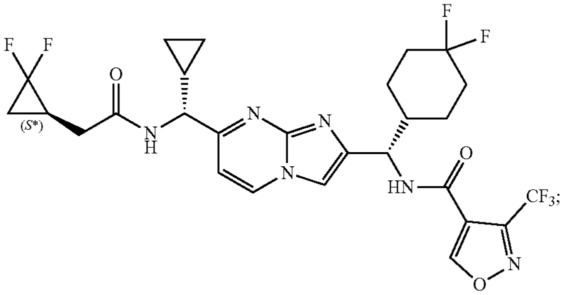
;
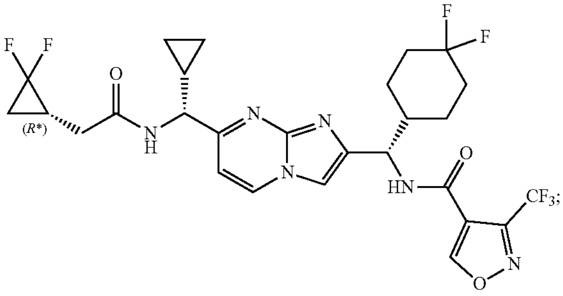
;
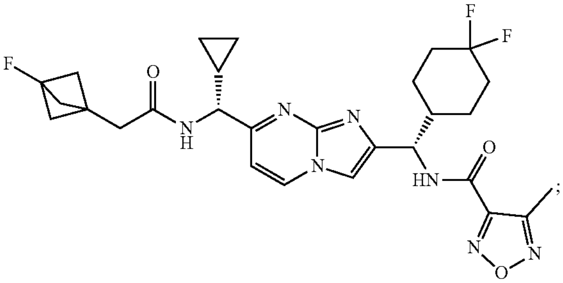
;
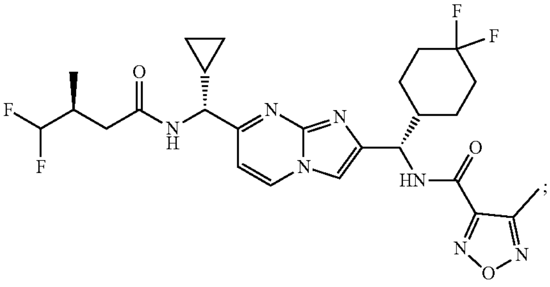
;
-continued
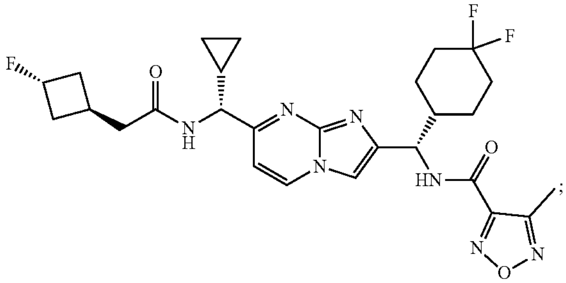
;
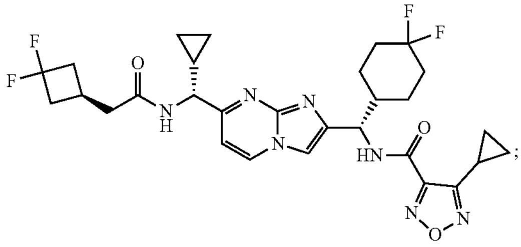
; and
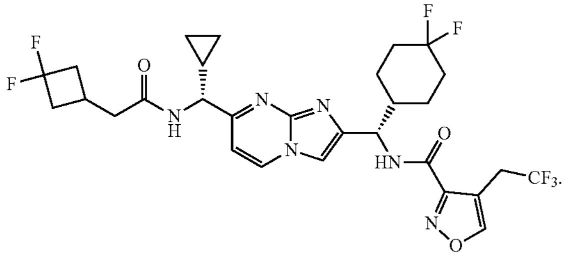
.
18. The compound of claim 17, or a pharmaceutically acceptable salt thereof, wherein the compound is selected from
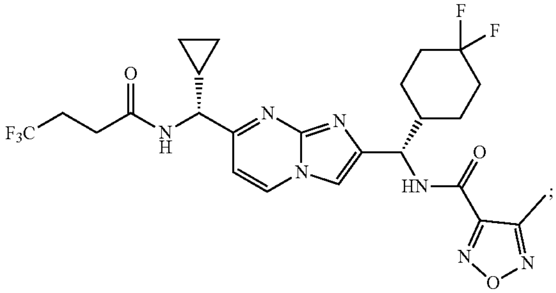
;
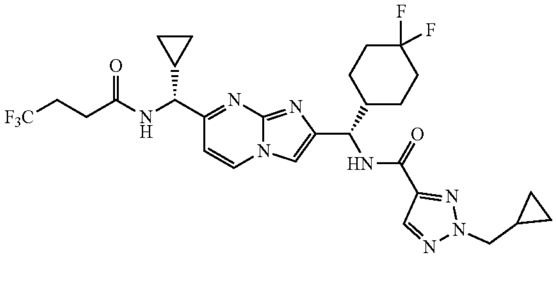
;

-continued
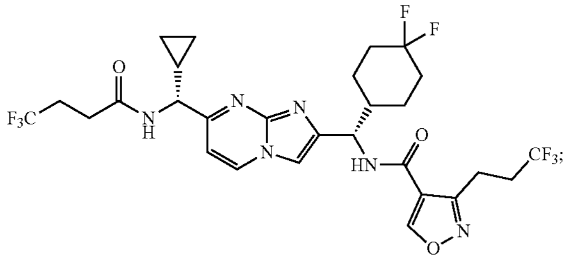
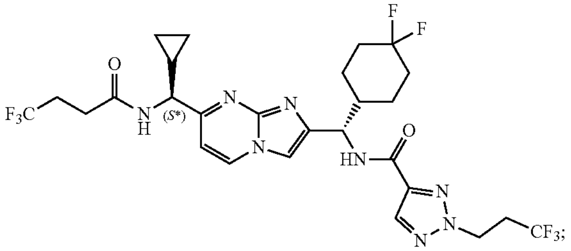
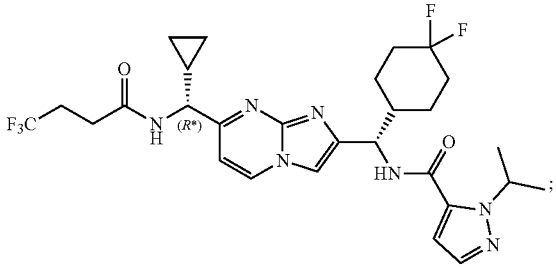
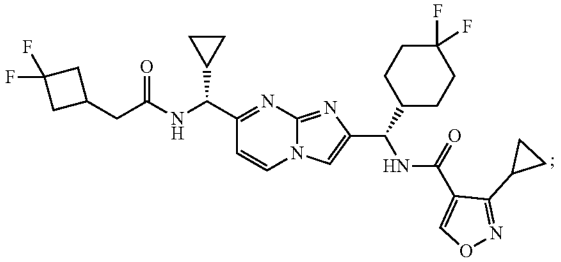
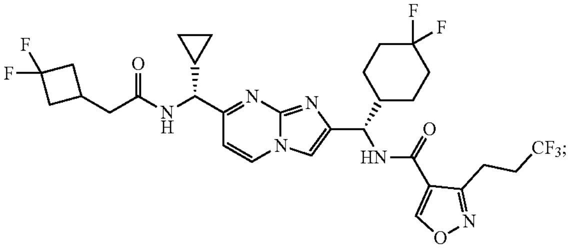
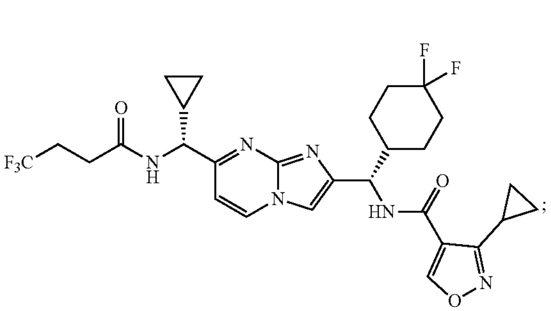
-continued
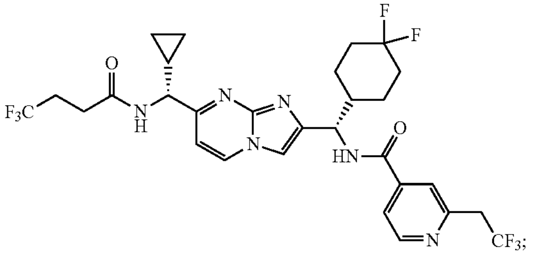
and
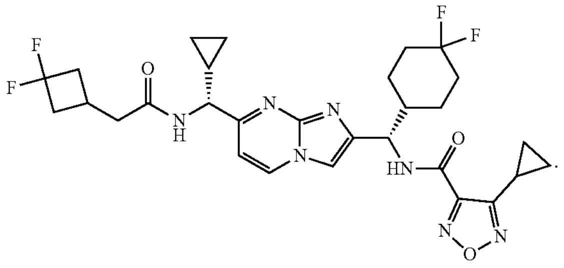
19. The compound of claim 18, or a pharmaceutically acceptable salt thereof, which is
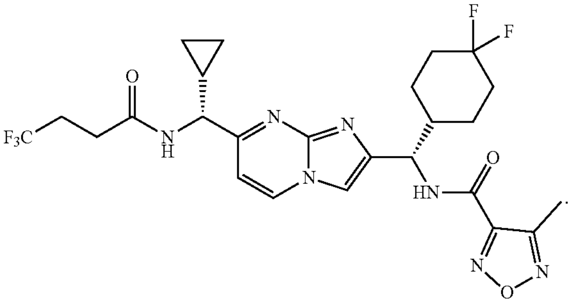
20. The compound of claim 18, or a pharmaceutically acceptable salt thereof, which is
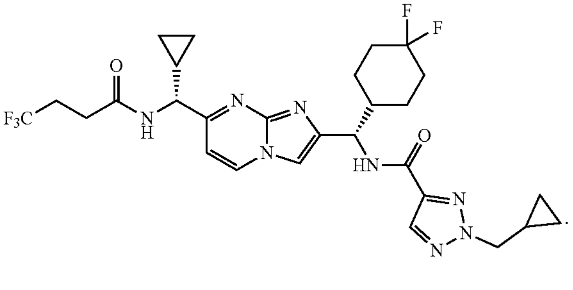 [SMILES: O=C(CCC(F)(F)F)N[C@@H](c1ccn2cc([C@@H](NC(=O)c3cnn(CC4CC4)n3)C3CCC(F)(F)CC3)nc2n1)C1CC1]
21. The compound of claim 18, or a pharmaceutically acceptable salt thereof, which is

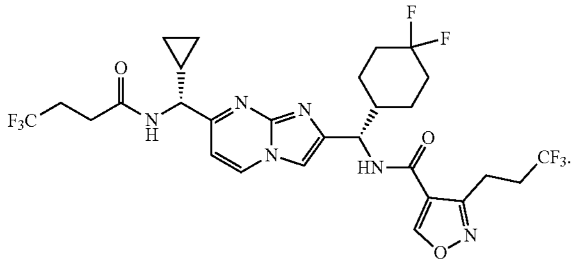 [SMILES: O=C(CCC(F)(F)F)N[C@@H](c1ccn2cc([C@@H](NC(=O)c3conc3CCC(F)(F)F)C3CCC(F)(F)CC3)nc2n1)C1CC1]

22. The compound of claim 18, or a pharmaceutically acceptable salt thereof, which is

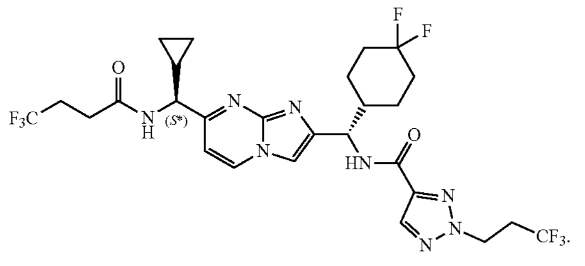 [SMILES: O=C(CCC(F)(F)F)N[C@H](c1ccn2cc([C@@H](NC(=O)c3cnn(CCC(F)(F)F)n3)C3CCC(F)(F)CC3)nc2n1)C1CC1]

23. The compound of claim 18, or a pharmaceutically acceptable salt thereof, which is

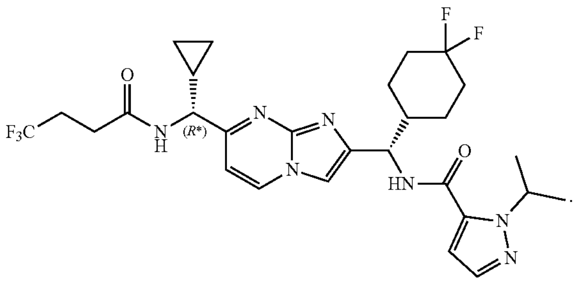 [SMILES: CC(C)n1nccc1C(=O)N[C@H](c1cn2ccc([C@H](NC(=O)CCC(F)(F)F)C3CC3)nc2n1)C1CCC(F)(F)CC1]

24. The compound of claim 18, or a pharmaceutically acceptable salt thereof, which is

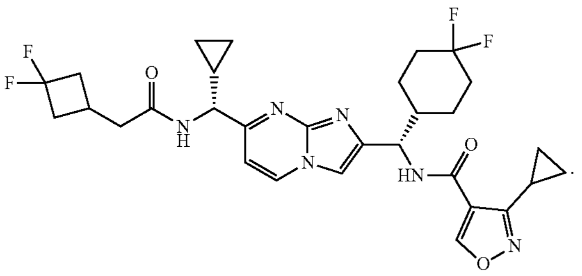 [SMILES: O=C(CC1CC(F)(F)C1)N[C@@H](c1ccn2cc([C@@H](NC(=O)c3conc3C3CC3)C3CCC(F)(F)CC3)nc2n1)C1CC1]

25. The compound of claim 18, or a pharmaceutically acceptable salt thereof, which is

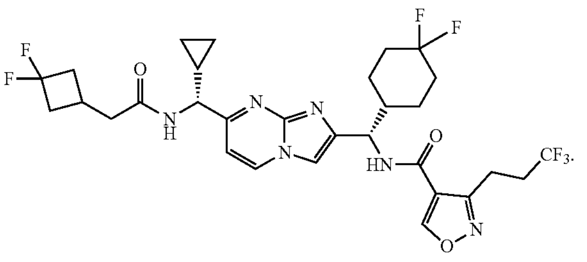 [SMILES: O=C(CC1CC(F)(F)C1)N[C@@H](c1ccn2cc([C@@H](NC(=O)c3conc3CCC(F)(F)F)C3CCC(F)(F)CC3)nc2n1)C1CC1]

26. The compound of claim 18, or a pharmaceutically acceptable salt thereof, which is

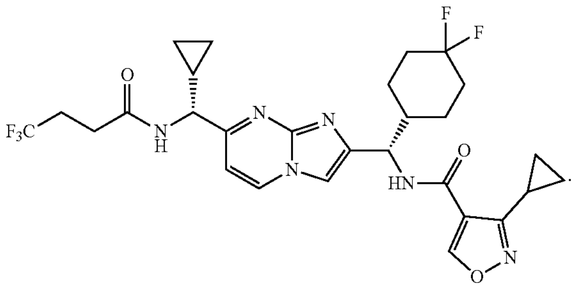 [SMILES: O=C(CCC(F)(F)F)N[C@@H](c1ccn2cc([C@@H](NC(=O)c3conc3C3CC3)C3CCC(F)(F)CC3)nc2n1)C1CC1]

27. The compound of claim 18, or a pharmaceutically acceptable salt thereof, which is

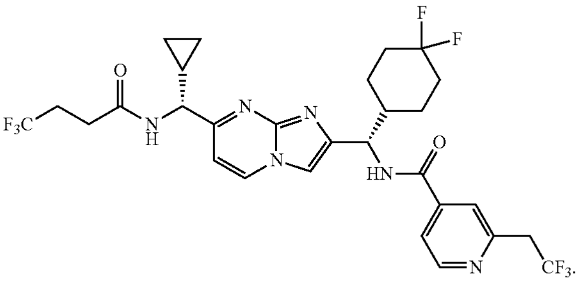 [SMILES: O=C(CCC(F)(F)F)N[C@@H](c1ccn2cc([C@@H](NC(=O)c3ccnc(CC(F)(F)F)c3)C3CCC(F)(F)CC3)nc2n1)C1CC1]

28. The compound of claim 18, or a pharmaceutically acceptable salt thereof, which is

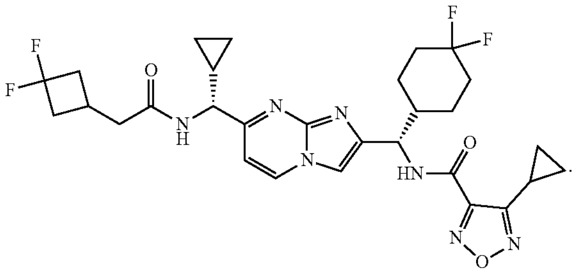 [SMILES: O=C(CC1CC(F)(F)C1)N[C@@H](c1ccn2cc([C@@H](NC(=O)c3nonc3C3CC3)C3CCC(F)(F)CC3)nc2n1)C1CC1]

29. A pharmaceutical composition, comprising a compound of claim 1, or a pharmaceutically acceptable salt thereof, and a pharmaceutically acceptable carrier.

30. A method for treating and/or ameliorating an IL-17A mediated inflammatory syndrome, disorder, or disease comprising administering to a subject in need thereof a therapeutically effective amount of a compound of claim 1, or a pharmaceutically acceptable salt thereof.

31. The method of claim 30, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigoid, atopic dermatitis, vitiligo, multiple sclerosis, asthma, uveitis, chronic obstructive pulmonary disorder, multiple myeloma, and systemic lupus erythematosus.

32. The method of claim 31, wherein the IL-17A mediated inflammatory syndrome, disorder, or disease is psoriasis.

33. The method of claim 31, wherein the IL-17A mediated inflammatory syndrome, disorder, or disease is psoriatic arthritis or rheumatoid arthritis.

34. The method of claim 31, wherein the IL-17A mediated inflammatory syndrome, disorder, or disease is atopic dermatitis.

35. The method of claim 31, wherein the IL-17A mediated inflammatory syndrome, disorder, or disease is systemic lupus erythematosus.

36. The method of claim 30, wherein the compound, or a pharmaceutically acceptable salt thereof, is administered orally.

37. The method of claim 36, wherein the compound, or a pharmaceutically acceptable salt thereof, is administered as a tablet or a capsule.

* * * * *